(12) United States Patent
Beconi et al.

(10) Patent No.: US 12,365,729 B2
(45) Date of Patent: Jul. 22, 2025

(54) ANTI-HEMOJUVELIN (HJV) ANTIBODIES FOR TREATING MYELOFIBROSIS

(71) Applicants: Disc Medicine, Inc., Watertown, MA (US); AbbVie Inc., North Chicago, IL (US); AbbVie Deutschland Gmbh & Co. KG, Wiesbaden (DE)

(72) Inventors: Maria Beconi, Cambridge, MA (US); John Quisel, Cambridge, MA (US); Brian MacDonald, Bend, OR (US); Steven Robinette, Fremont, NH (US); Bernhard Mueller, Hannover (DE); Andreas Popp, Sprockhovel (DE); Jennifer M. Perez, Worcester, MA (US)

(73) Assignees: Disc Medicine, Inc., Watertown, MA (US); Abb Vie Inc., North Chicago, IL (US); Abb Vie Deutschland Gmbh & Co. KG, Wiesbaden (DE)

( * ) Notice: Subject to any disclaimer, the term of this patent is extended or adjusted under 35 U.S.C. 154(b) by 0 days.

(21) Appl. No.: 18/896,718

(22) Filed: Sep. 25, 2024

(65) Prior Publication Data
US 2025/0084162 A1 Mar. 13, 2025

Related U.S. Application Data

(63) Continuation of application No. 17/924,672, filed as application No. PCT/US2021/032343 on May 13, 2021.
(Continued)

(51) Int. Cl.
| A61K 39/395 | (2006.01) |
| A61P 35/00 | (2006.01) |
| C07K 16/28 | (2006.01) |

(52) U.S. Cl.
CPC .............. *C07K 16/28* (2013.01); *A61P 35/00* (2018.01); *C07K 2317/24* (2013.01); *C07K 2317/565* (2013.01)

(58) Field of Classification Search
None
See application file for complete search history.

(56) References Cited

U.S. PATENT DOCUMENTS

| 4,526,938 A | 7/1985 | Churchill et al. |
| 4,554,101 A | 11/1985 | Hopp |

(Continued)

FOREIGN PATENT DOCUMENTS

| CA | 2855840 A1 | 6/2013 |
| CN | 1484652 A | 3/2004 |

(Continued)

OTHER PUBLICATIONS

Katagiri et al., Bone Morphogenetic Proteins, Cold Spring Harb. Perspect. Biol. 8:a021899, 29 pages, doi: 10.1101/cshperspect. a021899, 2016.*

(Continued)

*Primary Examiner* — Claire Kaufman
(74) *Attorney, Agent, or Firm* — Wolf, Greenfield & Sacks, P.C.

(57) ABSTRACT

Aspects of the application provide anti-hemojuvelin antibodies and methods of using the same in treating myelofibrosis and/or conditions associated with myelofibrosis.

30 Claims, 28 Drawing Sheets
Specification includes a Sequence Listing.

Related U.S. Application Data

(60) Provisional application No. 63/164,294, filed on Mar. 22, 2021, provisional application No. 63/047,828, filed on Jul. 2, 2020, provisional application No. 63/035,649, filed on Jun. 5, 2020, provisional application No. 63/024,416, filed on May 13, 2020.

(56) References Cited

U.S. PATENT DOCUMENTS

| | | |
|---|---|---|
| 4,628,027 A | 12/1986 | Gay |
| 4,704,692 A | 11/1987 | Ladner |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,223,409 A | 6/1993 | Ladner et al. |
| 5,225,539 A | 7/1993 | Winter |
| 5,241,070 A | 8/1993 | Law |
| 5,258,498 A | 11/1993 | Huston et al. |
| 5,290,540 A | 3/1994 | Prince et al. |
| 5,294,404 A | 3/1994 | Grandone et al. |
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,524 A | 6/1996 | Buechler et al. |
| 5,530,101 A | 6/1996 | Queen et al. |
| 5,543,524 A | 8/1996 | Mattingly et al. |
| 5,565,362 A | 10/1996 | Rosen et al. |
| 5,571,698 A | 11/1996 | Ladner et al. |
| 5,573,904 A | 11/1996 | Mattingly |
| 5,580,717 A | 12/1996 | Dower et al. |
| 5,585,089 A | 12/1996 | Queen et al. |
| 5,585,097 A | 12/1996 | Bolt et al. |
| 5,593,896 A | 1/1997 | Adamczyk et al. |
| 5,624,821 A | 4/1997 | Winter et al. |
| 5,627,052 A | 5/1997 | Schrader |
| 5,648,260 A | 7/1997 | Winter et al. |
| 5,658,727 A | 8/1997 | Barbas et al. |
| 5,677,425 A | 10/1997 | Bodmer et al. |
| 5,679,377 A | 10/1997 | Bernstein et al. |
| 5,679,526 A | 10/1997 | Buechler et al. |
| 5,693,762 A | 12/1997 | Queen et al. |
| 5,693,780 A | 12/1997 | Newman et al. |
| 5,698,426 A | 12/1997 | Huse |
| 5,714,352 A | 2/1998 | Jakobobits et al. |
| 5,723,323 A | 3/1998 | Kauffman et al. |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,780,225 A | 7/1998 | Wigler et al. |
| 5,783,699 A | 7/1998 | Mattingly et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,849,992 A | 12/1998 | Meade et al. |
| 5,851,776 A | 12/1998 | Valkirs |
| 5,855,913 A | 1/1999 | Hanes et al. |
| 5,869,046 A | 2/1999 | Presta et al. |
| 5,874,064 A | 2/1999 | Edwards et al. |
| 5,885,527 A | 3/1999 | Buechler |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Lloyd et al. |
| 5,939,272 A | 8/1999 | Buechler et al. |
| 5,939,598 A | 8/1999 | Kucherlapati et al. |
| 5,947,124 A | 9/1999 | Buechler et al. |
| 5,969,108 A | 10/1999 | Mccafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,998,209 A | 12/1999 | Jokobovits et al. |
| 6,017,517 A | 1/2000 | Park |
| 6,019,944 A | 2/2000 | Buechler |
| 6,019,968 A | 2/2000 | Platz et al. |
| 6,075,181 A | 6/2000 | Kucherlapati et al. |
| 6,091,001 A | 7/2000 | Jakobovits et al. |
| 6,096,311 A | 8/2000 | Fanger et al. |
| 6,111,166 A | 8/2000 | van de Winkel |
| 6,113,855 A | 9/2000 | Buechler |
| 6,114,598 A | 9/2000 | Kucherlapati et al. |
| 6,121,022 A | 9/2000 | Presta et al. |
| 6,130,364 A | 10/2000 | Jakobovits et al. |
| 6,143,576 A | 11/2000 | Buechler |
| 6,165,745 A | 12/2000 | Ward et al. |
| 6,180,370 B1 | 1/2001 | Queen et al. |
| 6,194,551 B1 | 2/2001 | Idusogie et al. |
| 6,204,023 B1 | 3/2001 | Robinson et al. |
| 6,270,765 B1 | 8/2001 | Deo et al. |
| 6,277,375 B1 | 8/2001 | Ward |
| 6,303,755 B1 | 10/2001 | Deo et al. |
| 6,365,116 B1 | 4/2002 | Barham et al. |
| 6,410,690 B1 | 6/2002 | Deo et al. |
| 6,632,926 B1 | 10/2003 | Chen et al. |
| 6,660,843 B1 | 12/2003 | Feige et al. |
| 6,682,928 B2 | 1/2004 | Keler et al. |
| 6,699,658 B1 | 3/2004 | Wittrup et al. |
| 6,737,056 B1 | 5/2004 | Presta |
| 6,890,763 B2 | 5/2005 | Jackowski et al. |
| 6,914,128 B1 | 7/2005 | Salfeld et al. |
| 6,925,389 B2 | 8/2005 | Hitt et al. |
| 6,984,720 B1 | 1/2006 | Korman et al. |
| 6,989,100 B2 | 1/2006 | Norton |
| 7,335,667 B2 | 2/2008 | Rodgers et al. |
| 7,411,048 B2 | 8/2008 | Kulaksiz et al. |
| 7,511,018 B2 | 3/2009 | Goldberg et al. |
| 7,528,143 B2 | 5/2009 | Noronha et al. |
| 7,534,764 B2 | 5/2009 | Ganz et al. |
| 7,598,257 B2 | 10/2009 | Rodgers et al. |
| 7,612,041 B2 | 11/2009 | Knopf et al. |
| 7,612,181 B2 | 11/2009 | Wu et al. |
| 7,658,921 B2 | 2/2010 | Dall'Acqua et al. |
| 7,709,605 B2 | 5/2010 | Knopf et al. |
| 7,763,634 B2 | 7/2010 | Young et al. |
| 7,767,816 B2 | 8/2010 | Farmer et al. |
| 7,820,163 B2 | 10/2010 | Leung et al. |
| 7,825,246 B2 | 11/2010 | Noronha et al. |
| 7,834,022 B2 | 11/2010 | Rodgers et al. |
| 7,842,663 B2 | 11/2010 | Knopf et al. |
| 7,906,293 B2 | 3/2011 | Mattingly et al. |
| 7,960,343 B2 | 6/2011 | Knopf et al. |
| 7,968,091 B2 | 6/2011 | Woolf et al. |
| 7,988,973 B2 | 8/2011 | Sherman |
| 8,058,229 B2 | 11/2011 | Seehra et al. |
| 8,088,767 B2 | 1/2012 | Galan et al. |
| 8,138,199 B2 | 3/2012 | Noronha et al. |
| 8,138,339 B2 | 3/2012 | Bauer et al. |
| 8,158,616 B2 | 4/2012 | Rodgers et al. |
| 8,183,245 B2 | 5/2012 | Guerin et al. |

(56) References Cited

U.S. PATENT DOCUMENTS

| | | | |
|---|---|---|---|
| 8,183,346 B2 | 5/2012 | Leung et al. |
| 8,193,189 B2 | 6/2012 | Gerspacher et al. |
| 8,202,881 B2 | 6/2012 | Purandare et al. |
| 8,258,144 B2 | 9/2012 | Song et al. |
| 8,278,335 B2 | 10/2012 | Machacek et al. |
| 8,293,881 B2 | 10/2012 | Seehra et al. |
| 8,304,258 B2 | 11/2012 | Kulaksiz et al. |
| 8,309,566 B2 | 11/2012 | Bhamidipati et al. |
| 8,309,718 B2 | 11/2012 | Li et al. |
| 8,318,167 B2 | 11/2012 | Lin et al. |
| 8,323,649 B2 | 12/2012 | Garcia-Martinez et al. |
| 8,328,308 B2 | 12/2012 | Kurashina et al. |
| 8,338,377 B2 | 12/2012 | Seehra |
| 8,344,144 B2 | 1/2013 | Machacek et al. |
| 8,349,851 B2 | 1/2013 | Abraham et al. |
| 8,349,865 B2 | 1/2013 | Siu et al. |
| 8,354,408 B2 | 1/2013 | Bourke et al. |
| 8,367,078 B2 | 2/2013 | Sayeski et al. |
| 8,367,706 B2 | 2/2013 | Altman et al. |
| 8,415,346 B2 | 4/2013 | Altman et al. |
| 8,415,362 B2 | 4/2013 | Rodgers et al. |
| 8,415,364 B2 | 4/2013 | Epstein et al. |
| 8,420,089 B2 | 4/2013 | Smith |
| 8,420,695 B2 | 4/2013 | Wilson et al. |
| 8,431,569 B2 | 4/2013 | Young et al. |
| 8,440,663 B2 | 5/2013 | Mann et al. |
| 8,440,679 B2 | 5/2013 | McAllister et al. |
| 8,445,199 B2 | 5/2013 | Collier et al. |
| 8,486,902 B2 | 7/2013 | Rodgers et al. |
| 8,486,941 B2 | 7/2013 | Burns et al. |
| 8,501,735 B2 | 8/2013 | Rosales et al. |
| 8,507,435 B2 | 8/2013 | Goldberg et al. |
| 8,507,501 B2 | 8/2013 | Yu et al. |
| 8,513,270 B2 | 8/2013 | Arvantis et al. |
| 8,530,619 B2 | 9/2013 | Kaplan et al. |
| 8,563,539 B2 | 10/2013 | Baldino et al. |
| 8,580,802 B2 | 11/2013 | Salituro et al. |
| 8,591,886 B2 | 11/2013 | Ponath et al. |
| 8,604,043 B2 | 12/2013 | Li et al. |
| 8,609,817 B2 | 12/2013 | Leung et al. |
| 8,629,168 B2 | 1/2014 | Gerspacher et al. |
| 8,629,250 B2 | 1/2014 | Sasu et al. |
| 8,633,205 B2 | 1/2014 | Ledeboer et al. |
| 8,633,206 B2 | 1/2014 | Promo et al. |
| 8,637,023 B2 | 1/2014 | Lin et al. |
| 8,637,526 B2 | 1/2014 | Blaney et al. |
| 8,648,069 B2 | 2/2014 | Akritopoulou-Zanze et al. |
| 8,673,891 B2 | 3/2014 | Fujihara et al. |
| 8,691,807 B2 | 4/2014 | Yao et al. |
| 8,710,016 B2 | 4/2014 | Seehra et al. |
| 8,716,303 B2 | 5/2014 | Rodgers et al. |
| 8,722,693 B2 | 5/2014 | Rodgers et al. |
| 8,741,912 B2 | 6/2014 | Ledeboer et al. |
| 8,765,385 B2 | 7/2014 | Kumar et al. |
| 8,765,727 B2 | 7/2014 | Combs et al. |
| 8,765,734 B2 | 7/2014 | Huang et al. |
| 8,779,001 B2 | 7/2014 | Tweardy et al. |
| 8,795,665 B2 | 8/2014 | Seo et al. |
| 8,809,359 B2 | 8/2014 | Burns |
| 8,814,840 B2 | 8/2014 | Evans et al. |
| 8,822,481 B1 | 9/2014 | Rodgers et al. |
| 8,829,013 B1 | 9/2014 | Rodgers et al. |
| 8,841,431 B2 | 9/2014 | Sell et al. |
| 8,846,908 B2 | 9/2014 | Singh et al. |
| 8,865,168 B2 | 10/2014 | Lin et al. |
| 8,871,753 B2 | 10/2014 | Combs et al. |
| 8,895,002 B2 | 11/2014 | Lin et al. |
| 8,901,145 B2 | 12/2014 | Baldino et al. |
| 8,912,200 B2 | 12/2014 | Brasca et al. |
| 8,915,875 B2 | 12/2014 | Passlock-Deetjen et al. |
| 8,921,376 B2 | 12/2014 | Ledeboer et al. |
| 8,933,085 B2 | 1/2015 | Rodgers et al. |
| 8,937,064 B2 | 1/2015 | Ledeboer et al. |
| 8,937,065 B2 | 1/2015 | Becker et al. |
| 8,957,065 B2 | 2/2015 | Cha et al. |
| 8,962,803 B2 | 2/2015 | Mueller et al. |
| 8,980,582 B2 | 3/2015 | Seo et al. |
| 8,999,998 B2 | 4/2015 | Gibbons et al. |
| 9,034,311 B2 | 5/2015 | Eastwood et al. |
| 9,034,884 B2 | 5/2015 | Rodgers et al. |
| 9,035,074 B2 | 5/2015 | Brown et al. |
| 9,040,052 B1 | 5/2015 | Clube |
| 9,051,382 B2 | 6/2015 | Trentmann et al. |
| 9,079,912 B2 | 7/2015 | Rodgers et al. |
| 9,085,615 B2 | 7/2015 | Garcia-Martinez et al. |
| 9,133,200 B2 | 9/2015 | Gonzalez Rodriguez et al. |
| 9,175,075 B2 | 11/2015 | Mueller |
| 9,175,078 B2 | 11/2015 | Arvedson et al. |
| 9,181,271 B2 | 11/2015 | Li et al. |
| 9,187,562 B1 | 11/2015 | Clube |
| 9,193,733 B2 | 11/2015 | Rodgers et al. |
| 9,206,183 B2 | 12/2015 | Bach Tana et al. |
| 9,206,188 B2 | 12/2015 | Vankayalapati et al. |
| 9,228,188 B2 | 1/2016 | Bettecourt et al. |
| 9,249,145 B2 | 2/2016 | Rodgers et al. |
| 9,249,454 B2 | 2/2016 | Woolf et al. |
| 9,265,825 B2 | 2/2016 | Smith |
| 9,283,224 B2 | 3/2016 | Brasca et al. |
| 9,315,577 B2 | 4/2016 | Foltz et al. |
| 9,358,229 B2 | 6/2016 | Vannucchi et al. |
| 9,359,358 B2 | 6/2016 | Rodgers et al. |
| 9,371,320 B2 | 6/2016 | Nara et al. |
| 9,382,231 B2 | 7/2016 | Li et al. |
| 9,439,963 B2 | 9/2016 | Clube |
| 9,452,227 B2 | 9/2016 | Garcia-Martinez et al. |
| 9,469,613 B2 | 10/2016 | Brown et al. |
| 9,469,654 B2 | 10/2016 | Pandey et al. |
| 9,518,027 B2 | 12/2016 | Silverman |
| 9,526,759 B2 | 12/2016 | Knopf et al. |
| 9,533,986 B2 | 1/2017 | Pandey et al. |
| 9,540,367 B2 | 1/2017 | Tung |
| 9,556,251 B2 | 1/2017 | Lin et al. |
| 9,605,069 B2 | 3/2017 | Mueller et al. |
| 9,610,356 B2 | 4/2017 | Hohlbaum et al. |
| 9,617,258 B2 | 4/2017 | Thorarensen et al. |
| 9,636,398 B2 | 5/2017 | Belligere et al. |
| 9,637,483 B2 | 5/2017 | Yoshida et al. |
| 9,650,399 B2 | 5/2017 | Gunning et al. |
| 9,657,098 B2 | 5/2017 | Westerman et al. |
| 9,676,756 B2 | 6/2017 | Bauer et al. |
| 9,682,983 B2 | 6/2017 | Alimardanov et al. |
| 9,688,661 B2 | 6/2017 | Brasca et al. |
| 9,701,747 B2 | 7/2017 | Smith |
| 9,708,379 B2 | 7/2017 | Lin et al. |
| 9,724,410 B2 | 8/2017 | Smith et al. |
| 9,738,636 B2 | 8/2017 | Hopkins et al. |
| 9,803,011 B2 | 10/2017 | Westerman et al. |
| 9,814,722 B2 | 11/2017 | Rodgers et al. |
| 9,862,764 B2 | 1/2018 | Cong et al. |
| 9,884,900 B2 | 2/2018 | Kumar et al. |
| 9,949,971 B2 | 4/2018 | Hamdy et al. |
| 9,993,480 B2 | 6/2018 | Vannucchi et al. |
| 10,001,571 B2 | 6/2018 | Rowland et al. |
| 10,011,571 B2 | 7/2018 | Lu et al. |
| 10,016,429 B2 | 7/2018 | Rodgers et al. |
| 10,064,866 B2 | 9/2018 | Scherle et al. |
| 10,106,602 B2 | 10/2018 | Mueller et al. |
| 10,111,897 B2 | 10/2018 | Wood et al. |
| 10,112,933 B2 | 10/2018 | Tweardy et al. |
| 10,118,958 B2 | 11/2018 | Mueller et al. |
| 10,189,882 B2 | 1/2019 | Attie et al. |
| 10,202,356 B2 | 2/2019 | Mollard et al. |
| 10,206,931 B2 | 2/2019 | Romero et al. |
| 10,233,186 B2 | 3/2019 | Brooijmans et al. |
| 10,239,941 B2 | 3/2019 | Westerman et al. |
| 10,245,268 B2 | 4/2019 | Koh et al. |
| 10,246,462 B2 | 4/2019 | Beck et al. |
| 10,273,273 B2 | 4/2019 | Lin et al. |
| 10,294,226 B2 | 5/2019 | Koudriakova et al. |
| 10,307,426 B2 | 6/2019 | Zak et al. |
| 10,307,455 B2 | 6/2019 | Kumar et al. |
| 10,323,088 B2 | 6/2019 | Westerman |
| 10,391,094 B2 | 8/2019 | Jayan et al. |
| 10,428,148 B2 | 10/2019 | Katagiri et al. |

(56) References Cited

U.S. PATENT DOCUMENTS

| | | |
|---|---|---|
| 10,669,277 B2 | 6/2020 | Wilson et al. |
| 10,822,403 B2 | 11/2020 | Mueller et al. |
| 12,098,189 B2 | 9/2024 | Mueller et al. |
| 12,098,192 B2 | 9/2024 | Mueller et al. |
| 2003/0170881 A1 | 9/2003 | Davis et al. |
| 2003/0186374 A1 | 10/2003 | Hufton et al. |
| 2004/0018577 A1 | 1/2004 | Emerson et al. |
| 2005/0042664 A1 | 2/2005 | Wu et al. |
| 2005/0054078 A1 | 3/2005 | Miller et al. |
| 2006/0104968 A1 | 5/2006 | Bookbinder et al. |
| 2006/0106020 A1 | 5/2006 | Rodgers et al. |
| 2006/0153852 A1 | 7/2006 | Coleman et al. |
| 2006/0160164 A1 | 7/2006 | Miller et al. |
| 2007/0004618 A1 | 1/2007 | Ganz et al. |
| 2007/0149506 A1 | 6/2007 | Arvantis et al. |
| 2008/0020401 A1 | 1/2008 | Grenier et al. |
| 2008/0021013 A1 | 1/2008 | Dobrzanski et al. |
| 2008/0213277 A1 | 9/2008 | Sasu et al. |
| 2008/0287475 A1 | 11/2008 | Feng et al. |
| 2008/0312259 A1 | 12/2008 | Rodgers et al. |
| 2009/0062302 A1 | 3/2009 | Buser-Doepner et al. |
| 2009/0104187 A1 | 4/2009 | Kovacevich et al. |
| 2009/0238825 A1 | 9/2009 | Kovacevich et al. |
| 2010/0008918 A1 | 1/2010 | Sherman et al. |
| 2010/0028340 A1 | 2/2010 | Mueller et al. |
| 2010/0035875 A1 | 2/2010 | Zhu et al. |
| 2010/0048557 A1 | 2/2010 | Zhu et al. |
| 2010/0093760 A1 | 4/2010 | Yu et al. |
| 2010/0160287 A1 | 6/2010 | Wannamaker et al. |
| 2010/0204246 A1 | 8/2010 | Davies et al. |
| 2010/0322941 A1 | 12/2010 | Fischer et al. |
| 2010/0324040 A1 | 12/2010 | Davies et al. |
| 2011/0020775 A1 | 1/2011 | Cecil |
| 2011/0070233 A1 | 3/2011 | Seehra et al. |
| 2011/0085973 A1 | 4/2011 | Kao et al. |
| 2011/0135664 A1 | 6/2011 | Mueller |
| 2011/0201628 A1 | 8/2011 | Chuaqui et al. |
| 2011/0243853 A1 | 10/2011 | Jamieson et al. |
| 2011/0293526 A1 | 12/2011 | Plikus et al. |
| 2012/0055573 A1 | 3/2012 | Adams |
| 2012/0064076 A1 | 3/2012 | Lin et al. |
| 2012/0115930 A1 | 5/2012 | Monia et al. |
| 2012/0164140 A1 | 6/2012 | Lin et al. |
| 2012/0196853 A1 | 8/2012 | Duerrenberger et al. |
| 2012/0202806 A1 | 8/2012 | Duerrenberger et al. |
| 2012/0214798 A1 | 8/2012 | Duerrenberger et al. |
| 2012/0214803 A1 | 8/2012 | Buhr et al. |
| 2013/0089512 A1 | 4/2013 | Eastwood et al. |
| 2013/0216498 A1 | 8/2013 | Eastwood et al. |
| 2013/0243743 A1 | 9/2013 | Seehra et al. |
| 2013/0330343 A1 | 12/2013 | Mueller et al. |
| 2013/0330359 A1 | 12/2013 | Beligere et al. |
| 2014/0057970 A1 | 2/2014 | Schwobel et al. |
| 2014/0073643 A1 | 3/2014 | Smith et al. |
| 2014/0073645 A1 | 3/2014 | Linder et al. |
| 2014/0086919 A1 | 3/2014 | Lin et al. |
| 2014/0127325 A1 | 5/2014 | Bettencourt et al. |
| 2014/0170110 A1 | 6/2014 | Eastwood et al. |
| 2014/0199314 A1 | 7/2014 | Lin et al. |
| 2014/0286964 A1 | 9/2014 | Hubbard et al. |
| 2015/0024046 A1 | 1/2015 | Bartholomaus et al. |
| 2015/0166672 A1 | 6/2015 | Clube |
| 2015/0197525 A1 | 7/2015 | Silverman et al. |
| 2015/0291675 A1 | 10/2015 | Trentmann et al. |
| 2015/0306112 A1 | 10/2015 | Wu et al. |
| 2015/0361163 A1 | 12/2015 | Kumar et al. |
| 2015/0369821 A1 | 12/2015 | Trentmann et al. |
| 2016/0115167 A1 | 4/2016 | Yu et al. |
| 2016/0122409 A1 | 5/2016 | Ganz et al. |
| 2016/0186172 A1 | 6/2016 | Bettencourt et al. |
| 2016/0263117 A1 | 9/2016 | Yu et al. |
| 2016/0317632 A1 | 11/2016 | Albrecht et al. |
| 2017/0029499 A1 | 2/2017 | Kakkar et al. |
| 2017/0190705 A1 | 7/2017 | Yu et al. |
| 2017/0196878 A1 | 7/2017 | Centore et al. |
| 2017/0197968 A1 | 7/2017 | Lee et al. |
| 2017/0224819 A1 | 8/2017 | Hamdy et al. |
| 2017/0239451 A1 | 8/2017 | Berkowitz |
| 2017/0247448 A1 | 8/2017 | Westerman |
| 2017/0274077 A1 | 9/2017 | Kumar et al. |
| 2017/0305883 A1 | 10/2017 | Yu et al. |
| 2017/0313754 A1 | 11/2017 | Bourne et al. |
| 2017/0333406 A1 | 11/2017 | Adler et al. |
| 2018/0001633 A1 | 1/2018 | Silverbrook et al. |
| 2018/0002328 A1 | 1/2018 | Li et al. |
| 2018/0016332 A1 | 1/2018 | Schurpf et al. |
| 2018/0021340 A1 | 1/2018 | Yu et al. |
| 2018/0050085 A1 | 2/2018 | Kumar et al. |
| 2018/0057812 A1 | 3/2018 | Peyssonnaux et al. |
| 2018/0118835 A1 | 5/2018 | Katagiri et al. |
| 2018/0148491 A1 | 5/2018 | Han et al. |
| 2018/0317602 A1 | 11/2018 | Rothbaum et al. |
| 2019/0040068 A1 | 2/2019 | Yin et al. |
| 2019/0135807 A1 | 5/2019 | Anderson et al. |
| 2019/0152949 A1 | 5/2019 | Cyr et al. |
| 2019/0169208 A1 | 6/2019 | Cui et al. |
| 2019/0204427 A1 | 7/2019 | Abari et al. |
| 2019/0218214 A1 | 7/2019 | Hopkins et al. |
| 2019/0241650 A1 | 8/2019 | Devalaraja et al. |
| 2019/0282663 A1 | 9/2019 | Seehra et al. |
| 2019/0284183 A1 | 9/2019 | Hopkins et al. |
| 2019/0322665 A1 | 10/2019 | Bacani et al. |
| 2019/0328857 A1 | 10/2019 | Andersen et al. |
| 2020/0054643 A1 | 2/2020 | Hopkins et al. |
| 2020/0055919 A1 | 2/2020 | Kumar et al. |
| 2020/0071303 A1 | 3/2020 | Wang et al. |
| 2020/0095250 A1 | 3/2020 | Vechorkin et al. |
| 2020/0101134 A1 | 4/2020 | Laadem et al. |
| 2020/0199131 A1 | 6/2020 | Pan et al. |
| 2021/0380669 A1 | 12/2021 | Nicholls et al. |
| 2022/0372135 A1 | 11/2022 | Quisel et al. |
| 2022/0372136 A1 | 11/2022 | Quisel et al. |
| 2023/0174645 A1 | 6/2023 | Beconi et al. |
| 2023/0183339 A1 | 6/2023 | Beconi et al. |
| 2024/0417458 A1 | 12/2024 | MacDonald et al. |

FOREIGN PATENT DOCUMENTS

| | | |
|---|---|---|
| CN | 101778864 A | 7/2010 |
| CN | 101816674 A | 9/2010 |
| CN | 103655542 A | 3/2014 |
| CN | 104136462 A | 11/2014 |
| CN | 104144947 A | 11/2014 |
| CN | 109789184 A | 5/2019 |
| EP | 404097 A2 | 12/1990 |
| EP | 471293 A2 | 2/1992 |
| EP | 2335708 A1 | 6/2011 |
| HN | 2010/000752 A | 8/2012 |
| JP | 2002-542770 A | 12/2002 |
| JP | 2011-512806 A | 4/2024 |
| WO | WO 1990/002809 A1 | 3/1990 |
| WO | WO 1991/005548 A1 | 5/1991 |
| WO | WO 1991/010737 A1 | 7/1991 |
| WO | WO 1991/010741 A1 | 7/1991 |
| WO | WO 1991/017271 A1 | 11/1991 |
| WO | WO 1992/001047 A1 | 1/1992 |
| WO | WO 1992/002551 A1 | 2/1992 |
| WO | WO 1992/009690 A2 | 6/1992 |
| WO | WO 1992/015679 A1 | 9/1992 |
| WO | WO 1992/018619 A1 | 10/1992 |
| WO | WO 1992/019244 A2 | 11/1992 |
| WO | WO 1992/020791 A1 | 11/1992 |
| WO | WO 1992/022324 A1 | 12/1992 |
| WO | WO 1993/001288 A1 | 1/1993 |
| WO | WO 1993/011161 A1 | 6/1993 |
| WO | WO 1993/011236 A1 | 6/1993 |
| WO | WO 1994/002602 A1 | 2/1994 |
| WO | WO 1994/029351 A2 | 12/1994 |
| WO | WO 1995/015982 A2 | 6/1995 |
| WO | WO 1995/020401 A1 | 8/1995 |
| WO | WO 1996/020698 A2 | 7/1996 |
| WO | WO 1996/033735 A1 | 10/1996 |
| WO | WO 1996/034096 A1 | 10/1996 |
| WO | WO 1997/029131 A1 | 8/1997 |

(56) References Cited

FOREIGN PATENT DOCUMENTS

| | | |
|---|---|---|
| WO | WO 1997/032572 A2 | 9/1997 |
| WO | WO 1997/034631 A1 | 9/1997 |
| WO | WO 1997/044013 A1 | 11/1997 |
| WO | WO 1998/016654 A1 | 4/1998 |
| WO | WO 1998/023289 A1 | 6/1998 |
| WO | WO 1998/024893 A2 | 6/1998 |
| WO | WO 1998/031346 A1 | 7/1998 |
| WO | WO 1998/031700 A1 | 7/1998 |
| WO | WO 1998/050433 A2 | 11/1998 |
| WO | WO 1999/015154 A1 | 4/1999 |
| WO | WO 1999/020253 A1 | 4/1999 |
| WO | WO 1999/025044 A1 | 5/1999 |
| WO | WO 1999/045031 A2 | 9/1999 |
| WO | WO 1999/053049 A1 | 10/1999 |
| WO | WO 1999/058572 A1 | 11/1999 |
| WO | WO 1999/066903 A2 | 12/1999 |
| WO | WO 2000/009560 A2 | 2/2000 |
| WO | WO 2000/037504 A2 | 6/2000 |
| WO | WO 2000/042072 A2 | 7/2000 |
| WO | WO 2000/056772 A1 | 9/2000 |
| WO | WO 2001/058956 A2 | 8/2001 |
| WO | WO 2002/002773 A2 | 1/2002 |
| WO | WO 2002/016436 A2 | 2/2002 |
| WO | WO 2002/060919 A2 | 8/2002 |
| WO | WO 2004/078140 A2 | 9/2004 |
| WO | WO 2005/047307 A2 | 5/2005 |
| WO | WO 2006/088972 A2 | 8/2006 |
| WO | WO 2007/024715 A2 | 3/2007 |
| WO | WO 2007/039256 A2 | 4/2007 |
| WO | WO 2008/047831 A1 | 4/2008 |
| WO | WO 2008/117050 A1 | 10/2008 |
| WO | WO 2008/124768 A1 | 10/2008 |
| WO | WO 2008/132502 A1 | 11/2008 |
| WO | WO 2008/144757 A1 | 11/2008 |
| WO | WO 2009/016410 A2 | 2/2009 |
| WO | WO 2009/017838 A2 | 2/2009 |
| WO | WO 2009/017954 A1 | 2/2009 |
| WO | WO 2009/027736 A2 | 3/2009 |
| WO | WO 2009/030500 A1 | 3/2009 |
| WO | WO 2007/024715 A9 | 4/2009 |
| WO | WO 2009/046416 A1 | 4/2009 |
| WO | WO 2009/049028 A1 | 4/2009 |
| WO | WO 2009/055674 A1 | 4/2009 |
| WO | WO 2009/095712 A2 | 8/2009 |
| WO | WO 2009/106356 A1 | 9/2009 |
| WO | WO 2010/020810 A1 | 2/2010 |
| WO | WO 2010/056981 A2 | 5/2010 |
| WO | WO 2010/065077 A2 | 6/2010 |
| WO | WO 2010/065079 A2 | 6/2010 |
| WO | WO 2010/065496 A1 | 6/2010 |
| WO | WO 2010/072823 A1 | 7/2010 |
| WO | WO 2010/141062 A1 | 12/2010 |
| WO | WO 2011/023722 A1 | 3/2011 |
| WO | WO 2011/029832 A1 | 3/2011 |
| WO | WO 2011/066369 A2 | 6/2011 |
| WO | WO 2011/066371 A2 | 6/2011 |
| WO | WO 2011/070045 A1 | 6/2011 |
| WO | WO 2011/153586 A1 | 12/2011 |
| WO | WO 2012/150973 A1 | 11/2012 |
| WO | WO 2013/063110 A1 | 5/2013 |
| WO | WO 2013/090633 A2 | 6/2013 |
| WO | WO 2013/090635 A2 | 6/2013 |
| WO | WO 2014/020531 A1 | 2/2014 |
| WO | WO 2014/058516 A1 | 4/2014 |
| WO | WO 2014/065661 A1 | 5/2014 |
| WO | WO 2015/051135 A2 | 4/2015 |
| WO | WO 2015/091531 A1 | 6/2015 |
| WO | WO 2015/118434 A1 | 8/2015 |
| WO | WO 2015/171691 A2 | 11/2015 |
| WO | WO 2016/090188 A1 | 6/2016 |
| WO | WO 2016/146651 A1 | 9/2016 |
| WO | WO 2016/180784 A1 | 11/2016 |
| WO | WO 2017/143014 A1 | 8/2017 |
| WO | WO 2017/191437 A1 | 11/2017 |
| WO | WO 2017/196261 A1 | 11/2017 |
| WO | WO 2017/216724 A1 | 12/2017 |
| WO | WO 2018/009624 A1 | 1/2018 |
| WO | WO 2018/053234 A1 | 3/2018 |
| WO | WO 2018/067740 A1 | 4/2018 |
| WO | WO 2018/096525 A2 | 5/2018 |
| WO | WO 2018/128828 A1 | 7/2018 |
| WO | WO 2018/136634 A1 | 7/2018 |
| WO | WO 2018/165186 A1 | 9/2018 |
| WO | WO 2018/185341 A1 | 10/2018 |
| WO | WO 2018/200855 A1 | 11/2018 |
| WO | WO 2019/057112 A1 | 3/2019 |
| WO | WO 2019/069844 A1 | 4/2019 |
| WO | WO 2019/079649 A1 | 4/2019 |
| WO | WO 2019/094751 A1 | 5/2019 |
| WO | WO 2019/107943 A1 | 6/2019 |
| WO | WO 2019/140283 A1 | 7/2019 |
| WO | WO 2019/161157 A1 | 8/2019 |
| WO | WO 2019/161162 A1 | 8/2019 |
| WO | WO 2019/204427 A1 | 10/2019 |
| WO | WO 2020/009740 A2 | 1/2020 |
| WO | WO 2020/041466 A1 | 2/2020 |
| WO | WO 2020/065252 A1 | 4/2020 |
| WO | WO 2020/068729 A1 | 4/2020 |
| WO | WO 2020/086730 A1 | 4/2020 |
| WO | WO 2020/086736 A1 | 4/2020 |
| WO | WO 2020/086963 A1 | 4/2020 |
| WO | WO 2020/092523 A1 | 5/2020 |
| WO | WO 2020/097396 A1 | 5/2020 |
| WO | WO 2020/097398 A1 | 5/2020 |
| WO | WO 2020/112086 A1 | 6/2020 |
| WO | WO 2021/062163 A1 | 4/2021 |
| WO | WO 2021/062171 A1 | 4/2021 |
| WO | WO 2021/231798 A1 | 11/2021 |
| WO | WO 2021/231800 A2 | 11/2021 |
| WO | WO 2023/091968 A1 | 5/2023 |

OTHER PUBLICATIONS

Fujita et al., The roles of RGMa-neogenin signaling in inflammation and angiogenesis, Inflamm. Regener. 37:6, 4 pages, doi.org/10.1186/s41232-017-0037-6, 2017.*
Chiu et al., Antibody Structure and Function: The Basis for Engineering Therapeutics, Antibodies, 8:55, 80 pages, doi:10.3390/antib8040055, 2019.*
International Preliminary Report on Patentability for Application No. PCT/US2023/068107 mailed Dec. 19, 2024.
Extended European Search Report for Application No. 20867029.9, mailed Aug. 7, 2023.
International Search Report and Written Opinion for Application No. PCT/US2020/052732 mailed Jan. 11, 2021.
International Preliminary Report on Patentability for Application No. PCT/US2020/052732 mailed Apr. 7, 2022.
Extended European Search Report for Application No. 20869747.4, mailed Sep. 18, 2023.
International Search Report and Written Opinion for Application No. PCT/US2020/052748 mailed Jan. 12, 2021.
International Preliminary Report on Patentability for Application No. PCT/US2020/052748 mailed Apr. 7, 2022.
Extended European Search Report for Application No. EP21803135.9, mailed May 2, 2024.
Invitation to Pay Additional Fees for Application No. PCT/US2021/032345 mailed Aug. 24, 2021.
International Search Report and Written Opinion for Application No. PCT/US2021/032345 mailed Nov. 26, 2021.
International Preliminary Report on Patentability for Application No. PCT/US2021/032345 mailed Nov. 24, 2022.
Extended European Search Report for Application No. EP21804008.7, mailed Apr. 8, 2024.
Invitation to Pay Additional Fees for Application No. PCT/US2021/032343 mailed Aug. 16, 2021.
International Search Report and Written Opinion for Application No. PCT/US2021/032343 mailed Oct. 29, 2021.
International Preliminary Report on Patentability for Application No. PCT/US2021/032343 mailed Nov. 24, 2022.

(56) References Cited

OTHER PUBLICATIONS

International Search Report and Written Opinion for Application No. PCT/US2022/079987 mailed Mar. 6, 2023.
International Preliminary Report on Patentability for Application No. PCT/US2022/079987 mailed May 30, 2024.
International Search Report and Written Opinion for Application No. PCT/US2023/068107 mailed Oct. 17, 2023.
[No Author Listed] Know About Different Types of Wounds, Wound Care Surgeons, 2022, https://www.woundcaresurgeons.org/blogs/know-about-different-types-of-wounds, 5 pages.
[No Author Listed] National Kidney Foundation. K/DOQI clinical practice guidelines for chronic kidney disease: evaluation, classification, and stratification. Am J Kidney Dis. Feb. 2002;39(2 Suppl 1):S1-266.
Akinc et al., Targeting the Hepcidin Pathway with RNAi Therapeutics for the Treatment of Anemia. Blood. Nov. 18, 2011;118(21):688. doi: http://doi.org/10.1182/blood.V118.21.688.688.
Alshemmari et al., Molecular Pathogenesis and Clinical Significance of Driver Mutations in Primary Myelofibrosis: A Review. Med Princ Pract. 2016;25(6):501-509. doi: 10.1159/000450956. Epub Sep. 21, 2016.
Alwahaibi et al., Spectrum of glomerular diseases in Arab countries: A systematic review. Saudi J Kidney Dis Transpl. Nov.-Dec. 2018;29(6):1256-1266. doi: 10.4103/1319-2442.248285.
Amylon et al., Prednisone stimulation of erythropoiesis in leukemic children during remission. Am J Hematol. Oct. 1986;23(2):179-81. doi: 10.1002/ajh.2830230213.
Andriopoulos et al., BMP6 is a key endogenous regulator of hepcidin expression and iron metabolism. Nat Genet. Apr. 2009;41(4):482-7. doi: 10.1038/ng.335. Epub Mar. 1, 2009. Author Manuscript, 16 pages.
Asshoff et al., Momelotinib inhibits ACVR1/ALK2, decreases hepcidin production, and ameliorates anemia of chronic disease in rodents. Blood. Mar. 30, 2017;129(13):1823-1830. doi: 10.1182/blood-2016-09-740092. Epub Feb. 10, 2017.
Babbitt et al., Mechanisms of anemia in CKD. J Am Soc Nephrol. Oct. 2012;23(10):1631-4. doi: 10.1681/ASN.2011111078. Epub Aug. 30, 2012.
Babbitt et al., Bone morphogenetic protein signaling by hemojuvelin regulated hepcidin expression. Nature Genetics. May 2006;38(5):531. doi:10.1038/ng1777. Epub Apr. 9, 2006.
Birgegard et al., Inflammatory functional iron deficiency common in myelofibrosis, contributes to anaemia and impairs quality of life. From the Nordic MPN study Group. Eur J Haematol. Mar. 2019;102(3):235-240. doi: 10.1111/ejh.13198. Epub Jan. 1, 2019.
Blanchette et al., Modulation of hepcidin to treat iron deregulation: potential clinical applications. Expert Rev Hematol. 2016;9(2):169-86. doi: 10.1586/17474086.2016.1124757. Epub Dec. 15, 2015.
Boser et al., Anti-repulsive Guidance Molecule C (RGMc) Antibodies Increases Serum Iron in Rats and Cynomolgus Monkeys by Hepcidin Downregulation. AAPS J. Jul. 2015;17(4):930-8. doi: 10.1208/s12248-015-9770-4. Epub Apr. 22, 2015.
Brasse-Lagnel et al., Immunoassay for human serum hemojuvelin. Haematologica. Dec. 2010;95(12):2031-7. doi: 10.3324/haematol.2010.022129. Epub Aug. 16, 2010.
Braunstein et al., Anemia of Chronic Disease. John Hopkins University School of Medicine. Sep. 2021. https://www.merckmanuals.com/professional/hematology-and-oncology/anemias-caused-by-deficient-erythropoiesis/anemia-of-chronic-disease [last accessed Nov. 16, 2022].
Browne et al., Potential role of bone morphogenetic protein (BMP) signalling as a potential therapeutic target for modification of iron balance. Nephrology Dialysis Transplantation. Jan. 1, 2009;24(1):28-30.
Bruhns et al., Specificity and affinity of human Fcgamma receptors and their polymorphic variants for human IgG subclasses. Blood. Apr. 16, 2009;113(16):3716-25. doi: 10.1182/blood-2008-09-179754. Epub Nov. 18, 2008.
Calpe et al., Comparison of newly developed anti-bone morphogenetic protein 4 llama-derived antibodies with commercially available BMP4 inhibitors. MAbs. May-Jun. 2016;8(4):678-88. doi: 10.1080/19420862.2016.1158380.
Canali et al., Activin B Induces Noncanonical SMAD1/5/8 Signaling via BMP Type I Receptors in Hepatocytes: Evidence for a Role in Hepcidin Induction by Inflammation in Male Mice. Endocrinology. Mar. 2016;157(3):1146-62. doi: 10.1210/en.2015-1747. Epub Jan. 6, 2016.
Capellini et al., Iron deficiency across chronic inflammatory conditions: International expert opinion on definition, diagnosis, and management. Am J Hematol. Oct. 2017;92(10):1068-1078. doi: 10.1002/ajh.24820. Epub Jul. 7, 2017.
Carvalho et al., ALK2 inhibitors display beneficial effects in preclinical models of ACVR1 mutant diffuse intrinsic pontine glioma. Commun Biol. May 9, 2019;2:156. doi: 10.1038/s42003-019-0420-8.
Cazzola, et al., From Janus kinase 2 to calreticulin: the clinically relevant genomic landscape of myeloproliferative neoplasms. Blood. Jun. 12, 2014;123(24):3714-9. doi: 10.1182/blood-2014-03-530865. Epub Apr. 30, 2014.
Chai et al., Danazol: An Effective and Underutilised Treatment Option in Diamond-Blackfan Anaemia. Case Rep Hematol. Jul. 1, 2019;2019:4684156. doi: 10.1155/2019/4684156.
Chelius et al., Formation of pyroglutamic acid from N-terminal glutamic acid in immunoglobulin gamma antibodies. Anal Chem. Apr. 1, 2006;78(7):2370-6. doi: 10.1021/ac051827k.
Chen et al., Differential roles for bone morphogenetic protein (BMP) receptor type IB and IA in differentiation and specification of mesenchymal precursor cells to osteoblast and adipocyte lineages. J Cell Biol. Jul. 13, 1998;142(1):295-305. doi: 10.1083/jcb.142.1.295.
Cheng et al., Hepcidin expression in anemia of chronic disease and concomitant iron-deficiency anemia. Clin Exp Med. Mar. 2011;11(1):33-42. doi: 10.1007/s10238-010-0102-9. Epub May 25, 2010.
Chothia et al., Canonical structures for the hypervariable regions of immunoglobulins. J Mol Biol. Aug. 20, 1987;196(4):901-17. doi: 10.1016/0022-2836(87)90412-8.
Cokic et al., Proinflammatory Cytokine IL-6 and JAK-STAT Signaling Pathway in Myeloproliferative Neoplasms. Mediators Inflamm. 2015;2015:453020. doi: 10.1155/2015/453020. Epub Sep. 29, 2015.
Cooke et al., A fully human anti-hepcidin antibody modulates iron metabolism in both mice and nonhuman primates. Blood. Oct. 24, 2013;122(17):3054-61. Doi: 10.1182/blood-2013-06-505792. Epub Aug. 14, 2013.
Coyne, Hepcidin: clinical utility as a diagnostic tool and therapeutic target. Kidney Int. Aug. 2011;80(3):240-4. doi: 10.1038/ki.2011.141. Epub Jun. 15, 2011.
Cullis, Diagnosis and management of anaemia of chronic disease: current status. Br J Haematol. Aug. 2011;154(3):289-300. doi: 10.1111/j.1365-2141.2011.08741.x. Epub May 25, 2011.
Daher et al., Heterozygous mutations in BMP-6 Pro-peptide Lead to Inappropriate Hepcidin Synethesis and Moderate Iron Overload in Humans. Gastroenterology. Mar. 2016;150(3): 672-683.e4. doi: 10.1053/j.gastro.2015.10.049. Epub Nov. 12, 2015.
Dall'Acqua et al., Properties of human IgG1s engineered for enhanced binding to the neonatal Fc receptor (FcRn). J Biol Chem. Aug. 18, 2006;281(33):23514-24. doi: 10.1074/jbc.M604292200. Epub Jun. 21, 2006.
D'Angelo, Role of hepcidin in the pathophysiology and diagnosis of anemia. Blood Res. Mar. 2013;48(1):10-5. doi: 10.5045/br.2013.48.1.10. Epub Mar. 25, 2013.
De Falco et al., Iron refractory iron deficiency anemia. Haemotologica. 2013;98(6): 845-53. doi: 10.3324/haematol.2012.075515.
De Pascalis et al., Grafting of "abbreviated" complementarity-determining regions containing specificity-determining residues essential for ligand contact to engineer a less immunogenic humanized monoclonal antibody. the Journal of Immunology. Sep. 15, 2002;169(6):3076-84.
Du et al., The serine protease TMPRSS6 is required to sense iron deficiency. Science. May 23, 2008;320(5879):1088-92. doi: 10.1126/science.1157121. Epub May 1, 2008. Author Manuscript, 9 pages.
Elala et al., 1599 Driver Mutations and Prognosis in 502 Patients with Essential Thrombocythemia. ASH. Dec. 5, 2015. Retrieved

(56) References Cited

OTHER PUBLICATIONS from internet: https://ash.confex.com/ash/2015/webprogramscheduler/Paper79911.html. [last accessed Nov. 22, 2022].

Eleftheriadis et al., The role of hepcidin in iron homeostasis and anemia in hemodialysis patients. Semin Dial. Jan.-Feb. 2009;22(1):70-7. doi: 10.1111/j.1525-139X.2008.00532.x.

Emanuel et al., Myeloproliferative neoplasm (MPN) symptom assessment form total symptom score: prospective international assessment of an abbreviated symptom burden scoring system among patients with MPNs. J Clin Oncol. Nov. 20, 2012;30(33):4098-103. doi: 10.1200/JCO.2012.42.3863. Epub Oct. 15, 2012. Erratum in: J Clin Oncol. Dec. 20, 2012;30(36):4590. Ferarri, Maria L. [corrected to Ferrari, Maria L].

Feder et al., A novel MHC class I-like gene is mutated in pateints with hereditary haemochromatosis. Nat Genet. Aug. 1996;13(4):399-408. doi: 10.1038/ng0896-399.

Finberg et al., Down-regulation of Bmp/Smad signaling by Tmprss6 is required for maintenance of systemic iron homeostasis. Blood. May 6, 2010;115(18):3817-26. doi: 10.1182/blood-2009-05-224808. Epub Mar. 3, 2010.

Fung et al., High-throughput screening of small molecules identifies hepcidin antagonists. Mol Pharmacol. Mar. 2013;83(3):681-90. doi: 10.1124/mol.112.083428. Epub Jan. 4, 2013.

Fung et al., Manipulation of the hepcidin pathway for therapeutic purposes. Haematologica. Nov. 2013;98(11):1667-76. doi: 10.3324/haematol.2013.084624.

Ganz et al., The Hepcidin-Ferroportin System as a Therapeutic Target in Anemias and Iron Overload Disorders. Hematology Am Soc Hematol Educ Program. 2011:538-42. doi: 10.1182/asheducation-2011.1.538.

Ganz, Hepcidin and iron regulation, 10 years later. Blood. Apr. 28, 2011;117(17):4425-33. doi: 10.1182/blood-2011-01-258467. Epub Feb. 23, 2011.

Genbank Submission; NIH/NCBI, Gene ID 148738, HJV hemojuvelin BMP co-receptor [*Homo sapiens* (human)], Jun. 15, 2023, 7 pages.

Genbank Submission; NIH/NCBI, Gene ID 310681, Hjv hemojuvelin BMP co-receptor [*Rattus norvegicus* (Norway rat)], Jun. 15, 2023, 4 pages.

Genbank Submission; NIH/NCBI, Gene ID 69585, Hjv hemojuvelin BMP co-receptor [*Mus musculus* (house mouse)], Apr. 12, 2023, 5 pages.

Genbank Submission; NIH/NCBI, Gene ID 698805, HJV hemojuvelin BMP co-receptor [*Macaca mulatta* (Rhesus monkey)], Aug. 15, 2022, 3pages.

Gomez-Puerto et al., Bone morphogenetic protein receptor signal transduction in human disease. J Pathol. Jan. 2019;247(1):9-20. doi: 10.1002/path.5170. Epub Nov. 27, 2018.

Gorrell et al., Identification of a bone mophogenic protein type 2 receptor neutralizing antibody. BMC Res Notes. 2019;12-331. doi: 10.1186/s13104-019-4367-0.

Guglielmelli et al., Anaemia characterises patients with myelofibrosis harbouring Mpl mutation. Br J Haematol. May 2007;137(3):244-7. doi: 10.1111/j.1365-2141.2007.06565.x.

Harrison et al., Momelotinib versus best available therapy in patients with myelofibrosis previously treated with ruxolitinib (Simplify 2): a randomized, open-label, phase 3 trial. Lancet Haematol. Feb. 2018;5(2):e73-e81. doi: 10.1016/S2352-3026(17)30237-5. Epub Dec. 20, 2017.

Hinton et al., Engineered Human IgG Antibodies with Longer Serum Half-lives in Primates, J Biol Chem. Feb. 20, 2004;279(8):6213-6. doi: 10.1074/jbc.C300470200. Epub Dec. 29, 2003.

Holliger et al., "Diabodies": small bivalent and bispecific antibody fragments. Proc Natl Acad Sci U S A. Jul. 15, 1993;90(14):6444-8. doi: 10.1073/pnas.90.14.6444.

Hudson et al., Novel Quinazolinone Inhibitors of ALK2 Flip between Alternate Binding Modes: Structure-Activity Relationship, Structural Characterization, Kinase Profiling, and Cellular Proof of Concept. J Med Chem. Aug. 23, 2018;61(16):7261-7272. doi: 10.1021/acs.jmedchem.8b00782. Epub Aug. 7, 2018.

Jabara et al., A missense mutaton in TFRC, encoding transferrin receptor 1, causes combined immunodeficiency. Nat Genet. Jan. 2016;48(1):74-8. doi: 10.1038/ng.3465. Epub Dec. 7, 2015.

Kang et al., BMP2 accelerates the motility and invasiveness of gastric cancer cells via activation of the phosphatidylinositol 3-kinase (PI3K)/Akt pathway. Exp Cell Res. Jan. 1, 2010;316(1):24-37. doi: 10.1016/j.yexcr.2009.10.010. Epub Oct. 14, 2009.

Katsarou et al., Hepcidin Therapeutics. Pharmaceuticals (Basel). Nov. 21, 2018;11(4):127. doi: 10.3390/ph11040127.

Kawakami et al., BMP signaling during bone pattern determination in the developing limb. Development. Nov. 1996;122(11):3557-66. doi: 10.1242/dev.122.11.3557.

Kinsley et al., Molecular characterization of a third case of human astransferrinemia. Blood. Oct. 15, 2004;104(8):2607.doi: 10.1182/blood-2004-05-1751.

Klampfl et al. Somatic mutations of calreticulin in myeloproliferative neoplasms. N Engl J Med. Dec. 19, 2013;369(25):2379-90. doi: 10.1056/NEJMoa1311347. Epub Dec. 10, 2013.

Kovac et al. Anti-Hemojuvelin Antibody Corrects Anemia Caused by Inappropriately High Hepcidin Level. Haematologica. May 2016;101(5):e173-6. doi: 10.3324/haematol.2015.140772. Epub Mar. 4, 2016.

Kralovics et al., A gain-of-function mutation of JAK2 in myeloproliferative disorders. N Engl J Med. Apr. 28, 2005;352(17):1779-90. doi: 10.1056/NEJMoa051113.

Kroot et al., Hepcidin in human iron disorders: diagnostic implications. Clin Chem. Dec. 2011;57(12):1650-69. doi: 10.1373/clinchem.2009.140053. Epub Oct. 11, 2011.

Kundranda et al., Role of Hepcidin in Anemia of Waldenstrom Macroglobulinemia. Blood. Nov. 11, 2010;116(21):4984. doi:https://doi.org/10.1182/blood.V116.21.4984.4984.

Kuninger et al., Complex biosynthesis of the muscle-enriched iron regulator RGMc. J Cell Sci. Aug. 15, 2006;119(Pt 16):3273-83. doi: 10.1242/jcs.03074. Epub Jul. 25, 2006.

Kuns-Hashimoto et al., Selective Binding of RGMc/hemojuvelin, a Key Protein in Systemic Iron Metabolism, to BMP-2 and Neogenin. Am J Physiol Cell Physiol. Apr. 2008;294(4):C994-C1003. doi: 10.1152/ajpcell.00563.2007. Epub Feb. 20, 2008.

Lasho et al., SF3B1 mutations in primary myelofibrosis: clinical, histopathology and genetic correlates among 155 patients. Leukemia. May 2012;26(5):1135-7. doi: 10.1038/leu.2011.320. Epub Nov. 8, 2011.

Lee et al., Neogenin Inhibits HJV Secretion and Regulates BMP-induced hepcidin expression and iron homeostasis. Blood. Apr. 15, 2010;115(15):3136-45. doi: 10.1182/blood-2009-11-251199. Epub Jan. 11, 2010. Erratum in: Blood. Jul. 8, 2010;116(1):151. Lee, Dai-Hoon [corrected to Lee, Dae-Hoon]; Zhou, Li-Juau [corrected to Zhou, Li-Juan]; Xie, Jiau-Xiu [corrected to Xie, Jian-Xin].

Lefranc et al., IMGT, the international ImMunoGeneTics database. Nucleic Acids Res. Jan. 1, 1999;27(1):209-12. doi: 10.1093/nar/27.1.209.

Lin et al., Competitive Regulation of Hepcidin mRNA by Soluble and Cell-Associated Hemojuvelin. Blood. Oct. 15, 2005;106(8):2884-9. doi: 10.1182/blood-2005-05-1845. Epub Jul. 5, 2005.

Litchford et al., Nutritional issues in the patient with diabetes and foot ulcers. In: Levin and O'Neal's The Diabetic Foot, Jan. 1, 2008 (pp. 199-217), Mosby.

Locatelli et al., Kidney Disease: Improving Global Outcomes guidelines on anaemia management in chronic kidney disease: a European Renal Best Practice position statement. Nephrol Dial Transplant. Jun. 2013;28(6):1346-59. doi: 10.1093/ndt/gft033. Epub Apr. 12, 2013.

MacDougall et al., FIND-CKD: a randomized trial of intravenous ferric carboxymaltose versus oral iron in patients with chronic kidney disease and iron deficiency anaemia. Nephrol Dial Transplant. Nov. 2014;29(11):2075-84. doi: 10.1093/ndt/gfu201. Epub Jun. 2, 2014.

Madu et al., Anaemia of Chronic Disease: An In-Depth Review. Med Princ Pract. Jan. 2017;26(1):1-9. doi: 10.1159/000452104. Epub Sep. 28, 2016.

(56) References Cited

OTHER PUBLICATIONS

Maes et al., In anemia of multiple myeloma, hepcidin is induced by increased bone morphogenetic protein 2. Blood. Nov. 4, 2010;116(18):3635-44. doi: 10.1182/blood-2010-03-274571. Epub Aug. 2, 2010.

Maliken et al., The hepcidin circuits act: balancing iron and inflammation. Hepatology. May 2011;53(5):1764-6. doi: 10.1002/hep.24267. Author Manuscript, 5 pages.

Mesa et al., The Myelofibrosis Symptom Assessment Form (MFSAF): an evidence-based brief inventory to measure quality of life and symptomatic response to treatment in myelofibrosis. Leuk Res. Sep. 2009;33(9):1199-203. doi: 10.1016/j.leukres.2009.01.035. Epub Feb. 27, 2009. Author Manuscript, 10 pages.

Metzgeroth et al., Iron deficiency anemia and anemia of chronic disorders. Internist (Berl). Aug. 1, 2015;56(9):978-88. German. doi: 10.1007/s00108-015-3711-2.

Meynard et al., Lack of the bone morphogenetic protein BMP6 induces massive iron overload. Nat Genet. Apr. 2009;41(4):478-81. doi: 10.1038/ng.320. Epub Mar. 1, 2009.

Mleczko-Sanecka et al., SMAD7 controls iron metabolism as a potent inhibitor of hepcidin expression. Blood. Apr. 1, 2010;115(13):2657-65. doi: 10.1182/blood-2009-09-238105. Epub Dec. 29, 2009.

Mueller et al., The role of repulsive guidance molecules in the embryonic and adult vertebrate central nervous system. Philos Trans R Soc Lond B Biol Sci. Sep. 29, 2006;361(1473):1513-29. doi: 10.1098/rstb.2006.1888.

Murtagh et al., Dialysis or not? A comparative survival study of patients over 75 years with chronic kidney disease stage 5. Nephrol Dial Transplant. Jul. 2007;22(7):1955-62. doi: 10.1093/ndt/gfm153. Epub Apr. 4, 2007.

Nangalia et al., Somatic CALR mutations in myeloproliferative neoplasms with nonmutated JAK2. N Engl J Med. Dec. 19, 2013;369(25):2391-2405. doi: 10.1056/NEJMoa1312542. Epub Dec. 10, 2013.

Naymagon et al., Myelofibrosis-Related Anemia and Emergings Therapeutic Strategies. HemaSphere. Dec. 20, 2017;1(1):e1. doi: 10.1097/HS9.0000000000000001.

Nemeth et al., Anti-hepcidin therapy for iron-restricted anemias. Blood. 2013;122(17):2929-31. doi: https://doi.org/10.1182/blood-2013-08-522466.

Nemeth et al., Hepcidin regulates cellular iron efflux by binding to ferroportin and inducing its internalization. Science. Dec. 17, 2004;306(5704):2090-3. doi: 10.1126/science.1104742. Epub Oct. 28, 2004.

Nemeth, Targeting the hepcidin-ferroportin axis in the diagnosis and treatment of anemias. Adv Hematol. 2010;2010:750643. doi: 10.1155/2010/750643. Epub Dec. 24, 2009.

Neubauer et al., Jak2 deficiency defines an essential developmental checkpoint in definitive hematopoiesis. Cell. May 1, 1998;93(3):397-409. doi: 10.1016/s0092-8674(00)81168-x.

Nili et al., Soluble repulsive guidance molecule c/hemojuvelin is a broad spectrum bone morphogenetic protein (BMP) antagonist and inhibits both BMP2- and BMP6-mediated signaling and gene expression. J Biol Chem. Aug. 6, 2010;285(32):24783-92. doi: 10.1074/jbc.M110.130286. Epub Jun. 8, 2010.

O'Mara et al., Anemia in patients with Chronic Kidney Disease. Diabetes Spectrum. 2008;21(1):12-19. doi: https://doi.org/10.2337/diaspect.21.1.12.

Ogun et al., Biochemistry, Transferrin. Nov. 16, 2022. In: StatPearls [Internet]. Treasure Island (FL): StatPearls Publishing; Jan. 2023. 4 pages.

Oh et al., Hepcidin Suppression by Momelotinib Is Associated with Increased Iron Availability and Erythropoiesis in Transfusion-Dependent Myelofibrosis Patients. Blood. Nov. 29, 2018;132:4282. doi: https://doi.org/10.1182/blood-2018-99-111349.

Papanikolaou et al., Mutations in HFE2 cause iron overload in chromosome 1q-linked juvenile hemochromatosis. Nature Genetics. Jan. 2004;36(1):77-82. doi:10.1038/ng1274. Epub Nov. 30, 2003.

Pardanani et al., Associations and prognostic interactions between circulating levels of hepcidin, ferritin and inflammatory cytokines in primary myelofibrosis. Am J Hematol. Apr. 2013;88(4):312-6. doi: 10.1002/ajh.23406. Epub Feb. 28, 2013.

Parganas et al., Jak2 is essential for signaling through a variety of cytokine receptors. Cell. May 1, 1998;93(3):385-95. doi: 10.1016/s0092-8674(00)81167-8.

Passamonti et al., A dynamic prognostic model to predict survival in primary myelofibrosis: a study by the IWG-MRT (International Working Group for Myeloproliferative Neoplasms Research and Treatment). Blood. Mar. 4, 2010;115(9):1703-8. doi: 10.1182/blood-2009-09-245837. Epub Dec. 14, 2009.

Petzer et al., Established and Emerging Concepts to Treat Imbalances of Iron Homeostasis in Inflammatory Diseases. Pharmaceuticals (Basel). Dec. 11, 2018;11(4):135. doi: 10.3390/ph11040135.

Pietrangelo, Hepcidin in human iron disorders: therapeutic implications. J Hepatol. Jan. 2011;54(1):173-81. doi: 10.1016/j.jhep.2010.08.004. Epub Aug. 26, 2010.

Poljak, Production and structure of diabodies. Structure. Dec. 15, 1994;2(12):1121-3. doi: 10.1016/s0969-2126(94)00113-8.

Pouliot et al., Overexpression of a dominant negative type II bone morphogenetic protein receptor inhibits the growth of human breast cancer cells. Cancer Res. Jan. 15, 2003;63(2):277-81.

Preza et al., Minihepcidins are rationally designed small peptides that mimic hepcidin activity in mice and may be useful for the treatment of iron overload. J Clin Invest. Dec. 2011;121(12):4880-8. doi: 10.1172/JCI57693.

Qiao et al., Hepcidin-induced endocytosis of ferroportin is dependent on ferroportin ubiquitination. Cell Metab. Jun. 6, 2012;15(6):918-24. doi: 10.1016/j.cmet.2012.03.018.

Rameshwar et al., Systemic transforming growth factor-beta in patients with bone marrow fibrosis-pathophysiological implications. Am J Hematol. Oct. 1998; 59(2):133-42. doi: 10.1002/(sici)1096-8652(199810)59:2<133:: aid-ajh6>3.0.co;2-z.

Ramos et al., Minihepcidins prevent iron overload in a hepcidin-deficient mouse model of severe hemochromatosis. Blood. Nov. 1, 2012;120(18):3829-36. doi: 10.1182/blood-2012-07-440743. Epub Sep. 18, 2012.

Roetto et al., Mutant antimicrobial peptide hepcidin is associated with severe juvenile hemochromatosis. Nat Genet. Jan. 2003;33(1):21-2. doi: 10.1038/ng1053. Epub Dec. 9, 2002.

Ross et al., Identification of Antibody and Small Molecule Antagonists of Ferroportin-Hepcidin Interaction. Front Pharmacol. Nov. 21, 2017;8:838. doi: 10.3389/fphar.2017.00838.

Rotwein et al., Variation in the repulsive guidance molecule family in human populations. Physiol Rep. Feb. 2019;7(3):e13959. Doi:10.14814/phy2.13959. Epub Feb. 11, 2019.

Schwoebel et al., The effects of the anti-hepcidin Spiegelmer NOX-H94 on inflammation-induced anemia in cynomolgus monkeys. Blood. Mar. 21, 2013;121(12):2311-5. doi: 10.1182/blood-2012-09-456756. Epub Jan. 24, 2013.

Sebastiani et al., Pharmacological Targeting of the Hepcidin/Ferroportin Axis. Front Pharmacol. Jun. 21, 2016;7:160. doi: 10.3389/fphar.2016.00160.

Sheetz et al., Targeting the hepcidin-ferroportin pathway in anaemia of chronic kidney disease. Br J Clin Pharmacol. May 2019;85(5):935-948. doi: 10.1111/bcp.13877. Epub Mar. 4, 2019.

Shi et al., BMP6 and BMP4 expression in patients with cancer-related anemia and its relationship with hepcidin and s-HJV. Genet Mol Res. Mar. 31, 2016;15(1). doi: 10.4238/gmr.15017130.

Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. doi: 10.1074/jbc.M009483200. Epub Nov. 28, 2000.

Smith et al., Mouse model recapitulating human Fcγ receptor structural and functional diversity. Proc Natl Acad Sci U S A. Apr. 17, 2012;109(16):6181-6. doi: 10.1073/pnas.1203954109. Epub Apr. 2, 2012.

Sullivan, Stored iron and vascular reactivity. Arterioscler Thromb Vasc Biol. Aug. 2005;25(8):1532-5. doi: 10.1161/01.ATV.0000174124.20147.22.

(56) References Cited

OTHER PUBLICATIONS

Sun et al., A hepcidin lowering agent mobilizes iron for incorporation into red blood cells in an adenine-induced kidney disease model of anemia in rats. Nephrol Dial Transplant. Jul. 2013;28(7):1733-43. doi: 10.1093/ndt/gfs584. Epub Jan. 22, 2013.

Tapper et al., Genetic variation at Mecom, Tert, JAK2 and HBS1L-MYB predisposes to myeloproliferative neoplasms. Nat Commun. Apr. 7, 2015;6:6691. doi: 10.1038/ncomms7691.

Tattersall et al., When to start dialysis: updated guidance following publication of the Initiating Dialysis Early and Late (IDEAL) study. Nephrol Dial Transplant. Jul. 2011;26(7):2082-6. doi: 10.1093/ndt/gfr168. Epub May 5, 2011.

Tefferi et al., An overview on CALR and CSF3R mutations and a proposal for revision of WHO diagnostic criteria for myeloproliferative neoplasms. Leukemia. Jul. 2014;28(7):1407-13. doi: 10.1038/leu.2014.35. Epub Jan. 20, 2014.

Tefferi et al., Targeted deep sequencing in primary myelofibrosis. Blood Adv. Nov. 30, 2016;1(2):105-111. doi: 10.1182/bloodadvances.2016000208.

Theurl et al., Pharmacologic inhibition of hepcidin expression reverses anemia of chronic inflammation in rats. Blood. Nov. 3, 2011;118(18):4977-84. doi: 10.1182/blood-2011-03-345066. Epub Jul. 5, 2011.

Tian et al., Repulsive guidance molecules (RGMs) and neogenin in bone morphogenetic protein (BMP) signaling. Mol Reprod Dev. Sep. 2013;80(9):700-17. doi: 10.1002/mrd.22199. Epub Jul. 19, 2013.

Toft et al., Anemia and clinical outcomes in patients with non-dialysis dependent or dialysis dependent severe chronic kidney disease: a Danish population-based study. J Nephrol. Feb. 2020;33(1):147-156. doi: 10.1007/s40620-019-00652-9. Epub Oct. 5, 2019.

Vadhan-Raj et al., Phase 1 Study of a Hepcidin Antagonist, LY2787106, in Cancer-Associated Anemia. Blood. Dec. 3, 2015;126(23):537. doi:http://doi.org/10.1182/blood.V126.23.537.537.

Vannucchi et al., Mutations and prognosis in primary myelofibrosis. Leukemia. Sep. 2013;27(9):1861-9. doi: 10.1038/leu.2013.119. Epub Apr. 26, 2013.

Vela et al., Differential regulation of hepcidin in cancer and non-cancer tissues and its clinical implications. Exp Mol Med. Feb. 2, 2018;50(2):e436. doi: 10.1038/emm.2017.273.

Verstovsek et al., A double-blind, placebo-controlled trial of ruxolitinib for myelofibrosis. N Engl J Med. Mar. 1, 2012;366(9):799-807. doi: 10.1056/NEJMoa1110557. Author Manuscript, 17 pages.

Verstovsek et al., Safety and efficacy of INCB018424, a JAK1 and JAK2 inhibitor, in myelofibrosis. N Engl J Med. Sep. 16, 2010;363(12):1117-27. doi: 10.1056/NEJMoa1002028.

Wang et al., Prognostic implications of predialysis patients' symptoms in peritoneal dialysis patients. Ren Fail. Dec. 2021;43(1):216-222. doi: 10.1080/0886022X.2021.1871920.

Wang, Hepcidin regulation in the anemia of inflammation. Curr Opin Hematol. May 2016;23(3):189-97. doi: 10.1097/MOH.0000000000000236. Author Manuscript, 15 pages.

Webster et al., Chronic Kidney Disease. Lancet. Mar. 25, 2017;389(10075):1238-1252. doi: 10.1016/S0140-6736(16)32064-5. Epub Nov. 23, 2016.

Wish et al., Positive Iron Balance in Chronic Kidney Disease: How Much is Too Much and How to Tell? Am J Nephrol. 2018;47(2):72-83. doi: 10.1159/000486968. Epub Feb. 13, 2018.

Wu et al., DISC-0974, An Anti-Hemojuvelin (HJV) Monoclonal Antibody, Reduced Hepcidin And Improved Anemia In A Rat Model Of Chronic Kidney Disease. American Society of Hematology, Blood, Nov. 15, 2022; vol. 140, (Supplement 1): 8153-8154. https://ashpublications.org/blood/article/140/Supplement%201/8153/489647/DISC-0974-an-Anti-Hemojuvelin-HJV-Monoclonal.

Xia et al., Hemojuvelin regulates hepcidin expression via a selective subset of BMP ligands and receptors independently of neogenin. Blood. May 15, 2008;111(10):5195-204. doi: 10.1182/blood-2007-09-111567. Epub Mar. 7, 2008.

Xu et al., In vitro characterization of five humanized OKT3 effector function variant antibodies. Cell Immunol. Feb. 25, 2000;200(1):16-26. doi: 10.1006/cimm.2000.1617.

Zhang et al., The Role of Hepatocyte Hemojuvelin in the Regulation of Bone Morphogenic Protein-6 and Hepcidin Expression in Vivo. J Biol Chem. May 28, 2010;285(22):16416-23. doi: 10.1074/jbc.M110.109488. Epub Apr. 2, 2010.

Zhang, Control of Systemic Iron Homeostasis by the Hemojuvelin-Hepcidin Axis. Adv Nutr. Nov. 2010;1(1):38-45. doi: 10.3945/an.110.1009. Epub Nov. 16, 2010.

Zhao et al., Neogenin Facilitates the Induction of Hepcidin Expression by Hemojuvelin in the Liver. J Biol Chem. Jun. 3, 2016;291(23):12322-35. doi: 10.1074/jbc.M116.721191. Epub Apr. 12, 2016.

Zhou et al., Hepcidin is elevated in primary and secondary myelofibrosis and remains elevated in patients treated with ruxolitinib. Blood. Nov. 29, 2018;132 (Supp 1):1760. 4 pages.

Zipfel et al., Complement Inhibitors in Clinical Trials for Glomerular Diseases. Front Immunol. Sep. 27, 2019;10:2166. doi: 10.3389/fimmu.2019.02166.

Zoller et al., Iron in Cancer Infection, Kidney and Liver Diseases: Innocent Bystander or Therapeutic Target? Bio Iron. May 6, 2019. Retrieved from internet: https://bioironforum.org/wp-content/uploads/2018/10/7.-Iron-in-cancer-infection-kidney-and-liver-diseases.Theurl-Zoller.pdf.

[No Author Listed] Leukemia & Lymphoma Society, Myelofibrosis Facts, <URL: https://www.lls.org/sites/default/files/file_assets/FS14_Myelofibrosis_Fact%20Sheet_Final9.12.pdf> [retrieved on Feb. 26, 2025], Apr. 2012. 9 pages.

Ganz, Anemia of Inflammation. N Engl J Med. Sep. 19, 2019;381(12):1148-1157. doi: 10.1056/NEJMra1804281.

* cited by examiner

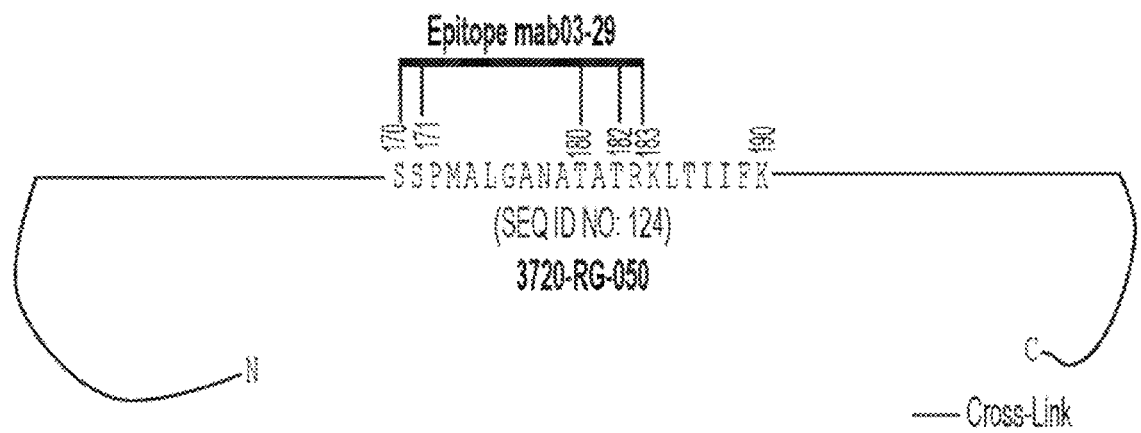
FIG. 14
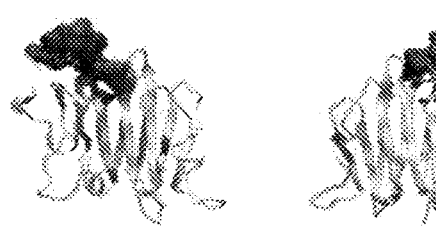
FIG. 15A  FIG. 15B  FIG. 15C
  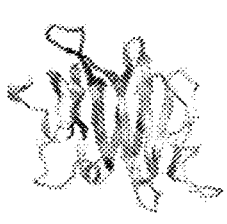
FIG. 15D  FIG. 15E  FIG. 15F
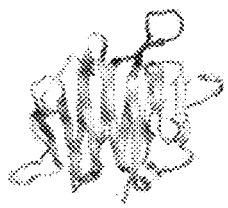   
FIG. 15G  FIG. 15H  FIG. 15I  FIG. 15J

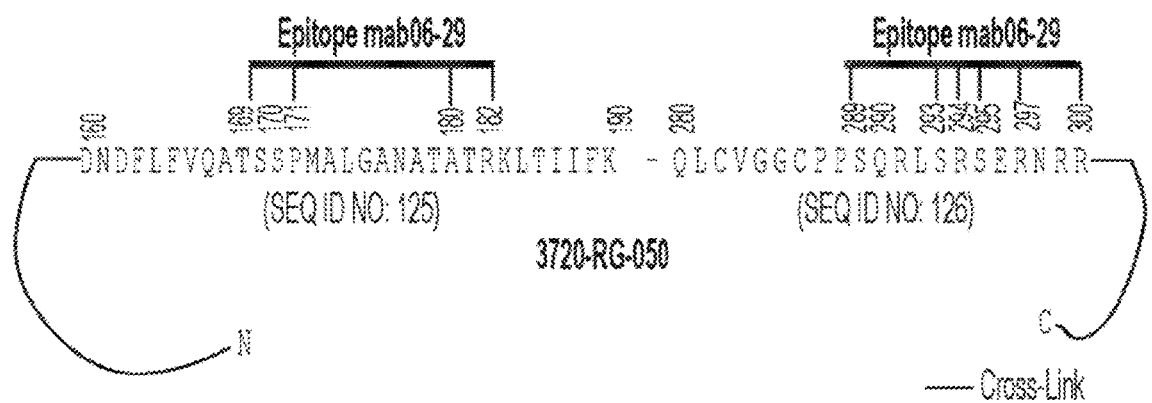
FIG. 16
 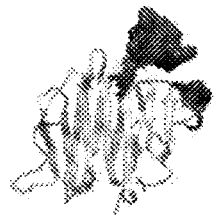 
FIG. 17A     FIG. 17B     FIG. 17C
  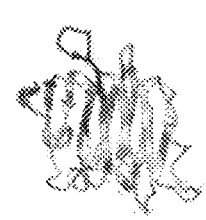
FIG. 17D     FIG. 17E     FIG. 17F
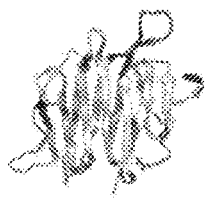   
FIG. 17G     FIG. 17H     FIG. 17I     FIG. 17J

ANTI-HEMOJUVELIN (HJV) ANTIBODIES FOR TREATING MYELOFIBROSIS

RELATED APPLICATIONS

This application is a continuation of U.S. patent application Ser. No. 17/924,672, filed Nov. 10, 2022, entitled ANTI-HEMOJUVELIN (HJV) ANTIBODIES FOR TREATING MYELOFIBROSIS, which is a national stage filing under 35 U.S.C. 371 International Patent Application Serial No. PCT/US2021/032343, filed May 13, 2021, entitled ANTI-HEMOJUVELIN (HJV) ANTIBODIES FOR TREATING MYELOFIBROSIS, which claims the benefit under 35 U.S.C. § 119(e) of U.S. provisional application Ser. No. 63/024,416, filed May 13, 2020, entitled "ANTI-HEMOJUVELIN (HJV) ANTIBODIES FOR TREATING MYELOFIBROSIS," 63/035,649, filed Jun. 5, 2020, entitled "ANTI-HEMOJUVELIN (HJV) ANTIBODIES FOR TREATING MYELOFIBROSIS," 63/047,828, filed Jul. 2, 2020, entitled "ANTI-HEMOJUVELIN (HJV) ANTIBODIES FOR TREATING MYELOFIBROSIS," and 63/164,294, filed Mar. 22, 2021, entitled "ANTI-HEMOJUVELIN (HJV) ANTIBODIES FOR TREATING MYELOFIBROSIS," the entire contents of each of which are incorporated herein by reference.

REFERENCE TO AN ELECTRONIC SEQUENCE LISTING

The contents of the electronic sequence listing (D084270003US04-SUBSEQ-LJG.xml; Size: 203,436 bytes; and Date of Creation: Mar. 25, 2025) is herein incorporated by reference in its entirety.

BACKGROUND

Iron is a key component of oxygen-transporting storage molecules, such as hemoglobin and myoglobin. Iron deficiency results in anemia, while iron overload leads to tissue damage and fibrosis. Hepcidin is a key peptide hormonal regulator of systemic iron homeostasis. It exerts its regulatory function by binding to the cellular iron exporter ferroportin, a transmembrane protein present on hepatocytes, enterocytes in the duodenum, macrophages, and adipocytes. The binding of hepcidin promotes ferroportin degradation, preventing the export of iron from cells and release of iron into the plasma.

SUMMARY

Aspects of the disclosure provide methods for treating high hepcidin disorders, such as myelofibrosis, myeloma, Waldenstrom macroglobulinemia, chronic kidney disease, anemias of chronic disease or iron restricted anemias that result in functional iron deficiency. In certain embodiments, methods are provided for treating myelofibrosis, which is generally characterized as a myeloproliferative disease associated with chronic inflammation and progressive marrow fibrosis. Anemia is a major clinical problem in myelofibrosis and is associated with negative outcomes. Such anemia is generally caused by, or associated with, bone marrow failure, splenomegaly and/or functional iron deficiency, which may contribute to inflammation. Moreover, in myelofibrosis, pro-inflammatory cytokines that induce hepcidin synthesis, such as IL-6 and oncostatin-M, are typically increased and associated with iron sequestration, macrophage iron loading, as well as myeloid proliferation and macrophage activation (See, e.g., FIG. 11). The resulting increases in hepcidin levels are associated with anemia and negative outcome.

Aspects of the present disclosure relates to effective bioavailability being achieved by subcutaneous administration of an isolated antibody that binds to hemojuvelin (HJV) to a subject having myelofibrosis together with beneficially low maximum serum concentrations ($C_{max}$). In some embodiments, subcutaneous administration of an anti-HJV antibody yields comparable pharmacodynamics effects (e.g., decreased circulating hepcidin-25 levels, increased TSAT %, and/or increased serum iron levels) at lower maximum concentration ($C_{max}$) of the anti-HJV antibody compared to intravenous administration of the same antibody. $C_{max}$ is the maximum (or peak) serum concentration that a drug (e.g., an anti-HJV antibody) after the agent/antibody has been administered and before the administration of a second dose. In some embodiments, achieving a low $C_{max}$ within a short period of time (e.g., within 12 hours, within 24 hours, etc) after administration of an anti-HJV antibody minimizes undesirable increases in serum iron response, and/or minimizes chances of off-target effects of the antibody (e.g., binding to RGMa). In some embodiments, blunting $C_{max}$ by subcutaneous administration of an anti-HJV antibody avoids an undesirably sharp increase in serum iron response. In some embodiments, blunting $C_{max}$ by subcutaneous administration of an anti-HJV antibody reduces the off-target effects of the antibody.

Aspects of the disclosure also relates to an isolated antibody that binds to human hemojuvelin (HJV) for use in a method of treating a subject having myelofibrosis, in which the subject is administered with the isolated antibody by subcutaneous administration, and wherein the antibody comprises a heavy chain variable region (VH) comprising an amino acid sequence of SEQ ID NO: 38, and a light chain variable region (VL) comprising an amino acid sequence of SEQ ID NO: 39.

Aspects of the disclosure also relates to an isolated antibody that binds to human hemojuvelin (HJV) for use in a method of inhibiting HJV activity in a subject having myelofibrosis, in which the subject is administered with the isolated antibody by subcutaneous administration, and wherein the antibody comprises a heavy chain variable region (VH) comprising an amino acid sequence of SEQ ID NO: 38, and a light chain variable region (VL) comprising an amino acid sequence of SEQ ID NO: 39.

In some embodiments, the administration (e.g., intravenous injection or subcutaneous injection) of an anti-HJV antibody reduces circulating hepcidin-25 (e.g., serum or plasma hepcidin-25), which is the active form of hepcidin.

In some aspects, the present disclosure provides a method for reducing hepcidin-25 in a subject having myelofibrosis, the method comprising: administering to the subject an effective amount of the isolated antibody that binds to human hemojuvelin (HJV), wherein the antibody comprises: a heavy chain variable region (VH) comprising an amino acid sequence of SEQ ID NO: 38, and a light chain variable region (VL) comprising an amino acid sequence of SEQ ID NO: 39. In some aspects, the present disclosure provides an isolated antibody that binds to hemojuvelin (HJV) for use in a method of reducing hepcidin-25 in a subject having myelofibrosis, wherein the antibody comprises: a heavy chain variable region (VH) comprising an amino acid sequence of SEQ ID NO: 38, and a light chain variable region (VL) comprising an amino acid sequence of SEQ ID NO: 39. In some embodiments, the subject is administered via subcutaneous injection. In some embodiments, the administration reduces hepcidin-25 with 4 hours, 6 hours, 8 hours, 12 hours, 28 hours, 24 hours, 2 days, 3 days, 4 days, 5 days, 6 days, 1 week, or two weeks of administration. In some embodiments, the administration reduces hepcidin-25 by at least 30%, least 40%, least 50%, least 60%, least 70%, least 80%, least 90%, or least 95% of hepcidin compared to the hepcidin level in the subject prior to administration.

Certain aspects of this disclosure relate to an observation that hemojuvelin (HJV) is a regulator of hepcidin synthesis and that loss of hemojuvelin function may be associated with iron overload. For example, in some embodiments, homozygous HJV knockdown animals fail to amplify hepcidin synthesis in response to IL-6 and are unable to mount an effective hypoferremic response to acute inflammation. Accordingly, in some embodiments, methods provided herein involve administering to a subject in need thereof a hepcidin antagonist, which may be a hemojuvelin antagonist, in an amount effective to treat a high-hepcidin disorder. In some embodiments, the hemojuvelin antagonist is an anti-hemojuvelin antibody. In some embodiments, the anti-hemojuvelin antibody binds RGMc as its primary mode of action (as compared with RGMa and RGMb). Accordingly, in some embodiments, the anti-hemojuvelin antibody preferentially binds RGMc versus RGMa and/or RGMb. In some embodiments, the anti-hemojuvelin antibody binds RGMc with an equilibrium dissociation constant ($K_D$) less than one hundred nanomolar (nM) ($K_D$<100 nM). However, in some embodiments, the anti-hemojuvelin antibody binds RGMc with a similar affinity as RGMa and/or RGMb.

In some aspects, the present disclosure provides a method of treating a subject having myelofibrosis. In some embodiments, the method comprises: administering to the subject an effective amount of the isolated antibody that binds to human hemojuvelin (HJV), wherein the antibody comprises: a heavy chain complementary determining region 1 (HC CDR1) set forth as $X_1$YGMN (SEQ ID NO: 105), in which $X_1$ can be N or Y; a heavy chain complementary determining region 2 (HC CDR2) set forth as MIYYDSSX$_2$KHYADSVKG (SEQ ID NO: 106), in which $X_2$ can be E or D; a heavy chain complementary determining region 3 (HC CDR3) set forth as GX$_3$TPDX$_4$ (SEQ ID NO: 107), in which $X_3$ can be T or S, and $X_4$ can be Y, V, or K; and/or a light chain complementary determining region 1 (LC CDR1) set forth as RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H, a light chain complementary determining region 2 (LC CDR2) set forth as $X_9$VSX$_{10}$RFS (SEQ ID NO: 109), in which $X_9$ can be E, D or A, and $X_{10}$ can be N, S, T, E or H, a light chain complementary determining region 3 (LC CDR3) set forth as $X_{11}$QX$_{12}$TX$_{13}$DPX$_{14}$X$_{15}$ (SEQ ID NO: 110), in which $X_{11}$ can be F or M, $X_{12}$ can be V or A, $X_{13}$ can be H or Y, $X_{14}$ can be M, L or V, and $X_{15}$ can be T or S.

In some embodiments, the antibody comprises a VH comprising an amino acid sequence at least 85% identical to SEQ ID NO: 38, and/or a VL comprising an amino acid sequence at least 85% identical to SEQ ID NO: 39. In some embodiments, the antibody comprises a VH comprising an amino acid sequence of SEQ ID NO: 38, and a VL comprising an amino acid sequence of SEQ ID NO: 39.

In some embodiments, the antibody is a humanized antibody. In some embodiments, the humanized antibody comprises a humanized VH and/or a humanized VL.

In some embodiments, the antibody is selected from the group consisting of a full-length IgG, a Fab fragment, a F(ab') fragment, a F(ab')2 fragment, a scFv, and a Fv.

In some embodiments, the antibody is a full-length IgG. In some embodiments, the antibody comprises a heavy chain constant region of the isotype IgG1, IgG2, IgG3, or IgG4. In some embodiments, the antibody further comprises a heavy chain constant region set forth in SEQ ID NOs: 46, 48, 112 or 113. In some embodiments, the antibody further comprises a light chain constant region set forth in SEQ ID NO: 47. In some embodiments, the antibody comprises: (i) a heavy chain comprising an amino acid sequence at least 85% identical to SEQ ID NO: 61 or 117, and/or a light chain comprising an amino acid sequence at least 85% identical to SEQ ID NO: 62; or (ii) a heavy chain comprising an amino acid sequence at least 85% identical to SEQ ID NO: 63 or 118, and/or a light chain comprising an amino acid sequence at least 85% identical to SEQ ID NO: 62. In some embodiments, the antibody comprises a heavy chain comprising an amino acid sequence of SEQ ID NO: 61 or 117, and a light chain comprising an amino acid sequence of SEQ ID NO: 62. In some embodiments, the antibody comprises a heavy chain comprising an amino acid sequence of SEQ ID NO: 63 or 118, and a light chain comprising an amino acid sequence of SEQ ID NO: 62.

In some embodiments, the subject has myelofibrosis initiating mutations in JAK2, MPL, ASXL1, TET2, NFE2, SH2B3, SF3B1, or CALR. In some embodiments, the myelofibrosis is associated with increased levels of pro-inflammatory cytokines (e.g., IL-6, oncostatin-M) in the subject. In some embodiments, the subject presents with a serum hemoglobin level of less than 10 g/dL. In some embodiments, the subject presents with a serum hemoglobin level of less than 8 g/dL. In some embodiments, the subject is erythrocyte-transfusion dependent. In some embodiments, the subject is anemic.

In some embodiments, the subject has previously received an erythropoietin stimulating agent, a JAK-STAT inhibitor, a growth factor ligand trap, or an anti-fibrotic agent.

In some embodiments, the method described herein further comprising administering to the subject one or more of an erythropoietin stimulating agent, a JAK-STAT inhibitor, a growth factor ligand trap, and an anti-fibrotic agent. In some embodiments, the erythropoietin stimulating agent is selected from the group consisting of danazol, prednisone, thalidomide, lenalidomide, and pomalidomide. In some embodiments, the JAK-STAT inhibitor is selected from the group consisting of ruxolitinib, fedratinib, momelotinib, pacritinib, INCB039110, AG490, and PpYLKTK (SEQ ID NO: 130). In some embodiments, the growth factor ligand trap is sotatercept or luspatercept. In some embodiments, the anti-fibrotic agent is PRM-151.

In some aspects, the present disclosure also provides an isolated antibody that binds to human hemojuvelin (HJV) and compositions comprising the same. In some embodiments, the antibody comprises: a heavy chain complementary determining region 1 (HC CDR1) set forth as $X_1$YGMN (SEQ ID NO: 105), in which $X_1$ can be N or Y; and/or a heavy chain complementary determining region 2 (HC CDR2) set forth as MIYYDSSX$_2$KHYADSVKG (SEQ ID NO: 106), in which $X_2$ can be E or D; and/or a heavy chain complementary determining region 3 (HC CDR3) set forth as GX$_3$TPDX$_4$ (SEQ ID NO: 107), in which $X_3$ can be T or S, and $X_4$ can be Y, V, or K. In some embodiments, a light chain complementary determining region 1 (LC CDR1) set forth as RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H; and/or a light chain complementary determining region 2 (LC CDR2) set forth as $X_9$VSX$_{10}$RFS (SEQ ID NO: 109), in which $X_9$ can be E, D or A, and $X_{10}$ can be N, S, T, E or H; and/or a light chain complementary determining region 3 (LC CDR3) set forth as X$_{11}$QX$_{12}$TX$_{13}$DPX$_{14}$X$_{15}$ (SEQ ID NO: 110), in which X$_{11}$ can be F or M, X$_{12}$ can be V or A, X$_{13}$ can be H or Y, X$_{14}$ can be M, L or V, and X$_{15}$ can be T or S.

In some aspects, the present disclosure also provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 8. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 4, a LC CDR2 of SEQ ID NO: 5, a LC CDR3 of SEQ ID NO: 6. In some embodiments, the antibody comprises a VH comprising an amino acid sequence at least 85% identical to SEQ ID NO: 7, and/or a VL comprising an amino acid sequence at least 85% identical to SEQ ID NO: 8.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 30. In some embodiments the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 4, a LC CDR2 of SEQ ID NO: 49, a LC CDR3 of SEQ ID NO: 24. In some embodiments, the antibody comprises a VH comprising an amino acid sequence at least 85% identical to SEQ ID NO: 7, and/or a VL comprising an amino acid sequence at least 85% identical to SEQ ID NO: 30.

In some aspects, the present disclosure provides an isolated antibody that binds to hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; (ii) and/or a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 31. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 4, a LC CDR2 of SEQ ID NO: 18, a LC CDR3 of SEQ ID NO: 25. In some embodiments, the antibody comprises a VH comprising an amino acid sequence at least 85% identical to SEQ ID NO: 7, and/or a VL comprising an amino acid sequence at least 85% identical to SEQ ID NO: 8.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 32. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 14, a LC CDR2 of SEQ ID NO: 19, a LC CDR3 of SEQ ID NO: 25. In some embodiments, the antibody comprises a VH comprising an amino acid sequence at least 85% identical to SEQ ID NO: 7, and/or a VL comprising an amino acid sequence at least 85% identical to SEQ ID NO: 32.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 33. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 15, a LC CDR2 of SEQ ID NO: 20, a LC CDR3 of SEQ ID NO: 26. In some embodiments, the antibody comprises a VH comprising an amino acid sequence at least 85% identical to SEQ ID NO: 7, and/or a VL comprising an amino acid sequence at least 85% identical to SEQ ID NO: 33.

In some aspects, the present disclosure provide an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 34; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 35. In some embodiments, the antibody comprises: a HC CDR1 of SEQ ID NO: 9, a HC CDR2 of SEQ ID NO: 2, a HC CDR3 of SEQ ID NO: 3, and/or a LC CDR1 of SEQ ID NO: 16, a LC CDR2 of SEQ ID NO: 21, a LC CDR3 of SEQ ID NO: 27. In some embodiments, the antibody comprises a VH comprising an amino acid sequence at least 85% identical to SEQ ID NO: 34, and/or a VL comprising an amino acid sequence at least 85% identical to SEQ ID NO: 35.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 36; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 37. In some embodiments, the antibody comprises: a HC CDR1 of SEQ ID NO: 1, a HC CDR2 of SEQ ID NO: 10, a HC CDR3 of SEQ ID NO: 11, and/or a LC CDR1 of SEQ ID NO: 17, a LC CDR2 of SEQ ID NO: 18, a LC CDR3 of SEQ ID NO: 28. In some embodiments, the antibody comprises a VH comprising an amino acid sequence at least 85% identical to SEQ ID NO: 36, and/or a VL comprising an amino acid sequence at least 85% identical to SEQ ID NO: 37.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 38; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 39. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 17, a LC CDR2 of SEQ ID NO: 5, a LC CDR3 of SEQ ID NO: 27. In some embodiments, the antibody comprises a VH comprising an amino acid sequence at least 85% identical to SEQ ID NO: 38, and/or a VL comprising an amino acid sequence at least 85% identical to SEQ ID NO: 39.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 38; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 41. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 50, a LC CDR2 of SEQ ID NO: 22, a LC CDR3 of SEQ ID NO: 28. In some embodiments, the antibody comprises a VH comprising an amino acid sequence at least 85% identical to SEQ ID NO: 38, and/or a VL comprising an amino acid sequence at least 85% identical to SEQ ID NO: 41.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 42; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 43. In some embodiments, the antibody comprises: a HC CDR1 of SEQ ID NO: 1, a HC CDR2 of SEQ ID NO: 2, a HC CDR3 of SEQ ID NO: 12, and/or a LC CDR1 of SEQ ID NO: 15, a LC CDR2 of SEQ ID NO: 23, a LC CDR3 of SEQ ID NO: 27. In some embodiments, the antibody comprises a VH comprising an amino acid sequence at least 85% identical to SEQ ID NO: 42, and/or a VL comprising an amino acid sequence at least 85% identical to SEQ ID NO: 43.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 44; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 45. In some embodiments, the antibody comprises: a HC CDR1 of SEQ ID NO: 1, a HC CDR2 of SEQ ID NO: 2, a HC CDR3 of SEQ ID NO: 13, and/or a LC CDR1 of SEQ ID NO: 16, a LC CDR2 of SEQ ID NO: 21, a LC CDR3 of SEQ ID NO: 29. In some embodiments, the antibody comprises a VH comprising an amino acid sequence at least 85% identical to SEQ ID NO: 44, and/or a VL comprising an amino acid sequence at least 85% identical to SEQ ID NO: 45.

In some aspects, the present disclosure provides an isolated antibody that binds to hemojuvelin (HJV), in which the antibody comprises: a HC CDR1, a HC CDR2, and a HC CDR3, which collectively contains no more than 10 amino acid variations, preferably no more than 8 amino acid variations, more preferably no more than 5 amino acid variations, and more preferably no more than 2 amino acid variation, as compared with the HC CDR1, a HC CDR2, and a HC CDR3 of any one of the antibodies listed in Table 1; and/or wherein the antibody comprises a LC CDR1, a LC CDR2, and a LC CDR3, which collectively contains no more than 10 amino acid variations, preferably no more than 8 amino acids variations, as compared with the a LC CDR1, a LC CDR2, and a LC CDR3 of any one of the antibodies listed in Table 1.

In some embodiments, any of the antibodies provided herein is a humanized antibody. In some embodiments, the humanized antibody comprises a humanized VH and/or a humanized VL. In some embodiments, the antibody is selected from the group consisting of a full-length IgG, a Fab fragment, a F(ab') fragment, a F(ab')2 fragment, a scFv, and a Fv. In some embodiments, the antibody is a full-length IgG. In some embodiments, the antibody comprises a heavy chain constant region of the isotype IgG1, IgG2, IgG3, or IgG4. In some embodiments, the antibody further comprises a heavy chain constant region set forth in SEQ ID NOs: 46, 48, 112 or 113. In some embodiments, the antibody further comprises a light chain constant region set forth in SEQ ID NO: 47. In some embodiments, the antibody comprises: (i) a heavy chain comprising an amino acid sequence at least 85% identical to SEQ ID NO: 51 or 114, and/or a light chain comprising an amino acid sequence at least 85% identical to SEQ ID NOs: 52-56; (ii) a heavy chain comprising an amino acid sequence at least 85% identical to SEQ ID NO: 57 or 115, and/or a light chain comprising an amino acid sequence at least 85% identical to SEQ ID NO: 58; (iii) a heavy chain comprising an amino acid sequence at least 85% identical to SEQ ID NO: 59 or 116, and/or a light chain comprising an amino acid sequence at least 85% identical to SEQ ID NO: 60; (iv) a heavy chain comprising an amino acid sequence at least 85% identical to SEQ ID NO: 61 or 117, and/or a light chain comprising an amino acid sequence at least 85% identical to SEQ ID NO: 62; (v) a heavy chain comprising an amino acid sequence at least 85% identical to SEQ ID NO: 63 or 118, and/or a light chain comprising an amino acid sequence at least 85% identical to SEQ ID NO: 62; (vi) a heavy chain comprising an amino acid sequence at least 85% identical to SEQ ID NO: 61 or 117, and/or a light chain comprising an amino acid sequence at least 85% identical to SEQ ID NO: 65; (vii) a heavy chain comprising an amino acid sequence at least 85% identical to SEQ ID NO: 66 or 119, and/or a light chain comprising an amino acid sequence at least 85% identical to SEQ ID NO: 67; or (viii) a heavy chain comprising an amino acid sequence at least 85% identical to SEQ ID NO: 68 or 120, and/or a light chain comprising an amino acid sequence at least 85% identical to SEQ ID NO: 69.

In some embodiments, the antibody binds HJV with an equilibrium dissociation constant (KD) less than 100 nM. In some embodiments, the antibody binds to HJV with an equilibrium dissociation constant (KD) less than 1 nM.

In some embodiments, the antibody is conjugated to a molecular payload. In some embodiments, the molecular payload is a detectable agent, a diagnostic agent, or a therapeutic agent.

In some aspects, the present disclosure also provides a nucleic acid encoding the isolated antibody described herein.

In some aspects, the present disclosure also provides vector comprising the nucleic acid encoding the antibody described herein. In some embodiments, the vector comprises a nucleic acid sequence of nucleic acid sequences as set forth in Table 3.

In some aspects, the present disclosure also provides a host cell comprising the nucleic acid encoding the isolated antibody described herein of and/or the vectors comprising the same.

In some aspects, the present disclosure also provides a pharmaceutical composition comprising the anti-HJV antibody described herein, and a pharmaceutically acceptable carrier.

In some aspects, the present disclosure also provides a method for producing an anti-human hemojuvelin (HJV) antibody, the method comprises: (i) culturing the host cell under conditions allowing for expressing of the antibody that binds human hemojuvelin (HJV); and (ii) harvesting the cultured host cell or culture medium for collection of the antibody that binds human hemojuvelin (HJV). In some embodiments, the method comprising purifying the antibody that binds human hemojuvelin (HJV).

In some aspects, the present disclosure also provides an isolated antibody that binds to human hemojuvelin (HJV) produced by expressing in a host cell (i) a nucleic acid sequence encoding a heavy chain, in which the nucleic acid sequence is at least 90% identical to SEQ ID NO: 92; and/or (ii) a nucleic acid sequence encoding a light chain, in which the nucleic acid sequence is at least 90% identical to SEQ ID NO: 93. In some aspects, the present disclosure also provides an isolated antibody that binds to human hemojuvelin (HJV) produced by expressing in a host cell (i) a nucleic acid sequence encoding a heavy chain, in which the nucleic acid sequence is at least 90% identical to SEQ ID NO: 94; and/or (ii) a nucleic acid sequence encoding a light chain, in which the nucleic acid sequence is at least 90% identical to SEQ ID NO: 93. In some embodiments, the host cell is Chinese hamster ovary (CHO) cells, dhfr-CHO cell, human embryonic kidney (HEK)-293 cells, verda reno (VERO) cells, nonsecreting null (NS0) cells, human embryonic retinal (PER.C6) cells, Sp2/0 cells, baby hamster kidney (BHK) cells, Madin-Darby Canine Kidney (MDCK) cells, Madin-Darby Bovine Kidney (MDBK) cells, or monkey kidney CV1 line transformed by SV40 (COS) cells.

In some aspects, the present disclosure provides an isolated antibody that binds to human hemojuvelin (HJV) for use in a method of treating a subject having myelofibrosis, wherein the antibody comprises a heavy chain variable region (VH) comprising an amino acid sequence of SEQ ID NO: 38, and a light chain variable region (VL) comprising an amino acid sequence of SEQ ID NO: 39.

In some embodiments, the subject having myelofibrosis has anemia resulting from hepcidin synthesis that is induced by pro-inflammatory cytokines, and wherein the administration of the antibody reduces the anemia.

In some embodiments, the pro-inflammatory cytokines comprises interleukin-6 (IL-6).

The foregoing and other aspects, implementations, acts, functionalities, features and embodiments of the present teachings can be more fully understood from the following description in conjunction with the accompanying drawings.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIG. 1A shows a schematic process of generation of the anti-hemojuvelin antibody, humanization, and affinity maturation. FIGS. 1B-1G shows the sensorgrams by BIAcore analysis of antibodies HA, hHA-004, hHA-008, hHA-009 and hHA-011.

FIG. 2A shows the general principle of HJV BMP reporter assay. FIG. 2B shows the effect of anti-HJV antibodies in inhibiting RGMc BMP signaling. FIG. 2C shows the effect of anti-HJV antibodies in inhibiting RGMa BMP signaling.

FIG. 4A shows the structure of hHA-008. FIG. 4B shows the structure of hHA-008-QL. FIG. 4C shows a comparison in antibody structure between hHA-008 and hHA-008-QL.

FIG. 6A shows maximal effect of hHA-008 measured by TSAT % occurred between 4-8 days post treatment. FIG. 6B shows hHA-008 reached maximum effect as measured by TSAT % about 1-4 days after injection in female cynos. FIG. 6C shows hHA-008 reached maximum effect as measured by TSAT % about 1-4 days after injection in male cynos, but one of the males did not respond to hHA-008 treatment.

FIG. 7A shows the maximum TSAT % increase occurred 1-4 days after injection ($T_{max}$=14 days), and one of the animals tested had a drastic decline of TSAT around day 34. FIG. 7B shows plasma hepcidin-25 concentration changes over time after hHA-008 injection. FIG. 7C shows plasma hHA-008 concentration changes over time after hHA-008 injection. FIGS. 7D-7F show that hHA-008 had robust PK/PD correlation of PK (plasma antibody concentration) to TSAT % and plasma hepcidin-25 concentration. The results of each tested Cyno are shown in FIG. 7D (Cyno 1), FIG. 7E (Cyno 2), and FIG. 7F (Cyno 3).

FIG. 8A shows TSAT % and hHA-008 concentrations after animals were treated with either 0 (vehicle control) or 0.6 mpk hHA-008. FIG. 8B shows TSAT % and hHA-008 concentrations after animals were treated with either 0 (vehicle control) or 3 mpk hHA-008. FIG. 8C shows TSAT % and hHA-008 concentrations after animals were treated with either 0 (vehicle control) or 60 mpk hHA-008.

FIG. 9A shows TSAT % changes over time in Cynos post treatment of hHA-008 or hHA-008-QL. FIG. 9A shows TSAT % changes over time in Cynos post treatment of hHA-008 or hHA-008-QL. FIG. 9B shows plasma concentration of the antibodies over time in Cynos post treatment of hHA-008 or hHA-008-QL. FIG. 9C shows a time course of decline of plasma concentration of hHA-008 and hHA-008-QL.

FIGS. 10A-10B show binding of FcRn of hHA-008 and hHA-008-QL at pH 6.0. FIGS. 10C-10D show binding of FcRn of hHA-008 and hHA-008-QL at pH 7.4. X axis: Time. Y Axis: Response.

FIG. 14 shows hHA-008 interacts with amino acids 170-183 (SSPMALGANATATR (SEQ ID NO: 121)) on 3720-RG-050. The interaction happens on amino acids 170, 171, 180, 182, 183 on 3720-RG-050.

FIGS. 15A-15J show the interaction of 3720-RG-050 and hHA-008. A 3720-RG-050 PDB structure was generated by homology using Swiss Model software. 3720-RG-050 amino acids 170-183 (SSPMALGANATATR (SEQ ID NO: 121)) are shown in FIGS. 15A, 15B, 15C, 15D, 15E: ribbon/surface representation of front view (FIG. 15A); back view (FIG. 15B), side view 1 (FIG. 15C), side view 2 (FIG. 15D) and top view (FIG. 15E). FIGS. 15F, 15G, 15H, 15I, 15J: ribbon representation of front view (FIG. 15F); back view (FIG. 15G), side view 1 (FIG. 15H), side view 2 (FIG. 15I) and top view (FIG. 15J).

FIG. 16 shows hHA-008-QL interacts with amino acids 169-182 (TSSPMALGANATAT (SEQ ID NO: 122)) and 289-300 (SQRLSRSERNRR (SEQ ID NO: 127)) of 3720-RG-050. The interaction happens on amino acids 169, 171, 180, 182; 289, 293, 294, 295, 297, 300 on 3720-RG-050.

FIGS. 17A-17J show the interaction 3720-RG-050/hHA-008-QL. A 3720-RG-050 PDB structure was generated by homology using Swiss Model software. 3720-RG-050 amino acids 169-182 (TSSPMALGANATAT (SEQ ID NO: 122)) and 289-291 (SQR) are shown in FIGS. 17A, 17B, 17C, 17D, 17E: ribbon/surface representation of front view (FIG. 17A); back view (FIG. 17B), side view 1 (FIG. 17C), side view 2 (FIG. 17D) and top view (FIG. 17E). FIGS. 17F, 17G, 17H, 17I, 17J: ribbon representation of front view (FIG. 17F); back view (FIG. 17G), side view 1 (FIG. 17H), side view 2 (FIG. 17I) and top view (FIG. 17J).

FIG. 20A shows serum concentration-time profiles became indistinguishable between SC injection and IV injection 4 days after administration. FIGS. 20B-20D show the return of serum iron to baseline levels was consistent with the decline in hHA-008 serum concentrations after 0.3 mpk, 0.6 mpk and 1 mpk injection of hHA-008 either by subcutaneous injection or intravenous injection.

DETAILED DESCRIPTION

Figure 1A:
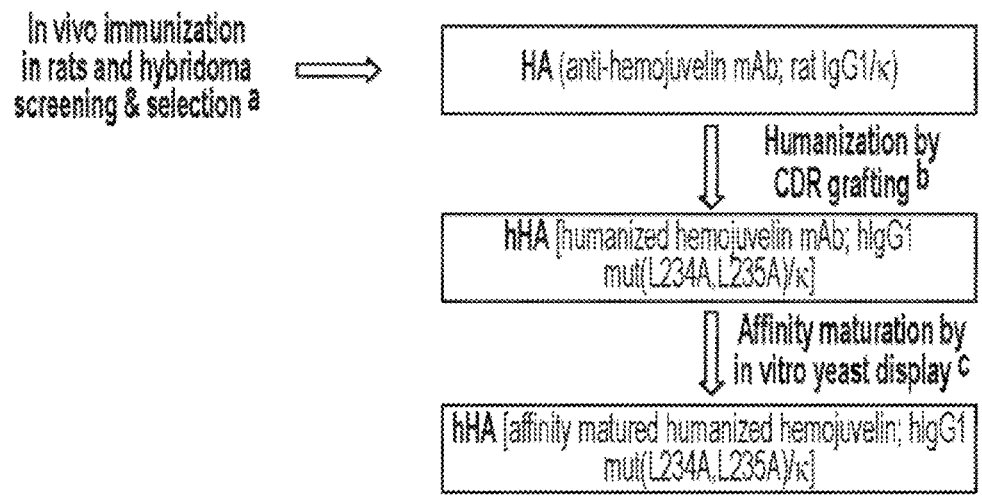
FIGS. 1A-1G are graphs showing generation and characterization of anti-HJV antibodies.
Figure 1B:
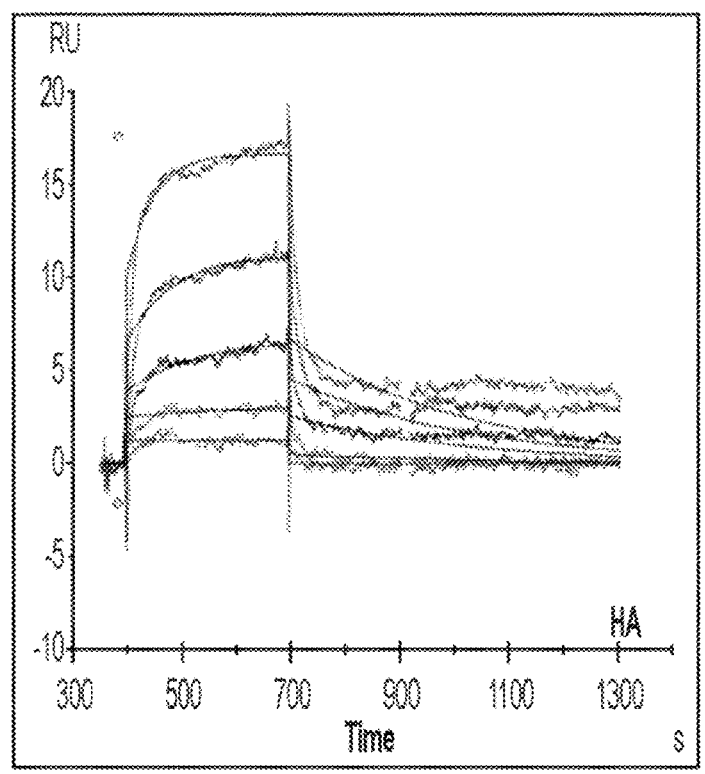
Figure 1C:
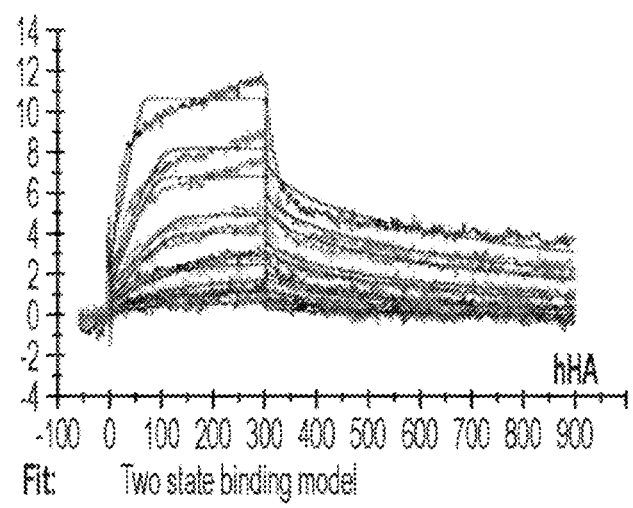
Figure 1D:
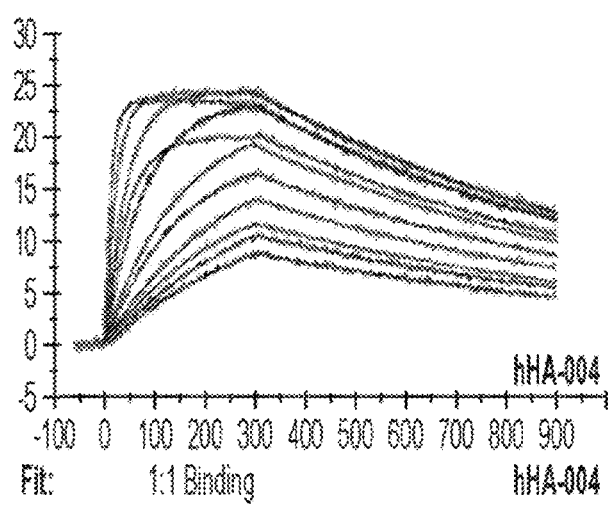
Figure 1E:
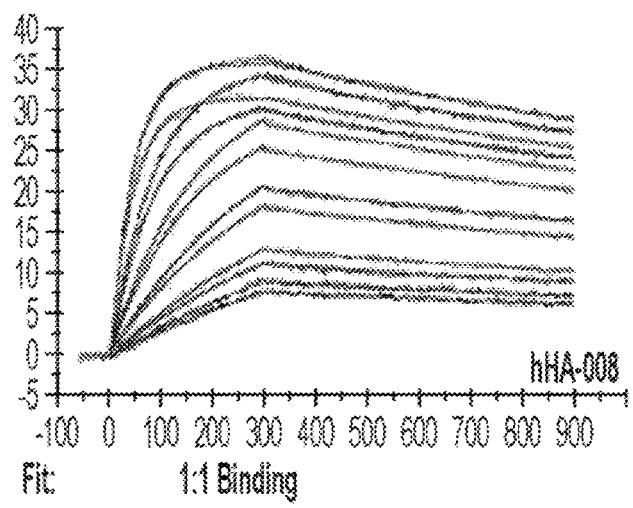
Figure 1F:
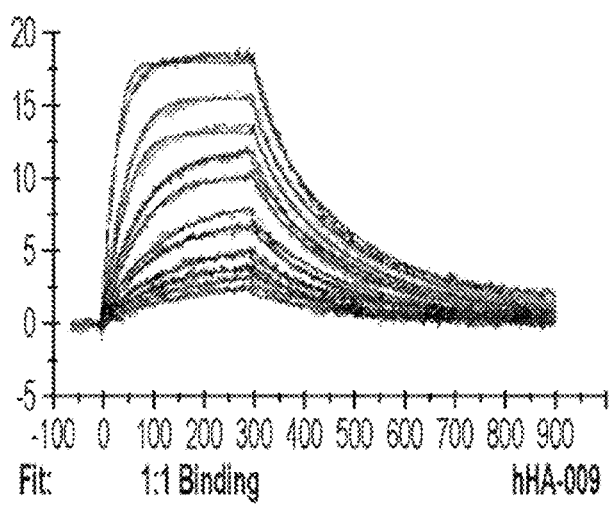
Figure 1G:
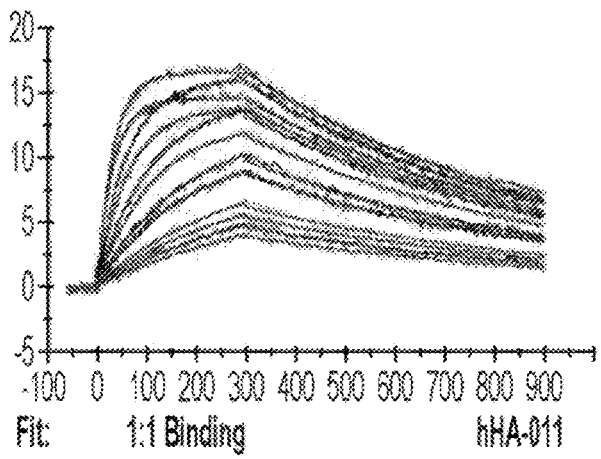

The present disclosure, at least in part, is based on the development of anti-Hemojuvelin (HJV) antibodies, e.g., antibodies listed in Table 1 and their variants, which showed high binding affinity and specificity to human hemojuvelin. Also provided are the use of the anti-HJV antibodies and their variants in research, diagnostic/detection, and therapeutic applications. In some embodiments, the disclosure provides anti-Hemojuvelin (HJV) antibodies for targeting hepcidin pathway that are effective for inhibiting hepcidin function and/or reducing hepcidin expression in cells, particularly for modulating iron homeostasis for the treatment of myelofibrosis and/or one or more symptoms or complications thereof. Accordingly, in related aspects, the disclosure provides compositions and methods for treating myelofibrosis, including primary myelofibrosis, myelofibrosis arising from a myeloproliferative neoplasm, and/or one or more symptoms or complications thereof, such as myelofibrosis-associated anemia, inflammation, bone marrow failure, splenomegaly, hypercatabolic symptoms, and/or fatigue.

In some embodiments, anti-hemojuvelin antibodies are provided that bind RGMc as a primary mode of action (as compared with RGMa and RGMb). Accordingly, in some embodiments, an anti-hemojuvelin antibody preferentially binds RGMc versus RGMa and/or RGMb. In some embodiments, an anti-hemojuvelin antibody binds RGMc with an equilibrium dissociation constant (KD) less than one hundred nanomolar (nM) (KD<100 nM). However, in some embodiments, the anti-hemojuvelin antibody binds RGMc with a similar affinity as RGMa and/or RGMb.

The foregoing and other aspects, implementations, acts, functionalities, features and embodiments of the present teachings can be more fully understood from the following description in conjunction with the accompanying drawings.

I. Definitions

Administering: As used herein, the terms "administering" or "administration" means to provide a complex to a subject in a manner that is physiologically and/or pharmacologically useful (e.g., to treat a condition in the subject).

Affinity Matured Antibody: "Affinity Matured Antibody" is used herein to refer to an antibody with one or more alterations in one or more CDRs, which result in an improvement in the affinity (i.e. KD, kd or ka) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies are known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha ($\alpha$), delta ($\Delta$), epsilon ($\epsilon$), gamma ($\gamma$) or mu ($\mu$) heavy chain. In some embodiments, the heavy chain of an antibody described herein can comprise a human alpha ($\alpha$), delta ($\Delta$), epsilon ($\epsilon$), gamma ($\gamma$) or mu ($\mu$) heavy chain. In a particular embodiment, an antibody described herein comprises a human gamma 1 CH1, CH2, and/or CH3 domain. In some embodiments, the amino acid sequence of the $V_H$ domain comprises the amino acid sequence of a human gamma ($\gamma$) heavy chain constant region, such as any known in the art. Non-limiting examples of human constant region sequences have been described in the art, e.g., see U.S. Pat. No. 5,693,780 and Kabat E A et al., (1991) supra. In some embodiments, the $V_H$ domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

CDR: As used herein, the term "CDR" refers to the complementarity determining region within antibody variable sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information System® http://www.imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). ee also hgmp.mrc.ac.uk and bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

Generally, there are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDR-grafted antibody: The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human hemojuvelin and non-human primate hemojuvelin) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

Effective Amount: As used herein, "an effective amount" refers to the amount of each active agent (e.g., anti-HJV antibody) required to confer therapeutic effect on the subject, either alone or in combination with one or more other active agents. In some embodiments, the therapeutic effect is reduced hepcidin level or activity, increased level of transferrin saturation (TSAT %), decreased level of circulating transferrin level, and/or alleviated disease conditions (e.g., reduced anemia or reduce myelofibrosis progression).

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Hemojuvelin (HJV): As used herein, the term "hemojuvelin (HJV)" (also known as repulsive guidance molecule C (RGMc) or hemochromatosis type 2 protein (HFE2)) refers to a membrane-bound and soluble form protein that regulates hepcidin production through the BMP/SMAD signaling pathway. The HFE2 gene encodes two known classes of GPI-anchored and glycosylated HJV molecules, which are targeted to the membrane and undergo distinct fates. HJV exists in multiple isoforms, including two soluble isoforms and two membrane-associated isoforms. In some embodiments, a predominant membrane-associated isoform is a disulfide-linked two-chain form composed of N- and C-terminal fragments. In some embodiments, a full-length single-chain isoform associates with the membrane, but is released from the cell surface and accumulates in extracellular fluid. In some embodiments, HJV may be of human (NCBI Gene ID 148738), non-human primate (e.g., NCBI Gene ID 698805), or rodent (e.g., NCBI Gene ID 69585 or NCBI Gene ID 310681) origin. In addition to HJV (RGMc), the repulsive guidance molecule family includes repulsive guidance molecule A (RGMa) and repulsive guidance molecule B (RGMb). RGMa and RGMb are expressed in the central nervous system during development and are thought to be involved in controlling axonal patterning and neuronal survival, while HJV is produced in the liver and in cardiac and skeletal muscle.

Hepcidin: As used herein, a "hepcidin" refers to an iron-regulating peptide hormone primarily made in the liver that is encoded by the HAMP gene. In some embodiments, hepcidin controls the delivery of iron to blood plasma from intestinal cells absorbing iron, from erythrocyte-recycling macrophages, and from iron-storing hepatocytes. In some embodiments, hepcidin inhibits iron transport by binding to the iron export channel ferroportin which is located on the basolateral surface of gut enterocytes and the plasma membrane of reticuloendothelial cells (macrophages). In some embodiments, inhibiting ferroportin prevents iron from being exported and the iron is sequestered in the cells. In some embodiments, by inhibiting ferroportin, hepcidin prevents enterocytes from allowing iron into the hepatic portal system, thereby reducing dietary iron absorption. Hepcidin expression involves multiple aspects, including, for example, transcription of the HAMP gene, translation of the transcribed mRNA, and the posttranslational processing of the hepcidin precursor into the bioactive hepcidin-25 peptide (DTHFPICIFCCGCCHRSKCGMCCKT (SEQ ID NO: 129)). In some embodiments, hepcidin expression is modulated via the hemojuvelin-induced BMP signaling pathway. In some embodiments, hepcidin expression is modulated via the IL-6-JAK-STAT signaling pathway.

HJV-induced BMP signaling: As used herein, the term "HJV-induced BMP signaling" refers to signaling through BMP receptors that is induced by Hemojuvelin (HJV), which is a membrane bound co-receptor for bone morphogenetic protein (BMP) signaling. As discussed in Xia Y, et al., *Hemojuvelin regulates hepcidin expression via a selective subset of BMP ligands and receptors independently of neogenin*, Blood. 2008 May 15; 111(10): 5195-5204, in hepatocytes, HJV-induced BMP signaling positively regulates hepcidin mRNA expression. In some embodiments, HJV binds to BMP2, BMP4, BMP5, or BMP6 to induce BMP signaling, e.g., to positively regulate hepcidin levels in hepatocytes. In some embodiments, cleavage of HJV by matripatase-2 reduces the amount of cell surface HJV available to participate in BMP signaling. In some embodiments, induction of BMP signaling by HJV is independent of neogenin. However, in some embodiments, neogenin facilitates induction of BMP signaling by HJV, as discussed in Zhao et al, Neogenin Facilitates the Induction of Hepcidin Expression by Hemojuvelin in the Liver, J Biol Chem. 2016 Jun. 3; 291(23): 12322-12335. In some embodiments, BMP6 is responsible for iron-dependent activation of the Smad signaling. In some embodiments, BMP6 is secreted from liver sinusoidal endothelial cells and binds to a BMP receptor (BMPR) on hepatocytes and thereby activates the SMAD signaling cascade. In such embodiments, HJV serves as a co-receptor for such BMP6, e.g., to positively regulate hepcidin levels in hepatocytes. In some embodiments, BMPs transduce signals by binding to one or a combination of type I and II serine/threonine kinase receptors. BMP type II receptors include BMPRII, ActRIIA, and ActRIIB. BMP type I receptors include ALK3, ALK6, and ALK2. In some embodiments, upon ligand binding, constitutively active type II receptors phosphorylate type I receptors, and type I receptors then phosphorylate intracellular receptor-activated Smads (R-Smads), namely Smad 1, Smad 5 and/or Smad 8. In such embodiments, activated R-Smads complex with the common partner Smad4 and translocate to the nucleus to regulate gene transcription, e.g., induction of hepcidin expression.

Hepcidin Antagonist: As used herein, a "hepcidin antagonist" refers to an agent that reduces hepcidin expression and/or hepcidin activity (directly or indirectly). In some embodiments, a hepcidin antagonist reduces hepcidin-25 levels and/or activity (directly or indirectly). In some embodiments, a hepcidin antagonist inhibits hepcidin-induced ferroportin degradation. Accordingly, in some embodiments, a hepcidin antagonist targets hepcidin function indirectly through the hepcidin stimulatory pathway to decrease hepcidin expression. In some embodiments, a hepcidin antagonist targets hepcidin function directly, e.g., by binding the hepcidin peptide to sequester free hepcidin or by binding ferroportin to inhibit the hepcidin-ferroportin binding interaction, thereby decreasing hepcidin-induced ferroportin degradation. In some embodiments, a hepcidin antagonist is a ferroportin inhibitor that disrupts ferroportin-hepcidin interactions, such as, for example, as disclosed in Ross S L, et al., *Identification of Antibody and Small Molecule Antagonists of Ferroportin-Hepcidin Interaction*. Front Pharmacol. 2017 Nov. 21; 8:838; Fung E., et al., *High-Throughput Screening of Small Molecules Identifies Hepcidin Antagonists. Molecular Pharmacology* March 2013, 83 (3) 681-690; and Angeliki Katsarou and Kostas Pantopoulos, *Hepcidin Therapeutics*. Pharmaceuticals (Basel). 2018 December; 11(4): 127, the relevant contents of each of which are incorporated herein by reference.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the $V_H$ and/or $V_L$ sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-hemojuvelin antibodies and antigen binding portions are provided. Such antibodies may be generated by obtaining murine anti-hemojuvelin monoclonal antibodies using traditional hybridoma technology followed by humanization using in vitro genetic engineering, such as those disclosed in Kasaian et al PCT publication No. WO 2005/123126 A2.

Isolated antibody: An "isolated antibody", as used herein, is intended to refer to an antibody that is substantially free of other antibodies having different antigenic specificities (e.g., an isolated antibody that specifically binds hemojuvelin is substantially free of antibodies that specifically bind antigens other than hemojuvelin). An isolated antibody that specifically binds hemojuvelin may, however, have cross-reactivity to other antigens, such as other repulsive guidance molecule (RGM) proteins (e.g., RGMa and/or RGMb). Moreover, an isolated antibody may be substantially free of other cellular material and/or chemicals.

JAK-STAT signaling: As used herein, the term "JAK-STAT signaling" refers to signaling through cellular receptors that recruits a Janus Kinase (JAK), such as, for example, Janus Kinase 1 (JAK1) or Janus Kinase 2 (JAK2), to activate a transcription factor signal transducer and activator of transcription (STAT), such as, for example, STAT3. In some embodiments, as discussed in Maliken, B D, et al., *The Hepcidin Circuits Act: Balancing Iron and Inflammation*, Hepatology. 2011 May; 53(5): 1764-1766, JAK-STAT signaling involves binding of the cytokine interleukin-6 (IL-6) to its cognate cellular receptor, which then recruits Janus Kinase 2 (JAK2) to phosphorylate STAT3. In some embodiments, STAT3 is then (following JAK2 activation/phosphorylation) translocated into the nucleus. In some embodiments, activated STAT3 then induces hepcidin transcription, e.g., by binding to the STAT3 binding motif in the hepcidin promoter region. Thus, in some embodiments, hepcidin expression is induced via JAK-STAT signaling during inflammation through activation STAT3 by IL-6.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Myelofibrosis: As used herein, the term "myelofibrosis" refers to a disorder characterized by pathological myeloproliferation and aberrant cytokine production resulting in progressive fibrosis, inflammation and/or functional compromise of the bone marrow niche of a subject. The fibrosis associated with myelofibrosis often results from a non-clonal fibroblastic response to inflammatory and fibrogenic cytokines produced by aberrant clonal myeloid cells, such as megakaryocytes. Myelofibrosis typically results in bone marrow failure, splenomegaly, hypercatabolic symptoms, and anemia. In some embodiments, myelofibrosis arises in a subject de novo. In such embodiments, the myelofibrosis is considered as a "primary" myelofibrosis. However, in some embodiments, the myelofibrosis arises from a preexisting myeloproliferative neoplasm. In some embodiments, the preexisting myeloproliferative neoplasm is a polycythemia. In some embodiments, the preexisting myeloproliferative neoplasm is an essential thrombocytosis.

Myelofibrosis-Associated Anemia: As used herein, the term "myelofibrosis-associated anemia" refers to a condition arising in the context of, or comorbid with, myelofibrosis and being characterized by a deficiency in the ability of blood to transport oxygen. In some embodiments, myelofibrosis-associated anemia is the result of a deficiency in red blood cells, a deficiency in hemoglobin, and/or a deficiency in total blood volume. In some embodiments, a myelofibrosis-associated anemia is an iron deficiency anemia or a myelophthisic anemia. In some embodiments, myelofibrosis-associated anemia is further associated with chronic inflammatory disease. In some embodiments, a myelofibrosis-associated anemia is associated with high circulating hepcidin level in a subject. In some embodiments, a myelofibrosis-associate anemia is associated with proinflammatory cytokine (e.g., IL-6) induced high circulating hepcidin level in a subject. Examples of anemias other than myelofibrosis-associated anemia include anemias related to rheumatoid arthritis, anemias of infection, autoimmune hemolytic anemia, aplastic anemia, hypoplastic anemia, pure red cell aplasia and anemia resulting from renal failure or endocrine disorders, megaloblastic anemias, anemia resulting from defects in heme or globin synthesis, anemia caused by a structural defect in red blood cells, e.g., sickle-cell anemia, sideroblastic anemia, anemia associated with chronic infections such as malaria, trypanosomiasis, HIV, hepatitis virus or other viruses, anemias caused by marrow deficiencies in absence of myelofibrosis, and chemotherapy-induced anemia.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O- methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. One embodiment of the disclosure provides fully human antibodies capable of binding human hemojuvelin which can be generated using techniques well known in the art, such as, but not limited to, using human Ig phage libraries such as those disclosed in Jermutus et al., PCT publication No. WO 2005/007699 A2.

Selective: As used herein, the term "selective" or "selectively" refers to the ability of a molecule to produce an effect in relation to its target molecule compared to a reference molecule. For example, a molecule that selectively inhibits its target molecule means that this molecule is capable of inhibiting its target molecule with a degree that is distinguishable from a reference molecule in an inhibition assay or other inhibitory context. For example, with respect to an inhibitor, the term, "selectively inhibits", refers to the ability of the inhibitor to inhibit its target molecule with a degree that is distinguishable from a reference molecule that is not substantially inhibited in an inhibition assay, e.g., to an extent that permit selective inhibition of the target molecule, as described herein. For example, the half maximal inhibitory concentration (IC50) for the target molecule and/or the reference molecule can be tested in a kinase potency assay as described in Asshoff, M. et al., Momelotinib inhibits ACVR1/ALK2, decreases hepcidin production, and ameliorates anemia of chronic disease in rodents. Blood. 2017 Mar. 30; 129(13): 1823-1830 (e.g., Kinase potency assay by Carna Biosciences). In this assay, inhibitor solution (e.g., solution containing the selective inhibitor to be tested)/kinase substrate is mixed with target molecule solution (e.g., ALK2) or reference molecule solution (e.g., JAK1 or JAK2), and incubated under room temperature for 1 hour. Once the reaction is terminated, the signal produced by enzymatic activity on the substrate can be measured. The half maximal inhibitor concentration for the target molecule and the reference molecule can be calculated. In some embodiments, a molecule described herein selectively binds to a target molecule. In some embodiments, a molecule described herein selectively inhibits to a target molecule. In some embodiments, a molecule described herein selectively antagonizes to a target molecule. In some embodiments, a molecule described herein selectively neutralizes to a target molecule.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to hemojuvelin.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having myelofibrosis and/or one or more conditions arising as a result of myelofibrosis.

Treatment: As used herein, the term "treating" or "treatment" refers to the application or administration of a composition including one or more active agents (e.g., anti-HJV antibodies) to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder. Alleviating a target disease/disorder includes delaying or preventing the development or progression of the disease, or reducing disease severity.

II. Anti-Hemojuvelin (HJV) Antibodies

In some embodiments, the hemojuvelin antagonist binds to one or more proteins of the repulsive guidance molecule (RGM) family, including RGMa, RGMb, and RGMc (HJV). In some embodiments, the hemojuvelin antagonist selectively binds hemojuvelin (RGMc) over RGMa and RGMb. In some embodiments, the hemojuvelin antagonist is an antisense oligonucleotide that reduces expression of hemojuvelin (see, e.g., U.S. Pat. No. 7,534,764; U.S. Patent Publication No. US 2014/127325; and International Publication No. WO 2016/180784, which are incorporated herein by reference). In some embodiments, the hemojuvelin antagonist is a small molecule compound that inhibits hemojuvelin, e.g., by competitive binding and/or chemical modification of hemojuvelin.

In some embodiments, the hemojuvelin antagonist is an antibody (e.g., HA001-HA012) specific for hemojuvelin and/or one or more proteins of the RGM protein family (e.g., RGMa, RGMb). Appropriate antibodies specific for hemojuvelin and/or one or more RGM proteins that may be useful in certain methods provided herein are provided for example, in U.S. Pat. Nos. 10,118,958; and 8,507,435; U.S. Patent Publication Nos. US 2013/330343; US 2015/166672; and US 2017/029499; and International Publication Nos. WO 2015/171691; and WO 2018/009624, which are incorporated herein by reference. Provided herein, in some aspects, are antibodies that bind to human hemojuvelin (HJV) with high specificity and affinity. In some embodiments, the anti-HJV antibody described herein specifically binds to any extracellular epitope of a HJV or an epitope that becomes exposed to an antibody. In some embodiments, anti-HJV antibodies provided herein bind specifically to HJV from human, non-human primates, mouse, rat, etc. In some embodiments, anti-HJV antibodies provided herein bind to human HJV. In some embodiments, the anti-HJV antibody described herein binds to an amino acid segment of a human or non-human primate HJV.

In some embodiments, the anti-HJV antibody described herein specifically binds to an epitope on human HJV. Human HJV is a 426 amino acid protein with a predicted N-terminal signal peptide of 31 amino acids and a C-terminal GPI-attachment signal of 45 amino acids. An exemplary human HJV amino acid sequence is set forth in SEQ ID NO: 128:

(SEQ ID NO: 128)
MGEPGQSPSPRSSHGSPPTLSTLTLLLLLCGHAHSQCKILRCNAEYVSST

LSLRGGGSSGALRGGGGGGRGGGVGSGGLCRALRSYALCTRRTARTCRGD

LAFHSAVHGIEDLMIQHNCSRQGPTAPPPPRGPALPGAGSGLPAPDPCDY

EGRFSRLHGRPPGFLHCASFGDPHVRSFHHHFHTCRVQGAWPLLDNDFLF

VQATSSPMALGANATATRKLTIIFKNMQECIDQKVYQAEVDNLPVAFEDG

SINGGDRPGGSSLSIQTANPGNHVEIQAAYIGTTIIIRQTAGQLSFSIKV

AEDVAMAFSAEQDLQLCVGGCPPSQRLSRSERNRRGAITIDTARRLCKEG

LPVEDAYFHSCVFDVLISGDPNFTVAAQAALEDARAFLPDLEKLHLFPSD

AGVPLSSATLLAPLLSGLFVLWLCIQ

In some embodiments, the anti-HJV antibody described herein may bind to a fragment of a human HJV. The fragment of HJV may be between about 5 and about 425 amino acids, between about 10 and about 400 amino acids, between about 50 and about 350 amino acids, between about 100 and about 300 amino acids, between about 150 and about 250 amino acids, between about 200 and about 300 amino acids, or between about 75 and about 150 amino acids in length. The fragment may comprise a contiguous number of amino acids from RGMc. An exemplary amino acid of a HJV fragment is set forth in SEQ ID NO: 123:

(SEQ ID NO: 123)
QCKILRCNAEYVSSTLSLRGGGSSGALRGGGGGGRGGGVGSGGLCRALRS

YALCTRRTARTCRGDLAFHSAVHGIEDLMIQHNCSRQGPTAPPPPRGPAL

PGAGSGLPAPDPCDYEGRFSRLHGRPPGFLHCASFGDPHVRSFHHHFHTC

RVQGAWPLLDNDFLFVQATSSPMALGANATATRKLTIIFKNMQECIDQKV

YQAEVDNLPVAFEDGSINGGDRPGGSSLSIQTANPGNHVEIQAAYIGTTI

IIRQTAGQLSFSIKVAEDVAMAFSAEQDLQLCVGGCPPSQRLSRSERNRR

GAITIDTARRLCKEGLPVEDAYFHSCVFDVLISGDPNFTVAAQAALEDAR

AFLPDLEKLHLFPSD

In some embodiments, the anti-HJV antibody described herein binds to different epitopes within a human HJV or a human HJV fragment.

In some embodiments, the anti-HJV antibody interacts with an epitope within amino acids 160-190 of SEQ ID NO: 123. In some embodiments, the anti-HJV antibody interacts with an epitope having an amino acid sequence of amino acids 170-183 of SEQ ID NO: 123. In some embodiments, the anti-HJV antibody interacts with an epitope having the amino acid sequence of SSPMALGANATATR (SEQ ID NO: 121). In some embodiments, the anti-HJV antibody interacts with different segments within SSPMALGANATATR (SEQ ID NO: 121). In some embodiments, the anti-HJV antibody interacts with amino acids 170-171, amino acids 171-180, amino acids 180-182, and amino acids 182-183 of SEQ ID NO: 123. In some embodiments, the antibody interacts with amino acids 170 (S), 171(S), 180 (T), 182 (T) and 183 (R) of SEQ ID NO: 123. In some embodiments, hHA-008 interacts with the epitope SSPMALGANATATR (SEQ ID NO: 121). In some embodiments, hHA-008 interacts with amino acids 170 (S), 171(S), 180 (T), 182 (T) and 183 (R) of SEQ ID NO: 123.

In some embodiments, the anti-HJV antibody interacts with an epitope within amino acids 160-190 of SEQ ID NO: 123 and/or amino acids 280-310 of SEQ ID NO: 123. In some embodiments, the anti-HJV antibody interacts with an epitope within amino acids 169-182 of SEQ ID NO: 123 and/or amino acids 289-300 of SEQ ID NO: 123. In some embodiments, the anti-HJV antibody interacts with an epitope within amino acids 169-182 of SEQ ID NO: 123 and amino acids 289-300 of SEQ ID NO: 123. In some embodiments, the anti-HJV antibody interacts with an epitope having the amino acid sequence of TSSPMALGANATAT (SEQ ID NO: 122) and amino acid sequence SQRLSRSERNRR (SEQ ID NO: 127). In some embodiments, the anti-HJV antibody interacts with different segments within TSSPMALGANATAT (SEQ ID NO: 122) and SQRLSRSERNRR (SEQ ID NO: 127). In some embodiments, the anti-HJV antibody interacts with amino acids 169-171, amino acids 171-180, and amino acids 180-182 of SEQ ID NO: 123, and amino acids 289-293, amino acids 293-294, amino acids 294-295, amino acids 295-297 and amino acids 297-300 of SEQ ID NO: 123. In some embodiments, the antibody interacts with amino acids 169 (T), 170 (S), 171(S), 180 (T), 182 (T), 289 (S), 293 (S), 294 (R), 295(S), 297(R), and 300 (R) of SEQ ID NO: 123. In some embodiments, hHA-008-QL interacts with different segments within TSSPMALGANATAT (SEQ ID NO: 122) and SQRLSRSERNRR (SEQ ID NO: 127). In some embodiments, hHA-008-QL interacts with amino acids 169 (T), 170 (S), 171(S), 180 (T), 182 (T), 289 (S), 293 (S), 294 (R), 295(S), 297(R), and 300 (R) of SEQ ID NO: 123.

In some embodiments, the anti-HJV antibodies described herein are affinity matured clones. In some embodiments, an anti-HJV antibody specifically binds a HJV (e.g., a human or non-human primate HJV) with binding affinity (e.g., as indicated by $K_D$) of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. For example, the anti-HJV antibodies of the present disclosure can bind to a hemojuvelin protein (e.g., human hemojuvelin) with an affinity between 5 pM and 500 nM, e.g., between 50 pM and 100 nM, e.g., between 500 pM and 50 nM. The disclosure also includes antibodies that compete with any of the antibodies described herein for binding to a hemojuvelin protein (e.g., human hemojuvelin) and that have an affinity of 100 nM or lower (e.g., 80 nM or lower, 50 nM or lower, 20 nM or lower, 10 nM or lower, 500 pM or lower, 50 pM or lower, or 5 pM or lower). The affinity and binding kinetics of the anti-HJV antibody can be tested using any suitable method including but not limited to biosensor technology (e.g., OCTET or BIACORE). In some embodiments, the anti-HJV antibodies described herein binds to HJV with a $K_D$ of sub-nanomolar range. In some embodiments, the anti-HJV antibodies described herein selectively binds to RGMc, but not RGMa or RGMb.

Binding affinity (or binding specificity) can be determined by a variety of methods including equilibrium dialysis, equilibrium binding, gel filtration, ELISA, surface plasmon resonance (SPR), florescent activated cell sorting (FACS) or spectroscopy (e.g., using a fluorescence assay). Exemplary conditions for evaluating binding affinity are in HBS-P buffer (10 mM HEPES pH7.4, 150 mM NaCl, 0.005% (v/v) surfactant P20) and PBS buffer (10 mM PO4-3, 137 mM NaCl, and 2.7 mM KCl). These techniques can be used to measure the concentration of bound proteins as a function of target protein concentration. The concentration of bound protein ([Bound]) is generally related to the concentration of free target protein ([Free]) by the following equation:

$$[Bound]=[Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The heavy chain (HC) and light chain (LC) sequences, heavy chain variable domain (VH) and light chain variable domain (VL), CDR sequences, and heavy chain and light chain constant region sequences of non-limiting examples of anti-HJV antibodies are provided in Table 1.

TABLE 1

Examples of anti-HJV antibodies
(CDRs according to the Kabat definition)

| humanized Hemojuvelin Antagonist (HA) Antibody | | Sequences | SEQ ID NO |
|---|---|---|---|
| hHA-001 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLETSDGDTFLE | 4 |
| | LC CDR2 | EVSTRFS | 5 |
| | LC CDR3 | FQVTHDPMT | 6 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLETSDGDTFLEW FQQRPGQSPRLLIYEVSTRFSGVPDRFSGSGSGTDFTLKI SRVEAEDVGVYYCFQVTHDPMTFGQGTKLEIK | 8 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLETSDGDTFLEW FQQRPGQSPRLLIYEVSTRFSGVPDRFSGSGSGTDFTLKI SRVEAEDVGVYYCFQVTHDPMTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 52 |
| hHA-002 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLETSDGDTFLE | 4 |
| | LC CDR2 | EVSSRFS | 49 |
| | LC CDR3 | MQVTHDPLT | 24 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLETSDGDTFLEW FQQRPGQSPRLLIYEVSSRFSGVPDRFSGSGSGTDFTLKI SRVEAEDVGVYYCMQVTHDPLTFGQGTKLEIK | 30 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLETSDGDTFLEW FQQRPGQSPRLLIYEVSSRFSGVPDRFSGSGSGTDFTLKI SRVEAEDVGVYYCCMQVTHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 53 |
| hHA-003 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLETSDGDTFLE | 4 |
| | LC CDR2 | EVSNRFS | 18 |
| | LC CDR3 | FQVTHDPVT | 25 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLETSDGDTFLEW FQQRPGQSPRLLIYEVSNRFSGVPDRFSGSGSGTDFTLKI SRVEAEDVGVYYCFQVTHDPVTFGQGTKLEIK | 31 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̄FNW YVDGVEVHNAKT K̄PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̄FNW YVDGVEVHNAKT K̄PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̄FNWYVDGV EVHNAKT K̄PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̄FNWYVDGV EVHNAKT K̄PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLETSDGDTFLEW FQQRPGQSPRLLIYEVSNRFSGVPDRFSGSGSGTDFTLKI SRVEAEDVGVYYCFQVTHDPVTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 54 |
| hHA-004 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLESSDGDTFLE | 14 |
| | LC CDR2 | DVSTRFS | 19 |
| | LC CDR3 | FQVTHDPVT | 25 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | VL | DVVLTQSPLSLPVTLGQPASISCRSSQSLESSDGDTFLEW FQQRPGQSPRLLIYDVSTRFSGVPDRFSGSGSGTDFTLKI SRVEAEDVGVYYCFQVTHDPVTFGQGTKLEIK | 32 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLESSDGDTFLEW FQQRPGQSPRLLIYDVSTRFSGVPDRFSGSGSGTDFTLKI SRVEAEDVGVYYCFQVTHDPVTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 55 |
| hHA-005 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLEESDGYTFLE | 15 |
| | LC CDR2 | DVSERFS | 20 |
| | LC CDR3 | FQATYDPLT | 26 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLEESDGYTFLEW FQQRPGQSPRLLIYDVSERFSGVPDRFSGSGSGTDFTLKI SRVEAEDVGVYYCFQATYDPLTFGQGTKLEIK | 33 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̄FNW YVDGVEVHNAKT̄KPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̄FNW YVDGVEVHNAKT̄KPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̄FNWYVDGV EVHNAKT̄KPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̄FNWYVDGV EVHNAKT̄KPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLEESDGYTFLEW FQQRPGQSPRLLIYDVSERFSGVPDRFSGSGSGTDFTLKI SRVEAEDVGVYYCFQATYDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 56 |
| hHA-006 | HC CDR1 | YYGMN | 9 |
| | HC CDR2 | MIYYDSSEKHYADSVKG | 2 |
| | HC CDR3 | GTTPDY | 3 |
| | LC CDR1 | RSSQSLEDSDGGTFLE | 16 |
| | LC CDR2 | DVSSRFS | 21 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | LC CDR3 | FQATHDPLT | 27 |
| | VH | EVQLVESGGGLVQPGGSLRLSCAASGFTFSYYGMNWIRQA PGKGLEWIGMIYYDSSEKHYADSVKGRFTISRDNSKNTLY LQMNSLRAEDTAVYYCAKGTTPDYWGQGTMVTVSS | 34 |
| | VL | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLTFGQGTKLEIK | 35 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSYYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 57 |
| | | EVQLVESGGGLVQPGGSLRLSCAASGFTFSYYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEGGAAPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 115 |
| | Light Chain | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 58 |
| hHA-007 | HC CDR1 | NYGMN | 1 |
| | HC CDR2 | MIYYDSSDKHYADSVKG | 10 |
| | HC CDR3 | GTTPDV | 11 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | LC CDR1 | RSSQSLEESDGYTFLH | 17 |
| | LC CDR2 | EVSNRFS | 18 |
| | LC CDR3 | FQATHDPVT | 28 |
| | VH | EVQLVESGGGLVQPGGSLRLSCAASGFTFSNYGMNWIRQA PGKGLEWIGMIYYDSSDKHYADSVKGRFTISRDNSKNTLY LQMNSLRAEDTAVYYCAKGTTPDVWGQGTMVTVSS | 36 |
| | VL | DVVLTQSPLSLPVTLGQPASISCRSSQSLEESDGYTFLHW FQQRPGQSPRLLIYEVSNRFSGVPDRFSGSGSGTDFTLKI SRVEAEDVGVYYCFQATHDPVTFGQGTKLEIK | 37 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSDKHYADSVKGRFTISRDNSKNTLY LQMNSLRAEDTAVYYCAKGTTPDVWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 59 |
| | | EVQLVESGGGLVQPGGSLRLSCAASGFTFSNYGMNWIRQA PGKGLEWIGMIYYDSSDKHYADSVKGRFTISRDNSKNTLY LQMNSLRAEDTAVYYCAKGTTPDVWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 116 |
| | Light Chain | DVVLTQSPLSLPVTLGQPASISCRSSQSLEESDGYTFLHW FQQRPGQSPRLLIYEVSNRFSGVPDRFSGSGSGTDFTLKI SRVEAEDVGVYYCFQATHDPVTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 60 |
| hHA-008 | HC CDR1 | NYGMN | 1 |
| | HC CDR2 | MIYYDSSEKHYADSVKG | 2 |

TABLE 1-continued

Examples of anti-HJV antibodies
(CDRs according to the Kabat definition)

| humanized Hemojuvelin Antagonist (HA) Antibody | Sequences | SEQ ID NO |
|---|---|---|
| HC CDR3 | GTTPDY | 3 |
| LC CDR1 | RSSQSLEESDGYTFLH | 17 |
| LC CDR2 | EVSTRFS | 5 |
| LC CDR3 | FQATHDPLT | 27 |
| VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSS | 38 |
| VL | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIK | 39 |
| HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK$\underline{\text{F}}$NW YVDGVEVHNAKT$\underline{\text{K}}$PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSV$\underline{\text{M}}$HEALHNHYT QKSLSLSPGK | 46 |
| | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK$\underline{\text{F}}$NW YVDGVEVHNAKT$\underline{\text{K}}$PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSV$\underline{\text{M}}$HEALHNHYT QKSLSLSPG | 112 |
| LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK$\underline{\text{F}}$NWYVDGV EVHNAKT$\underline{\text{K}}$PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSV$\underline{\text{M}}$HEALHNHYTQKSLS LSPGK | 61 |
| | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK$\underline{\text{F}}$NWYVDGV EVHNAKT$\underline{\text{K}}$PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSV$\underline{\text{M}}$HEALHNHYTQKSLS LSPG | 117 |
| Light Chain | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 62 |

TABLE 1-continued

Examples of anti-HJV antibodies
(CDRs according to the Kabat definition)

| humanized Hemojuvelin Antagonist (HA) Antibody | Sequences | SEQ ID NO |
|---|---|---|
| hHA-008-QL HC CDR1 | NYGMN | 1 |
| HC CDR2 | MIYYDSSEKHYADSVKG | 2 |
| HC CDR3 | GTTPDY | 3 |
| LC CDR1 | RSSQSLEESDGYTFLH | 17 |
| LC CDR2 | EVSTRFS | 5 |
| LC CDR3 | FQATHDPLT | 27 |
| VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSS | 38 |
| VL | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIK | 39 |
| HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDQLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVLHEALHNHYT QKSLSLSPGK | 48 |
| | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDQLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVLHEALHNHYT QKSLSLSPG | 113 |
| LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDQLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVLHEALHNHYTQKSLS LSPGK | 63 |
| | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDQLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVLHEALHNHYTQKSLS LSPG | 118 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | Light Chain | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 62 |
| hHA-009 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLADSDGDTFLH | 50 |
| | LC CDR2 | AVSHRFS | 22 |
| | LC CDR3 | FQATHDPVT | 28 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSS | 38 |
| | VL | DVVLTQSPLSLPVTLGQPASISCRSSQSLADSDGDTFLHW FQQRPGQSPRLLIYAVSHRFSGVPDRFSGSGSGTDFTLKI SRVEAEDVGVYYCFQATHDPVTFGQGTKLEIK | 41 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 61 |
| | | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL | 117 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | | FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | |
| | Light Chain | DVVLTQSPLSLPVTLGQPASISCRSSQSLADSDGDTFLHW FQQRPGQSPRLLIYAVSHRFSGVPDRFSGSGSGTDFTLKI SRVEAEDVGVYYCFQATHDPVTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 65 |
| hHA-010 | HC CDR1 | NYGMN | 1 |
| | HC CDR2 | MIYYDSSEKHYADSVKG | 2 |
| | HC CDR3 | GTTPDK | 12 |
| | LC CDR1 | RSSQSLEESDGYTFLE | 15 |
| | LC CDR2 | EVSHRFS | 23 |
| | LC CDR3 | FQATHDPLT | 27 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDKWGQGTMVTVSS | 42 |
| | VL | DVVLTQSPLSLPVTLGQPASISCRSSQSLEESDGYTFLEW FQQRPGQSPRLLIYEVSHRFSGVPDRFSGSGSGTDFTLKI SRVEAEDVGVYYCFQATHDPLTFGQGTKLEIK | 43 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDKWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 66 |
| | | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDKWGQGTMVTVSSASTKG | 119 |

TABLE 1-continued

Examples of anti-HJV antibodies
(CDRs according to the Kabat definition)

| humanized Hemojuvelin Antagonist (HA) Antibody | | Sequences | SEQ ID NO |
|---|---|---|---|
| | | PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | |
| | Light Chain | DVVLTQSPLSLPVTLGQPASISCRSSQSLEESDGYTFLEW FQQRPGQSPRLLIYEVSHRFSGVPDRFSGSGSGTDFTLKI SRVEAEDVGVYYCFQATHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 67 |
| hHA-011 | HC CDR1 | NYGMN | 1 |
| | HC CDR2 | MIYYDSSEKHYADSVKG | 2 |
| | HC CDR3 | GSTPDY | 13 |
| | LC CDR1 | RSSQSLEDSDGGTFLE | 16 |
| | LC CDR2 | DVSSRFS | 21 |
| | LC CDR3 | FQATHDPLS | 29 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGSTPDYWGQGTMVTVSS | 44 |
| | VL | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLSFGQGTKLEIK | 45 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGSTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 68 |

TABLE 1-continued

Examples of anti-HJV antibodies
(CDRs according to the Kabat definition)

| humanized Hemojuvelin Antagonist (HA) Antibody | Sequences | SEQ ID NO |
|---|---|---|
|  | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGSTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 120 |
| Light Chain | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLSFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 69 |

In some embodiments, the N-terminal of the heavy chain of the anti-HJV antibody described herein is glutamic acid (E). In some embodiments, the glutamic acid can cyclize spontaneously to pyroglutamic acid by post-translational modification. Spontaneous cyclization of glutamic acid to pyroglutamic acid has been previously described, e.g., Chelius et al., Formation of Pyroglutamic Acid From N-terminal Glutamic Acid in Immunoglobulin Gamma Antibodies, Anal Chem. 2006; 78(7):2370-2376. In some embodiments, the N-terminal of the heavy chain of the anti-HJV antibody described herein is a pyroglutamic acid. In some embodiments, the anti-HJV antibodies having N-terminal pyroglutamic acid are impurities in the population of anti-HJV antibodies (e.g., less than 5%, less than 4%, less than 3%, less than 2%, less than 1%, less than 0.5%, less than 0.1%, less than 0.05%, or less than 0.01%) in the population of anti-HJV antibody. In some embodiments, the population of the anti-HJV antibodies comprises a mixture of anti-HJV antibodies having glutamic acid or pyroglutamic acid at the N-terminal of the heavy chain.

In some embodiments, the anti-HJV antibodies of the present disclosure comprises one or more of the HC CDRs (e.g., HC CDR1, HC CDR2, or HC CDR3) amino acid sequences from any one of the anti-HJV antibodies selected from Table 1. In some embodiments, the anti-HJV antibodies of the present disclosure comprise the HC CDR1, HC CDR2, and HC CDR3 as provided for any one of the antibodies elected from Table 1. In some embodiments, the anti-HJV antibodies of the present disclosure comprises one or more of the LC CDRs (e.g., LC CDR1, LC CDR2, or LC CDR3) amino acid sequences from any one of the anti-HJV antibodies selected from Table 1. In some embodiments, the anti-HJV antibodies of the present disclosure comprise the LC CDR1, LC CDR2, and LC CDR3 as provided for any one of the anti-HJV antibodies selected from Table 1.

In some embodiments, the anti-HJV antibodies of the present disclosure comprises the HC CDR1, HC CDR2, HC CDR3, LC CDR1, LC CDR2, and LC CDR3 as provided for any one of the anti-HJV antibodies selected from Table 1. In some embodiments, antibody heavy and light chain CDR3 domains may play a particularly important role in the binding specificity/affinity of an antibody for an antigen. Accordingly, the anti-HJV antibodies of the disclosure may include at least the heavy and/or light chain CDR3s of any one of the anti-HJV antibodies selected from Table 1.

In some embodiments, the isolated anti-HJV antibody comprises a heavy chain variable region that comprises a heavy chain CDR1 (HC CDR1), a heavy chain CDR2 (HC CDR2), and a heavy chain CDR3 (HC CDR3).

In some embodiments, following the Kabat definition, the HC CDR1 may comprise the amino acid sequence of $X_1$YGMN (SEQ ID NO: 105), in which $X_1$ can be N or Y. Alternatively or in addition, the HC CDR2 may comprise the amino acid sequence of MIYYDSS$X_2$KHYADSVKG (SEQ ID NO: 106), in which $X_2$ can be E or D. Alternatively or in addition, the HC CDR3 may comprise the amino acid sequence of G$X_3$TPD$X_4$ (SEQ ID NO: 107), in which $X_3$ can be T or S, and $X_4$ can be Y, V, or K.

In some embodiments, following the Kabat definition, the anti-HJV antibody may comprise a light chain variable region that comprises a light chain CDR1 (LC CDR1), a light chain CDR2 (LC CDR2), and a light chain CDR3 (LC CDR3). In some embodiments, the LC CDR1 may comprise the amino acid sequence of RSSQSL$X_5X_6$SDG$X_7$TFL$X_8$ (SEQ ID NO: 108), in which $X_5$ can be A or E, $X_6$ can be T, S, E, or D, $X_7$ can be D, Y, or G, and $X_8$ can be E or H. Alternatively or in addition, the LC CDR2 may comprise the amino acid sequence of $X_9$VS$X_{10}$RFS (SEQ ID NO: 109), in which $X_9$ can be E, D or A, and $X_{10}$ can be N, S, T, E or H. Alternatively or in addition, the LC CDR3 may comprise the amino acid sequence of $X_{11}$Q$X_{12}$T$X_{13}$DP$X_{14}X_{15}$ (SEQ ID NO: 110), in which $X_{11}$ can be F or M, $X_{12}$ can be V or A, $X_{13}$ can be H or Y, $X_{14}$ can be M, L or V, and $X_{15}$ can be T or S.

Also within the scope of the present disclosure are functional variants of any of the exemplary anti-HJV antibodies as disclosed herein. A functional variant may contain one or more amino acid residue variations in the $V_H$ and/or $V_L$, or in one or more of the HC CDRs and/or one or more of the LC CDRs as relative to the reference antibody, while retaining substantially similar binding and biological activities (e.g., substantially similar binding affinity, binding specificity, inhibitory activity, anti-inflammatory activity, or a combination thereof) as the reference antibody.

In some embodiments, any of the anti-HJV antibodies of the disclosure have one or more CDRs (e.g., HC CDR or LC CDR) sequences substantially similar to any of the HC CDR1, HC CDR2, HC CDR3, LC CDR1, LC CDR2, and/or LC CDR3 sequences from one of the anti-HJV antibodies selected from Table 1. In some embodiments, the position of one or more CDRs along the VH (e.g., HC CDR1, HC CDR2, or HC CDR3) and/or VL (e.g., LC CDR1, LC CDR2, or LC CDR3) region of an antibody described herein can vary by one, two, three, four, five, or six amino acid positions so long as immunospecific binding to hemojuvelin (e.g., human hemojuvelin) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or C-terminal boundary of the CDR by one, two, three, four, five, or six amino acids, relative to the CDR position of any one of the antibodies described herein, so long as immunospecific binding to hemojuvelin (e.g., human hemojuvelin) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., HC CDR1, HC CDR2, or HC CDR3) and/or VL (e.g., LC CDR1, LC CDR2, or LC CDR3) region of an antibody described herein can vary (e.g., be shorter or longer) by one, two, three, four, five, or more amino acids, so long as immunospecific binding to hemojuvelin (e.g., human hemojuvelin) is maintained (e.g., substantially maintained, for example, at least 50%, at least 60%, at least 70%, at least 80%, at least 90%, at least 95% of the binding of the original antibody from which it is derived).

Accordingly, in some embodiments, a HC CDR1, HC CDR2, HC CDR3, LC CDR1, LC CDR2, and/or LC CDR3 described herein may be one, two, three, four, five or more amino acids shorter than one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, a HC CDR1, HC CDR2, HC CDR3, LC CDR1, LC CDR2, and/or LC CDR3 described herein may be one, two, three, four, five or more amino acids longer than one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, the amino portion of a HC CDR1, HC CDR2, HC CDR3, LC CDR1, LC CDR2, and/or LC CDR3 described herein can be extended by one, two, three, four, five or more amino acids compared to one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a HC CDR1, HC CDR2, HC CDR3, LC CDR1, LC CDR2, and/or LC CDR3 described herein can be extended by one, two, three, four, five or more amino acids compared to one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, the amino portion of a HC CDR1, HC CDR2, HC CDR3, LC CDR1, LC CDR2, and/or LC CDR3 described herein can be shortened by one, two, three, four, five or more amino acids compared to one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a HC CDR1, HC CDR2, HC CDR3, LC CDR1, LC CDR2, and/or LC CDR3 described herein can be shortened by one, two, three, four, five or more amino acids compared to one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to hemojuvelin (e.g., human hemojuvelin) is maintained, for example, using binding assays and conditions described in the art.

In some examples, any of the anti-HJV antibodies of the disclosure have one or more CDR (e.g., HC CDR or LC CDR) sequences substantially similar to any one of the anti-HJV antibodies selected from Table 1. For example, the antibodies may include one or more CDR sequence(s) from any of the anti-HJV antibodies selected from Table 1 containing up to 5, 4, 3, 2, or 1 amino acid residue variations as compared to the corresponding CDR region in any one of the CDRs provided herein (e.g., CDRs from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a hemojuvelin protein (e.g., a human hemojuvelin protein), for example, as determined based on a crystal structure. Some aspects of the disclosure provide anti-HJV antibodies that comprise one or more of the heavy chain variable (VH) and/or light chain variable (VL) domains provided herein. In some embodiments, any of the VH domains provided herein include one or more of the HC CDR sequences (e.g., HC CDR1, HC CDR2, and HC CDR3) provided herein, for example, any of the CDR-H sequences provided in any one of the anti-HJV selected from Table 1. In some embodiments, any of the VL domains provided herein include one or more of the CDR-L sequences (e.g., LC CDR1, LC CDR2, and LC CDR3) provided herein, for example, any of the LC CDR sequences provided in any one of the anti-HJV antibodies selected from Table 1.

In some embodiments, the anti-HJV antibodies of the disclosure include any antibody that includes a heavy chain variable domain and/or a light chain variable domain of any one of the anti-HJV antibodies selected from Table 1, and variants thereof. In some embodiments, anti-HJV antibodies of the disclosure include any antibody that includes the heavy chain variable and light chain variable pairs of any anti-HJV antibodies selected from Table 1.

Aspects of the disclosure provide anti-HJV antibodies having a heavy chain variable (VH) and/or a light chain variable (VL) domain amino acid sequence homologous to any of those described herein. In some embodiments, the anti-HJV antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any one of the anti-HJV antibodies selected from Table 1. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein. In some embodiments, any of the anti-HJV antibodies provided herein comprise a heavy chain variable sequence and a light chain variable sequence that comprises a framework sequence that is at least 75%, 80%, 85%, 90%, 95%, 98%, or 99% identical to the framework sequence of any anti-HJV antibodies selected from Table 1.

In some embodiments, the anti-HJV antibody of the present disclosure is a humanized antibody (e.g., a humanized variant containing one or more CDRs of Table 1). In some embodiments, the anti-HJV antibody of the present disclosure comprises a HC CDR1, a HC CDR2, a HC CDR3, a LC CDR1, a LC CDR2, and a LC CDR3 that are the same as the HC CDR1, HC CDR2, HC CDR3, LC CDR1, LC CDR2, and LC CDR3 shown in Table 1, and comprises a humanized heavy chain variable region and/or a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 1) into the human variable domains (e.g., IGKV1-NL1*01 and IGHV1-3*01 human variable domain). In some embodiments, the anti-HJV antibody of the present disclosure is a humanized variant comprising one or more amino acid substitutions (e.g., in the VH framework region) as compared with any one of the VHs listed in Table 1, and/or one or more amino acid substitutions (e.g., in the VL framework region) as compared with any one of the VLs listed in Table 1.

In some embodiments, the anti-HJV antibody of the present disclosure is a humanized antibody comprising a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH of any of the anti-HJV antibodies listed in Table 1. Alternatively or in addition, the anti-HJV antibody of the present disclosure is a humanized antibody comprising a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL of any one of the anti-HJV antibodies listed in Table 1.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of a light chain variable domain having the amino acid sequence of SEQ ID NO: 8.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 4, a LC CDR2 having the amino acid sequence of SEQ ID NO: 5, and a LC CDR3 having the amino acid sequence of SEQ ID NO: 6.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 4, LC CDR2 having the amino acid sequence of SEQ ID NO: 5, and LC CDR3 having the amino acid sequence of SEQ ID NO: 6.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 4, LC CDR2 having the amino acid sequence of SEQ ID NO: 5, and LC CDR3 having the amino acid sequence of SEQ ID NO: 6.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 4; a LC CDR2 having no more than 3 amino acid variations (e.g., no more than 3, 2, or 1 amino acid variation) as compared with the LC CDR2 having the amino acid sequence of SEQ ID NO: 5; and/or a LC CDR3 having no more than 3 amino acid variations (e.g., no more than 3, 2, or 1 amino acid variation) as compared with the LC CDR3 having the amino acid sequence of SEQ ID NO: 6.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 8.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 8.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 8.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of a light chain variable domain having the amino acid sequence of SEQ ID NO: 30.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 4, a LC CDR2 having the amino acid sequence of SEQ ID NO: 49, and a LC CDR3 having the amino acid sequence of SEQ ID NO: 24.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 4, LC CDR2 having the amino acid sequence of SEQ ID NO: 49, and LC CDR3 having the amino acid sequence of SEQ ID NO: 24.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 4, LC CDR2 having the amino acid sequence of SEQ ID NO: 49, and LC CDR3 having the amino acid sequence of SEQ ID NO: 24.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 4; a LC CDR2 having no more than 3 amino acid variations (e.g., no more than 3, 2, or 1 amino acid variation) as compared with the LC CDR2 having the amino acid sequence of SEQ ID NO: 49; and/or a LC CDR3 having no more than 3 amino acid variations (e.g., no more than 3, 2, or 1 amino acid variation) as compared with the LC CDR3 having the amino acid sequence of SEQ ID NO: 24.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 30.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 30.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 30.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of a light chain variable domain having the amino acid sequence of SEQ ID NO: 31.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 4, a LC CDR2 having the amino acid sequence of SEQ ID NO: 18, and a LC CDR3 having the amino acid sequence of SEQ ID NO: 25.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 4, LC CDR2 having the amino acid sequence of SEQ ID NO: 18, and LC CDR3 having the amino acid sequence of SEQ ID NO: 25.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 4, LC CDR2 having the amino acid sequence of SEQ ID NO: 18, and LC CDR3 having the amino acid sequence of SEQ ID NO: 25.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 4; a LC CDR2 having no more than 3 amino acid variations (e.g., no more than 3, 2, or 1 amino acid variation) as compared with the LC CDR2 having the amino acid sequence of SEQ ID NO: 18; and/or a LC CDR3 having no more than 3 amino acid variations (e.g., no more than 3, 2, or 1 amino acid variation) as compared with the LC CDR3 having the amino acid sequence of SEQ ID NO: 25

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 31

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 31

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 31.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of a light chain variable domain having the amino acid sequence of SEQ ID NO: 32.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 14, a LC CDR2 having the amino acid sequence of SEQ ID NO: 19, and a LC CDR3 having the amino acid sequence of SEQ ID NO: 25.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 14, LC CDR2 having the amino acid sequence of SEQ ID NO: 19, and LC CDR3 having the amino acid sequence of SEQ ID NO: 25.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 14, LC CDR2 having the amino acid sequence of SEQ ID NO: 19, and LC CDR3 having the amino acid sequence of SEQ ID NO: 25.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 14; a LC CDR2 having no more than 3 amino acid variations (e.g., no more than 3, 2, or 1 amino acid variation) as compared with the LC CDR2 having the amino acid sequence of SEQ ID NO: 19; and/or a LC CDR3 having no more than 3 amino acid variations (e.g., no more than 3, 2, or 1 amino acid variation) as compared with the LC CDR3 having the amino acid sequence of SEQ ID NO: 25.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 32.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 32.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 32.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of a light chain variable domain having the amino acid sequence of SEQ ID NO: 33.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 15, a LC CDR2 having the amino acid sequence of SEQ ID NO: 20, and a LC CDR3 having the amino acid sequence of SEQ ID NO: 26.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 15, LC CDR2 having the amino acid sequence of SEQ ID NO: 20, and LC CDR3 having the amino acid sequence of SEQ ID NO: 26.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 15, LC CDR2 having the amino acid sequence of SEQ ID NO: 20, and LC CDR3 having the amino acid sequence of SEQ ID NO: 26.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 15; a LC CDR2 having no more than 3 amino acid variations (e.g., no more than 3, 2, or 1 amino acid variation) as compared with the LC CDR2 having the amino acid sequence of SEQ ID NO: 20; and/or a LC CDR3 having no more than 3 amino acid variations (e.g., no more than 3, 2, or 1 amino acid variation) as compared with the LC CDR3 having the amino acid sequence of SEQ ID NO: 26.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 33.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 33.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 33.

In some embodiments, the anti-HJV antibody of the present disclosure comprises a HC CDR1, HC CDR2 and HC CDR3 of a heavy chain variable domain having the amino acid sequence of SEQ ID NO: 34. Alternatively or in addition, the anti-HJV antibody of the present disclosure comprises a LC CDR1, LC CDR2 and LC CDR3 of a light chain variable domain having the amino acid sequence of SEQ ID NO: 35.

In some embodiments, according to the Kabat definition system, the anti-HJV antibody of the present disclosure comprises a HC CDR1 having the amino acid sequence of SEQ ID NO: 9, a HC CDR2 having the amino acid sequence of SEQ ID NO: 2, a HC CDR3 having the amino acid sequence of SEQ ID NO: 3, a LC CDR1 having the amino acid sequence of SEQ ID NO: 16, a LC CDR2 having the amino acid sequence of SEQ ID NO: 21, and a LC CDR3 having the amino acid sequence of SEQ ID NO: 27.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 9, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 16, LC CDR2 having the amino acid sequence of SEQ ID NO: 21, and LC CDR3 having the amino acid sequence of SEQ ID NO: 27.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 9, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 16, LC CDR2 having the amino acid sequence of SEQ ID NO: 21, and LC CDR3 having the amino acid sequence of SEQ ID NO: 27.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 9; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 16; a LC CDR2 having no more than 3 amino acid variations (e.g., no more than 3, 2, or 1 amino acid variation) as compared with the LC CDR2 having the amino acid sequence of SEQ ID NO: 21; and/or a LC CDR3 having no more than 3 amino acid variations (e.g., no more than 3, 2, or 1 amino acid variation) as compared with the LC CDR3 having the amino acid sequence of SEQ ID NO: 27.

In some embodiments, the anti-HJV antibody of the present disclosure comprises a VH comprising the amino acid sequence of SEQ ID NO: 34. Alternatively or in addition, the anti-HJV antibody of the present disclosure comprises a VL comprising the amino acid sequence of SEQ ID NO: 35.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 34. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 35.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 34. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 35.

In some embodiments, the anti-HJV antibody of the present disclosure comprises a HC CDR1, HC CDR2 and HC CDR3 of a heavy chain variable domain having the amino acid sequence of SEQ ID NO: 36. Alternatively or in addition, the anti-HJV antibody of the present disclosure comprises a LC CDR1, LC CDR2 and LC CDR3 of a light chain variable domain having the amino acid sequence of SEQ ID NO: 37.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 10, a HC CDR3 having the amino acid sequence of SEQ ID NO: 11, a LC CDR1 having the amino acid sequence of SEQ ID NO: 17, a LC CDR2 having the amino acid sequence of SEQ ID NO: 18, and a LC CDR3 having the amino acid sequence of SEQ ID NO: 28.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 10, and HC CDR3 having the amino acid sequence of SEQ ID NO: 11. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 17, LC CDR2 having the amino acid sequence of SEQ ID NO: 18, and LC CDR3 having the amino acid sequence of SEQ ID NO: 28.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 10, and HC CDR3 having the amino acid sequence of SEQ ID NO: 11. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 17, LC CDR2 having the amino acid sequence of SEQ ID NO: 18, and LC CDR3 having the amino acid sequence of SEQ ID NO: 28.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 10; and/or a HC CDR3 having no more than 3 amino acid variations (e.g., no more than 3, 2, or 1 amino acid variation) as compared with the HC CDR3 having the amino acid sequence of SEQ ID NO: 11. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 17; a LC CDR2 having no more than 3 amino acid variations (e.g., no more than 3, 2, or 1 amino acid variation) as compared with the LC CDR2 having the amino acid sequence of SEQ ID NO: 18; and/or a LC CDR3 having no more than 3 amino acid variations (e.g., no more than 3, 2, or 1 amino acid variation) as compared with the LC CDR3 having the amino acid sequence of SEQ ID NO: 28.

In some embodiments, the anti-HJV antibody of the present disclosure comprises a VH comprising the amino acid sequence of SEQ ID NO: 36. Alternatively or in addition, the anti-HJV antibody of the present disclosure comprises a VL comprising the amino acid sequence of SEQ ID NO: 37.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 36. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 37.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 36. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 37.

In some embodiments, the anti-HJV antibody of the present disclosure comprises a HC CDR1, HC CDR2 and HC CDR3 of a heavy chain variable domain having the amino acid sequence of SEQ ID NO: 38. Alternatively or in addition, the anti-HJV antibody of the present disclosure comprises a LC CDR1, LC CDR2 and LC CDR3 of a light chain variable domain having the amino acid sequence of SEQ ID NO: 39.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 17, a LC CDR2 having the amino acid sequence of SEQ ID NO: 5, and a LC CDR3 having the amino acid sequence of SEQ ID NO: 27.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 17, LC CDR2 having the amino acid sequence of SEQ ID NO: 5, and LC CDR3 having the amino acid sequence of SEQ ID NO: 27.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 17, LC CDR2 having the amino acid sequence of SEQ ID NO: 5, and LC CDR3 having the amino acid sequence of SEQ ID NO: 27.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 17; a LC CDR2 having no more than 3 amino acid variations (e.g., no more than 3, 2, or 1 amino acid variation) as compared with the LC CDR2 having the amino acid sequence of SEQ ID NO: 5; and/or a LC CDR3 having no more than 3 amino acid variations (e.g., no more than 3, 2, or 1 amino acid variation) as compared with the LC CDR3 having the amino acid sequence of SEQ ID NO: 27.

In some embodiments, the anti-HJV antibody of the present disclosure comprises a VH comprising the amino acid sequence of SEQ ID NO: 38. Alternatively or in addition, the anti-HJV antibody of the present disclosure comprises a VL comprising the amino acid sequence of SEQ ID NO: 39.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 38. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 39.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 38. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 39.

In some embodiments, the anti-HJV antibody of the present disclosure comprises a HC CDR1, HC CDR2 and HC CDR3 of a heavy chain variable domain having the amino acid sequence of SEQ ID NO: 38. Alternatively or in addition, the anti-HJV antibody of the present disclosure comprises a LC CDR1, LC CDR2 and LC CDR3 of a light chain variable domain having the amino acid sequence of SEQ ID NO: 41.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 50, a LC CDR2 having the amino acid sequence of SEQ ID NO: 22, and a LC CDR3 having the amino acid sequence of SEQ ID NO: 28.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 50, LC CDR2 having the amino acid sequence of SEQ ID NO: 22, and LC CDR3 having the amino acid sequence of SEQ ID NO: 28.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 50, LC CDR2 having the amino acid sequence of SEQ ID NO: 22, and LC CDR3 having the amino acid sequence of SEQ ID NO: 28.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 50; a LC CDR2 having no more than 3 amino acid variations (e.g., no more than 3, 2, or 1 amino acid variation) as compared with the LC CDR2 having the amino acid sequence of SEQ ID NO: 22; and/or a LC CDR3 having no more than 3 amino acid variations (e.g., no more than 3, 2, or 1 amino acid variation) as compared with the LC CDR3 having the amino acid sequence of SEQ ID NO: 28.

In some embodiments, the anti-HJV antibody of the present disclosure comprises a VH comprising the amino acid sequence of SEQ ID NO: 38. Alternatively or in addition, the anti-HJV antibody of the present disclosure comprises a VL comprising the amino acid sequence of SEQ ID NO: 41.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 38. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 41.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 38. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 41.

In some embodiments, the anti-HJV antibody of the present disclosure comprises a HC CDR1, HC CDR2 and HC CDR3 of a heavy chain variable domain having the amino acid sequence of SEQ ID NO: 42. Alternatively or in addition, the anti-HJV antibody of the present disclosure comprises a LC CDR1, LC CDR2 and LC CDR3 of a light chain variable domain having the amino acid sequence of SEQ ID NO: 43.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 12, a LC CDR1 having the amino acid sequence of SEQ ID NO: 15, a LC CDR2 having the amino acid sequence of SEQ ID NO: 23, and a LC CDR3 having the amino acid sequence of SEQ ID NO: 27.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 12. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 15, LC CDR2 having the amino acid sequence of SEQ ID NO: 23, and LC CDR3 having the amino acid sequence of SEQ ID NO: 27.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 12. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 15, LC CDR2 having the amino acid sequence of SEQ ID NO: 23, and LC CDR3 having the amino acid sequence of SEQ ID NO: 27.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 12. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 15; a LC CDR2 having no more than 3 amino acid variations (e.g., no more than 3, 2, or 1 amino acid variation) as compared with the LC CDR2 having the amino acid sequence of SEQ ID NO: 23; and/or a LC CDR3 having no more than 3 amino acid variations (e.g., no more than 3, 2, or 1 amino acid variation) as compared with the LC CDR3 having the amino acid sequence of SEQ ID NO: 27.

In some embodiments, the anti-HJV antibody of the present disclosure comprises a VH comprising the amino acid sequence of SEQ ID NO: 42. Alternatively or in addition, the anti-HJV antibody of the present disclosure comprises a VL comprising the amino acid sequence of SEQ ID NO: 43.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 42. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 43.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 42. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 43.

In some embodiments, the anti-HJV antibody of the present disclosure comprises a HC CDR1, HC CDR2 and HC CDR3 of a heavy chain variable domain having the amino acid sequence of SEQ ID NO: 44. Alternatively or in addition, the anti-HJV antibody of the present disclosure comprises a LC CDR1, LC CDR2 and LC CDR3 of a light chain variable domain having the amino acid sequence of SEQ ID NO: 45.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 13, a LC CDR1 having the amino acid sequence of SEQ ID NO: 16, a LC CDR2 having the amino acid sequence of SEQ ID NO: 21, and a LC CDR3 having the amino acid sequence of SEQ ID NO: 29.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 13. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 16, LC CDR2 having the amino acid sequence of SEQ ID NO: 21, and LC CDR3 having the amino acid sequence of SEQ ID NO: 29.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 13. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the LC CDR1 having the amino acid sequence of SEQ ID NO: 16, LC CDR2 having the amino acid sequence of SEQ ID NO: 21, and LC CDR3 having the amino acid sequence of SEQ ID NO: 29.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 13. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 16; a LC CDR2 having no more than 3 amino acid variations (e.g., no more than 3, 2, or 1 amino acid variation) as compared with the LC CDR2 having the amino acid sequence of SEQ ID NO: 21; and/or a LC CDR3 having no more than 3 amino acid variations (e.g., no more than 3, 2, or 1 amino acid variation) as compared with the LC CDR3 having the amino acid sequence of SEQ ID NO: 29.

In some embodiments, the anti-HJV antibody of the present disclosure comprises a VH comprising the amino acid sequence of SEQ ID NO: 44. Alternatively or in addition, the anti-HJV antibody of the present disclosure comprises a VL comprising the amino acid sequence of SEQ ID NO: 45.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 44. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 45.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 44. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 45.

The CDRs of an antibody may have different amino acid sequences when different definition systems are used (e.g., the IMGT definition, the Kabat definition, or the Chothia definition). A definition system annotates each amino acid in a given antibody sequence (e.g., VH or VL sequence) with a number, and numbers corresponding to the heavy chain and light chain CDRs are provided in Table 2. The CDRs listed in Table 1 are defined in accordance with the Kabat definition. One skilled in the art is able to derive the CDR sequences using the different numbering systems for the anti-HJV antibodies provided in Table 1.

TABLE 2

CDR Definitions

|  | IMGT[1] | Kabat[2] | Chothia[3] |
|---|---|---|---|
| HC CDR1 | 27-38 | 31-35 | 26-32 |
| HC CDR2 | 56-65 | 50-65 | 53-55 |
| HC CDR3 | 105-116/117 | 95-102 | 96-101 |
| LC CDR1 | 27-38 | 24-34 | 26-32 |
| LC CDR2 | 56-65 | 50-56 | 50-52 |
| LC CDR3 | 105-116/117 | 89-97 | 91-96 |

[1]IMGT ®, the international ImMunoGeneTics information system ®, imgt.org, Lefranc, M.-P. et al., Nucleic Acids Res., 27: 209-212 (1999)
[2]Kabat et al. (1991) Sequences of Proteins of Immunological Interest, Fifth Edition, U.S. Department of Health and Human Services, NIH Publication No. 91-3242
[3]Chothia et al., J. Mol. Biol. 196: 901-917 (1987))

In some embodiments, the anti-HJV antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-HJV antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-HJV antibody of the present disclosure comprises a VL domain and/or VH domain of any one of the anti-HJV antibodies selected from Table 1, and comprises a constant region comprising the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra. An example of a human IgG1 constant region is given below:

```
                                      (SEQ ID NO: 103)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In some embodiments, the heavy chain of any of the anti-HJV antibodies described herein comprises a mutant human IgG1 constant region. For example, the introduction of LALA mutations (a mutant derived from mAb b12 that has been mutated to replace the lower hinge residues Leu234 Leu235 with Ala234 and Ala235) in the CH2 domain of human IgG1 is known to reduce Fcg receptor binding (Bruhns, P., et al. (2009) and Xu, D. et al. (2000)). The mutant human IgG1 constant region is provided below (mutations bonded and underlined):

```
                                      (SEQ ID NO: 46)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In some embodiments, the heavy chain of any of the anti-HJV antibodies described herein further comprises mutations in human IgG1 constant region. For example, the introduction of T250Q and M248L substitutions. In some embodiments, such substitution may affect FcRn binding and serum half-life (WO2005047307 and WO2013063110). An exemplary IgG1 constant region comprising the LALA mutation and the QL mutation is provided below (mutations bonded and underlined):

```
                                      (SEQ ID NO: 48)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDQLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVLHEALHNHYTQKSLSLSPGK
```

In some embodiments, during the production of the antibodies, particularly with Chinese Hamster Ovary Cells (CHO cells), it can be appreciated that the lysine at the C-terminus of the heavy chain is cleaved. Accordingly, a human IgG1 constant region within a secreted antibody can be:

```
                                      (SEQ ID NO: 111)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK
```

```
                                                        -continued
EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG
```

In some embodiments, a mutant human IgG1 comprising the LALA mutations in a secreted antibody can be:

```
                                              (SEQ ID NO: 112)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG
```

In some embodiments, a mutant human IgG1 comprising the LALA mutations and the QL mutations can be:

```
                                              (SEQ ID NO: 113)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDQLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVLHEALHNHYTQKSLSLSPG
```

In some embodiments, the light chain of any of the anti-HJV antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

```
                                               (SEQ ID NO: 47)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

Other antibody heavy and light chain constant regions are well known in the art, e.g., those provided in the IMGT database (www.imgt.org) or at www.vbase2.org/vbstat.php., both of which are incorporated by reference herein.

In some embodiments, the anti-HJV antibody described herein comprises a heavy chain comprising any one of the VH as listed in Table 1 or any variants thereof and a heavy chain constant region that is at least 80%, at least 85%, at least 90%, at least 95%, or at least 99% identical to SEQ ID NO: 46, SEQ ID NO: 48, SEQ ID NO: 112, or SEQ ID NO: 113.

In some embodiments, the anti-HJV antibody described herein comprises a heavy chain comprising any one of the VH as listed in Table 1 or any variants thereof and a heavy chain constant region that contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with SEQ ID NO: 46, SEQ ID NO: 48, SEQ ID NO: 112, or SEQ ID NO: 113. In some embodiments, the anti-HJV antibody described herein comprises a heavy chain comprising any one of the VH as listed in Table 1 or any variants thereof and a heavy chain constant region as set forth in SEQ ID NO: 46. In some embodiments, the anti-HJV antibody described herein comprises heavy chain comprising any one of the VH as listed in Table 1 or any variants thereof and a heavy chain constant region as set forth in SEQ ID NO: 48. In some embodiments, the anti-HJV antibody described herein comprises heavy chain comprising any one of the VH as listed in Table 1 or any variants thereof and a heavy chain constant region as set forth in SEQ ID NO: 112. In some embodiments, the anti-HJV antibody described herein comprises heavy chain comprising any one of the VH as listed in Table 1 or any variants thereof and a heavy chain constant region as set forth in SEQ ID NO: 113.

In some embodiments, the anti-HJV antibody described herein comprises a light chain comprising any one of the VL as listed in Table 1 or any variants thereof and a light chain constant region that is at least 80%, at least 85%, at least 90%, at least 95%, or at least 99% identical to SEQ ID NO: 47. In some embodiments, the anti-HJV antibody described herein comprises a light chain comprising any one of the VL as listed in Table 1 or any variants thereof and a light chain constant region contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with SEQ ID NO: 47. In some embodiments, the anti-HJV antibody described herein comprises a light chain comprising any one of the VL as listed in Table 1 or any variants thereof and a light chain constant region set forth in SEQ ID NO: 47.

Examples of IgG heavy chain and light chain amino acid sequences of the anti-HJV antibodies described are provided in Table 1 above.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51, 57, 59, 61, 63, 66, 68, 114, 115, 116, 117, 118, 119 or 120. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 52, 53, 54, 55, 56, 58, 60, 62, 65, 67 or 69. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51, 57, 59, 61, 63, 66, 68, 114, 115, 116, 117, 118, 119 or 120. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 52, 53, 54, 55, 56, 58, 60, 62, 65, 67 or 69. In some embodiments, the anti-HJV antibody described herein comprises a heavy chain comprising the amino acid sequence of any one of SEQ ID NOs: 51, 57, 59, 61, 63, 66, 68, 114, 115, 116, 117, 118, 119 or 120. Alternatively or in addition, the anti-HJV antibody described herein comprises a light chain comprising the amino acid sequence of any one of SEQ ID NOs: 52, 53, 54, 55, 56, 58, 60, 62, 65, 67 or 69.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 52. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 52. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 52.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 53. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 53. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 53.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 54. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 54. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 54.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 55. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 55. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 55.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 56. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 56. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 56.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 57 or 115. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 58. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 57 or 115. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 58. In some embodiments, the anti-HJV antibody described herein comprises a heavy chain comprising the amino acid sequence of any one of SEQ ID NOs: 57 or 115. Alternatively or in addition, the anti-HJV antibody described herein comprises a light chain comprising the amino acid sequence of any one of SEQ ID NOs: 58.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 59 or 116. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 60. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 59 or 116. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 60. In some embodiments, the anti-HJV antibody described herein comprises a heavy chain comprising the amino acid sequence of any one of SEQ ID NOs: 59 or 116. Alternatively or in addition, the anti-HJV antibody described herein comprises a light chain comprising the amino acid sequence of any one of SEQ ID NOs: 60.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 61 or 117. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 62. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 61 or 117. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 62. In some embodiments, the anti-HJV antibody described herein comprises a heavy chain comprising the amino acid sequence of any one of SEQ ID NOs: 61 or 117. Alternatively or in addition, the anti-HJV antibody described herein comprises a light chain comprising the amino acid sequence of any one of SEQ ID NOs: 62.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 63 or 118. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 62. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 63 or 118. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 62. In some embodiments, the anti-HJV antibody described herein comprises a heavy chain comprising the amino acid sequence of any one of SEQ ID NOs: 63 or 118. Alternatively or in addition, the anti-HJV antibody described herein comprises a light chain comprising the amino acid sequence of any one of SEQ ID NOs: 62.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 61 or 117. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 65. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 61 or 117. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 65. In some embodiments, the anti-HJV antibody described herein comprises a heavy chain comprising the amino acid sequence of any one of SEQ ID NOs: 61 or 117. Alternatively or in addition, the anti-HJV antibody described herein comprises a light chain comprising the amino acid sequence of any one of SEQ ID NOs: 65.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 66 or 119. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 67. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 66 or 119. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 67. In some embodiments, the anti-HJV antibody described herein comprises a heavy chain comprising the amino acid sequence of any one of SEQ ID NOs: 66 or 119. Alternatively or in addition, the anti-HJV antibody described herein comprises a light chain comprising the amino acid sequence of any one of SEQ ID NOs: 67.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 68 or 120. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 69. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 68 or 120. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 69. In some embodiments, the anti-HJV antibody described herein comprises a heavy chain comprising the amino acid sequence of any one of SEQ ID NOs: 68 or 120. Alternatively or in addition, the anti-HJV antibody described herein comprises a light chain comprising the amino acid sequence of any one of SEQ ID NOs: 69.

The anti-HJV antibodies described herein can be in any antibody form, including, but not limited to, intact (i.e., full-length) antibodies, antigen-binding fragments thereof (such as Fab, F(ab'), F(ab')2, Fv), single chain antibodies, bi-specific antibodies, or nanobodies. In some embodiments, the anti-HJV antibody described herein is a scFv. In some embodiments, the anti-HJV antibody described herein is a scFv-Fab (e.g., scFv fused to a portion of a constant region).

In some embodiments, conservative mutations can be introduced into antibody sequences (e.g., CDRs or framework sequences) at positions where the residues are not likely to be involved in interacting with a target antigen (e.g., hemojuvelin), for example, as determined based on a crystal structure. In some embodiments, one, two or more mutations (e.g., amino acid substitutions) are introduced into the Fc region of an anti-HJV antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-HJV antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-HJV antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of an anti-HJV antibody described herein can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcγ receptor. This approach is described further in International Publication No. WO 00/42072.

In some embodiments, the heavy and/or light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind hemojuvelin, such that the variant, CDR-grafted, chimeric, humanized, or composite antibody has at least 50%, at least 60%, at least 70%, at least 80%, at least 90%, at least 95% or more binding to hemojuvelin relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

In some embodiments, any one of the anti-HJV antibodies described herein may comprise a signal peptide in the heavy and/or light chain sequence (e.g., a N-terminal signal peptide). In some embodiments, the anti-HJV antibody described herein comprises any one of the VH and VL sequences, any one of the IgG heavy chain and light chain sequences, or any one of the F(ab') heavy chain and light chain sequences described herein, and further comprises a signal peptide (e.g., a N-terminal signal peptide). In some embodiments, the signal peptide comprises the amino acid sequence of MEFGLSWLFLVAILKGVQC (SEQ ID NO: 104).

III. Preparation of the Anti-HJV Antibodies

Antibodies capable of binding hemojuvelin as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., HJV) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, CA) and HuMAb-Mouse® and TC Mouse™ from Medarex, Inc. (Princeton, NJ) or H2L2 mice from Harbour Antibodies BV (Holland). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, human HEK293 cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Alternatively, techniques described for the production of single chain antibodies (U.S. Pat. Nos. 4,946,778 and 4,704,692) can be adapted to produce a phage or yeast scFv library and scFv clones specific to HJV can be identified from the library following routine procedures. Positive clones can be subjected to further screening to identify those that has high HJV binding affinity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In one example, epitope mapping can be accomplished use H/D-Ex (hydrogen deuterium exchange) coupled with proteolysis and mass spectrometry. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. Alternatively, competition assays can be performed using other antibodies known to bind to the same antigen to determine whether an antibody binds to the same epitope as the other antibodies. Competition assays are well known to those of skill in the art.

In some examples, an anti-HJV antibody is prepared by recombinant technology as exemplified below. Nucleic acids encoding the heavy and light chain of an anti-HJV antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV promoter, and the herpes simplex tk virus promoter.

Regulatable promoters can also be used. Such regulatable promoters include those using the lac repressor from *E. coli* as a transcription modulator to regulate transcription from lac operator bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-555115 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad, among others.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551(1992)] combined the tetracycline repressor (tetR) with the transcription activator (VP 16) to create a tetR-mammalian cell transcription activator fusion protein, tTa (tetR-VP 16), with the tetO bearing minimal promoter derived from the human cytomegalovirus (hCMV) promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells trans-activator or repressor fusion protein, which in some instances can be toxic to cells (Gossen 5 et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art. Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies (e.g., the nucleic acid coding sequence listed in Table 3) may be introduced into suitable host cells for producing the antibodies. Non-limiting examples of the host cells include Chinese hamster ovary (CHO) cells, dhfr-CHO cell, human embryonic kidney (HEK)-293 cells, verda reno (VERO) cells, nonsecreting null (NS0) cells, human embryonic retinal (PER.C6) cells, Sp2/0 cells, baby hamster kidney (BHK) cells, Madin-Darby Canine Kidney (MDCK) cells, Madin-Darby Bovine Kidney (MDBK) cells, and monkey kidney CV1 line transformed by SV40 (COS) cells. In some embodiments, the host cell expressing the anti-HJV antibodies are CHO cells. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody. In some embodiments, the host cell comprises the nucleic acid encoding the heavy chain of the anti-HJV antibody. In some embodiments, the host cell comprises the nucleic acid encoding the light chain of the anti-HJV antibody. In some embodiments, the host cell comprises the nucleic acid encoding the heavy chain and the nucleic acid encoding the light chain.

In some embodiments, methods for preparing an antibody described herein involve a recombinant expression vector that encodes both the heavy chain and the light chain of an anti-HJV antibody, as also described herein. The recombinant expression vector can be introduced into a suitable host cell (e.g., a dhfr-CHO cell) by a conventional method, e.g., calcium phosphate mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-HJV antibody and the other encoding the light chain of the anti-HJV antibody. Both of the two recombinant expression vectors can be introduced into a suitable host cell (e.g., dhfr-CHO cell) by a conventional method, e.g., calcium phosphate-mediated transfection.

Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-HJV antibody as described herein (e.g., as provided in Table 3), vectors (e.g., expression vectors) containing such; and host cells comprising the vectors are within the scope of the present disclosure.

TABLE 3

Nucleic acids Sequences encoding the VH/VL of anti-HJV antibodies listed in Table 1

| humanized HA Antibody | | Nucleic Acid Sequences | SEQ ID NO |
|---|---|---|---|
| hHA-001 | VH | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAATTGGATTAGACAAGCGCCCGGAAAAGGATTGGAATGGATAGGAATG<br>ATATACTACGATAGCTCAGAAAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGAACA<br>ACACCAGATTATTGGGGTCAAGGAACAATGGTAACCGTGTCAAGC | 70 |
| | VL | GACGTAGTACTGACCCAAAGCCCCCTTTCTCTCCCAGTAACCCTCGGACA<br>ACCAGCCTCAATTTCATGCAGATCATCACAATCACTTGAGACGAGCGACG<br>GAGACACTTTTCTTGAGTGGTTCCAACAAAGACCCGGACAAAGCCCACGC<br>CTGCTTATTTACGAGGTATCAACGAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTTCAAGTCACCCACGACCCC<br>ATGACGTTCGGACAAGGAACTAAGCTCGAAATCAAA | 72 |
| | Heavy Chain | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAATTGGATTAGACAAGCGCCCGGAAAAGGATTGGAATGGATAGGAATG<br>ATATACTACGATAGCTCAGAAAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGAACA<br>ACACCAGATTATTGGGGTCAAGGAACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | 71 |
| | Light Chain | GACGTAGTACTGACCCAAAGCCCCCTTTCTCTCCCAGTAACCCTCGGACA<br>ACCAGCCTCAATTTCATGCAGATCATCACAATCACTTGAGACGAGCGACG<br>GAGACACTTTTCTTGAGTGGTTCCAACAAAGACCCGGACAAAGCCCACGC<br>CTGCTTATTTACGAGGTATCAACGAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTTCAAGTCACCCACGACCCC<br>ATGACGTTCGGACAAGGAACTAAGCTCGAAATCAAAGAACGGTGGCTGC<br>ACCATCTGTCTTCATCTTCCCGCCATCTGATGAGCAGTTGAAATCTGGAA | 73 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | | CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | |
| hHA-002 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGC | 70 |
| | VL | GACGTAGTACTGACCCAAAGCCCCCTTTCTCTCCCAGTAACCCTCGGACA ACCAGCCTCAATTTCATGCAGATCATCACAATCACTTGAGACGAGCGACG GAGACACTTTTCTTGAGTGGTTCCAACAAAGACCCGGACAAAGCCCACGC CTGCTTATTTACGAGGTATCAAGCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTATGCAAGTCACCCACGACCCC CTGACCTTCGGACAAGGAACTAAGCTCGAAATCAAA | 74 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 71 |
| | Light Chain | GACGTAGTACTGACCCAAAGCCCCCTTTCTCTCCCAGTAACCCTCGGACA ACCAGCCTCAATTTCATGCAGATCATCACAATCACTTGAGACGAGCGACG GAGACACTTTTCTTGAGTGGTTCCAACAAAGACCCGGACAAAGCCCACGC CTGCTTATTTACGAGGTATCAAGCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTATGCAAGTCACCCACGACCCC CTGACCTTCGGACAAGGAACTAAGCTCGAAATCAAAAGAACGGTGGCTGC ACCATCTGTCTTCATCTTCCCGCCATCTGATGAGCAGTTGAAATCGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 75 |
| hHA-003 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGC | 70 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | VL | GACGTAGTACTGACCCAAAGCCCCCTTTCTCTCCCAGTAACCCTCGGACA<br>ACCAGCCTCAATTTCATGCAGATCATCACAATCACTTGAGACCAGCGACG<br>GAGATACTTTTCTTGAGTGGTTCCAACAAAGACCCGGACAAAGCCCACGC<br>CTGCTTATTTACGAGGTATCAAACAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGTCACCCACGACCCC<br>GTCACGTTCGGACAAGGAACTAAGCTCGAAATCAAA | 76 |
| | Heavy Chain | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAATTGGATTAGACAAGCGCCCGGAAAAGGATTGGAATGGATAGGAATG<br>ATATACTACGATAGCTCAGAAAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGAACA<br>ACACCAGATTATTGGGGTCAAGGAACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | 71 |
| | Light Chain | GACGTAGTACTGACCCAAAGCCCCCTTTCTCTCCCAGTAACCCTCGGACA<br>ACCAGCCTCAATTTCATGCAGATCATCACAATCACTTGAGACCAGCGACG<br>GAGATACTTTTCTTGAGTGGTTCCAACAAAGACCCGGACAAAGCCCACGC<br>CTGCTTATTTACGAGGTATCAAACAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGTCACCCACGACCCC<br>GTCACGTTCGGACAAGGAACTAAGCTCGAAATCAAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | 77 |
| hHA-004 | VH | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAATTGGATTAGACAAGCGCCCGGAAAAGGATTGGAATGGATAGGAATG<br>ATATACTACGATAGCTCAGAAAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGAACA<br>ACACCAGATTATTGGGGTCAAGGAACAATGGTAACCGTGTCAAGC | 70 |
| | VL | GACGTAGTACTGACCCAAAGCCCCCTTTCTCTCCCAGTAACCCTCGGACA<br>ACCAGCCTCAATTTCATGCAGATCATCACAATCACTTGAGTCCAGCGACG<br>GAGACACTTTTCTTGAGTGGTTCCAACAAAGACCCGGACAAAGCCCACGC<br>CTGCTTATTTACGATGTATCAACTAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTTCAAGTCACCCATGACCCC<br>GTGACCTTCGGACAAGGAACTAAGCTCGAAATCAAA | 78 |
| | Heavy Chain | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAATTGGATTAGACAAGCGCCCGGAAAAGGATTGGAATGGATAGGAATG<br>ATATACTACGATAGCTCAGAAAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGAACA<br>ACACCAGATTATTGGGGTCAAGGAACAATGGTAACCGTGTCAAGCGCGTC | 71 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | | GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | |
| | Light Chain | GACGTAGTACTGACCCAAAGCCCCCTTTCTCTCCCAGTAACCCTCGGACA ACCAGCCTCAATTTCATGCAGATCATCACAATCACTTGAGTCCAGCGACG GAGACACTTTTCTTGAGTGGTTCCAACAAAGACCCGGACAAAGCCCACGC CTGCTTATTTACGATGTATCAACTAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTTCAAGTCACCCATGACCCC GTGACCTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 79 |
| hHA-005 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGC | 70 |
| | VL | GACGTAGTACTGACCCAAAGCCCCCTTTCTCTCCCAGTAACCCTCGGACA ACCAGCCTCAATTTCATGCAGATCATCACAATCACTTGAGGAAAGCGACG GATACACTTTTCTTGAATGGTTCCAACAAAGACCCGGACAAAGCCCACGC CTGCTTATTTACGATGTATCAGAAAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCGACCTACGACCCC CTCACCTTCGGACAAGGAACTAAGCTCGAAATCAAA | 80 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT | 71 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | | CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | |
| | Light Chain | GACGTAGTACTGACCCAAAGCCCCCTTTCTCTCCCAGTAACCCTCGGACA<br>ACCAGCCTCAATTTCATGCAGATCATCACAATCACTTGAGGAAAGCGACG<br>GATACACTTTTCTTGAATGGTTCCAACAAAGACCCGGACAAAGCCCACGC<br>CTGCTTATTTACGATGTATCAGAAAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCGACCTACGACCCC<br>CTCACCTTCGGACAAGGAACTAAGCTCGAAATCAAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | 81 |
| hHA-006 | VH | GAAGTACAGTTGGTAGAAAGCGGCGGAGGACTTGTGCAGCCAGGTGGATC<br>TCTCAGACTTTCATGTGCCGCAAGCGGTTTTACTTTTAGTTACTATGGAA<br>TGAACTGGATTAGACAAGCGCCCGGAAAAGGATTGGAATGGATAGGCATG<br>ATATACTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACG<br>ACGCCCGATTACTGGGGTCAAGGAACAATGGTAACCGTGTCAAGC | 82 |
| | VL | GACGTAGTACTGACCCAAAGCCCCCTTTCTCTCCCAGTAACCCTCGGACA<br>ACCAGCCTCAATTTCATGCAGATCATCACAATCACTTGAGGACAGCGACG<br>GAGGAACTTTTCTTGAGTGGTTCCAACAAAGACCCGGACAAAGCCCACGC<br>CTGCTTATTTACGACGTATCAAGCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTTCAAGCGACCCACGACCCC<br>CTGACGTTCGGACAAGGAACTAAGCTCGAAATCAAA | 83 |
| | Heavy Chain | GAAGTACAGTTGGTAGAAAGCGGCGGAGGACTTGTGCAGCCAGGTGGATC<br>TCTCAGACTTTCATGTGCCGCAAGCGGTTTTACTTTTAGTTACTATGGAA<br>TGAACTGGATTAGACAAGCGCCCGGAAAAGGATTGGAATGGATAGGCATG<br>ATATACTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACG<br>ACGCCCGATTACTGGGGTCAAGGAACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | 84 |
| | Light Chain | GACGTAGTACTGACCCAAAGCCCCCTTTCTCTCCCAGTAACCCTCGGACA<br>ACCAGCCTCAATTTCATGCAGATCATCACAATCACTTGAGGACAGCGACG<br>GAGGAACTTTTCTTGAGTGGTTCCAACAAAGACCCGGACAAAGCCCACGC<br>CTGCTTATTTACGACGTATCAAGCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTTCAAGCGACCCACGACCCC<br>CTGACGTTCGGACAAGGAACTAAGCTCGAAATCAAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA | 85 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | | GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | |
| hHA-007 | VH | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAACTGGATAAGACAAGCGCCCGGAAAAGGATTGGAATGGATAGGCATG<br>ATATACTACGACAGCTCGGACAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACG<br>ACGCCGGATGTATGGGGTCAAGGAACAATGGTAACCGTGTCAAGC | 86 |
| | VL | GACGTAGTACTGACCCAAAGCCCCCTTTCTCTCCCAGTAACCCTCGGACA<br>ACCAGCCTCAATTTCATGCAGATCATCACAATCACTTGAAGAGAGCGACG<br>GATACACTTTTCTTCATTGGTTCCAACAAAGACCCGGACAAAGCCCACGC<br>CTGCTTATTTACGAGGTATCAAACAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>GTGACGTTCGGACAAGGAACTAAGCTCGAAATCAAA | 87 |
| | Heavy<br>Chain | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAACTGGATAAGACAAGCGCCCGGAAAAGGATTGGAATGGATAGGCATG<br>ATATACTACGACAGCTCGGACAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACG<br>ACGCCGGATGTATGGGGTCAAGGAACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | 88 |
| | Light<br>Chain | GACGTAGTACTGACCCAAAGCCCCCTTTCTCTCCCAGTAACCCTCGGACA<br>ACCAGCCTCAATTTCATGCAGATCATCACAATCACTTGAAGAGAGCGACG<br>GATACACTTTTCTTCATTGGTTCCAACAAAGACCCGGACAAAGCCCACGC<br>CTGCTTATTTACGAGGTATCAAACAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>GTGACGTTCGGACAAGGAACTAAGCTCGAAATCAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | 89 |
| hHA-008 | VH | GAAGTACAGTTGGTAGAAAGCGGCGGAGGACTTGTGCAACCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGCATG<br>ATATATTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACC<br>ACCCCCGATTACTGGGGTCAAGGAACAATGGTAACCGTGTCAAGC | 90 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | VL | GACGTAGTACTGACCCAAAGCCCCCTTTCTCTCCCAGTAACCCTCGGACA<br>ACCAGCCTCAATTTCATGCAGATCATCACAATCACTTGAAGAAAGCGACG<br>GATACACTTTTCTTCACTGGTTCCAACAAAGACCCGGACAAAGCCCACGC<br>CTGCTTATTTACGAGGTATCAACCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>CTGACCTTCGGACAAGGAACTAAGCTCGAAATCAAA | 91 |
| | Heavy<br>Chain | GAAGTACAGTTGGTAGAAAGCGGCGGAGGACTTGTGCAACCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGCATG<br>ATATATTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACC<br>ACCCCCGATTACTGGGGTCAAGGAACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | 92 |
| | Light<br>Chain | GACGTAGTACTGACCCAAAGCCCCCTTTCTCTCCCAGTAACCCTCGGACA<br>ACCAGCCTCAATTTCATGCAGATCATCACAATCACTTGAAGAAAGCGACG<br>GATACACTTTTCTTCACTGGTTCCAACAAAGACCCGGACAAAGCCCACGC<br>CTGCTTATTTACGAGGTATCAACCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>CTGACCTTCGGACAAGGAACTAAGCTCGAAATCAAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | 93 |
| hHA-008-QL | VH | GAAGTACAGTTGGTAGAAAGCGGCGGAGGACTTGTGCAACCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGCATG<br>ATATATTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACC<br>ACCCCCGATTACTGGGGTCAAGGAACAATGGTAACCGTGTCAAGC | 90 |
| | VL | GACGTAGTACTGACCCAAAGCCCCCTTTCTCTCCCAGTAACCCTCGGACA<br>ACCAGCCTCAATTTCATGCAGATCATCACAATCACTTGAAGAAAGCGACG<br>GATACACTTTTCTTCACTGGTTCCAACAAAGACCCGGACAAAGCCCACGC<br>CTGCTTATTTACGAGGTATCAACCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>CTGACCTTCGGACAAGGAACTAAGCTCGAAATCAAA | 91 |
| | Heavy<br>Chain | GAAGTACAGTTGGTAGAAAGCGGCGGAGGACTTGTGCAACCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGCATG<br>ATATATTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACC<br>ACCCCCGATTACTGGGGTCAAGGAACAATGGTAACCGTGTCAAGCGCGTC | 94 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | | GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACCAACTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGCTGCATGAGGCTCTGCACAACCACT<br>ACACGCAGAAGAGCCTCTCCCTGTCTCCGGGTAAATGA | |
| | Light<br>Chain | GACGTAGTACTGACCCAAAGCCCCCTTTCTCTCCCAGTAACCCTCGGACA<br>ACCAGCCTCAATTTCATGCAGATCATCACAATCACTTGAAGAAAGCGACG<br>GATACACTTTTCTTCACTGGTTCCAACAAAGACCCGGACAAAGCCCACGC<br>CTGCTTATTTACGAGGTATCAACCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>CTGACCTTCGGACAAGGAACTAAGCTCGAAATCAAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | 93 |
| hHA-009 | VH | GAAGTACAGTTGGTAGAAAGCGGCGGAGGACTTGTGCAACCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGCATG<br>ATATATTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACC<br>ACCCCCGATTACTGGGGTCAAGGAACAATGGTAACCGTGTCAAGC | 90 |
| | VL | GACGTAGTACTGACCCAAAGCCCCCTTTCTCTCCCAGTAACCCTCGGACA<br>ACCAGCCTCAATTTCATGCAGATCATCACAATCACTTGCGGACAGCGACG<br>GAGATACTTTTCTTCACTGGTTCCAACAAAGACCCGGACAAAGCCCACGC<br>CTGCTTATTTACGCGGTATCACACAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCATGACCCC<br>GTCACGTTCGGACAAGGAACTAAGCTCGAAATCAAA | 95 |
| | Heavy<br>Chain | GAAGTACAGTTGGTAGAAAGCGGCGGAGGACTTGTGCAACCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGCATG<br>ATATATTACGACAGCTCGGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGGACC<br>ACCCCCGATTACTGGGGTCAAGGAACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT | 92 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | | CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | |
| | Light Chain | GACGTAGTACTGACCCAAAGCCCCCTTTCTCTCCCAGTAACCCTCGGACA ACCAGCCTCAATTTCATGCAGATCATCACAATCACTTGCGGACAGCGACG GAGATACTTTTCTTCACTGGTTCCAACAAAGACCCGGACAAAGCCCACGC CTGCTTATTTACGCGGTATCACACAGATTCTCAGGAGTTCCAGACAGATT TTCAGGCAGCGGATCCGGCACAGACTTCACCCTTAAAATTGCAGAGTAG AAGCAGAAGATGTAGGAGTGTATTATTGTTTCCAAGCCACCCATGACCCC GTCACGTTCGGACAAGGAACTAAGCTCGAAATCAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 96 |
| hHA-010 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG ATATACTACGACAGCTCCGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGCACG ACGCCCGATAAATGGGGTCAAGGAACAATGGTAACCGTGTCAAGC | 97 |
| | VL | GACGTAGTACTGACCCAAAGCCCCCTTTCTCTCCCAGTAACCCTCGGACA ACCAGCCTCAATTTCATGCAGATCATCACAATCACTTGAGGAGAGCGACG GATACACTTTTCTTGAGTGGTTCCAACAAAGACCCGGACAAAGCCCACGC CTGCTTATTTACGAGGTATCACATAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCGACCCACGACCCC CTGACGTTCGGACAAGGAACTAAGCTCGAAATCAAA | 98 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG ATATACTACGACAGCTCCGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGCACG ACGCCCGATAAATGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 99 |
| | Light Chain | GACGTAGTACTGACCCAAAGCCCCCTTTCTCTCCCAGTAACCCTCGGACA ACCAGCCTCAATTTCATGCAGATCATCACAATCACTTGAGGAGAGCGACG GATACACTTTTCTTGAGTGGTTCCAACAAAGACCCGGACAAAGCCCACGC CTGCTTATTTACGAGGTATCACATAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCGACCCACGACCCC CTGACGTTCGGACAAGGAACTAAGCTCGAAATCAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA | 100 |

TABLE 3-continued

Nucleic acids Sequences encoding the VH/VL of anti-HJV antibodies listed in Table 1

| humanized HA Antibody | | Nucleic Acid Sequences | SEQ ID NO |
|---|---|---|---|
| | | GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | |
| hHA-011 | VH | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGAATG<br>ATATACTACGACAGCTCCGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGCTCG<br>ACCCCCGATTACTGGGGTCAAGGAACAATGGTAACCGTGTCAAGC | 101 |
| | VL | GACGTAGTACTGACCCAAAGCCCCCTTTCTCTCCCAGTAACCCTCGGACA<br>ACCAGCCTCAATTTCATGCAGATCATCACAATCACTTGAGGACAGCGACG<br>GAGGCACTTTTCTTGAGTGGTTCCAACAAAGACCCGGACAAAGCCCACGC<br>CTGCTTATTTACGACGTATCAAGCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>CTCAGCTTCGGACAAGGAACTAAGCTCGAAATCAAA | 102 |
| | Heavy<br>Chain | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAACTGGGTTAGACAAGCGCCCGGAAAAGGATTGGAATGGATAGGAATG<br>ATATACTACGACAGCTCCGAGAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGCTCG<br>ACCCCCGATTACTGGGGTCAAGGAACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | 40 |
| | Light<br>Chain | GACGTAGTACTGACCCAAAGCCCCCTTTCTCTCCCAGTAACCCTCGGACA<br>ACCAGCCTCAATTTCATGCAGATCATCACAATCACTTGAGGACAGCGACG<br>GAGGCACTTTTCTTGAGTGGTTCCAACAAAGACCCGGACAAAGCCCACGC<br>CTGCTTATTTACGACGTATCAAGCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTCCAAGCCACCCACGACCCC<br>CTCAGCTTCGGACAAGGAACTAAGCTCGAAATCAAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | 64 |

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 73.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 75.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 77.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 79.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 81.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 84, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 85.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 88, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 89.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 92, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 93.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 94, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 93.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 92, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 96.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 99, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 100.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 40, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 64.

In some embodiments, the anti-HJV antibodies described herein can be used for delivering a molecular payload to a target cell or a target tissue (e.g., a cell or tissue that expresses HJV). Accordingly, the anti-HJV antibody described herein can be linked to a molecular payload. The complexes described herein may be used in various applications, e.g., diagnostic or therapeutic applications.

In some embodiments, the complex described herein is used to modulate the activity or function of at least one gene, protein, and/or nucleic acid. In some embodiments, the molecular payload is responsible for the modulation of a gene, protein, and/or nucleic acids. A molecular payload may be a small molecule, protein, nucleic acid, oligonucleotide, or any molecular entity capable of modulating the activity or function of a gene, protein, and/or nucleic acid in a cell. In some embodiments, a molecular payload is an oligonucleotide that targets a disease-associated repeat in muscle cells.

IV. Pharmaceutical Composition

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The anti-HJV antibody containing pharmaceutical composition disclosed herein may further comprise a suitable buffer agent. A buffer agent is a weak acid or base used to maintain the pH of a solution near a chosen value after the addition of another acid or base. In some examples, the buffer agent disclosed herein can be a buffer agent capable of maintaining physiological pH despite changes in carbon dioxide concentration (produced by cellular respiration). Exemplary buffer agents include, but are not limited to a HEPES (4-(2-hydroxyethyl)-1-piperazineethanesulfonic acid) buffer, Dulbecco's phosphate-buffered saline (DPBS) buffer, or Phosphate-buffered Saline (PBS) buffer. Such buffers may comprise disodium hydrogen phosphate and sodium chloride, or potassium dihydrogen phosphate and potassium chloride.

In some embodiments, the buffer agent in the pharmaceutical composition described herein may maintain a pH value of about 5-8. For example, the pH of the pharmaceutical composition can be about 7.1, 7.2, 7.3, 7.4, 7.5, 7.6, 7.7, 7.8, 7.9, or 8.0. In other examples, the pharmaceutical composition may have a pH value lower than 7, for example, about 7, 6.8, 6.5, 6.3, 6, 5.8, 5.5, 5.3, or 5.

The pharmaceutical composition described herein comprises one or more suitable salts. A salt is an ionic compound that can be formed by the neutralization reaction of an acid and a base. (Skoog, D. A; West, D. M.; Holler, J. F.; Crouch, S. R. (2004). "chapters 14-16". Fundamentals of Analytical Chemistry (8th ed.)). Salts are composed of related numbers of cations (positively charged ions) and anions (negative ions) so that the product is electrically neutral (without a net charge).

In some embodiments, the pharmaceutical compositions can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). In some embodiments, the pharmaceutical composition can be formulated for intravenous injection. In some embodiments, the pharmaceutical composition can be formulated for subcutaneous injection.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous or subcutaneous solution bag or vial having a stopper pierceable by a hypodermic injection needle.

V. Methods of Use

Aspects of the disclosure relate to compositions and methods for treating myelofibrosis and/or one or more conditions arising as a result of myelofibrosis in a subject.

Figure 12:
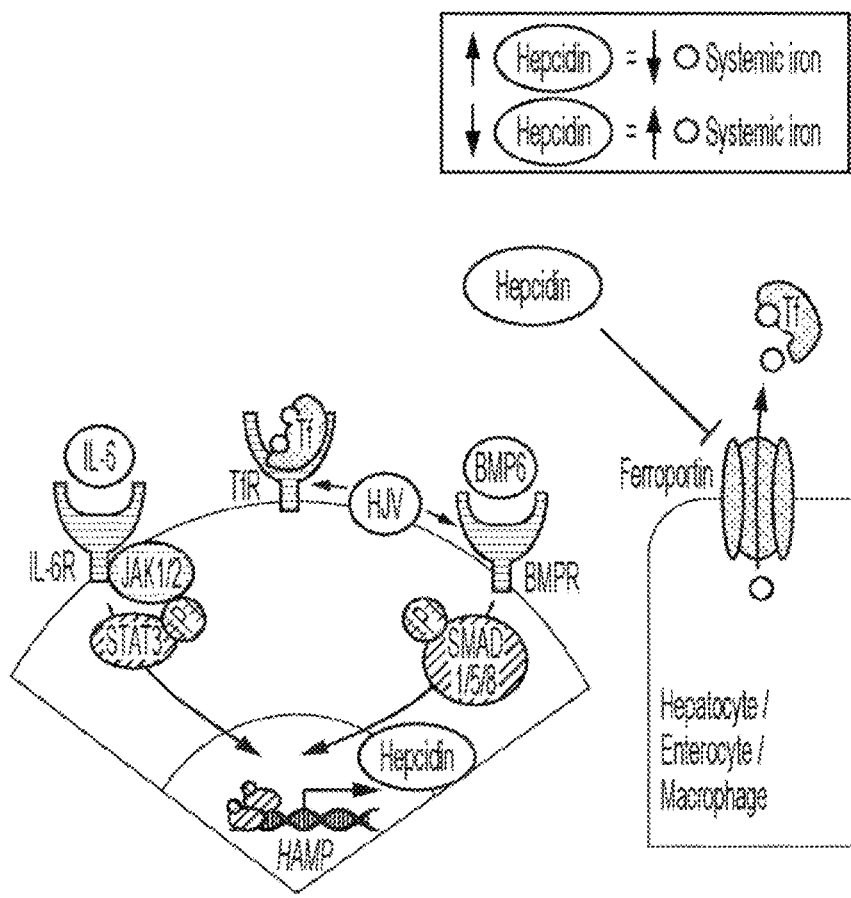
FIG. 12 depicts the hepcidin stimulatory pathway and the physiological regulation of iron homeostasis by hepcidin.

FIG. 12 depicts the hepcidin stimulatory pathway and the physiological regulation of iron homeostasis by hepcidin. As generically shown, Hepcidin operates by binding to the iron exporter Ferroportin in iron-releasing target cells (e.g., hepatocytes, duodenal enterocytes, tissue macrophages, and other cell types). The binding of hepcidin blocks iron efflux and triggers ubiquitination, internalization, and lysosomal degradation of ferroportin. This leads to intracellular iron retention and eventually decreased systemic iron levels.

The HAMP gene encodes hepcidin precursor protein, which is primarily expressed by hepatocytes in the liver, and at lower levels by other cells in extrahepatic tissues. The precursor protein is subsequently cleaved to yield bioactive hepcidin. In some embodiments, a hepcidin antagonist of the present disclosure is a HAMP antagonist, which antagonizes hepcidin function by binding HAMP or a transcription or translation product thereof, or by inhibiting a transcriptional or translational regulator of HAMP to reduce HAMP expression. Examples of transcriptional regulators of HAMP include, without limitation, SMAD1/5/8 (e.g., BMP-SMAD signaling pathway) and STAT3 (e.g., JAK-STAT signaling pathway). Accordingly, in some embodiments, the HAMP antagonist is a BMP-SMAD signaling pathway inhibitor or a JAK-STAT signaling pathway inhibitor.

Increases in serum or tissue iron trigger transcriptional induction of hepcidin via the BMP-SMAD signaling pathway. The mechanism involves secretion of bone morphogenetic protein 6 (BMP6) from liver sinusoidal endothelial cells, which binds to a BMP receptor (BMPR) on hepatocytes and thereby activates the SMAD signaling cascade. Examples of BMP receptors include type I (e.g., ALK2, ALK3, ALK6) and type II (e.g., ActRIIA, BMPRII) BMP receptors. A central regulator of the BMP-SMAD signaling pathway for hepcidin stimulation is the BMP co-receptor, hemojuvelin (HJV). Accordingly, in some aspects, the disclosure relates to hemojuvelin antagonists (e.g., anti-HJV antibodies and compositions thereof) for targeting hepcidin, e.g., for modulating iron homeostasis for the treatment of myelofibrosis and/or one or more conditions arising as a result of myelofibrosis.

In some embodiments, the disclosure provides methods for modulating iron homeostasis for the treatment of myelofibrosis that involve direct inhibition of binding of hepcidin to the iron exporter ferroportin. In some embodiments, the hepcidin antagonist is an anti-HJV antibody. Myelofibrosis (MF) is a myeloproliferative disorder characterized by proliferation of abnormal blood stem cells leading to bone marrow fibrosis. Production of healthy blood cells (megakaryocytes responsible for platelet production and erythrocytes) is impaired. MF can be categorized as primary MF (PMF) and secondary MF (SMF). PMF and SMF have similar clinical profiles which include anemia, fatigue, and splenomegaly are common presenting symptoms. Primary myelofibrosis (PMF) is characterized as MF that occurs on its own. In some embodiments, PMF may be associated with increased level of proinflammatory cytokines (e.g., IL-6) in the subject (see, e.g., Cokid et al. Proinflammatory Cytokine IL-6 and JAK-STAT Signaling Pathway in Myeloproliferative Neoplasms, Mediators Inflamm. 2015; 2015: 453020). Secondary myelofibrosis (SMF) occurs as the result of a separate disease, e.g. scar tissue in the bone marrow as a complication of an autoimmune disease. In some embodiments, a subject described herein is has or is suspected of having PMF. In some embodiments, a subject described herein is has or is suspected of having SMF.

In some embodiments, a subject having or suspect of having myelofibrosis (e.g., PMF and/or SMF) comprises one or more mutations in one or more genes (e.g., a JAK2 gene, a Thrombopoietin Receptor (MPL) gene, a calreticulin (CALR) gene, a Lymphocyte-Specific Adapter Protein Lnk (LNK) gene, a ASXL Transcriptional Regulator 1 (ASXL1) gene, a Serine And Arginine Rich Splicing Factor 2 (SRSF2) gene, a Protein Phosphatase, $Mg^{2+}/Mn^{2+}$ Dependent 1D (PPM1D) gene, Isocitrate Dehydrogenase (NADP(+)) 1/Isocitrate Dehydrogenase (NADP(+)) 2 (IDH1/2) genes, a Tet Methylcytosine Dioxygenase 2 (TET2) gene, a Enhancer Of Zeste 2 Polycomb Repressive Complex 2 Subunit (EZH2) gene, a U2 Small Nuclear RNA Auxiliary Factor 1 (U2AF1) gene, a Nuclear Factor, Erythroid 2 (NFE2) gene, a SH2B Adaptor Protein 3 (SH2B3) gene, a Splicing Factor 3b Subunit 1 (SF3B1) gene, a Cbl Proto-Oncogene (CBL) gene or a combination thereof.

In some embodiments, the subject has one or more mutations in the JAK2 gene. JAK2 plays an integral role in transducing signals from receptors involved in myeloid cell lineage proliferation by EPO, TPO, and/or G-CSF (see, e.g., Alshemmari et al., *Molecular Pathogenesis and Clinical Significance of Driver Mutations in Primary Myelofibrosis: A Review*, Med Princ Pract, 2016; 25(6):501-509). In some embodiments, the subject contains a human JAK2 gene having initiating mutations in an exon 12 or exon 14. In some embodiments, the initiating mutation in the JAK2 gene is in exon 14 and results in a V617F substitution. In some embodiments, the V617F mutation leads or over-activation of JAK2 and its associated signaling pathways. In some embodiments, the over-activation of JAK2 leads to myelofibrosis (e.g., PMF, and/or SMF).

In some embodiments, a subject has one or more mutations in the Thrombopoietin Receptor (MPL) gene. MPL is the cognate receptor of thrombopoietin (TPO), and mutations that result in gain of function of the MPL gene lead to impairment in megakaryocytes production. In some embodiments, the subject comprises a W515L/K mutation of MPL. In some embodiments, the some embodiments, a subject having one or more mutations in MPL gene has a greater chance (e.g., more than 10%, more than 20%, more than 30%, more than 40%, more than 50%, more than 60%, more than 70%, more than 80%, more than 90%, more than 2-fold, more than 3-fold, more than 4-fold, more than 5-fold, more than 6-fold, more than 7-fold, more than 8-fold, more than 9-fold, or more than 10-fold) of developing anemia compared to the overall subjects having MF (Guglielmelli P et al., Anaemia characterises patients with myelofibrosis harboring Mpl mutation. Br J Haematol 2007; 137: 244-247).

In some embodiments, a subject has one or more mutations in the calreticulin (CALR) gene. The CALR gene encodes the calreticulin protein, which is a multifactorial protein that regulates calcium homeostasis, cell signaling, gene expression, cell adhesion, autoimmunity and apoptosis. About 140 CALR mutations have been identified with 19 variant to be associated with MF. In some embodiments, the subject has or is suspect of having MF has an Exon 9 mutation in the CALR gene.

Additional mutations in other gene that are associated with MF have been identified. Non-limiting examples of genes associated with MF include, e.g., JAK2, MPL, CLAR, LNK, ASXL1, SRSF2, PPM1D, IDH1/2, TET2, EZH2, U2AF1, NFE2, SH2B3, SF3B1 or CBL. In some embodiments, a subject has or is suspect of having MF comprises one or more mutations in one or more of the genes described herein.

In some embodiments, the subject has one or more mutations in genes involved in epigenetic regulation or splicing. In some embodiments the one or more mutations in genes involved in epigenetic regulation or splicing is ASXL1, DNMT3A, TET2, SRSF2, U2AF1, EZH2 or SF3B1. In some embodiments, the subject has mutations in IDH1/2 associated with risk of progression to MBN-BP.

In some aspects, the disclosure relates to compositions (e.g., anti-HJV antibodies and compositions thereof) and methods for treating myelofibrosis in a subject. In some embodiments, a subject to be treated in accordance with the disclosure may be identified based on an appropriate diagnostic or prognostic methodology. For example, the Dynamic International Prognostic Scoring System (DIPSS) and age-adjusted DIPSS provide models of patient outcome based on several patient-specific variables, including age, hemoglobin level, white blood cell count, peripheral blood blasts, and constitutional symptoms (see, e.g., Passamonti, F., et al. Blood. 2010 Mar. 4; 115(9):1703-8, which is incorporated herein by reference). The DIPSS model calculates a DIPSS score which allows for allocating a patient into a risk category for prognosis purposes. A DIPSS score of 0 identifies a "low risk" patient, a DIPSS score of 1-2 identifies an "intermediate-1 risk" patient, a DIPSS score of 3-4 identifies an "intermediate-2 risk" patient, and a DIPSS score of 5-6 identifies a "high risk" patient. Accordingly, in some embodiments, a subject in need of treatment in accordance with the application may have a DIPSS score of at least 1. In some embodiments, the subject has a DIPSS score of 1-4 (e.g., 1, 2, 3, or 4). In some embodiments, the subject has a DIPSS score of 5 or 6 (e.g., 5 or 6).

In some embodiments, a subject to be treated in accordance with the disclosure may be assessed by an appropriate diagnostic or prognostic methodology. For example, the Myeloproliferative Neoplasm-Symptom Assessment Form Total Symptom Score (MPN-SAF TSS) provides a 10-item instrument designed to assess the most representative and clinically relevant symptoms among patients with MPNs. The tool records the patient's assessment of the incidence and severity of these disease-related symptoms. It can be used to track symptoms over time and guide subsequent management decisions (see e.g., Emanuel R M, et al. Myeloproliferative neoplasm (MPN) symptom assessment form total symptom score: prospective international assessment of an abbreviated symptom burden scoring system among patients with MPNs, J Clin Oncol. 2012; 30(33):4098-4103, which is incorporated herein by reference). The MPN-SAF TSS includes symptoms such as fatigue, early satiety, inactivity, concentration problems, abdominal discomfort, night sweats, bone pain, itching, unintentional weight loss, and fever. Each symptom is rated by a Symptom severity on a 0 (absent/as good as it can be) to 10 (worst imaginable/as bad as it can be) scale. The MPN-SAF TSS has a possible range of 0 to 100, with 100 representing the highest level of symptom severity. In some embodiments, a Myelofibrosis Symptom Assessment Form (MFSAF) is derived from MPN-SAF TSS. MFSAF is an instrument that measures the symptoms reported by >10% of MF patients, and includes a measure of quality of life (QoL). MFSAF includes a comprehensive evaluation of fatigue, an assessment of splenomegaly and associated mechanical symptoms, and an evaluation of other symptoms such as night sweats, itching (pruritus), bone pain, fever, unintentional weight loss and overall quality of life (see e.g., Mesa et al., The Myelofibrosis Symptom Assessment Form (MFSAF): An Evidence-based Brief Inventory to Measure Quality of Life and Symptomatic Response to Treatment in Myelofibrosis, Leuk Res. 2009 September; 33(9): 1199-1203, which is incorporated herein by reference). MFSAF can be used to track symptoms over time and guide subsequent management decisions. In some embodiments, a patient has a MPN-SAF TSS of 0-100 (e.g., any score number between 0 and 100), $10^{-100}$ (e.g., any score number between 10 and 100), 20-100 (e.g., any score number between 20 and 100), 30-100 (e.g., any score number between 30 and 100), 40-100 (e.g., any score number between 40 and 100), 50-100 (e.g., any score number between 50 and 100), 60-100 (e.g., any score number between 60 and 100), 70-100 (e.g., any score number between 70 and 100), 80-100 (e.g., any score number between 80 and 100), or 90-100 (e.g., any score number between 00 and 100).

In some aspects, a subject having MF (e.g., PMF or SMF) develops anemia. Anemia in MF is the result of a multifactorial process.

In some embodiments, anemia in MF may be therapy related. In some embodiments, MF patients have been previously treated with JAK inhibitors (e.g., Ruxolitinib or Fedratinib). In some embodiments, patients receiving JAK inhibitors (e.g., Ruxolitinib or Fedratinib) exhibits higher chance of developing MF-related anemia. Inhibition of JAK-STAT signaling pathway leads to inhibition of erythropoietin-mediated JAK2 signaling, which is essential for erythropoiesis. In some embodiments, new-onset anemia has been identified as a major adverse event associated JAK inhibitor (e.g., ruxolitinib) treatment (see, e.g., Verstovsek S, Kantarjian H, Mesa R A, et al. *Safety and efficacy of INCB*018424, *a JAK*1 *and JAK*2 *inhibitor, in myelofibrosis*. N Engl J Med. 2010; 363(12):1117-1127; Verstovsek S, Mesa R A, Gotlib J, et al. *A doubleblind, placebo-controlled trial of ruxolitinib for myelofibrosis*. N Engl J Med. 2012; 366(9):799-807; Parganas E, Wang D, Stravopodis D, et al. *Jak2 is essential for signaling through a variety of cytokine receptors*. Cell. 1998; 93(3):385-395; Neubauer H, Cumano A, M"uller M, Wu H, Huffstadt U, Pfeffer K. *Jak2 deficiency defines an essential developmental checkpoint in definitive hematopoiesis*. Cell. 1998; 93(3):397-409, the entire contents of each of which are incorporated herein by reference).

In some embodiments, the subject has or is at risk of having constitutional or microvascular symptoms associated with Myeloproliferative neoplasms (MPN). In some embodiments, the subject has or is at risk of having thromboembolic or hemorrhagic complications. In some embodiments, the subject has or is at risk of having MPN-blast phase acute myeloid leukemia (AML). In some embodiments, the subject exhibits ribosomopathy in megakaryocytes. In some embodiments, the subject exhibits reduced GATA1 expression, particularly in megakaryocytes. In some embodiments, the subject exhibits defects in megakaryocytic function or maturation. In some embodiments, the subject does not have a nutritional iron deficiency. In some embodiments, the subject presents with thrombocytopenia, anemia, and/or neutropenia.

In some embodiments, myelofibrosis-associated anemia is caused by ineffective erythropoiesis due to bone marrow suppression and deficiencies in iron metabolism, increased destruction of red blood cell due to splenomegaly, increased plasma volume, abnormal pro-inflammatory environment in the bone marrow, or a combination thereof.

In some embodiments, the myelofibrosis-associated anemia is associated with abnormal iron metabolism. In some embodiments, the abnormal iron metabolism in MF patients is functional iron deficiency (FID). FID represents a state of iron-restricted erythropoiesis characterized by an imbalance between iron demand and serum iron that is readily available for effective erythropoiesis. In FID, even when the body has adequate or increased systemic iron stores, iron is sequestered and not available for erythropoiesis. In some embodiments, FID is caused by an increase of hepcidin relative to the iron store levels. In some embodiments, increased hepcidin expression is caused by upregulation of pro-inflammatory cytokines. For example, IL-6 was reported to be higher in anemic MF patients (Birgegard et al., Inflammatory Functional Iron Deficiency Common in Myelofibrosis, Contributes to Anaemia and Impairs Quality of Life. From the Nordic MPN Study Group, Eur J Haematol. 2019 March; 102(3):235-240).

In some embodiments, the myelofibrosis-associated anemia is characterized by high serum pro-inflammatory cytokine levels.

In myelofibrosis (e.g., PMF), pro-inflammatory cytokines that induce hepcidin synthesis, such as IL-6 and oncostatin-M, are typically increased and associated with iron sequestration, macrophage iron loading, as well as myeloid proliferation and macrophage activation. These increased hepcidin levels may lead to anemia.

In some embodiments, the pro-inflammatory cytokine is IL-6. Normal range of IL-6 (e.g., in subjects without disease) is equal or less than 1.8 pg/ml. In some embodiments, the subject has a higher-than-normal serum IL-6 levels, e.g., greater than 1.8 pg/ml.

In some embodiments, the present disclosure provides a method of treating a subject having myelofibrosis. In some embodiments, the subject has anemia resulting from hepcidin synthesis that is induced by pro-inflammatory cytokines. In some embodiments, the pro-inflammatory cytokine that increases hepcidin synthesis is IL-6. In some embodiments, administration of the anti-HJV antibody to the subject reduces hepcidin synthesis induced by pro-inflammatory cytokines (e.g., IL-6). In some embodiments, the administration of the anti-HJV antibody ameliorates FID associated with increased hepcidin synthesis induced by proinflammatory cytokines (e.g., IL-6).

Determination of whether an amount of the antibody (e.g., anti-HJV antibody) achieved the therapeutic effect would be evident to one of skill in the art based on the teachings provided herein. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. The particular dosage regimen, i.e., dose, timing and repetition, used in the method described herein will depend on the particular subject and that subject's medical history, as discussed herein.

Empirical considerations, such as time to maximum effect, the half-life, and/or time above a specific concentration generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Other reasons for dose-adjusting include differences in pharmacokinetics or pharmacodynamic response driven by sex, age, individual response, polymorphisms on the antibody target and/or receptors involved in antibody clearance. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In some embodiments, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Dosing frequencies may vary in accordance with the claimed methods. In some embodiments, a composition may be administered once. In some embodiments, a composition will be administered on multiple occasions. In some embodiments, dosing frequency is every week, every 2 weeks, every 3 weeks, every 4 weeks, every 5 weeks, every 6 weeks, every 7 weeks, every 8 weeks, every 9 weeks, or every 10 weeks; or once every month, every 2 months, or every 3 months, or longer. In some embodiments, a composition will be administered daily, biweekly, weekly, bimonthly, monthly, or at any time interval that provide suitable (e.g., maximal) efficacy while minimizing safety risks to the subject. Generally, the efficacy and the treatment and safety risks may be monitored throughout the course of treatment.

Figure 7A:
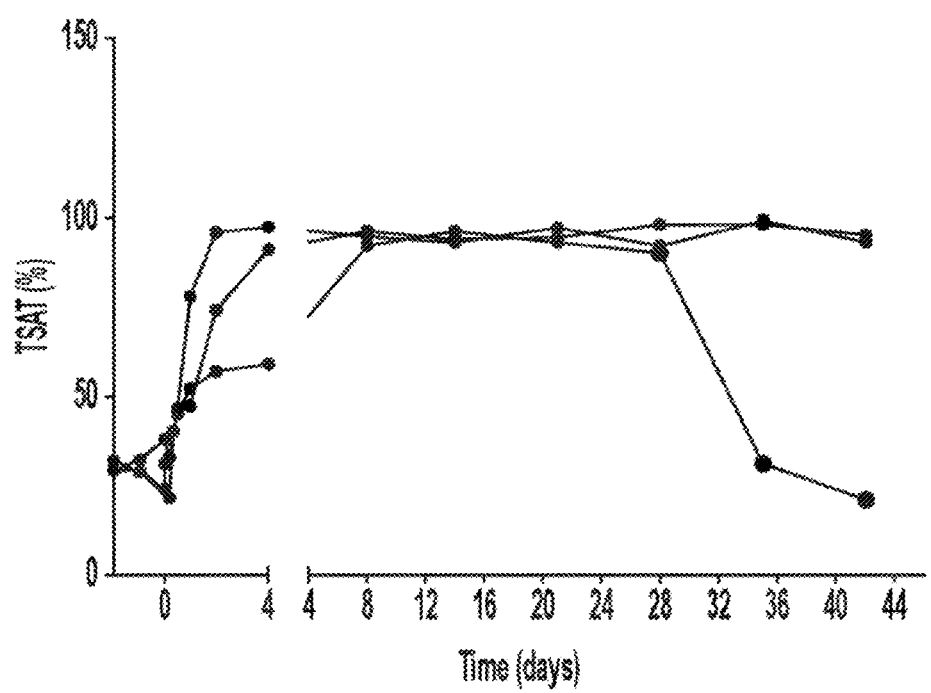
FIGS. 7A-7F shows PK/PD correlation in Cynos with single IV dose of 6 mpk.

In some embodiments, administration of anti-HJV antibody results in a decrease in circulating hepcidin-25 concentration and/or increase serum TSAT % (see, e.g., FIGS. 7D-7E), and in some embodiments, these effects persist for a period of time (e.g., one month or more). Accordingly, in some embodiments, timing and frequency of administration of anti-HJV antibody can be determined by monitoring one or more biomarkers, e.g., criteria to assess iron availability or flag possible iron overload. For example, in some embodiments, anti-HJV antibody is administered intermittently or in accordance with the level of a particular biomarker such as circulating hepcidin-25 levels, circulating transferrin level, or transferrin saturation percentage (TSAT %). In some embodiments, a biomarker level can be used to determine whether a subject is a candidate for treatment. However, in some embodiments, a biomarker may be used to determine whether to continue treatment or to resume a treatment or to halt a treatment, e.g., halt treatment with an anti-HJV antibody.

For example, in some embodiments, a subject may be considered as not being a candidate for treatment if TSAT % of the subject is at or above 70%, at or above 75%, at or above 80%, at or above 85%, at or above 90%, or at or above 95%. In some cases, if TSAT % of the subject is at or above 70%, at or above 75%, at or above 80%, at or above 85%, at or above 90%, or at or above 95%, an ongoing treatment with an anti-HJV antibody may be stopped or temporarily stopped, e.g., to prevent iron overload. In other embodiments, administration of an anti-HJV antibody may be performed when a TSAT % of a subject is at or below 95%, at or below 90%, at or below 80%, at or below 70%, at or below 65%, at or below 60%, at or below 55%, at or below 50%, at or below 45%, at or below 40%, at or below 35%, or at or below 30%. Thus, in some embodiments, TSAT % of a subject can be monitored, e.g., continuously or periodically, while a patient is receiving a treatment or under care of a treating physician, e.g., for anemia, to prevent iron overload or otherwise to assess whether further treatments are appropriate. It should be appreciated, however, that other suitable markers may be monitored to determine dosage and dosage frequency (including, for example, ferritin levels, serum iron levels, creatinine levels, etc.) in accordance with the methods provided herein.

In some embodiments, a subject may be administered a composition provided herein (e.g., an anti-HJV antibody) at one or more intervals during a set period of time. In some cases, periods of time during which a subject is administered a composition at one or more intervals may be separated by periods of time in which the subject is not administered the composition. In some embodiments, the relative durations of respective periods of time may depend on the subject's response to treatment or severity of disease or both and/or may be determined based on the judgment of a treating physician. For example, in some embodiments, during the course of a year a subject may be administered a composition weekly, biweekly or monthly for two months and then the administration is stopped for ten months. In some embodiments, during the course of a year a subject may be administered a composition weekly, biweekly or monthly for three months and then the administration is stopped for nine months. In some embodiments, during the course of a year a subject may be administered a composition weekly, biweekly or monthly for four months and then the administration is stopped for eight months. In some embodiments, during the course of a year a subject may be administered a composition weekly, biweekly or monthly for five months and then the administration is stopped for seven months. In some embodiments, during the course of a year a subject may be administered a composition weekly, biweekly or monthly for six months and then the administration is stopped for six months. In some embodiments, during the course of a year a subject may be administered a composition weekly, biweekly or monthly for seven months and then the administration is stopped for five months. In some embodiments, during the course of a year a subject may be administered a composition weekly, biweekly or monthly for eight months and then the administration is stopped for four months. In some embodiments, during the course of a year a subject may be administered a composition weekly, biweekly or monthly for nine months and then the administration is stopped for three months. In some embodiments, during the course of a year a subject may be administered a composition weekly, biweekly or monthly for ten months and then the administration is stopped for two months. In some embodiments, during the course of a year a subject may be administered a composition weekly, biweekly or monthly for two months on, two months off; or for three months on, three months off, or for four months on, four months off.

Generally, for administration of any of the antibodies described herein, a dose may be about 0.01 mg/kg, 0.05 mg/kg. 0.1 mg/kg, 0.2 mg/kg, 0.3 mg/kg, 0.4 mg/kg, 0.5 mg/kg, 0.6 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg or 100 mg/kg.

In some embodiments, the dosage the anti-HJV antibody is up to 0.01 mg/kg, up to 0.05 mg/kg, up to 0.1 mg/kg, up to 0.2 mg/kg, up to 0.3 mg/kg, up to 0.4 mg/kg, up to 0.5 mg/kg, up to 0.6 mg/kg, up to 1 mg/kg, mg/kg, up to 2 mg/kg, up to 3 mg/kg, up to 4 mg/kg, up to 5 g/kg, up to 6 mg/kg, up to 7 mg/kg, up to 8 mg/kg, up to 9 mg/kg, up to 10 mg/kg, up to 20 mg/kg, up to 30 mg/kg, up to 40 mg/kg, up to 50 mg/kg, up to 60 mg/kg, up to 70 mg/kg, 80 mg/kg, up to 90 mg/kg, up to 100 mg/kg or more.

However, in some embodiments, the dose of the anti-HJV antibody can be in a range of 0.01 mg/kg to 100 mg/kg, 0.01 mg/kg to 10 mg/kg, 0.5 mg/kg to 15 mg/kg, 1 mg/kg to 15 mg/kg, 5 mg/kg to 25 mg/kg, 10 mg/kg to 30 mg/kg, 20 mg/kg to 40 mg/kg, 30 mg/kg to 50 mg/kg, 40 mg/kg to 60 mg/kg, 50 mg/kg to 75 mg/kg, or 50 mg/kg to 100 mg/kg In some embodiments, the antibodies described herein are administered to a subject in need of the treatment at an amount sufficient to inhibit the activity of the target antigen (e.g., an amount sufficient to inhibit HJV-induced BMP signaling) by at least 20% (e.g., 30%, 40%, 50%, 60%, 70%, 80%, 90% or greater) in vivo. In other embodiments, the antibody is administered in an amount effective in reducing the activity level of a target antigen by at least 20% (e.g., 30%, 40%, 50%, 60%, 70%, 80%, 90% or greater).

In some embodiments, an antibody can be administered parenterally. For example, a parenterally administered composition may be administered by subcutaneous, intracutaneous, intravenous, intraperitoneal, intratumor, intramuscular, intraarticular, intraarterial, or infusion techniques. In addition, it can be administered to the subject via injectable depot routes of administration such as using 1-, 3-, or 6-month depot injectable or biodegradable materials and methods.

In some embodiments, an antibody (e.g., an anti-HJV antibody) is administered intravenously. In some embodiments, an antibody (e.g., an anti-HJV antibody) is administered subcutaneously. In some embodiments, subcutaneous administration of an ani-HJV antibody results in similar bioavailability compared to intravenous administration of the same antibody at the same dose.

In some embodiments, subcutaneous administration of the anti-HJV antibody yields the comparable pharmacodynamics effects (e.g., decreased circulating hepcidin-25 levels, increased TSAT %, and/or increased serum iron levels) at lower maximum concentrations ($C_{max}$) of the anti-HJV antibody compared to intravenous administration of the same antibody. $C_{max}$ is the maximum (or peak) serum concentration that a drug (e.g., an anti-HJV antibody) after the drug has been administered and before the administration of a second dose. In some embodiments, achieving a low $C_{max}$ within a short period of time (e.g., within 12 hours, within 24 hours) after administration of an anti-HJV antibody minimizes undesirable increases in serum iron response, and/or minimizes chances of off-target effects of the antibody (e.g., binding to RGMa). In some embodiments, blunting $C_{max}$ by subcutaneous administration of an anti-HJV antibody avoids an undesirably sharp increase in serum iron response. In some embodiments, blunting $C_{max}$ by subcutaneous administration of an anti-HJV antibody reduces the off-target effects of the antibody. In some embodiments, the $C_{max}$ reached by subcutaneous administration is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the $C_{m}ax$ reached by intravenous administration of an anti-HJV antibody.

For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Other injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). In some cases, preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents. Treatment efficacy for a target disease/disorder can be assessed by methods well-known in the art.

The anti-HJV antibody and treatment methods involving such as described in the present disclosure may be utilized in combination with other types of therapy for the target disease or disorder disclosed herein. In this context, an antibody composition and a therapeutic agent may be given either simultaneously or sequentially. Examples include chemotherapy, immune therapy (e.g. therapies involving other hepcidin antagonists), surgery, radiation, gene therapy, and so forth, or anti-infection therapy. Such therapies can be administered simultaneously or sequentially (in any order) with the treatment according to the present disclosure.

For example, the combination therapy can include the anti-HJV antibody and pharmaceutical composition described herein, co-formulated with and/or co-administered with, at least one additional therapeutic agent. Such combination therapies may advantageously utilize lower dosages of the administered therapeutic agents, thus preventing possible toxicities or complications associated with the various monotherapies. Moreover, the additional therapeutic agents disclosed herein may act on pathways in addition to or distinct from the hepcidin/BMP pathway, and thus may enhance and/or synergize with the effects of the anti-HJV antibodies.

In some aspects, the disclosure relates to compositions (e.g., anti-HJV antibodies and compositions thereof) and methods for treating myelofibrosis-associated anemia. The myelofibrosis-associated anemia may be characterized as a mild to moderate anemia or a severe anemia in accordance with appropriate diagnostic threshold parameters. For example, in some embodiments, the myelofibrosis-associated anemia is characterized based on a level of hemoglobin (Hgb), wherein the severity of the anemia increases with decreasing levels of Hgb. In some embodiments, mild to moderate anemia is associated with Hgb levels of at least 8 g/dL and less than the lower limit of normal (e.g., between about 8 and about 14 g/dL, between about 8 and about 12 g/dL, between about 8 and about 10 g/dL, between about 10 and about 14 g/dL, or between about 10 and about 12 g/dL). In some embodiments, severe anemia is associated with Hgb levels of about 8 g/dL or lower (e.g., between about 2 and about 8 g/dL, between about 4 and about 8 g/dL, or between about 6 and about 8 g/dL). In some embodiments, severe anemia is associated with erythrocyte-transfusion dependence. In some embodiments, severe anemia is associated with erythrocyte-transfusion independence resulting from a therapeutic intervention (e.g., therapeutic reversal of a transfusion dependent state), where a subject is dependent upon ongoing therapeutic treatment to maintain transfusion independence.

In some aspects, the disclosure provides compositions and methods for treating a subject that is known to have, or is suspected of having, a hematologic disorder characterized by low systemic iron levels. In some embodiments, the subject has myelofibrosis and/or one or more conditions arising as a result of myelofibrosis, as described elsewhere herein. In some embodiments, the subject is erythrocyte-transfusion dependent. In some embodiments, the subject is erythrocyte-transfusion independent.

Accordingly, in some embodiments, a subject in need of treatment in accordance with the disclosure has previously received therapeutic intervention for a hematologic disorder. In some embodiments, the subject has previously undergone a surgical procedure for treating one or more hematologic disorders. In some embodiments, the subject has previously undergone a splenectomy. In some embodiments, the subject has previously received a therapeutic agent for treating one or more hematologic disorders.

In some embodiments, a subject has previously received an erythropoietin stimulating agent. In some embodiments, the erythropoietin stimulating agent is selected from the group consisting of danazol, prednisone, thalidomide, lenalidomide, and pomalidomide.

In some embodiments, a subject has previously received a JAK-STAT pathway inhibitor. In some embodiments, the JAK-STAT pathway inhibitor is a JAK inhibitor or a STAT inhibitor. In some embodiments, the JAK inhibitor is selective for one or both of subtypes JAK1 and JAK2 (e.g., a JAK1/2 inhibitor). In some embodiments, the STAT inhibitor is a STAT3 inhibitor. In some embodiments, the JAK1/2 or STAT3 inhibitor is selected from the group consisting of ruxolitinib, fedratinib, momelotinib, pacritinib, INCB039110, AG490, and PpYLKTK (SEQ ID NO: 130).

In some embodiments, a subject has previously received a growth factor ligand trap. In some embodiments, the growth factor ligand trap is a transforming growth factor beta (TGF-β) ligand trap. In some embodiments, the TGF-β ligand trap is sotatercept or luspatercept. In some embodiments, a subject has previously received an anti-fibrotic agent. In some embodiments, the anti-fibrotic agent is PRM-151.

In some embodiments, a subject in need of treatment in accordance with the disclosure continues to receive a therapeutic treatment for a hematologic disorder. The disclosure therefore provides, in some aspects, compositions and methods for treating myelofibrosis and/or one or more conditions arising as a result of myelofibrosis by administering to a subject in need thereof a hepcidin antagonist (e.g., anti-HJV antibodies and compositions thereof) in combination with one or more therapeutic treatments for a hematologic disorder.

In some embodiments, a subject is administered a hemojuvelin antagonist (e.g., anti-HJV antibodies and compositions thereof) in combination with an erythropoietin stimulating agent. In some embodiments, the erythropoietin stimulating agent is selected from the group consisting of danazol, prednisone, thalidomide, lenalidomide, and pomalidomide.

In some embodiments, a subject is administered a hemojuvelin antagonist (e.g., anti-HJV antibodies and compositions thereof) in combination with a JAK-STAT pathway inhibitor. In some embodiments, the JAK-STAT pathway inhibitor is a JAK inhibitor or a STAT inhibitor. In some embodiments, the JAK inhibitor is selective for one or both of subtypes JAK1 and JAK2 (e.g., a JAK1/2 inhibitor). In some embodiments, the STAT inhibitor is a STAT3 inhibitor. In some embodiments, the JAK1/2 or STAT3 inhibitor is selected from the group consisting of ruxolitinib, fedratinib, momelotinib, pacritinib, INCB039110, AG490, and PpYLKTK (SEQ ID NO: 130). In some embodiments, a subject is administered a hemojuvelin antagonist (e.g., anti-HJV antibodies and compositions thereof) in combination with ruxolitinib.

In some embodiments, the hemojuvelin antagonist (e.g., anti-HJV antibodies and compositions thereof) reduces the extent to which a subject exhibits an anemic response to the JAK-STAT pathway inhibitor. For example, in some embodiments, a subject treated with a JAK-STAT pathway inhibitor as a monotherapy may be characterized as having a deficiency in the ability of blood to transport oxygen as compared to the subject's pretreatment state, a deficiency in red blood cells as compared to the subject's pretreatment state, a deficiency in hemoglobin as compared to the subject's pretreatment state, an/or a deficiency in total blood volume as compared to the subject's pretreatment state. Accordingly, in some embodiments, the hemojuvelin antagonist (e.g., anti-HJV antibodies and compositions thereof) reduces the extent to which a subject exhibits an anemic response to a JAK-STAT pathway inhibitor selected from the group consisting of ruxolitinib, fedratinib, momelotinib, pacritinib, INCB039110, AG490, and PpYLKTK (SEQ ID NO: 130). In some embodiments, the hemojuvelin antagonist (e.g., anti-HJV antibodies and compositions thereof) reduces the extent to which a subject exhibits an anemic response to ruxolitinib administration.

In some embodiments, a subject is administered a hemojuvelin antagonist (e.g., anti-HJV antibodies and compositions thereof) in combination with a growth factor ligand trap. In some embodiments, the growth factor ligand trap is a transforming growth factor beta (TGF-β) ligand trap. In some embodiments, the TGF-β ligand trap is sotatercept or luspatercept. In some embodiments, a subject is administered a hemojuvelin antagonist (e.g., anti-HJV antibodies and compositions thereof) in combination with an anti-fibrotic agent. In some embodiments, the anti-fibrotic agent is PRM-151.

Successful treatment of a subject in accordance with the disclosure may be determined by methods known in the art or by a skilled practitioner. In some embodiments, HJV antagonist (e.g., anti-HJV antibodies and compositions thereof) treatment is evaluated based on hepcidin levels (e.g., circulating hepcidin-25 levels) in a subject. For example, in some embodiments, baseline hepcidin levels (e.g., circulating hepcidin-25 levels) in a subject are determined (e.g., before treatment with anti-HJV antibody or otherwise in absence of anti-HJV antibody treatment at the time of determining) and compared to post-treatment hepcidin levels (e.g., circulating hepcidin-25 levels) in the subject. In some embodiments, a subject is successfully treated where an anti-HJV antibody decreases hepcidin levels (e.g., circulating hepcidin-25 levels) in the subject by between about 1 ng/mL and about 300 ng/mL. In some embodiments, the anti-HJV antibody decreases hepcidin levels (e.g., circulating hepcidin-25 levels) in a subject by between about 1 ng/mL and about 200 ng/mL, between about 1 ng/mL and about 100 ng/mL, between about 1 ng/mL and about 50 ng/mL, between about 1 ng/mL and about 10 ng/mL, between about 10 ng/mL and about 100 ng/mL, or between about 10 ng/mL and about 50 ng/mL. In some embodiments, the present disclosure provides a method for reducing hepcidin (e.g., circulating hepcidin-25 levels) in a subject having myelofibrosis. In some embodiments, the administration reduces hepcidin-25 within 4 hours, 6 hours, 8 hours, 12 hours, 28 hours, 24 hours, 2 days, 3 days, 4 days, 5 days, 6 days, 1 week, or two weeks of administration. In some embodiments, the administration reduces hepcidin (e.g., circulating hepcidin-25 levels) by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of hepcidin (e.g., circulating hepcidin-25 levels) compared to the hepcidin (e.g., circulating hepcidin-25 levels) level in the subject prior to administration.

In some embodiments, anti-HJV antibody treatment is evaluated based on serum ferritin levels in a subject. For example, in some embodiments, baseline serum ferritin levels in a subject are determined (e.g., before treatment with an anti-HJV antibody or otherwise in absence of anti-HJV antibody treatment at the time of determining) and compared to post-treatment serum ferritin levels in the subject. In some embodiments, a subject is successfully treated where an anti-HJV antibody decreases serum ferritin levels in the subject by between about 1 ng/mL and about 200 ng/mL. In some embodiments, the anti-HJV antibody decreases serum ferritin levels in a subject by between about 1 ng/mL and about 100 ng/mL, between about 1 ng/mL and about 50 ng/mL, between about 1 ng/mL and about 25 ng/mL, between about 1 ng/mL and about 10 ng/mL, between about 10 ng/mL and about 100 ng/mL, or between about 10 ng/mL and about 50 ng/mL.

In some embodiments, anti-HJV antibody treatment is evaluated based on serum hemoglobin levels in a subject. For example, in some embodiments, baseline serum hemoglobin levels in a subject are determined (e.g., before treatment with an anti-HJV antibody or otherwise in absence of anti-HJV antibody treatment at the time of determining) and compared to post-treatment serum hemoglobin levels in the subject. In some embodiments, a subject is successfully treated where an anti-HJV antibody decreases serum hemoglobin levels in the subject by between about 0.01 g/dL and about 5 g/dL. In some embodiments, the anti-HJV antibody decreases serum ferritin levels in a subject by between about 0.01 g/dL and about 1 g/dL, between about 0.1 g/dL and about 5 g/dL, between about 1 g/dL and about 5 g/dL, between about 0.01 g/dL and about 0.1 g/dL, between about 0.5 g/dL and about 2.5 g/dL, or between about 0.1 g/dL and about 1 g/dL.

In some aspects, other hepcidin antagonist can be a hepcidin inhibitor. In some embodiments, the hepcidin inhibitor is a molecule that specifically binds hepcidin (e.g., an antibody, an anticalin, or an aptamer). Examples of molecules that specifically bind hepcidin include, without limitation, PRS-080, LY2787106, NOX-H94 (Lexaptepid Pegol), 12B9m, LS-B4534, lipocalin mutein, and hNGAL mutein (see also U.S. Pat. Nos. 8,629,250; 9,315,577; 9,051, 382; 9,657,098; 9,610,356; 8,530,619; and U.S. Patent Publication Nos. US 2015/0291675, US 2018/0057812, and US 2017/0247448, which are incorporated herein by reference).

In some embodiments, other hepcidin antagonist can be a molecule that specifically binds ferroportin (e.g., an antibody, an anticalin, or an aptamer). In some embodiments, the molecule that specifically binds ferroportin is LY2928057. Molecules that bind ferroportin to inhibit hepcidin binding without affecting ferroportin activity have been described (see also U.S. Pat. No. 8,183,346, which is incorporated herein by reference). In some embodiments, the hepcidin inhibitor is a chemical modifier compound that modifies hepcidin or ferroportin to inhibit the hepcidin-ferroportin binding interaction. For example, in some embodiments, the hepcidin inhibitor is fursultiamine (see, e.g., Fung and Nemeth. Haematologica. 2013 November; 98(11):1667-76).

In yet other aspects, other hepcidin antagonist can be of the disclosure is a HAMP antagonist that binds HAMP or a transcription or translation product thereof. Examples of such HAMP antagonists include, without limitation, antisense oligonucleotides, small molecule inhibitor compounds, and antibodies, anticalins, or aptamers specific for a HAMP transcription or translation product. An antisense oligonucleotide may be single-stranded or double-stranded. As a set of non-limiting examples, an antisense oligonucleotide may be, but is not limited to, a small interfering RNA (siRNA), microRNA (miRNA), short hairpin RNA (shRNA), dicer substrate interfering RNA (dsiRNA), short siRNA, or single-stranded siRNA. In some embodiments, a double-stranded antisense oligonucleotide is an RNAi oligonucleotide. Specific examples of HAMP antisense oligonucleotides include, without limitation, siHepcidin and XEN701 (see also U.S. Patent Publication Nos. US 2016/0186172 and US 2012/0115930, which are incorporated herein by reference).

In some embodiments, the HAMP antagonist binds to or otherwise downregulates a molecule involved in the BMP-SMAD and/or JAK-STAT signaling pathways. In some embodiments, the HAMP antagonist is an antisense oligonucleotide, a small molecule compound, an antibody, an anticalin, or an aptamer. Examples of molecules targeted by HAMP antagonists of the disclosure include, without limitation, HFE, BMP6, BMP receptors, transferrin, transferrin receptors, SMAD1/5/8 and SMAD4, IL-6, IL-6 receptors, JAK1/2, and STAT3. In some embodiments, hepcidin antagonists of the disclosure are antagonists (e.g., inhibitors) of any one or more of these molecules.

In some embodiments, other hepcidin antagonist can be of the present disclosure is a BMP6 antagonist, which reduces hepcidin function by binding BMP6 and/or a BMP receptor to inhibit activation of the BMP-SMAD signaling pathway. In some embodiments, the BMP6 antagonist is an ALK2 inhibitor, such as, for example, LDN-212854, LDN-193189, LDN-214117, BLU-782, and others as disclosed in Hudson, L. et al., *Novel Quinazolinone Inhibitors of ALK2 Flip between Alternate Binding Modes: Structure-Activity Relationship, Structural Characterization, Kinase Profiling, and Cellular Proof of Concept. Med. Chem.* 2018, 61, 16, 7261-7272 and Carvalho D, et al., *ALK2 inhibitors display beneficial effects in preclinical models of ACVR1 mutant diffuse intrinsic pontine glioma.* Communications Biologyvolume 2, Article number: 156 (2019), the relevant contents of each of which are incorporated herein by reference. In some embodiments, the BMP6 antagonist is a soluble HJV polypeptide, including fragments and/or fusion molecules thereof (e.g., HJV-Fc), for example as described in U.S. Pat. No. 7,534,764; U.S. Publication No. US 2012/064076; and International Publication Nos. WO 2008/124768 and WO 2012/150973, which are incorporated herein by reference. Additional examples of BMP6 antagonists include, without limitation, TP-0184, FKBP12, a twisted gastrulation protein, dorsomorphin, noggin, chordin, ventroptin, follistatin, follistatin-related gene (FLRG), heparin, sulphated glycosaminoglycan, and Sclerostin domain-containing 1 protein (SOSTDC1). Additional examples of BMP6 antagonists that may be useful in certain methods provided herein are provided, for example, in U.S. Pat. Nos. 8,318,167; 9,556,251; 9,862,764; 10,202,356; 9,682,983; 8,507,501; 9,738,636; and 8,795,665; U.S. Publication Nos. US 2010/0093760; US 2014/0199314; US 2014/0086919; US 2016/0263117; US2016/0115167; US2017/0197968; US2017/0190705; US2017/0305883; US 2018/0021340; and US 2018/0118835; and PCT Publication Nos. WO 2017/216724; WO 2018/136634; WO 2018/053234; WO 2018/185341; WO 2016/146651; and WO 2018/200855; which are incorporated herein by reference.

Efficient iron signaling via the BMP-SMAD signaling pathway involves auxiliary factors, such as the diferric transferrin (Tf) sensor transferrin receptor 2 (TfR) to stimulate hepcidin expression (FIG. 12). In some embodiments, a hepcidin antagonist of the present disclosure is a transferrin antagonist, which antagonizes hepcidin function by binding transferrin and/or transferrin receptor 2 to inhibit activation of the BMP-SMAD signaling pathway. In some embodiments, the transferrin antagonist is an antisense oligonucleotide targeting Tf and/or TfR, such as siTfR2 (see, e.g., U.S. Pat. No. 9,228,188, which is incorporated herein by reference).

As detailed in the above, STAT3 is a transcriptional regulator of HAMP expression. Accordingly, in some embodiments, the HAMP antagonist is a JAK-STAT signaling pathway inhibitor. In some embodiments, the JAK-STAT signaling pathway inhibitor is a JAK inhibitor or a STAT inhibitor. In some embodiments, the JAK inhibitor is selective for one or both of subtypes JAK1 and JAK2 (e.g., a JAK1/2 inhibitor). In some embodiments, the STAT inhibitor is a STAT3 inhibitor. Examples of JAK1/2 and STAT3 inhibitors include, without limitation, ruxolitinib, fedratinib, momelotinib, pacritinib, INCB039110, AG490, and PpYLKTK (SEQ ID NO: 130).

The JAK-STAT3 signaling pathway is activated by the inflammatory cytokine IL-6. The binding of IL-6 to an IL-6 receptor (IL-6R) triggers receptor dimerization on hepatocytes, which leads to activation of the JAK-STAT3 signaling pathway (FIG. 12). Accordingly, in some embodiments, the JAK-STAT signaling pathway inhibitor is an IL-6 antagonist, which antagonizes hepcidin function by binding IL-6 and/or an IL-6 receptor to inhibit activation of the JAK-STAT3 signaling pathway. In some embodiments, the IL-6 antagonist is selected from the group consisting of Infliximab, Curcumin, 3,3'-Diindolyl-methane, Tocilizumab, and Siltuximab. Additional examples of IL-6 and IL-6R inhibitors that may be useful in certain methods provided herein are provided, for example, in U.S. Patent Publication No. US 2017/0029499, which is incorporated herein by reference.

Any of the anti-HJV antibodies disclosed herein can also be used for detecting presence of HJV (e.g., soluble HJV) in vitro or in vivo. Results obtained from such detection methods can be used for diagnostic purposes (e.g., diagnosing diseases associated with HJV) or for scientific research purposes (e.g., identifying new HJV secreting cell types, studying bioactivity and/or regulation of secreted HJV). For assay uses such as diagnostic uses, an anti-HJV antibody as described herein may be conjugated with a detectable label (e.g., an imaging agent such as a contrast agent) for detecting presence of HJV (e.g., soluble HJV), either in vivo or in vitro. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker.

Conjugated or attached can include covalent or noncovalent bonding as well as other forms of association, such as entrapment, e.g., of one entity on or within the other, or of either or both entities on or within a third entity, such as a micelle.

In other embodiments, an anti-HJV antibody as described herein can be attached to a detectable label, which is a compound that is capable of releasing a detectable signal, either directly or indirectly, such that the aptamer can be detected, measured, and/or qualified, in vitro or in vivo. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the aptamer, directly or indirectly, by conventional methods.

In some embodiments, the detectable label is an agent suitable for detecting HJV expressing cells in vitro, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99}$mTc Mebrofenin, and $^{99}$mTc Red Blood Cells, $^{123}$I Sodium iodide, $^{99}$mTc Exametazime, $^{99}$mTc Macroaggregate Albumin, $^{99}$mTc Medronate, $^{99}$mTc Mertiatide, $^{99}$mTc Oxidronate, $^{99}$mTc Pentetate, $^{99}$mTc Pertechnetate, $^{99}$mTc Sestamibi, $^{99}$mTc Sulfur Colloid, $^{99}$mTc Tetrofosmin, Thallium-201, or Xenon-133.

The reporting agent can also be a dye, e.g., a fluorophore, which is useful in detecting a disease mediated by HJV expressing cells in tissue samples.

To perform a diagnostic assay in vitro, an anti-HJV antibody can be brought in contact with a sample suspected of containing HJV, e.g., HJV expressing cells or soluble HJV in disease microenvironment. The antibody and the sample may be incubated under suitable conditions for a suitable period to allow for binding of the antibody to the HJV antigen. Such an interaction can then be detected via routine methods, e.g., ELISA, histological staining or FACS.

To perform a diagnostic assay in vivo, a suitable amount of anti-HJV antibodies, conjugated with a label (e.g., an imaging agent or a contrast agent), can be administered to a subject in need of the examination. Presence of the labeled antibody can be detected based on the signal released from the label by routine methods.

To perform scientific research assays, an anti-HJV antibody can be used to study bioactivity of HJV, detect the presence of HJV intracellularly, and or regulating the effect of HJV. For example, a suitable amount of anti-HJV can be brought in contact with a sample (e.g. a new cell type that is not previously identified as HJV producing cells) suspected of producing HJV. The cells are permeabilized prior to contacting the anti-HJV antibody. The antibody and the sample may be incubated under suitable conditions for a suitable period to allow for binding of the antibody to the HJV antigen. Such an interaction can then be detected via routine methods, e.g., ELISA, histological staining or FACS.

VI. Kits for Therapeutic and Diagnostic Applications

The present disclosure also provides kits for the therapeutic or diagnostic applications as disclosed herein. Such kits can include one or more containers comprising an anti-HJV antibody, e.g., any of those described herein.

In some embodiments, the kit can comprise instructions for use in accordance with any of the methods described herein. The included instructions can comprise a description of administration of the anti-HJV antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-HJV antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like.

Also contemplated are packages for use in combination with a specific device, such as an infusion device, such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-HJV antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Also provided herein are kits for use in detecting hemojuvelin in a sample. Such a kit may comprise any of the anti-HJV antibodies described herein. In some instances, the anti-HJV antibody can be conjugated with a detectable label as those described herein. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

Alternatively or in addition, the kit may comprise a secondary antibody capable of binding to anti-HJV antibody. The kit may further comprise instructions for using the anti-HJV antibody for detecting hemojuvelin.

EXAMPLES

Example 1: Anti-HJV Antibodies Generation and Characterization

From rats immunized with human hemojuvelin, hybridoma clones capable of binding to human hemojuvelin were identified. The anti-hemojuvelin monoclonal antibodies (mAb with rat IgG1/κ) were humanized by CDR grafting (hHA antibodies with hIgG1 constant region carrying the L234A, L235A mutations). Affinity matured anti-HJV (e.g., HA-001 to HA-0il) in vitro yeast display assay. A general process for generation of humanized affinity matured anti-HJV antibodies is illustrated in FIG. 1A.

Binding affinities of the anti-HJV antibodies to soluble human RGMa, Rat RGMa and human RGMc were measured by BIAcore analysis. Table 4 shows the affinity of the anti-hemojuvelin antibodies to human RGMa. Table 5 shows the affinity of the anti-hemojuvelin antibodies to rat RGMa. Table 6 shows the affinity of the anti-hemojuvelin antibodies to human RGMc.

TABLE 4

Binding Affinity (by BIAcore) of anti-HJV antibodies to Human RGMa

| Ab Name | $K_a$ (1/MS) | $K_d$ (1/s) | KD (M) |
|---|---|---|---|
| hHA-001 | 1.8E+06 | 6.7E−05 | 3.8E−11 |
| hHA-002 | 1.4E+06 | 5.0E−05 | 3.7E−11 |
| hHA-003 | 1.1E+06 | 1.4E−04 | 1.2E−10 |
| hHA-004 | 1.4E+06 | 2.2E−05 | 1.5E−11 |
| hHA-005 | 1.9E+06 | 2.5E−04 | 1.3E−10 |
| hHA-006 | 1.2E+06 | 1.4E−04 | 1.2E−10 |
| hHA-007 | 5.9E+05 | 8.9E−05 | 1.5E−10 |
| hHA-008 | 8.7E+05 | 2.7E−05 | 3.1E−11 |
| hHA-009 | 8.6E+05 | 4.0E−04 | 4.7E−10 |
| hHA-010 | 8.5E+05 | 1.0E−04 | 1.2E−10 |
| hHA-011 | 9.3E+05 | 9.9E−05 | 1.1E−10 |
| hHA | 6.0E+06 | 2.2E−03 | 3.7E−09 |
| HA | 1.2E+06 | 2.9E−03 | 2.4E−09 |

TABLE 5

Binding Affinity (by BIAcore) of anti-HJV antibodies to rat RGMa

| Ab Name | $K_a$ (1/MS) | $K_d$ (1/s) | KD (M) |
|---|---|---|---|
| hHA-001 | 1.2E+06 | 3.6E−05 | 3.1E−11 |
| hHA-002 | 1.0E+06 | 5.5E−05 | 5.3E−11 |
| hHA-003 | 8.7E+05 | 3.1E−05 | 3.6E−11 |
| hHA-004 | 1.1E+06 | <1e−6 | <9.4e−13 |
| hHA-005 | 1.4E+06 | 2.1E−04 | 1.5E−10 |
| hHA-006 | 9.4E+05 | 3.0E−05 | 3.2E−11 |
| hHA-007 | 5.1E+05 | <1e−6 | <2.0e−12 |
| hHA-008 | 6.6E+05 | <1e−6 | <1.5e−12 |
| hHA-009 | 6.8E+05 | 2.1E−04 | 3.1E−10 |
| hHA-010 | 6.6E+05 | 2.6E−05 | 3.9E−11 |
| hHA-011 | 7.0E+05 | 5.2E−05 | 7.4E−11 |
| hHA | 8.3E+05 | 1.7E−03 | 2.1E−09 |
| HA | 8.3E+05 | 2.5E−03 | 3.0E−09 |

TABLE 6

Binding Affinity (by BIAcore) of anti-HJV antibodies to Human RGMc

| Ab Name | $K_a$ (1/MS) | $K_d$ (1/s) | KD (M) |
|---|---|---|---|
| hHA-001 | 1.08E+07 | 1.65E−03 | 1.6E−10 |
| hHA-002 | 7.65E+06 | 1.70E−03 | 2.25E−10 |
| hHA-003 | 8.10E+06 | 2.40E−03 | 3E−10 |
| hHA-004 | 7.85E+06 | 1.04E−03 | 1.3E−10 |
| hHA-005 | 4.15E+07 | 1.36E−02 | 3.2E−10 |
| hHA-006 | 6.65E+06 | 2.55E−03 | 3.85E−10 |
| hHA-007 | 5.05E+06 | 2.15E−03 | 4.25E−10 |
| hHA-008 | 3.95E+06 | 3.90E−04 | 1.05E−10 |
| hHA-009 | 1.55E+07 | 1.07E−02 | 7.1E−10 |
| hHA-010 | 9.90E+06 | 4.40E−03 | 4.45E−10 |
| hHA-011 | 5.05E+06 | 1.40E−03 | 2.85E−10 |
| hHA | 8.3E+05 | | 2.1E−08 |

Within these antibodies, at lease hHA-004, hHA-008, hHA-009 and hHA-011 showed strong binding to human RGMc, and were selected for further testing. Sensorgrams by BIAcore analysis of antibodies HA, hHA-004, hHA-008, hHA-009 and hHA-011 are shown in FIGS. 1B-1G. hHA-008 was further tested for its binding affinity to human RGMa, Cyno RGMa, Rat RGMa, human RGMc, Cyno RGMc, Rat RGMc, and human RGMb, and the respective binding affinity is shown in Table 7. hHA-008 showed high affinity binding to human RGMa and RGMc with strong cross-reactivity to cyno and rodent species.

TABLE 7

Binding affinities of hHA-008 to human RGMa, Cyno RGMa, Rat RGMa, human RGMc, Cyno RGMc, Rat RGMc, and Human RGMb.

| RGM antigen | hHA-008 | | | hHA | | |
|---|---|---|---|---|---|---|
| in solution | ka (1/Ms) | kd (1/s) | KD (M) | ka (1/Ms) | kd (1/s) | KD (M) |
| Human RGMa | 4.9E+05 | 3.6E−05 | 7.4E−11 | 2.7E+05 | 2.3E−03 | 8.3E−09 |
| Cyno RGMa | 5.5E+05 | 3.5E−04 | 6.4E−10 | 2.1E+05 | 6.6E−04 | 3.1E−09 |
| Rat RGMa | 3.1E+05 | 3.6E−05 | 1.2E−10 | 2.3E+05 | 2.1E−03 | 9.1E−09 |
| Human RGMc | 2.5E+06 | 2.9E−04 | 1.2E−10 | 1.4E+06 | n/a | 4.0E−08* |
| cyno RGMc | 2.6E+06 | 3.1E−04 | 1.2E−10 | 1.8E+06 | n/a | 3.2E−08* |
| Rat RGMc | 1.4E+06 | 3.2E−04 | 2.3E−10 | | | 6.6E−08** |
| Human RGMb | no significant binding | | | no significant binding | | |

Figure 2A:
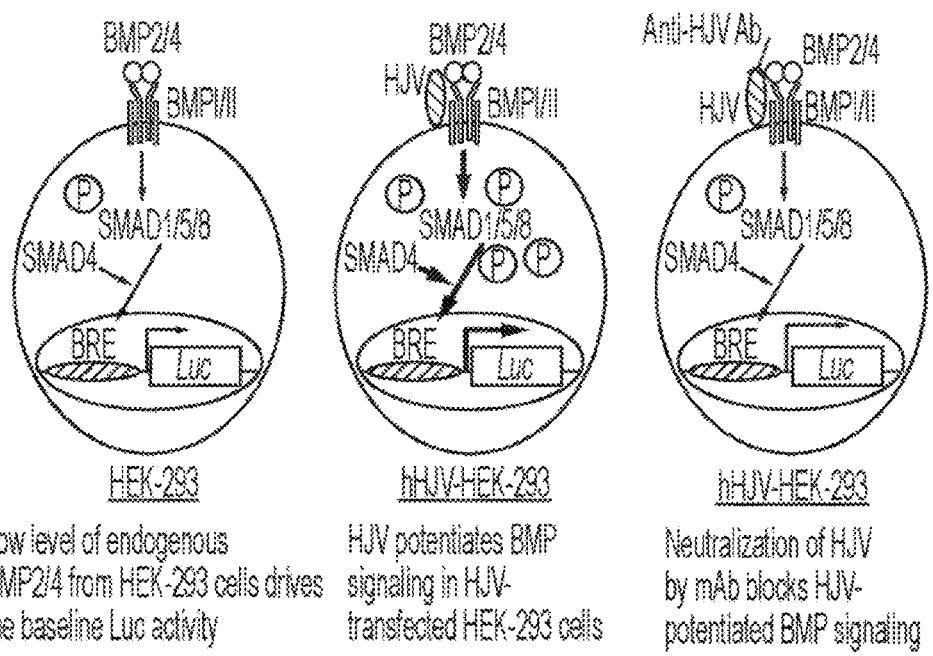
FIGS. 2A-2C are graphs showing the BMP reporter gene assay for anti-HJV antibodies.

*Data for the hHA with human and cyno RGMc was fitted to a two-state model. $k_{a1}$ represents the Ab Ag association in a two-state binding model
**Data for the hHA with Rat RGMc was fitted to a steady state affinity model The RGMc (HJV) BMP reporter gene assay was used for screening and characterization potency of anti-HJV antibodies in blocking membrane-bound RGMc induced BMP/Smad1/5/8 signaling. The assay is directly related to the mechanism of action of the anti-HJV mAbs in inhibiting RGMc/BMP/Smad1/5/8 signaling pathway that is responsible for induction of iron hormone hepcidin gene expression. The principle of HJV BMP reporter assay is illustrated in FIG. 2A.

The BRE-Luc reporter gene vector initially described by Korchynskyi and Dijke (J. Biol. Chem. 2002; 277:4883c) was used to transiently transfect porcine kidney epithelial cell line LLC-PK1 with or without co-transfection of an RGMa expression vector by Babbit et al (J. Biol. Chem. 2005; 280:29820) to determine if RGMa expression modulates BMP signaling. In BRE-Luc transiently transfected cells, RGMa was demonstrated to enhance BMP signaling through the Smad1/5/8 signaling pathway, consistent with a role for RGMa as a BMP co-receptor. All RGM members (RGMa, RGMb, and RGMc) act as BMP co-receptor and enhance BMP signaling. The BRE-Luc reporter vector was constructed and established the RGM BMP reporter gene assay in HEK293 cells. Human RGMc expression vector used in the assay was pcDNA-hRGMc.

Figure 2B:
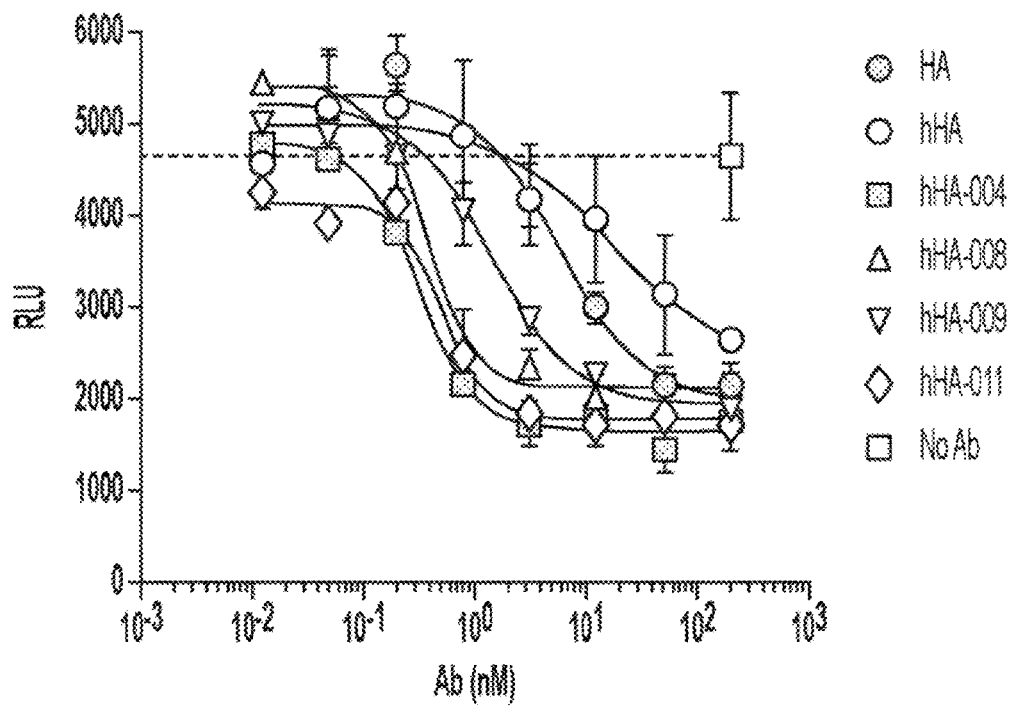

HEK293 cells were cultured in growth media (base media DMEM (Invitrogen catalog #11965-092) containing 10% fetal bovine serum (Gibco #10438-026) and 1% sodium pyruvate (Invitrogen, catalog #11360-070)). To prepare cells for transfection, $9 \times 10^6$ cells HEK293 cells were plated in 10 cm dishes and incubated at 37° C., 5% $CO_2$ for 6 hours. The cells were then transfected using PolyJet (μL): DNA (μg) ratio of 2:1, specifically 20 μl PolyJet (SignaGen, cat #SL100688) with 5 μg pGL[luc2P/BRE/Hygro] DNA (Abbvie) and 5 μg pcDNA-hRGMc (Abbvie) for 16 hours at 37° C., 5% $CO_2$. The media was replaced with fresh HEK293 growth media for 6 hours. The cells were then trypsinized with TrpLE (ThermoFisher, cat #12605010), counted, and plated in 96-well white assay plates (Thermo Scientific Nunclon delta F96, cat #136102) at $1 \times 10^5$ cells per well. The cells were treated with anti-RGMc mAb, anti-BMP2/4 mAb (R&D Systems, cat #MAB3552) (as a positive control), or an isotype control mAb for 16 hours at 37° C., 5% $CO_2$. Luciferase activity was detected using the One-Glo Luciferase kit (Promega, cat #E6120) and measurement on a TopCount luminescence counter. The results showed that anti-HJV antibodies dose-dependently inhibit RGMc potentiated BMP signaling (FIG. 2B). The IC50 (nM) of each of the antibodies tested in inhibiting RGMc signaling in BMP reporter assay are shown in Table 8.

TABLE 8

IC50 of the anti-HJV antibodies in BMP reporter assay for RGMc.

| | HA | hHA | hHA-004 | hHA-008 | hHA-009 | hHA-011 |
|---|---|---|---|---|---|---|
| IC50 (nM) | 5.713 | 17.08 | 0.3124 | 0.3772 | 1.362 | 0.0554 |

Figure 2C:
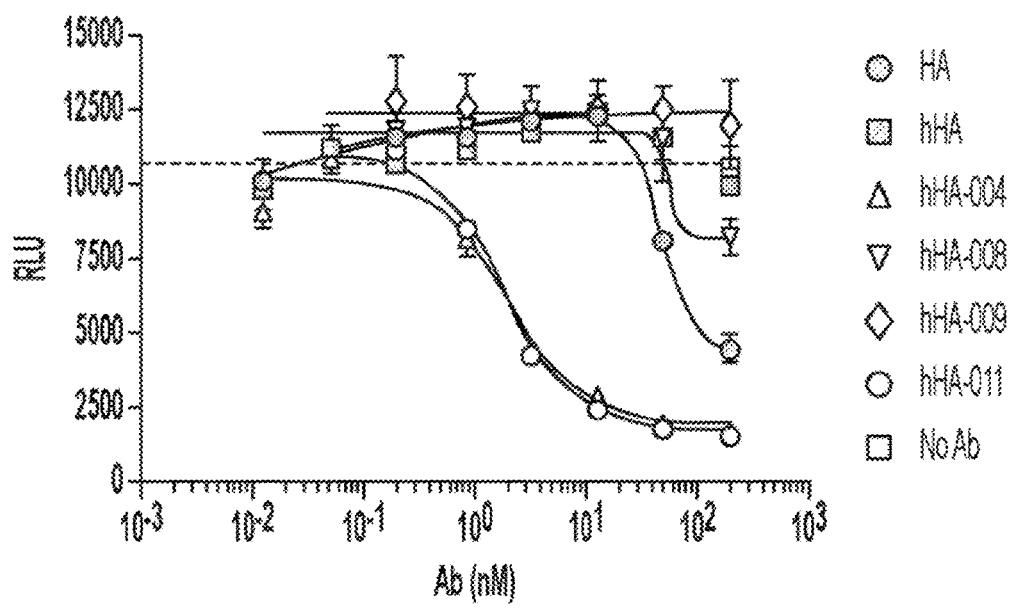

Further, the anti-HJV antibodies were tested for their ability to inhibit RGMa signaling in BMP reporter assays. The hHA-004 and hHA-011 showed potent inhibition on membrane-bound human RGMa in RGMa BMP reporter gene assay, whereas hHA-008 and hHA-009 showed no to minimal inhibition on RGMa activity. The hHA antibody showed no inhibition to membrane bound RGMa. The rat mAb HA showed inhibition on RGMa but to much less extent as compared to hHA-004 and hHA-011. FIG. 2C. The IC50 (nM) of each of the antibodies tested in inhibiting RGMa signaling in BMP reporter assay are shown in Table 9.

TABLE 9

IC50 of the anti-HJV antibodies in BMP reporter assay for RGMa

| | HA | hHA-004 | hHA-008 | hHA-009 | hHA-011 |
|---|---|---|---|---|---|
| IC50 (nM) | 47.63 | 2.014 | ~56.54 | 1.566E−008 | 1.657 |

The above data showed that the potency of the anti-HJV antibodies in neutralizing membrane RGMc in BMP reporter assay correlates with binding affinity on soluble RGMc. A summary of the anti-HJV antibody binding affinity to soluble human RGMc, and their capability to inhibit membrane bound RGMc and RGMa signaling are shown in Table 10.

TABLE 10

Anti-HJV antibody binding affinity to soluble human RGMc, and their capability to inhibit membrane bound RGMc and RGMa signaling.

| IgG | Binding Affinity (BIAcore) on soluble hRGMc | | | Potency on membrane hRGMc (RGMc/BMP reporter assay) | Potency on membrane hRGMa (RGMa/BMP reporter assay) |
|---|---|---|---|---|---|
| | Ka (1/MS) | Kd (1/s) | $K_D$ (M) | $IC_{50}$ (nM) | $IC_{50}$ (nM) |
| hHA-004 | 7.85E+06 | 1.04E−03 | 1.30E−10 | 0.31 | 2 |
| hHA-008 | 3.95E+06 | 3.90E−04 | 1.05E−10 | 0.37 | Minimal inhibition |
| hHA-009 | 1.55E+07 | 1.07E−02 | 7.10E−10 | 1.36 | No inhibition |
| hHA-011 | 5.05E+06 | 1.40E−03 | 2.85E−10 | 0.52 | 1.7 |
| hHA | 8.3E+05 ($k_{a1}$)* | n/a | 2.9E−08 | 17 | No inhibition |
| HA | 3.40E+06 | 5.00E−03 | 1.60E−10 | 5.7 | 48 |

Figure 3:
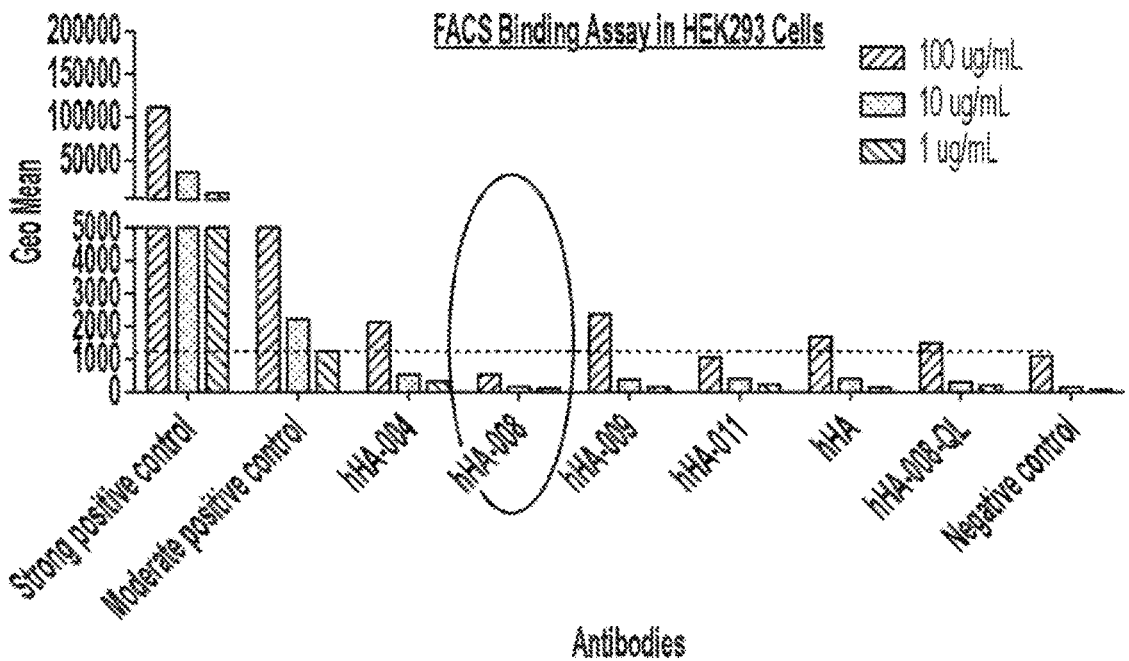
FIG. 3 is a graph showing anti-HJV antibodies non-specific binding to HEK293 cells. Bars from left to right in each group: 100 g/ml, 10 g/ml, and 1 g/ml.

The antibodies, including hHA, hHA-004, hHA-008, hHA-008-QL, hHA-009, and hHA-011 were tested for non-specific cell binding to HEK293 cells by FACS analysis. The data showed hHA and its hHA-008, hHA-008-QL and hHA-011 showed no to minimal non-specific cell binding on HEK293 cells at conc. up to 100 ug/ml. hHA-004 and hHA-009 showed some non-specific cell binding at higher concentrations, but to a much less extent compared to positive control IgGs (FIG. 3)

Figure 4A:
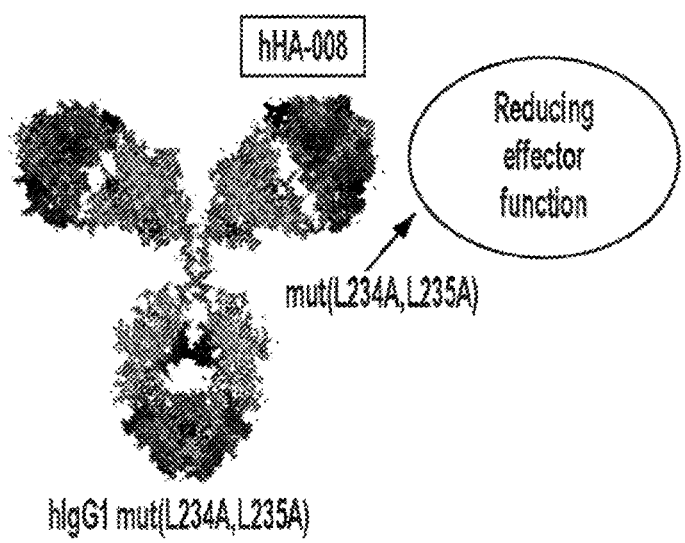
FIGS. 4A-4C are schematic illustrations showing the structure and designs of hHA-008 and hHA-008-QL.
Figure 4B:
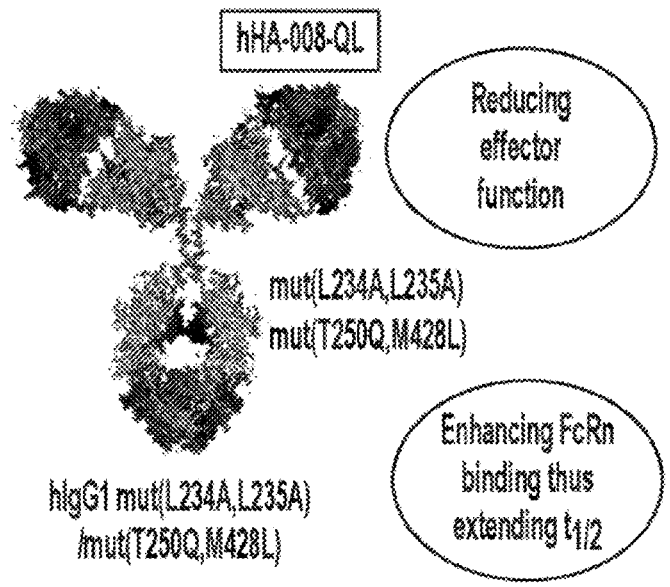
Figure 4C:
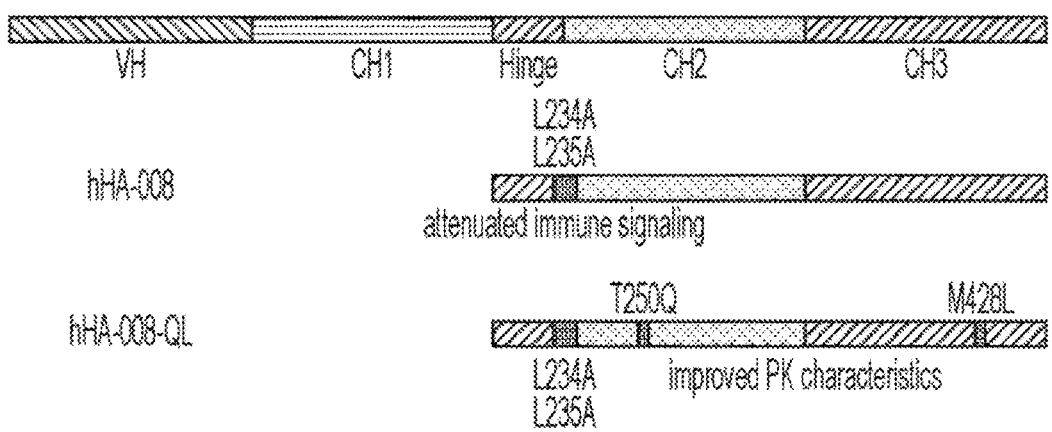

Example 2: Generation of hHA-008-QL hHA-008-QL was developed to prolong IgG serum half-line ($t_{1/2}$). Previous studies have shown that neonatal Fc receptor (FcRn) protects IgG from catabolism, thereby increasing IgG serum half-life. Accordingly, the Fc portion of hHA-008-QL was engineered to have T250Q and M428L mutations (QL mutations) such that it has enhanced binding to FcRn. FIGS. 4A and 4B illustrates the structure of hHA-008 and hHA-008-QL respectively. A further illustration of hHA-008 and hHA-008-QL is shown in FIG. 4C.

First, hHA-008-QL was tested for its RGMa and RGMc binding capabilities, and the data showed that hHA-008-QL had binding affinities to RGMa and RGMc comparable to that of hHA-008 (Table 11)

TABLE 11 hHA-008-QL and hHA-008 binding affinities to RGMa and RGMc

| IgG | huRGMa | | | huRGMc | | |
|---|---|---|---|---|---|---|
| | ka (1/Ms) | kd (1/s) | KD (M) | ka (1/Ms) | kd (1/s) | KD (M) |
| hHA-008-QL (hIgG1mut (LALA)/QL/k) | 4.3E+05 | 3.3E−05 | 7.7E−11 | 2.7E+06 | 3.3E−04 | 1.2E−10 |
| hHA-008 (hIgG1mut(LALA)/k | 5.4E+05 | 4.2E−05 | 7.8E−11 | 3.0E+06 | 3.2E−04 | 1.1E−10 |

Figure 5A:
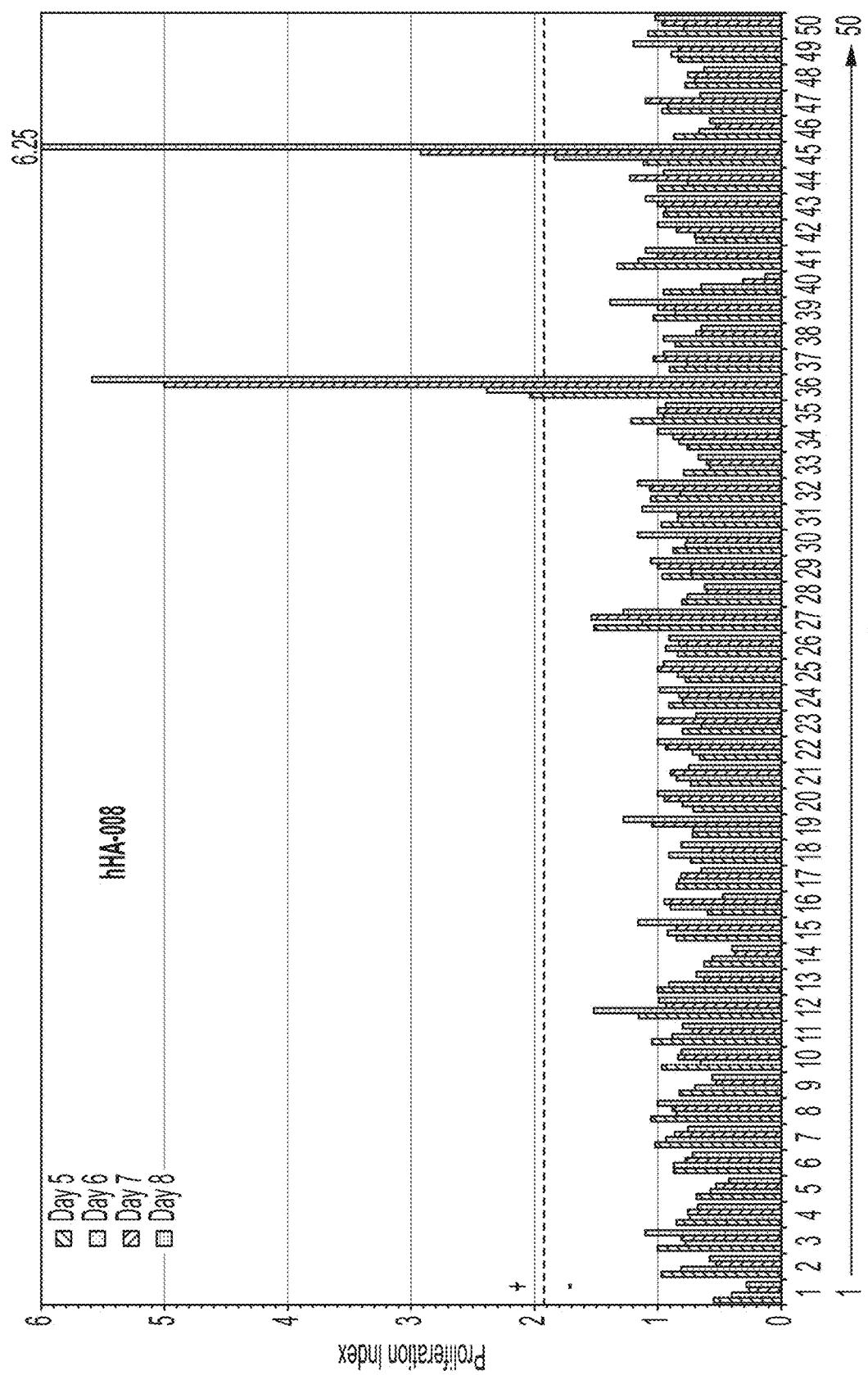
FIGS. 5A-5B are graphs showing the CD4+ T cell response peripheral blood mononuclear cells (PBMCs) challenged with hHA-008 or hHA-008-QL.
Figure 5B:
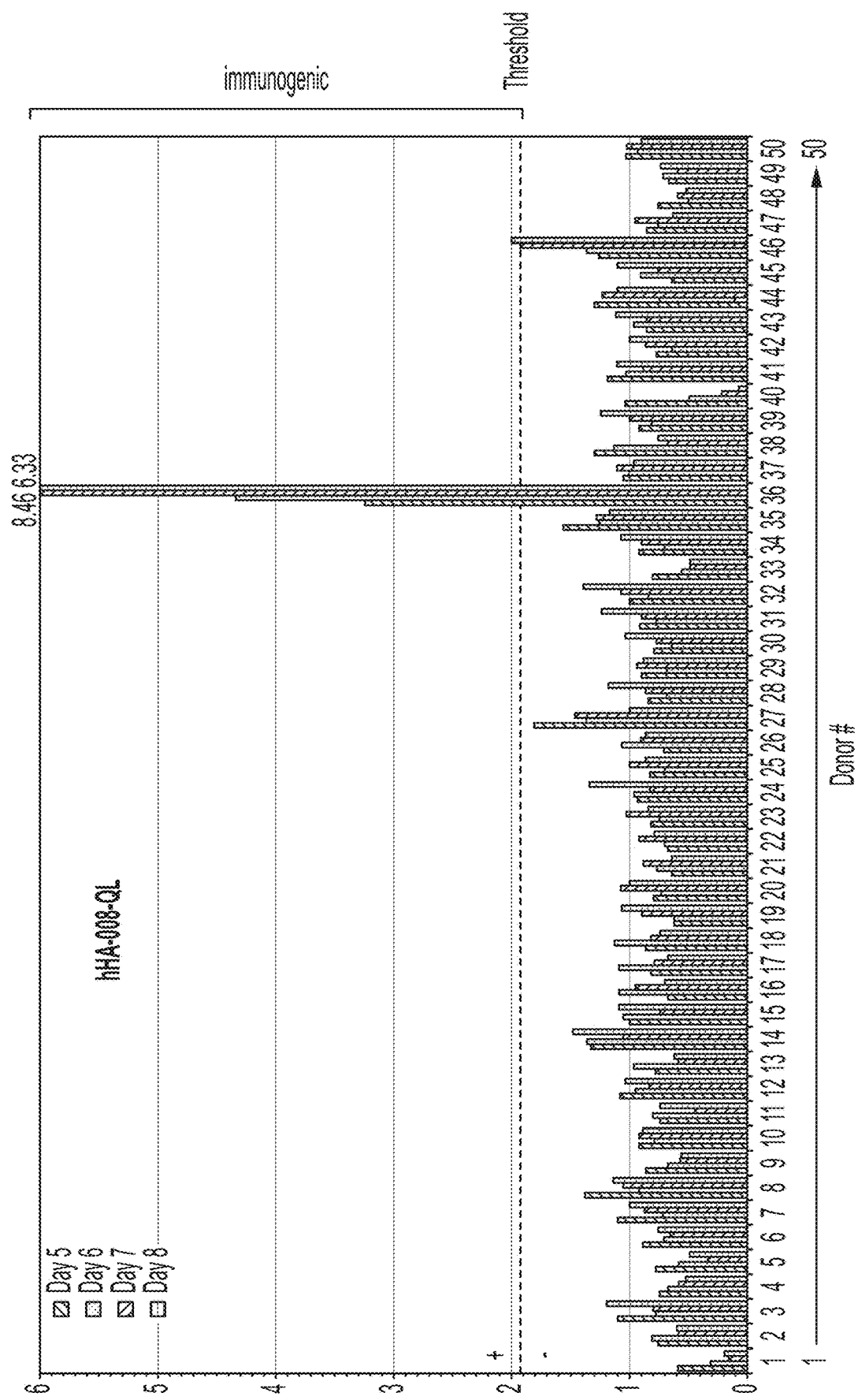

Example 3: Immunogenicity Studies of hHA-008 and hHA-008-QL hHA-008 and hHA-008-QL were tested for their immunogenicity using peripheral blood mononuclear cells (PBMCs) from 50 donors (representing all major HLA0DR and HLA-DQ haplotypes) challenged with hHA-008 or hHA-008-QL in a CD4$^+$ T cell response assay. The results showed only 4% of the 50 donors (2/50) showed a T cell response suggesting that both antibodies have low risk of immunogenicity. In this assay, Herceptin were used as negative control, to which 8% of the donors had a T cell response. Bydureon and keyhole limpet haemocyanin (KLH) were used as positive control. 32% of the donors showed T cell response to Bydureon and 100% donor had a T cell response to KLH. FIGS. 5A-5B showed T cell response in 50 donors for hHA-008 and hHA-008-QL.

Further, FcγR binding was tested for hHA-008 and hHA-008-QL as another parameter for immunogenicity. The control group, wild-type irrelevant IgG1 had significant binding to both the high and low affinity Fc gamma receptors. As expected, the binding of the wild-type irrelevant IgG4 is significantly lower than that of wild-type irrelevant IgG1. Binding to the high affinity and low affinity receptors is significantly reduced for both hHA-008 and hHA-008-QL compared to wild-type IgG1, suggesting low immunogenicity for both antibodies.

Figure 6A:
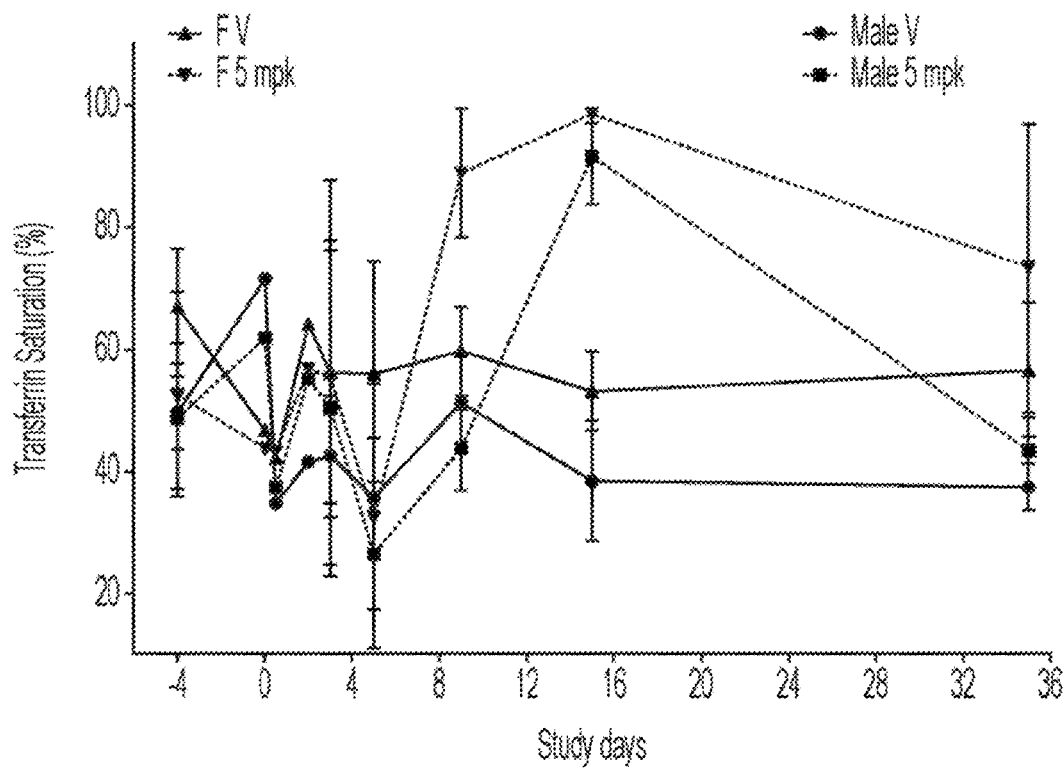
FIGS. 6A-6C are graphs showing PK/PD analysis of hHA-008 in rats and Cynomolgus macaque (cyno).

Example 4: Pharmacokinetics/Pharmacodynamics (PK/PD) Modeling of hHA-008 and hHA-008-QL In an initial study for PK/PD of hHA-008, male rats were treated with a single dose of hHA-008 at 5 mg per kilogram of body weight (mpk) by intravenous injection. Transferrin saturation (TSAT %; determined as the percentage of serum iron over serum total iron binding capacity) were tested over time. The data showed that maximal effect of increased TSAT occurred between 4-8 days post treatment (FIG. 6A).

Figure 6B:
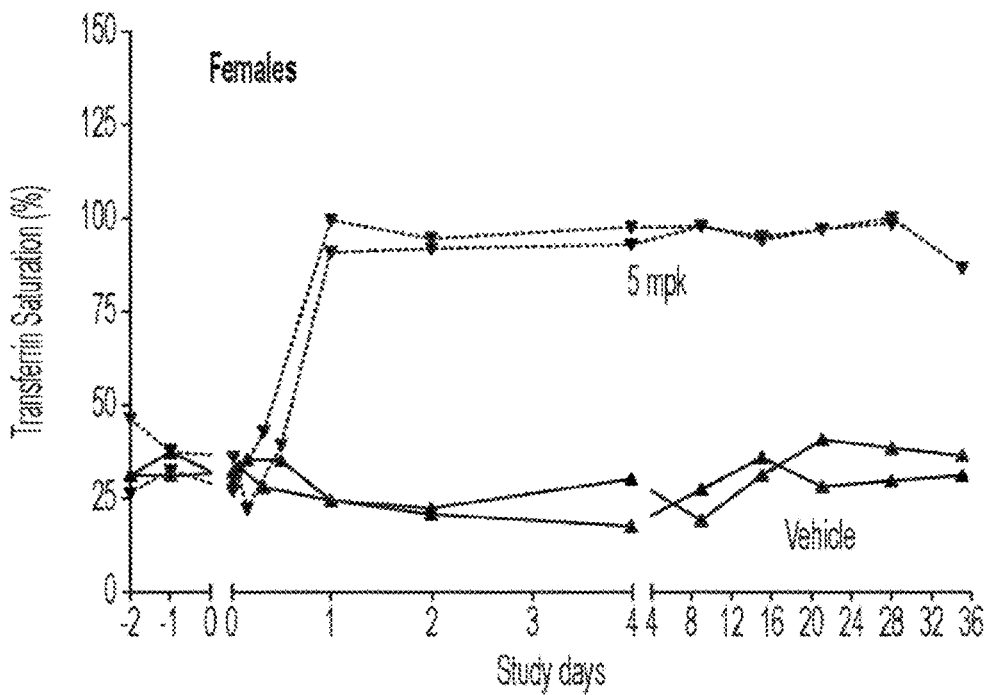
Figure 6C:
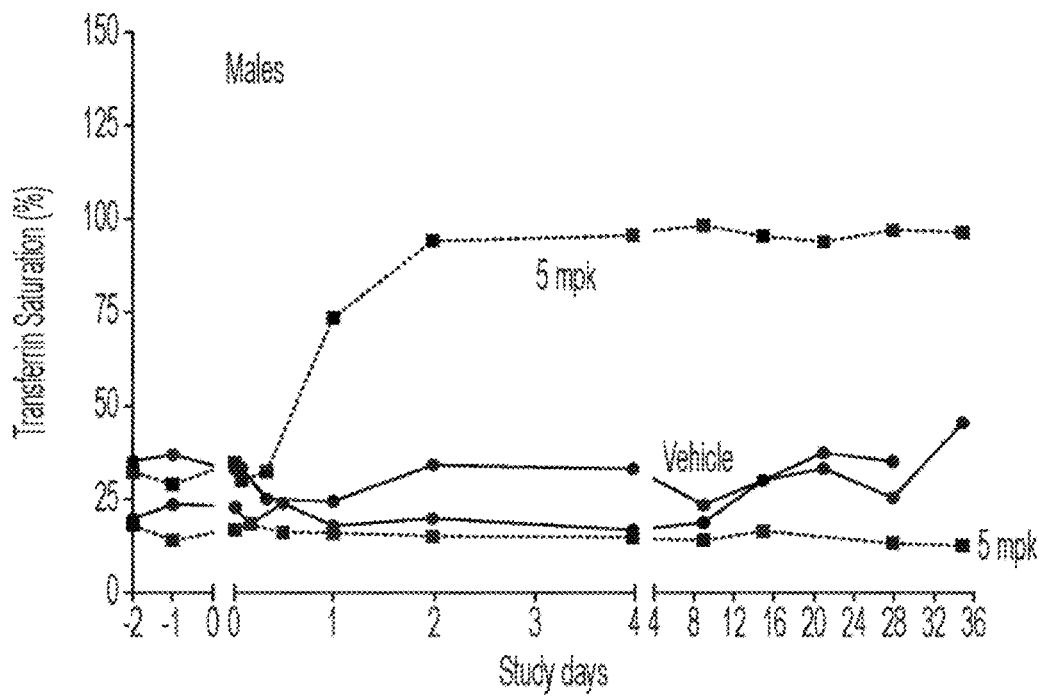

Further, a similar study was conducted in non-human primate Cynomolgus macaque (cyno). Both female (n=2) and male (n=2) cynos received a single dose of hHA-008 at 5 mg per kilogram of body weight (mpk) by intravenous injection. Transferrin saturation (TSAT %) were tested over time. Both female cynos showed maximum effect of increased TSAT % about 1-4 days after injection (FIG. 6B). One of the males showed the same effect, while the other one didn't respond to hHA-008 treatment (FIG. 6C). It was subsequently determined by examining the hematological profile of this male, that the lack of response was the result of this cyno having plasma hepcidin-25 level that was below the limit of detection (below 2 ng/mL). Further, before the injection, this male cyno had a lower baseline TSAT % and serum iron level than other cynos in the group: two days before the injection, it had a baseline TSAT % level at 18% and a serum iron level at 77 µg/dL; one day before the injection, it had a baseline TSAT % level at 14% and a serum iron level at 61 µg/dL. The low baseline TSAT % and serum iron levels, in combination with the low hepcidin-25 levels, was indicative that this male cyno had absolute iron deficiency instead of functional iron deficiency.

Further studies examining the effects of hHA-008 administration in more than 70 cynos revealed that animals having normal baseline serum iron levels (e.g., in the range of 80 µg/dL to 180 µg/dL) and hepcidin-25 levels greater than 2 ng/mL were responsive to hHA-008 treatment in that they exhibited pronounced increase in TSAT % levels shortly after injection (e.g., within 1-2 days post treatment) in response to reduced hepcidin-25 expression.

Figure 7B:
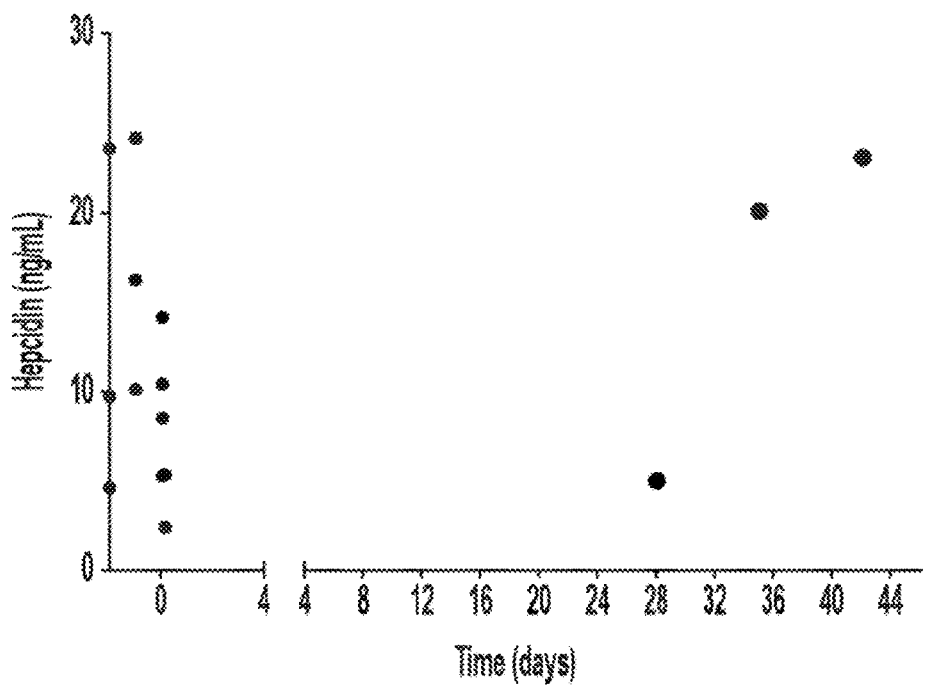
Figure 7C:
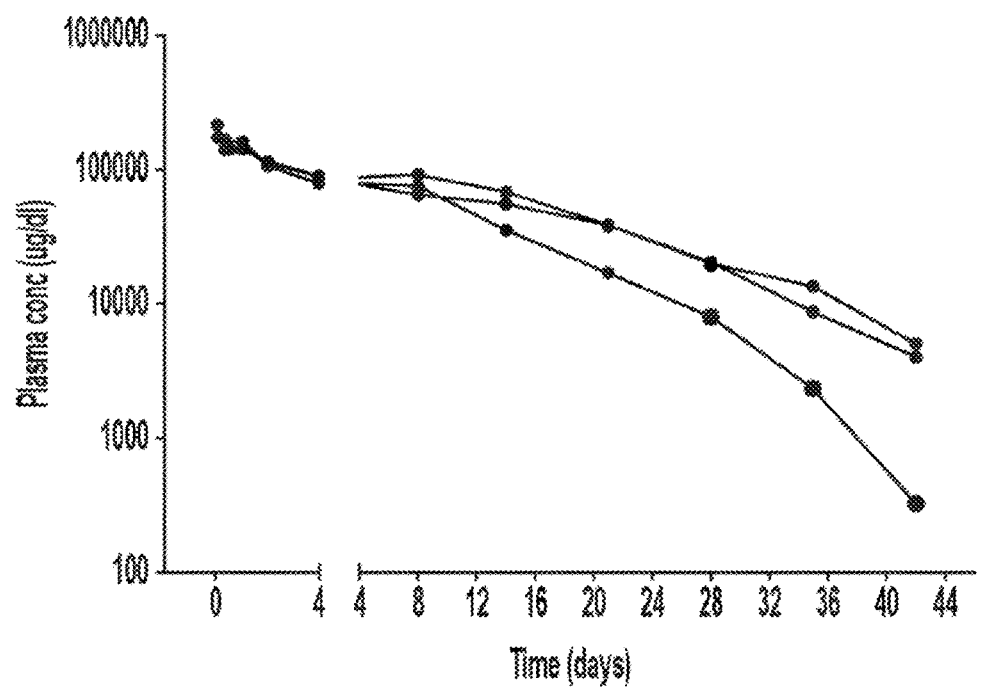

Additional experiments were conducted in cynos. Single dose of 6 mpk of hHA-008 were administered to three cynos via intravenous injection, and TSAT % (determined as serum iron over total iron binding capacity), plasma hepcidin-25 concentration, and hHA-008 concentrations were tested for each animal and time point. Similarly, the data showed that the maximum effect of increased TSAT % occurred 1-4 days after injection ($T_{max}$=14 days), which was consistent with the increase of hHA-008 concentrations. One of the animals had a drastic decline of TSAT % around day 34 (FIG. 7A), which was consistent with the declining of plasma hHA-008 concentration around that time. Plasma hepcidin-25 concentration correlated inversely with the concentrations of hHA-008, in that hepcidin-25 was undetectable after antibody injection, and for the animal which had the drastic decline of TSAT %, hepcidin level increased around the same time (FIG. 7B). In this cyno, hHA-008 had a plasma $t_{1/2}$ of about 5 days. The animal showed decline of TSAT % and increased hepcidin-25 levels at approximately day 34, which correlated well with the decrease of hHA-008 from plasma (FIG. 7C). $T_{1/2}$ of ~7 days in Cyno supports ≥one/month dosing frequency in human.

Figure 7D:
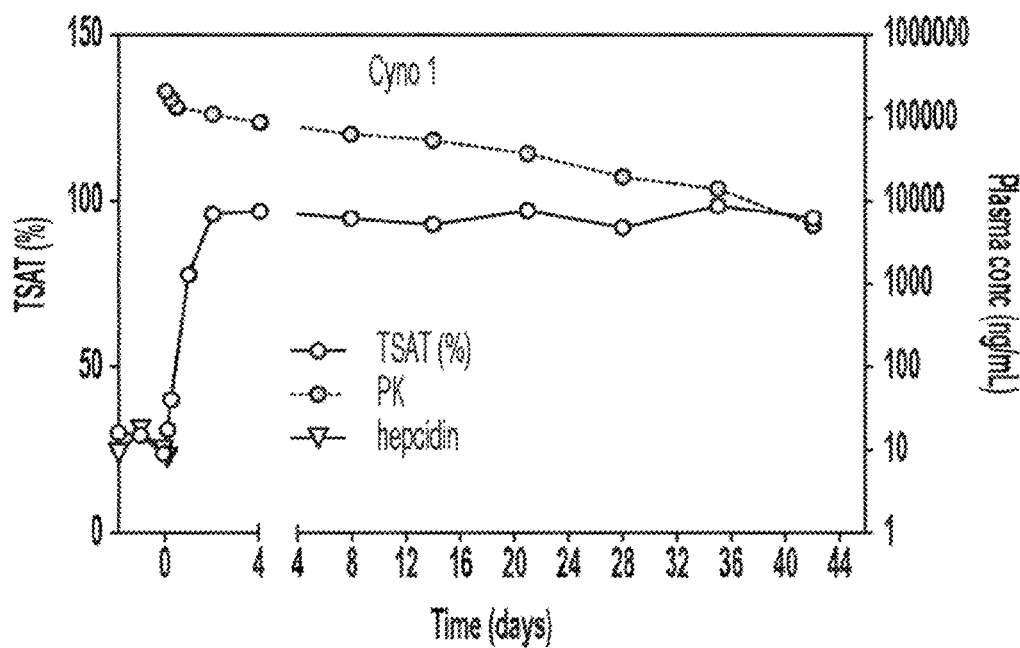
Figure 7E:
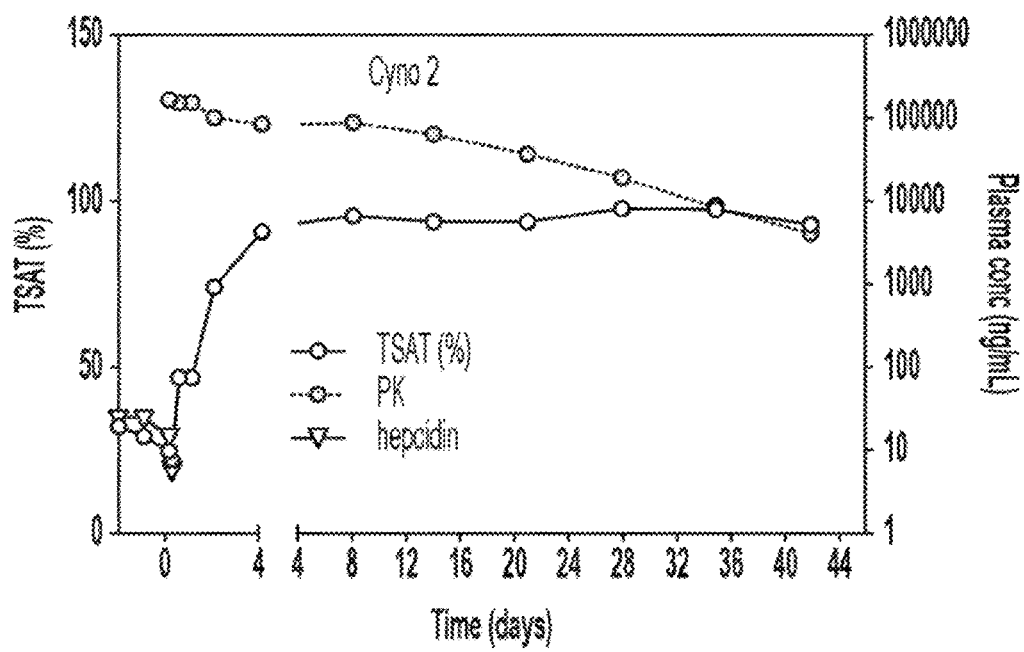
Figure 7F:
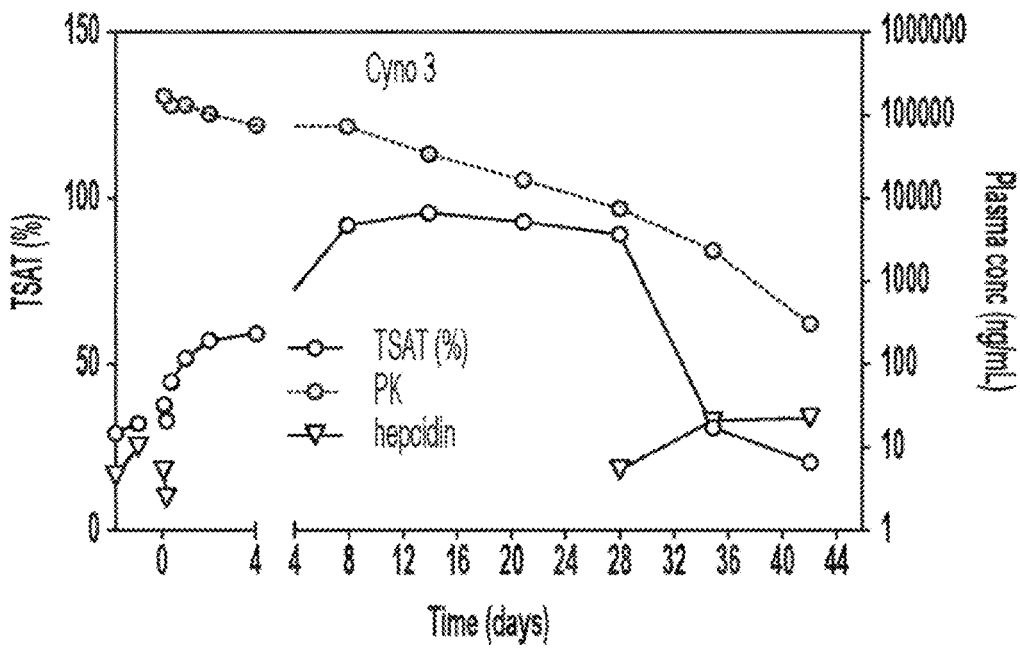
Figure 8A:
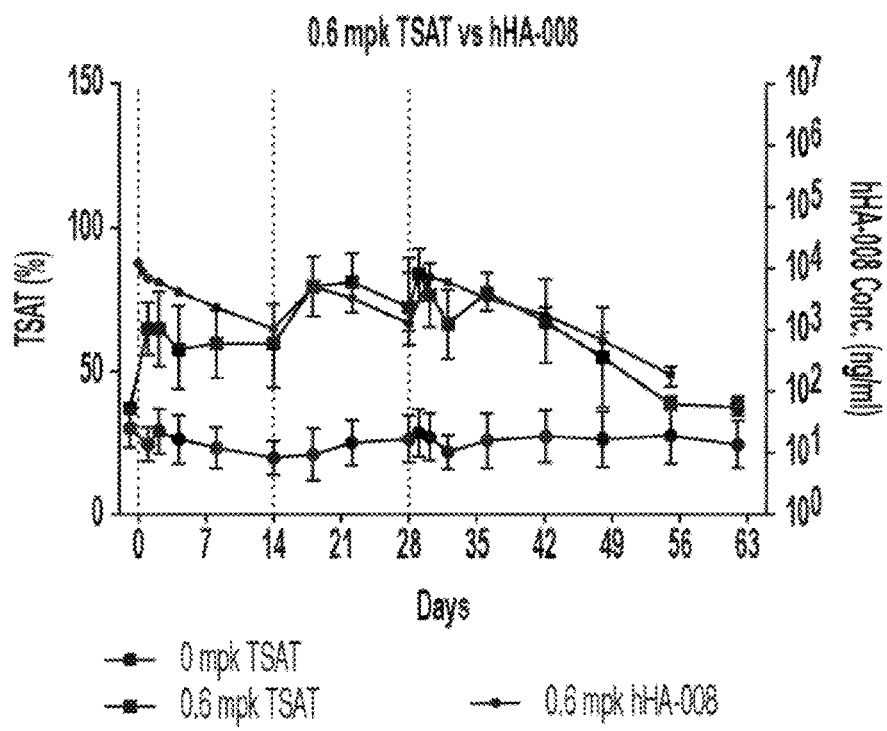
FIGS. 8A-8C show that hHA-008 antibody modulates TSAT % in a dose-dependent manner.
Figure 8B:
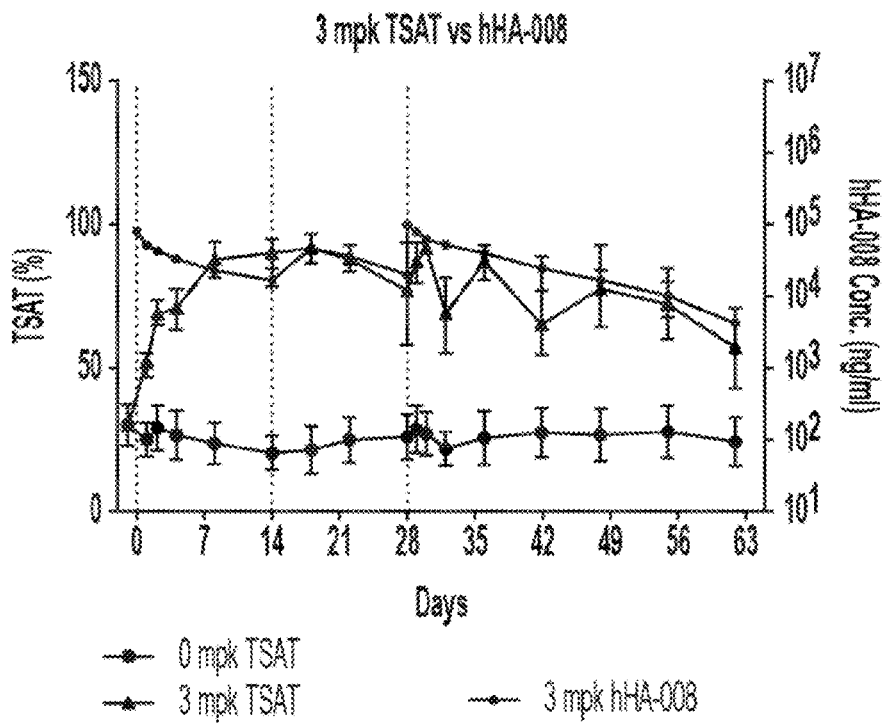
Figure 8C:
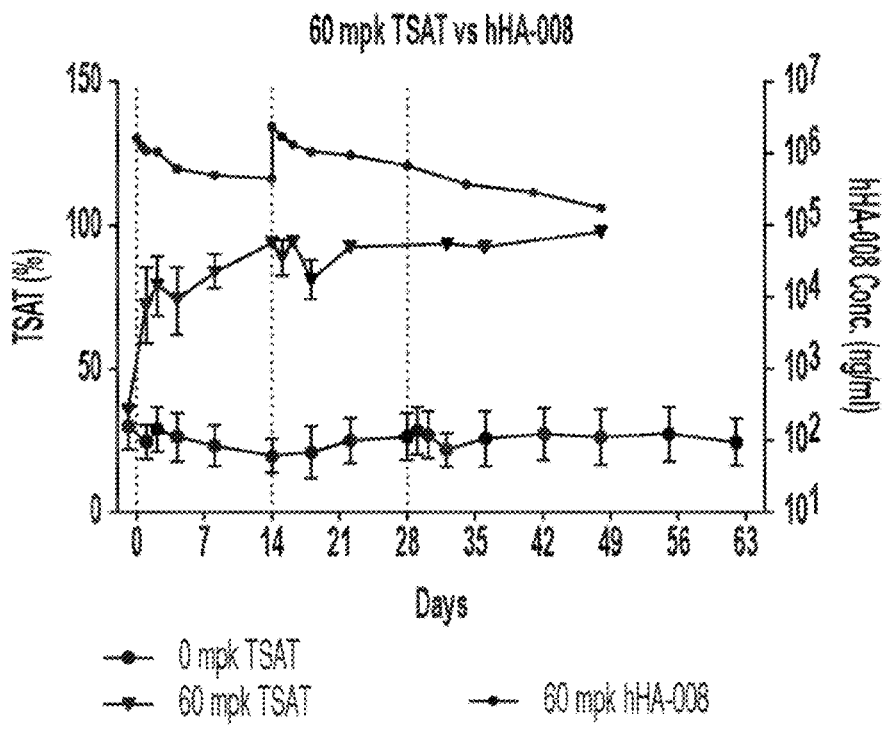

Moreover, hHA-008 had showed robust PK/PD correlation of PK (plasma antibody concentration) to TSAT % and plasma hepcidin-25 concentrations. The results of each tested Cyno are shown in FIG. 7D (Cyno 1), FIG. 7E (Cyno 2), and FIG. 7F (Cyno 3). hHA-008 showed a $t_{1/2}$ of 10.3 days in Cyno 1, $t_{1/2}$ of 8.8 days in Cyno 2, and $t_{1/2}$ of 5.1 days in Cyno 3. Hepcidin level drops to undetectable (<2 ng/ml) after hHA-008 treatment. Interestingly, return of hepcidin level to circulation was well correlated with the $t_{1/2}$ of hHA-008 in Cyno 3 (FIG. 7F).

hHA-008 antibody modulates TSAT % in a dose-dependent manner. Multiple dose studies were conducted in Cynos. The cynos (n=4 per dose level with 2 males and 2 females) were treated with either 0 (vehicle control), 0.6 mpk hHA-008, 3 mpk hHA-008, or 60 mpk hHA-008. The resulting concentrations of hHA-008 and the corresponding TSAT % response are presented in FIG. 8A, FIG. 8B and FIG. 8C for the 0.6, 3 and 60 mpk treatments respectively, all plotted vs the vehicle control. Cynos were dosed every 14 days. Dotted lines represent dose day. TSAT % increased after dosing, and the percent modulation was consistent with the dose levels: at 0.6 mpk, TSAT reached ~60%, and at 3 mpk and 60 mpk, TSAT % was saturated, indicating that hHA-008 modulates TSAT % in a dose dependent manner. Further, after the first dose at 0.6 mpk, TSAT % levels were maintained at ~60%, while at higher dose levels, TSAT % reached 100%, suggesting that TSAT can be modulated by selection of appropriate dose-level/regimen (FIGS. 8A-8C).

Example 5: hHA-008-QL Confers Longer Serum Half-Life and Takes Longer Time to Reach Maximal Effect Compared to hHA-008

Figure 9A:
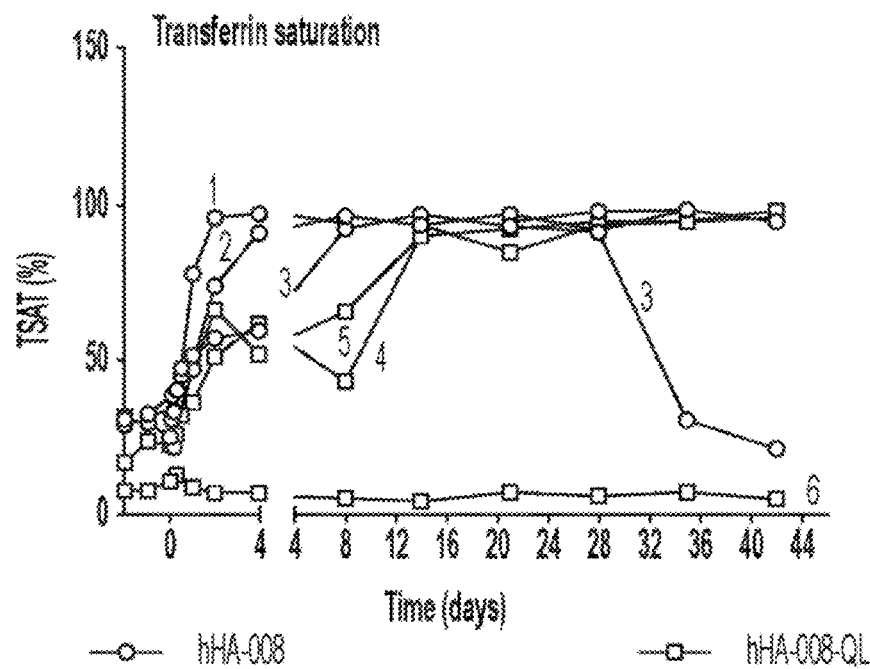
FIGS. 9A-9C are graphs showing the PK/PD comparison between hHA-008 and hHA-008-QL.
Figure 9B:
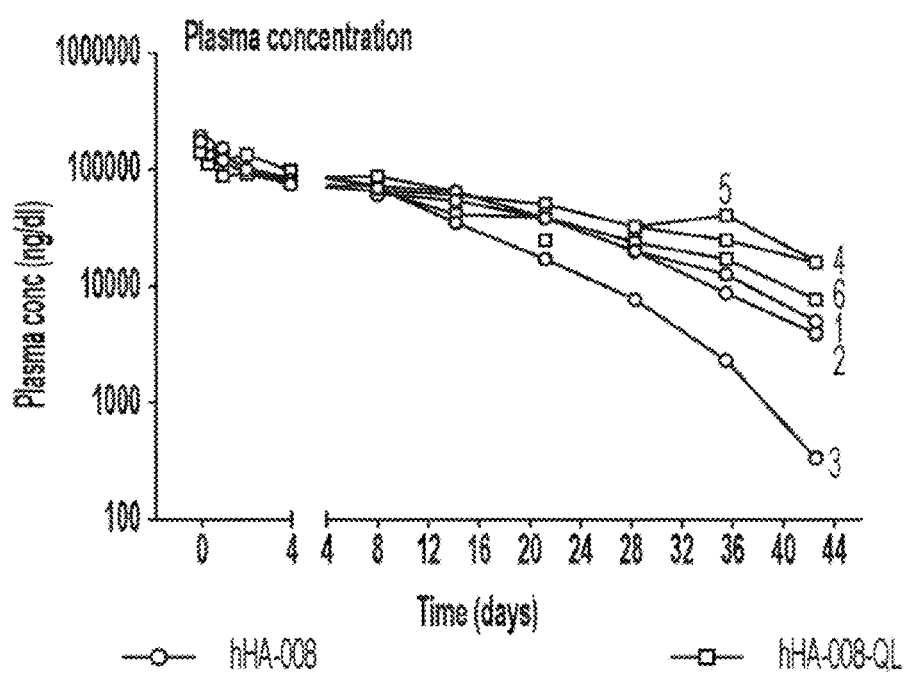
Figure 9C:
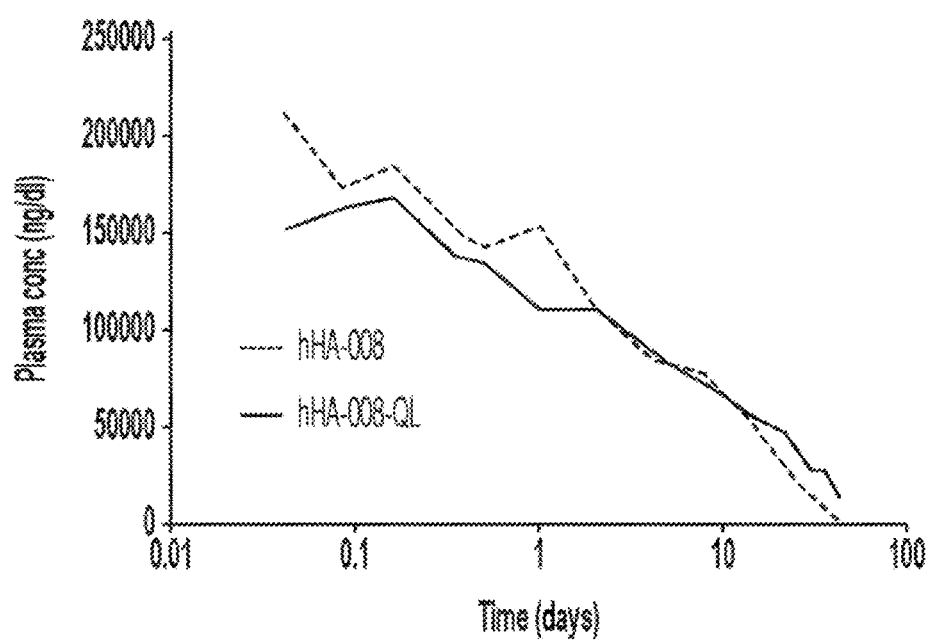

This study was designed to administer hHA-008 or hHA-008-QL at 6 mpk intravenously to Cynos (n=3). Samples were collected from each animal at 48 and 24 hr prior to treatment, and at 0, 0.04, 0.08, 0.167, 0.333, 0.5, 1, 2, 4, 8, 14, 21, 28, 35 and 42 days after treatment. TSAT % and plasma hepcidin-25 level were measured in each sample. The data showed that hHA-008 took shorter time to reach maximal effect ($T_{max}$) of increased TSAT % as compared to hHA-008-QL (FIG. 9A). Note that there was a non-responder in animals treated with hHA-008-QL. As discussed above, the non-responder had low hepcidin levels and low serum iron at base line prior to antibody treatment. On the other hand, hHA-008-QL had longer serum half-life (T½=12.1 days) compared to hHA-008 (T½=6.76 days) (FIG. 9B). Plasma concentrations of both antibodies were measured over time, as shown in FIG. 9C. Peak plasma concentrations were determined. A summary of the data between hHA-008 and hHA-008-QL are shown in Table 12.

TABLE 12 hHA-008 v. hHA-008-QL

| Parameter | Units | hHA-008 | hHA-008-QL |
|---|---|---|---|
| $C_{max}$ | µg/mL | 211.15 | 168.4 |
| $T_{max}$ | days | 0.083 | 2 |
| T ½ | days | 6.76 | 12.1 |

Figure 10A:
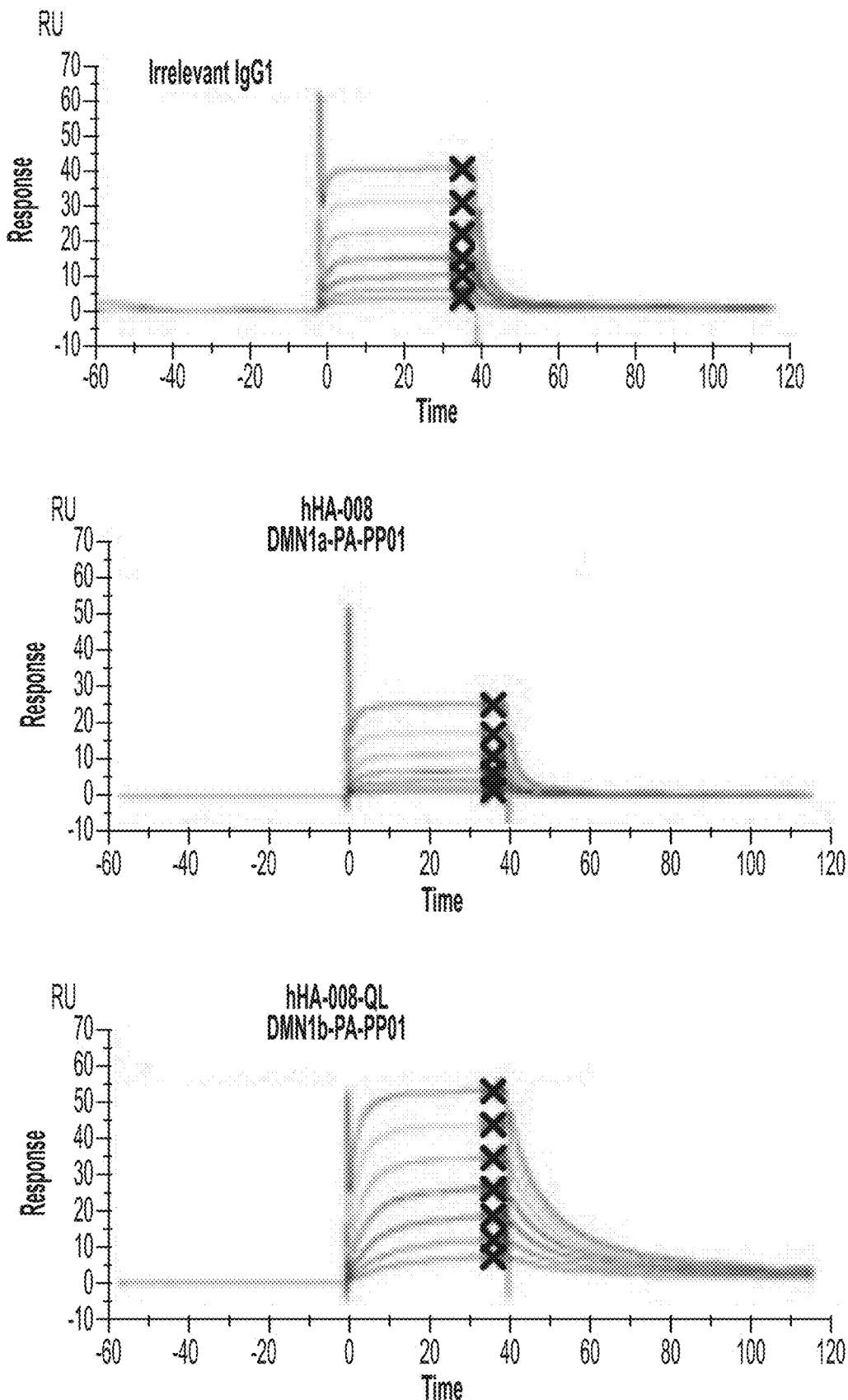
FIGS. 10A-10D are graphs showing binding of FcRn of hHA-008 and hHA-008-QL at pH 6.0 or 7.4.
Figure 10B:
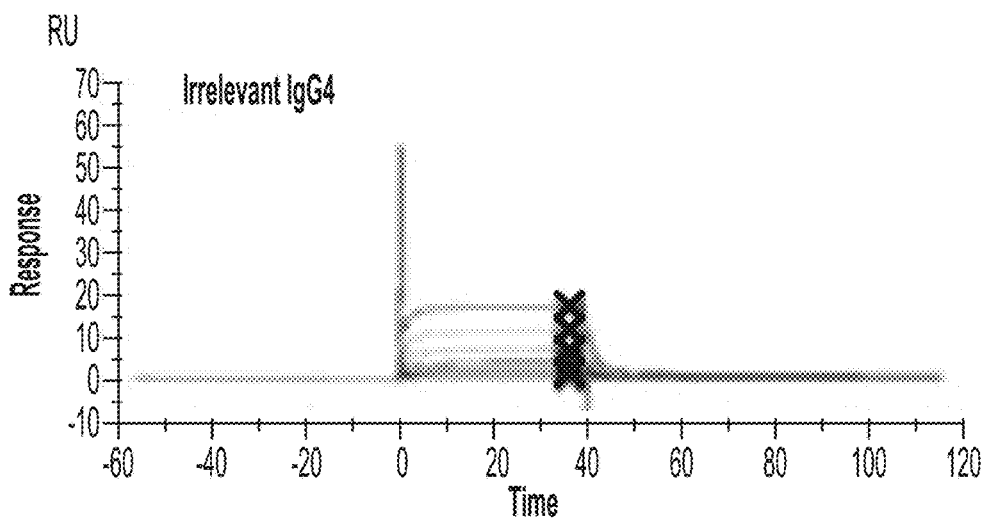
Figure 10B:
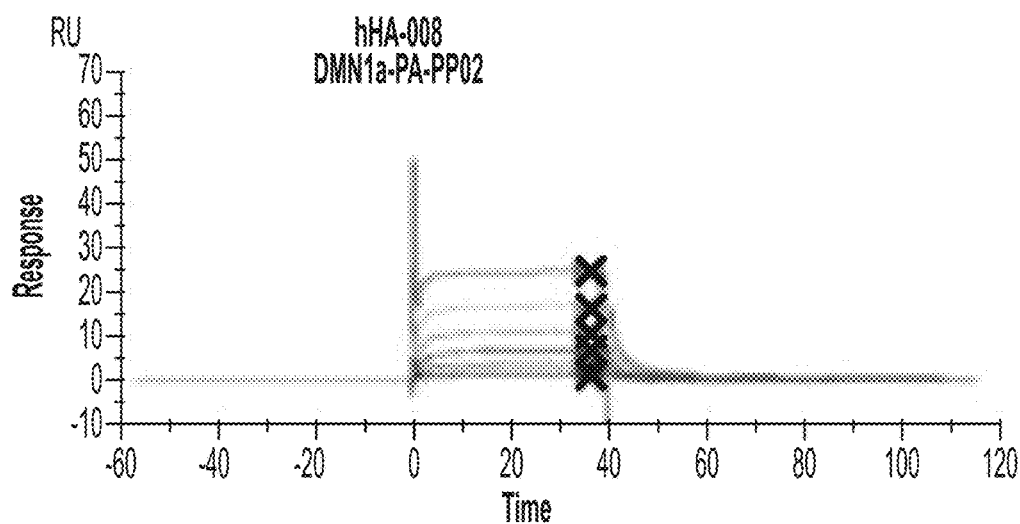
Figure 10B:
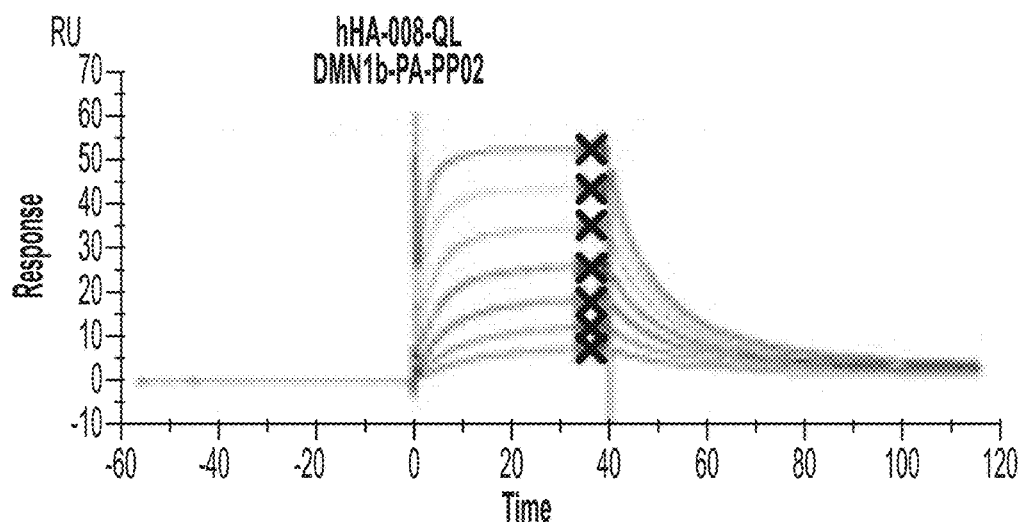
Figure 10C:
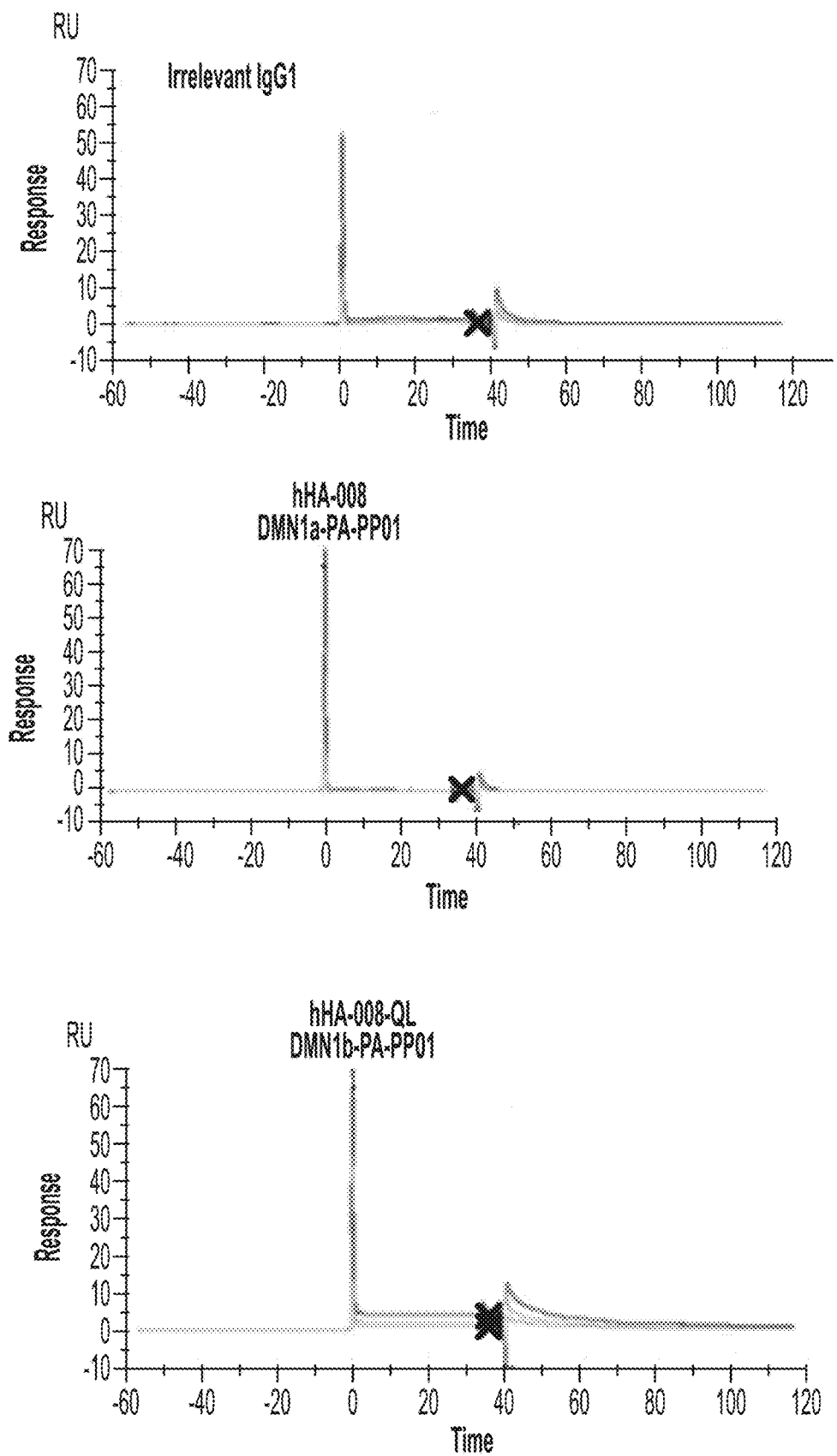
Figure 10D:
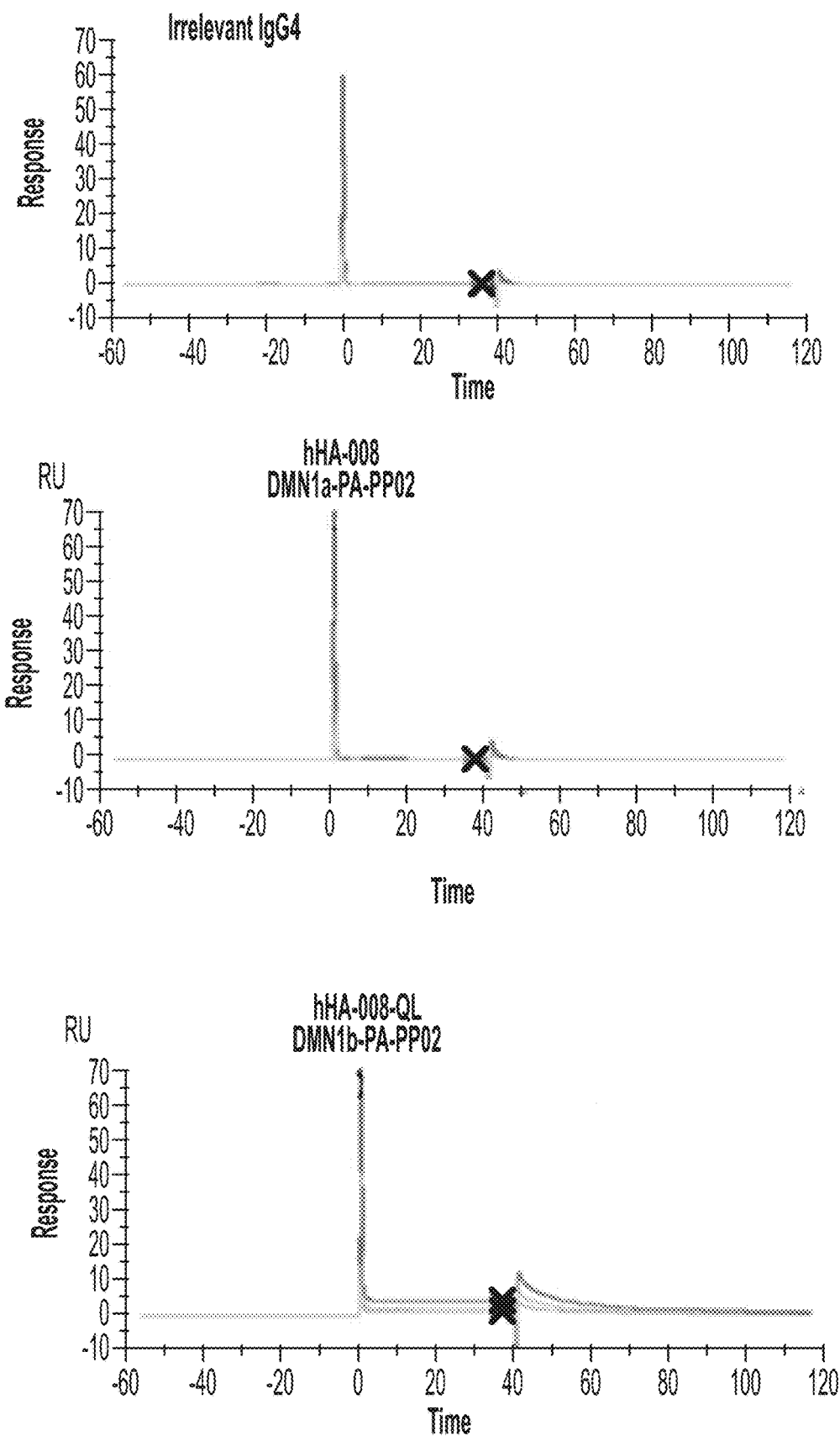

To investigate whether the longer serum life for hHA-008-QL was attributed to higher affinity to FcRn, both antibodies were analyzed for binding to FcRn at pH 6.0 and pH 7.4 using BIAcore. Non-specific IgG1 and IgG4 were used as controls. The dissociation constant (KD) of each of the antibody and the controls to FcRn at pH 6.0 and 7.4 were shown in Table 13, and the response curve were shown in FIGS. 10A-10D. No binding was observed of neither antibodies at pH 7.4 (FIGS. 10C-10D).

TABLE 13

KD for FeRn at pH 6.0 and pH 7.4

|  | KD (M) at pH 6.0 | KD(M) at pH 7.4 |
|---|---|---|
| IgG1 | 1.64E−06 | no binding |
| IgG4 | 3.64E−06 | no binding |
| hHA-008 | 2.95E−06 | no binding |
| hHA-008 | 2.96E−06 | no binding |
| hHA-008-QL | 9.00E−07 | no binding |
| hHA-008-QL | 8.82E−07 | no binding |

The mutations L247A and L248A (Kabat) (L234A and L235A, EU Numbering) do not appear to significantly affect FcRn binding. The overall affinity and response (RMax) for binding of FcRn at pH 6.0 is increased for hHA-008-QL compared to hHA-008, suggesting that the QL mutation confers the longer t ½ via the binding to the receptor.

Figure 11:
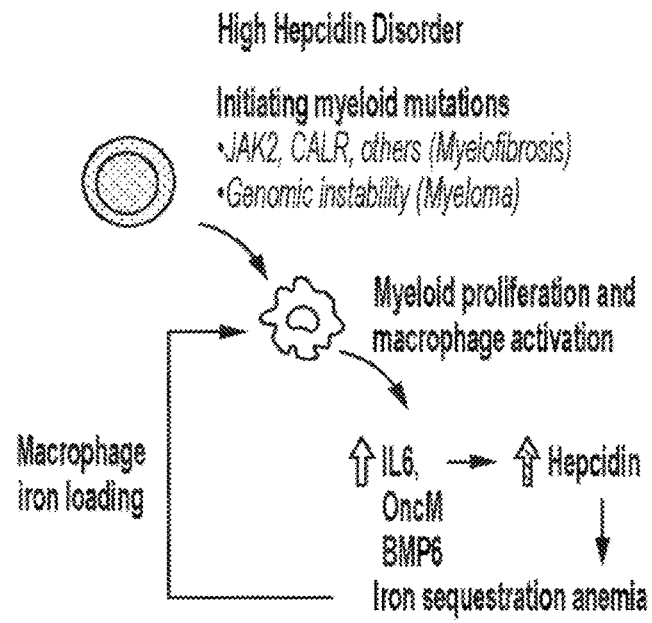
FIG. 11 depicts a myeloproliferation cycle characteristic certain high hepcidin disorders.
Figure 13:
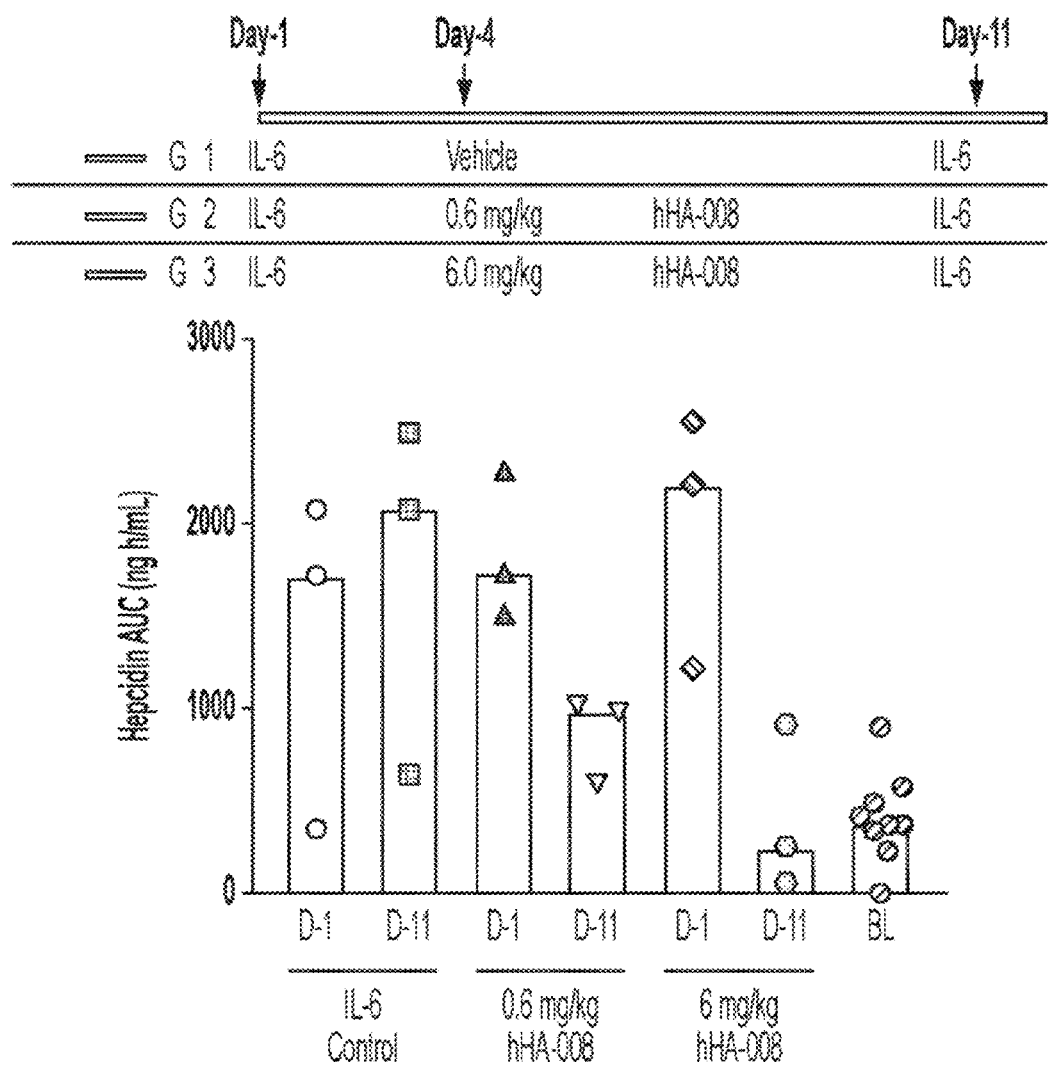
FIG. 13 is a graph showing that IL-6 induces hepcidin expression in Cynos, and hHA-008 treatment prevents inflammation-induced (IL 6) hepcidin-25 increase in a dose-dependent manner in cynos.

Example 6: hHA-008 Decreases IL-6 Induced Hepcidin Expression in Non-Human Primates As depict in FIG. 11, in myelofibrosis, pro-inflammatory cytokines that induce hepcidin synthesis, such as IL-6 and oncostatin-M, are typically increased and associated with iron sequestration, macrophage iron loading, as well as myeloid proliferation and macrophage activation. To test whether IL-6 indeed increases hepcidin expression and whether anti-HJV antibody is capable of inhibiting hepcidin expression induced by IL-6 in non-human primates, cynos were challenged with IL-6 on day 1, and divided into three groups. On day 4, cynos in Group 1 received vehicle control, cynos in Group 2 received hHA-008 antibody at 0.6 mg/kg, and cynos in Group 3 received hHA-008 antibody at 6.0 mg/kg. On day 11, cynos in all three groups were challenged with IL-6 again, and plasma hepcidin-25 in all cynos was measured. As shown in FIG. 13, IL-6 challenge increased plasma hepcidin-25 concentrations on Day 1, compared to pre-challenge baseline (BL) in all three groups of cynos. After the second IL-6 challenge on Day 11, cynos in group 1 showed an increase in plasma hepcidin-25 similar to that observed on Day 1. However, for cynos in groups 2 (0.6 mg/kg hHA-008) and 3 (6 mg/kg hHA-008), the presence hHA-008 prevented the IL-6 induced increase in plasma hepcidin-25 on Day 11 in a dose-dependent manner. That is, hHA-008 was effective in preventing inflammation-induced (IL 6) hepcidin increase in a dose-dependent manner in cynos. These results suggest that anti-HJV antibody are capable of inhibiting hepcidin expression induced by the IL-6 signaling pathway.

Example 7: Epitope Mapping

Epitope mapping was performed on hHA-008 and hHA-008-QL, using 3720-RG-050 (Hemojuvelin (HJV) fragment, SEQ ID NO: 123).

Before epitope mapping, High-Mass MALDI mass spectrometry and chemical cross-linking was used to confirm no non-covalent aggregates of hHA-008 and hHA-008-QL and multimers of the 3720-RG-050 were detected in sample preparation.

In order to determine the epitopes of hHA-008 and hHA-008-QL on 3720-RG-050 with high resolution, 3720-RG-050/hHA-008 and 3720-RG-050/hHA-008-QL complexes were incubated with deuterated cross-linkers and subjected to multi-enzymatic cleavage. After enrichment of the cross-linked peptides, the samples were analyzed by high resolution mass spectrometry (nLC-LTQ-Orbitrap MS) and the data generated were analyzed using XQuest and Stavrox software.

3720-RG-050/hHA-008 (HJV Fragment/hHA-008)

After Trypsin, Chymotrypsin, ASP-N, Elastase and Thermolysin proteolysis of the protein complex 3720-RG-050/hHA-008 with deuterated d0d12, the nLC-orbitrap MS/MS analysis detected 8 cross-linked peptides between 3720-RG-050 and hHA008.

The sequences and positions of cross-links are presented in Table 14 below.

TABLE 14

Cross-linked peptides detected between 3720-RG-050 and hHA-008.
hHA-008-Chymotrypsin and Thermolysin results in interlink between
hHA-008 complementarity determining regions and 3720-RG-050

| Enzyme | hHA-008 HC/ hHA-008 LC | 3720-RG-050 | Amino Acid Residues of hHA-008 HC/ hHA-008 LC | Amino acid Residues of 3720-RG-050 | nAA1 | nAA2 | Identified on StavroX |
|---|---|---|---|---|---|---|---|
| Chymotrypsin | hHA-008_HC (SEQ ID NO: 38) | SEQ ID NO: 123 | 48-53 | 166-189 | 52 | 170 | YES |
| Chymotrypsin | hHA-008_LC (SEQ ID NO: 39) | SEQ ID NO: 123 | 95-101 | 165-185 | 97 | 170 | YES |
| Chymotrypsin | hHA-008_LC (SEQ ID NO: 39) | SEQ ID NO: 123 | 95-101 | 165-185 | 98 | 171 | YES |
| Chymotrypsin | hHA-008_LC (SEQ ID NO: 39) | SEQ ID NO: 123 | 95-101 | 165-185 | 98 | 180 | YES |
| Chymotrypsin | hHA-008_LC (SEQ ID NO: 39) | SEQ ID NO: 123 | 95-101 | 165-185 | 98 | 182 | YES |
| Thermolysin | hHA-008_HC (SEQ ID NO: 38) | SEQ ID NO: 123 | 50-60 | 177-184 | 53 | 182 | YES |
| Chymotrypsin | hHA-008_LC (SEQ ID NO: 39) | SEQ ID NO: 123 | 95-101 | 165-185 | 98 | 183 | YES |
| Thermolysin | hHA-008_HC (SEQ ID NO: 38) | SEQ ID NO: 123 | 51-63 | 181-186 | 58 | 183 | YES |

Using chemical cross-linking, High-Mass MALDI mass spectrometry and nLC-Orbitrap mass spectrometry, molecular interface between 3720-RG-050 and hHA-008 was characterized. FIG. 14 shows hHA-008 interacts with amino acids 170-183 (SSPMALGANATATR (SEQ ID NO: 121)) on 3720-RG-050. The interaction happens on amino acids 170, 171, 180, 182, 183 on 3720-RG-050. FIGS. 15A-15J show the interaction of 3720-RG-050 and hHA-008. A 3720-RG-050 PDB structure was generated by homology using Swiss Model software. 3720-RG-050 amino acids 170-183 (SSPMALGANATATR (SEQ ID NO: 121)) of 3720-RG-050 sequence are shown in FIGS. 15A-15E: ribbon/surface representation of front view (FIG. 15A); back view (FIG. 15B), side view 1 (FIG. 15C), side view 2 (FIG. 15D) and top view (FIG. 15E). FIGS. 15F, 15G, 15H, 15I, 15J: ribbon representation of front view (FIG. 15F); back view (FIG. 15G), side view 1 (FIG. 15H), side view 2 (FIG. 15I) and top view (FIG. 15J). 3720-RG-050 hHA-008-QL (HJV fragment/hHA-008-QL)

After Trypsin, Chymotrypsin, ASP-N, Elastase and Thermolysin proteolysis of the protein complex 3720-RG-050/hHA-008-QL with deuterated d0d12, the nLC-orbitrap MS/MS analysis detected 16 cross-linked peptides between 3720-RG-050 and hHA-008-QL. The sequences and positions of cross-links are presented in Table 15 below.

TABLE 15

Cross-linked peptides detected between 3720-RG-050 and HA-008-QL.
hHA-008-QL- Trypsin, Chymotrypsin, AspN, Elastase and Thermolysin results Interlink
between hHA-008-QLcomplementarity determining regions and 3720-RG-050

| Enzyme | hHA-008-QL HC/ hHA-008-QL LC | 3720-RG-050 | Amino Acid Residues of hHA-008-QL HC/hHA-008-QL LC | Amino acid Residues of 3720-RG-050 | nAA1 | nAA2 | Identified on StavroX |
|---|---|---|---|---|---|---|---|
| Chymotrypsin | hHA-008-QL_LC (SEQ ID NO: 39) | SEQ ID NO: 123 | 95-101 | 165-185 | 97 | 169 | YES |
| Chymotrypsin | hHA-008-QL_LC (SEQ ID NO: 39) | SEQ ID NO: 123 | 95-101 | 165-185 | 98 | 169 | YES |
| Chymotrypsin | hHA-008-QL_LC (SEQ ID NO: 39) | SEQ ID NO: 123 | 95-101 | 165-185 | 98 | 171 | YES |
| Chymotrypsin | hHA-008-QL_LC (SEQ ID NO: 39) | SEQ ID NO: 123 | 95-101 | 165-185 | 98 | 180 | YES |
| Chymotrypsin | hHA-008-QL_LC (SEQ ID NO: 39) | SEQ ID NO: 123 | 53-67 | 176-185 | 59 | 180 | YES |
| Chymotrypsin | hHA-008-QL_LC (SEQ ID NO: 39) | SEQ ID NO: 123 | 53-67 | 176-185 | 61 | 180 | YES |
| Chymotrypsin | hHA-008-QL_LC (SEQ ID NO: 39) | SEQ ID NO: 123 | 95-101 | 165-185 | 98 | 182 | YES |
| Chymotrypsin | hHA-008-QL_HC (SEQ ID NO: 38) | SEQ ID NO: 123 | 96-104 | 280-292 | 100 | 289 | YES |
| Thermolysin | hHA-008-QL_HC (SEQ ID NO: 38) | SEQ ID NO: 123 | 29-44 | 283-302 | 32 | 293 | YES |
| Elastase | hHA-008-QL_HC (SEQ ID NO: 38) | SEQ ID NO: 123 | 31-42 | 290-295 | 32 | 294 | YES |
| Thermolysin | hHA-008-QL_HC (SEQ ID NO: 38) | SEQ ID NO: 123 | 29-44 | 283-302 | 32 | 295 | YES |
| Trypsin | hHA-008-QL_HC (SEQ ID NO: 38) | SEQ ID NO: 123 | 39-58 | 292-299 | 52 | 295 | YES |
| Trypsin | hHA-008-QL HC (SEQ ID NO: 38) | SEQ ID NO: 123 | 20-43 | 295-300 | 32 | 297 | YES |
| Thermolysin | hHA-008-QL_HC (SEQ ID NO: 38) | SEQ ID NO: 123 | 29-44 | 283-302 | 30 | 300 | YES |
| Elastase | hHA-008-QL_HC (SEQ ID NO: 38) | SEQ ID NO: 123 | 31-42 | 294-302 | 32 | 300 | YES |
| Elastase | hHA-008-QL_HC (SEQ ID NO: 38) | SEQ ID NO: 123 | 31-42 | 294-302 | 38 | 300 | YES |

Using chemical cross-linking, High-Mass MALDI mass spectrometry and nLC-Orbitrap mass spectrometry, molecular interface between 3720-RG-050 and hHA-008-QL was characterized. FIG. 16 shows hHA-008-QL interacts with amino acids 169-182 (TSSPMALGANATAT (SEQ ID NO: 122)) and 289-300 (SQRLSRSERNRR (SEQ ID NO: 127)) of 3720-RG-050. The interaction happens on amino acids 169, 171, 180, 182; 289, 293, 294, 295, 297, 300 on 3720-RG-050. FIGS. 17A-17J show the interaction 3720-RG-050/hHA-008-QL. A 3720-RG-050 PDB structure was generated by homology using Swiss Model software. 3720-RG-050 amino acids 169-182 (TSSPMALGANATAT (SEQ ID NO: 122) and 289-291 (SQR) are shown as FIGS. 17A-17E: ribbon/surface representation of front view (FIG. 17A); back view (FIG. 17B), side view 1 (FIG. 17C), side view 2 (FIG. 17D) and top view (FIG. 17E). FIGS. 17F, 17G, 17H, 17I, 17J: ribbon representation of front view (FIG. 17F); back view (FIG. 17G), side view 1 (FIG. 17H), side view 2 (FIG. 17I) and top view (FIG. 17J).

Example 8: hHA-008-QL Decreases Circulating Transferrin Level

Circulating transferrin level can be used as an indicator of the iron level in the body along with other markers (e.g., total iron binding capacity, serum ferritin level, etc.). Circulating transferrin is an iron-transport protein that reflects both protein and iron status. Transferrin increases with iron deficiency and decreases when iron status improves (see, e.g., Litchford et al., NUTRITIONAL ISSUES IN THE PATIENT WITH DIABETES AND FOOT ULCERS, Levin and O'Neal's The Diabetic Foot (Seventh Edition), 2008; Ogun et al., Biochemistry, Transferrin, Treasure Island (FL): StatPearls Publishing; 2021 January).

To test whether circulating transferrin level decreases after hHA-008-QL treatment, baseline transferrin level was established for each health Cynomolgus macaque (cynos) in the experiment 11 days before hHA-008-QL dosing on Day 1. Cynos were dosed with 0 mg/kg, 3 mg/kg, 30 mg/kg or 160 mg/kg of hHA-008-QL on day 1, day 15 and day 29 (n=5 in each group). Blood from each cyno was collected 96 hours, 192 hours, and 336 hours after the dosing on day 1; 48 hours, 96 hours, 192 hours, and 336 hours after the dosing on day 15; and 48 hours after the dosing on day 29. Note that blood for the 336-hour timepoint after day 1 dosing was collected 2 hours before the day 15 dosing, and blood for the 336-hour time point after day 15 dosing was collect 2 hours before the day 29 dosing. Transferrin levels were measured in all samples for each cyno, and was compared to its own baseline to calculate the percent change at each time point. The data in Table 16 show that treatment of hHA-008-QL reduced circulating transferrin levels compared to the baseline level.

TABLE 16

Circulating transferrin levels and the change over baseline in cynos treated with hHA-008-QL

| Day(s) Relative to Start Date | Males | | | | Females | | | |
|---|---|---|---|---|---|---|---|---|
| | 0 mg/kg/dose | 3 mg/kg/dose | 30 mg/kg/dose | 160 mg/kg/dose | 0 mg/kg/dose | 3 mg/kg/dose | 30 mg/kg/dose | 160 mg/kg/dose |
| Transferrin Day −11 (mg/dL; Baseline) | 241.96 ± 14.74 | 227.82 ± 22.69 | 239.14 ± 18.75 | 227.58 ± 10.21 | 241.96 ± 14.74 | 227.82 ± 22.69 | 239.14 ± 18.75 | 227.58 ± 10.21 |
| Transferrin Day 1, 96 h (mg/dL) | 259.28 ± 10.46 | 223.74 ± 20.49 ** | 226.74 ± 13.64 ** | 217.74 ± 9.88 ** | 259.28 ± 10.46 | 223.74 ± 20.49 ** | 226.74 ± 13.64 ** | 217.74 ± 9.88 ** |
| Day 1, 96 h tCtrl | — | 0.86 | 0.87 | 0.84 | — | 0.86 | 0.87 | 0.84 |
| Transferrin Day 1, 192 h (mg/dL) | 263.06 ± 19.77 | 224.92 ± 21.07 ** | 226.62 ± 11.34 ** | 221.64 ± 10.96 ** | 263.06 ± 19.77 | 224.92 ± 21.70 ** | 226.62 ± 11.34 ** | 221.64 ± 10.96 ** |
| Day 1, 192 h tCtrl | — | 0.86 | 0.86 | 0.84 | — | 0.86 | 0.86 | 0.84 |
| Transferrin Day 1, 336 h (mg/dL) | 260.68 ± 20.70 | 223.36 ± 24.75 * | 228.82 ± 8.80 | 225.72 ± 8.08 * | 260.68 ± 20.70 | 223.36 ± 24.75 * | 228.82 ± 8.80 | 225.72 ± 8.08 * |
| Day 1, 336 h tCtrl | — | 0.86 | 0.88 | 0.87 | — | 0.86 | 0.88 | 0.87 |
| Transferrin Day 15, 48 h (mg/dL) | 259.76 ± 18.52 | 218.06 ± 28.28 * | 225.86 ± 10.73 | 221.78 ± 9.85 * | 259.76 ± 18.52 | 218.06 ± 28.28 * | 225.86 ± 10.73 | 221.78 ± 9.85 * |
| Day 15, 48 h tCtrl | — | 0.84 | 0.87 | 0.85 | — | 0.84 | 0.87 | 0.85 |
| Transferrin Day 15, 96 h (mg/dL) | 253.88 ± 19.14 | 211.48 ± 22.48 ** | 219.52 ± 11.17 * | 209.26 ± 10.27 ** | 253.88 ± 19.14 | 211.48 ± 22.48 ** | 219.52 ± 11.17 * | 209.26 ± 10.27 ** |
| Day 15, 96 h tCtrl | — | 0.83 | 0.86 | 0.82 | — | 0.83 | 0.86 | 0.82 |
| Transferrin Day 15, 192 h (mg/dL) | 254.78 ± 24.23 | 215.88 ± 27.37 | 219.92 ± 10.13 | 211.30 ± 8.73 * | 254.78 ± 24.23 | 215.88 ± 27.37 | 219.92 ± 10.13 | 211.30 ± 8.73 * |
| Day 15, 192 h tCtrl | — | 0.85 | 0.86 | 0.83 | — | 0.85 | 0.86 | 0.83 |
| Transferrin Day 15, 336 h (mg/dL) | 268.04 ± 24.56 | 222.58 ± 26.20 ** | 235.52 ± 16.40 | 231.42 ± 11.07 * | 268.04 ± 24.56 | 222.58 ± 26.20 ** | 235.52 ± 16.40 | 231.42 ± 11.07 * |
| Day 15, 336 h tCtrl | — | 0.83 | 0.88 | 0.86 | — | 0.83 | 0.88 | 0.86 |
| Transferrin Day 29, 48 h (mg/dL) | 236.04 ± 14.11 | 198.48 ± 19.87 ** | 209.30 ± 14.41 * | 198.12 ± 10.25 ** | 236.04 ± 14.11 | 198.48 ±1 9.87 ** | 209.30 ± 14.41 * | 198.12 ± 10.25 ** |
| Day 29, 48 h tCtrl | — | 0.84 | 0.89 | 0.84 | — | 0.84 | 0.89 | 0.84 |
| Transferrin Day 29, 96 h (mg/dL) | 252.24 ± 12.39 | 209.24 ± 24.21 ** | 225.80 | 209.90 ± 8.04 ** | 252.24 ± 12.39 | 209.24 ± 24.21 ** | 225.80 ± 15.43 | 209.90 ± 8.04 ** |
| Day 29, 96 h tCtrl | — | 0.83 | 0.90 | 0.83 | — | 0.83 | 0.90 | 0.83 |

Anova & Dunnett:
* = p ≤ 0.05;
** = p ≤ 0.01

Figure 18:
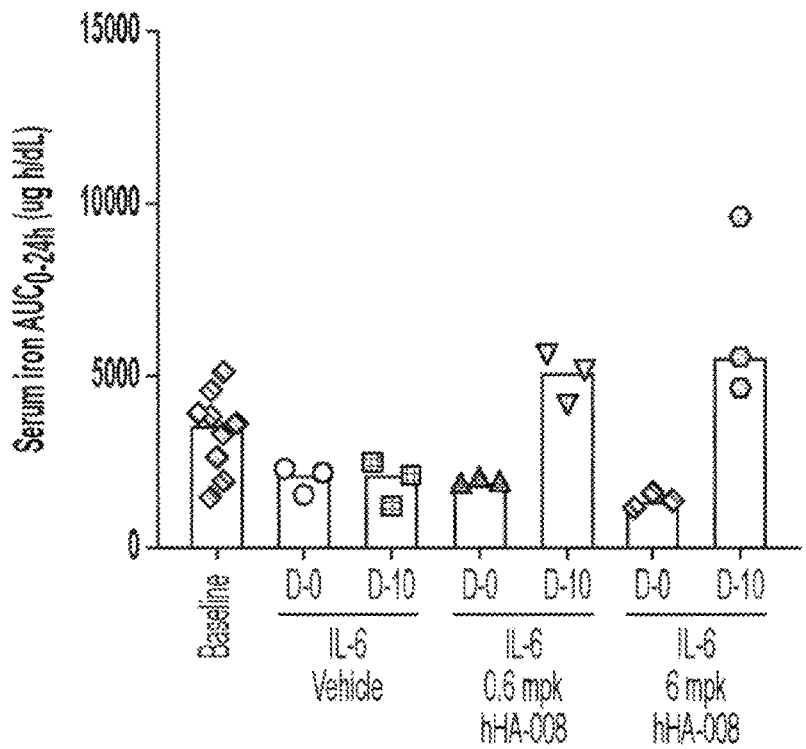
FIG. 18 shows that hHA-008 was effective in preventing IL-6-induced serum iron suppression in a dose-dependent manner in cynomolgus monkeys.

Example 9: hHA-008 Prevents Inflammation-Induced (IL-6) Iron Suppression in Cynomolgus Macaque Prevention of iron suppression by hHA-008 following IL-6 challenge was investigated in this study. On Day 0, three groups of cynos (N=3/group) were challenged with $6 \times 10^4$ international units (IU) IL-6/kg subcutaneously. On Day 3 each group of 3 animals received 0 (vehicle), 0.6 or 6 mg/kg of hHA-008 intravenously, respectively. On Day 10 all groups received a second challenge of $6 \times 10^4$ IU IL-6/kg subcutaneously. Blood was collected from all cynos to evaluate serum iron level at 48 hours and 24 hours prior to each IL-6 challenge, and 2, 4, 8 and 24 hours after each IL-6 dose. The average baseline value of the samples taken 48 and 24 hours prior to each IL-6 dose were used as D0 value. The results showed that hHA-008 was effective in preventing IL-6-induced serum iron suppression in a dose-dependent manner in cynomolgus monkeys (FIG. 18).

Example 10: Subcutaneous Injection of hHA-008 in Sprague-Dawley Rats

Sprague-Dawley Rats (6 females and 6 males) were injected with hHA-008 subcutaneously at 6 mg/kg (mpk). pharmacokinetics (SC PK) and pharmacodynamics (SC PD) were evaluated 35 days after dosing. Serum mean pharmacokinetics parameters (e.g., Cmax, Tmax, t½, and $AUC_{0-inf}$) were shown in Table 17:

TABLE 17

Serum Mean Pharmacokinetic (PK) Parameters of hHA-008 Following a Single SC Administration in Sprague-Dawley Rats

| Dose (mg/kg) | $C_{MAX}$ (μg/ml) (mean ± SD) | $T_{MAX}$ (DAYS) (mean ± SD) | $T_{1/2}$ (DAYS) (mean ± SD) | $AUC_{0\text{-}INF}$ (HR*MG/ML) (mean ± SD) |
|---|---|---|---|---|
| 6 | 37.6 ± 6.02 | 3.8 ± 0.6 | 4.3 ± 1.4 | 13,357 ± 1,437.4 |

Bioavailability of hHA-008 after subcutaneous administration was similar to bioavailability of hHA-008 after intravenous administration at 6 mg/kg, as evidenced by that subcutaneous injection bioavailability (SC bioavailability) of hHA-008 was about 84.7% of intravenous injection bioavailability of hHA-008 (IV bioavailability) (SC bioavailability=SC DN_AUC$_{0\text{-}inf}$/IV DN_AUC$_{0\text{-}inf}$×100; DN: Dose normalized). Further, the time to reach maximum concentration ($C_{max}$) was 3.6-4 days after SC administration with a much lower Cmax as compared to the Cmax after IV administration.

Figure 19:
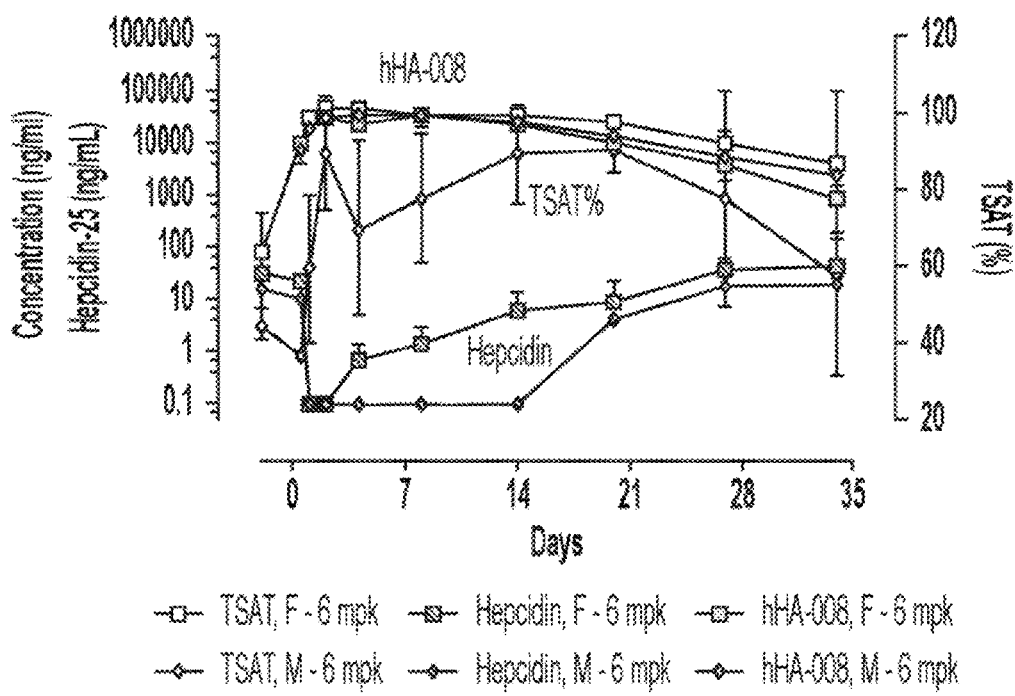
FIG. 19 shows that decline in PD response (e.g., hepcidin-25 concentration and TSAT %) was consistent with the decrease of hHA-008 serum concentration (FIG. 19) after subcutaneous administration of hHA-008 to Sprague-Dawley Rats.

At similar dose level, the PD response between the IV or SC was indistinguishable: serum hHA-008 concentration became saturated 1-2 days after dosing, remained elevated through at least 21 days and the decline in PD response (e.g., hepcidin-25 concentration and TSAT %) was consistent with the decrease of hHA-008 serum concentration (FIG. 19).

Example 11. Subcutaneous Dose Administration in Cynomolgus Monkeys

PK/PD of subcutaneous hHA-008 treatment were also evaluated in Cynomolgus (cynos). Cynos were injected with hHA-008 subcutaneously at 0.3 mpk, 0.6 mpk, 1 mpk and 6 mpk.

In the 6 mpk dosing group, 2 male and 1 female cynos received a single subcutaneous injection of hHA-008, and blood samples were collected for 61 days. Cynos received IV injection of hHA-008 at 6 mpk were used for comparison.

In the 0.3 mpk, 0.6 mpk, and 1.0 mpk groups, each group included 3 male cynos that received a single subcutaneous injection of hHA-008. Blood samples were collected for 27 days. Cynos received the same dose of hHA-008 by IV were used for comparison for each group.

Figure 20A:
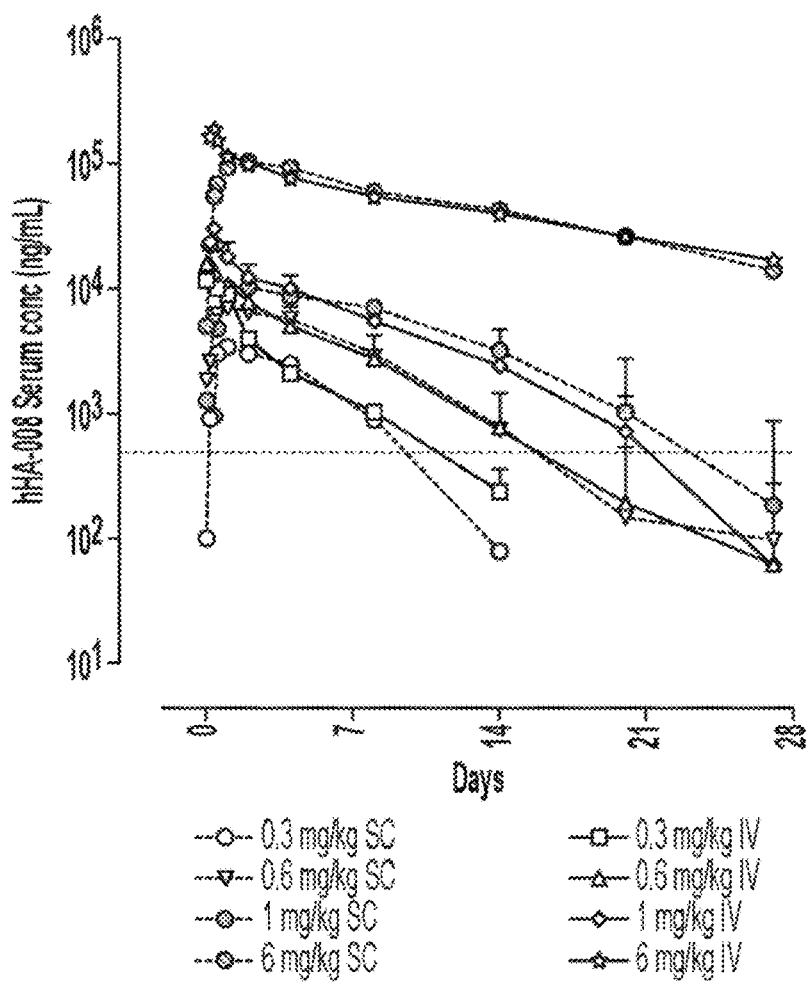
FIGS. 20A-20D show PK/PD analysis in cynomolgus monkeys after subcutaneous administration of hHA-008.

After SC administration of hHA-008 in cynomolgus monkeys, bioavailability was high and increased with dose levels (55.0% at 0.3 mpk, 81.9% at 0.6 mpk, 89.5% at 1 mpk and 100% at 6 mg/kg), when compared to animals injected at the same doses via IV. Tmax was reached rapidly after dosing in a dose dependent manner (1.33 to 2.67 days). Table 18 shows serum mean Pharmacokinetic (PK) parameters of hHA-008 following a single SC administration in cynos. hHA-008 serum concentration-time profiles became indistinguishable between SC injection and IV injection 4 days after administration (FIG. 20A).

Figure 20B:
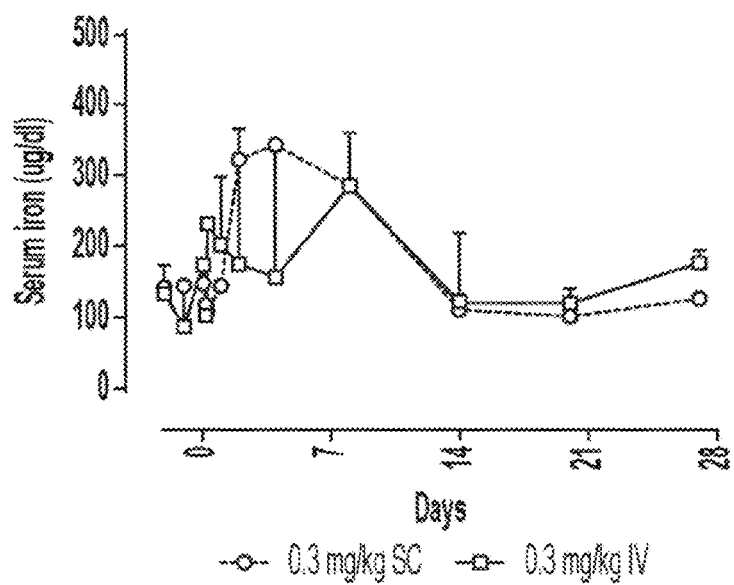
Figure 20C:
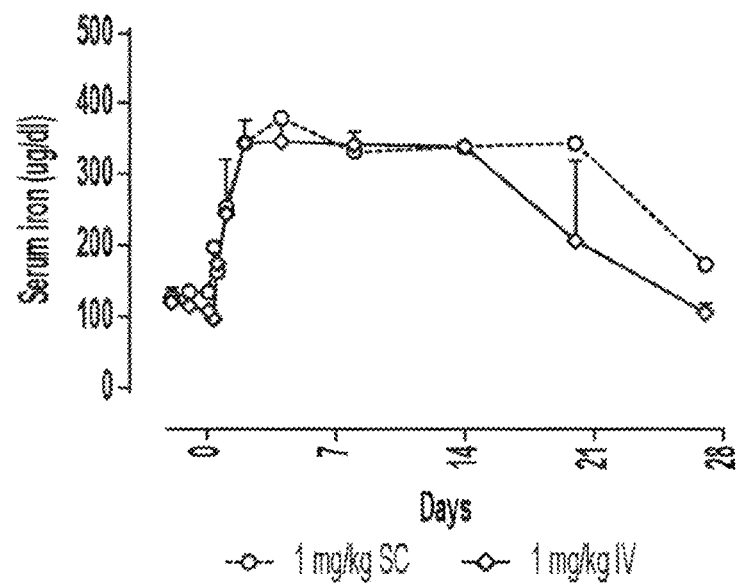
Figure 20D:
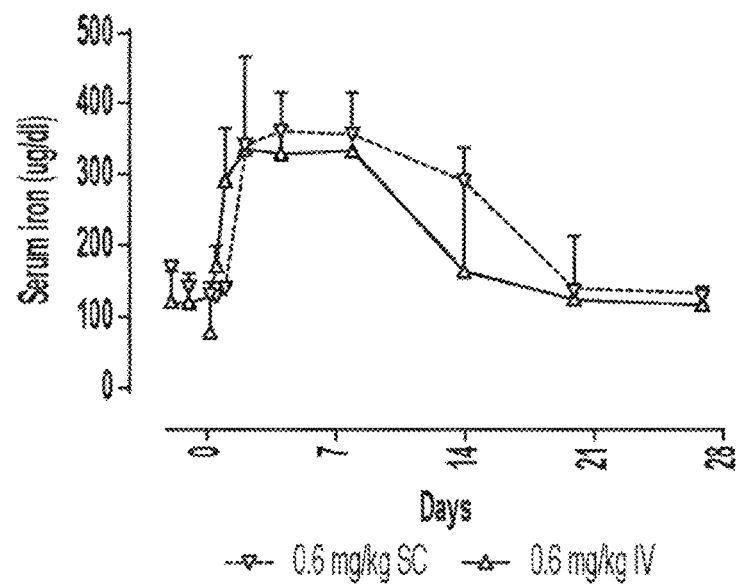

The PD response after SC dose was variable between animals, relatively proportional to the dose-level, and similar to the PD response observed after IV dosing at 0.1 mpk, 0.6 mpk, and 1.0 mpk. For all animals, the PD response was functionally maximal (TSAT >80% and hepcidin-25<LOQ) between 1-2 days after dosing. The return of the PD markers (e.g., serum iron) to baseline levels was consistent with the decline in hHA-008 serum concentrations (FIGS. 20B-20D). At 6 mpk, serum iron concentrations in both SC injected group and IV injected group were too saturated to reflect the change (data not shown).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also set forth as follows:

1. A method of treating a subject having myelofibrosis, the method comprising: administering to the subject an effective amount of the isolated antibody that binds to human hemojuvelin (HJV), wherein the antibody comprises: a heavy chain complementary determining region 1 (HC CDR1) set forth as $X_1$YGMN (SEQ ID NO: 105), in which $X_1$ can be N or Y; a heavy chain complementary determining region 2 (HC CDR2) set forth as MIYYDSSX$_2$KHYADSVKG (SEQ ID NO: 106), in which $X_2$ can be E or D; a heavy chain complementary determining region 3 (HC CDR3) set forth as GX$_3$TPDX$_4$ (SEQ ID NO: 107), in which $X_3$ can be T or S, and $X_4$ can be Y, V, or K; and/or a light chain complementary determining region 1 (LC CDR1) set forth as RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H, a light chain complementary determining region 2 (LC CDR2) set forth as $X_9$VSX$_{10}$RFS (SEQ ID NO: 109), in which $X_9$ can be E, D or A, and $X_{10}$ can be N, S, T, E or H, a light chain complementary determining region 3 (LC CDR3) set forth as $X_{11}$QX$_{12}$TX$_{13}$DPX$_{14}$X$_{15}$ (SEQ ID NO: 110), in which $X_{11}$ can be F or M, $X_{12}$ can be V or A, $X_{13}$ can be H or Y, $X_{14}$ can be M, L or V, and $X_{15}$ can be T or S.

2. The method of embodiment 1, wherein the antibody comprises a VH comprising an amino acid sequence at least

TABLE 18

Serum Mean Pharmacokinetic (PK) Parameters of hHA-008 Following a Single SC Administration in Cynos

| Dose (mg/kg) | $C_{max}$ (μg/mL) (mean ± SD) | $T_{max}$ (day) (mean ± SD) | $t_{1/2}$ (day) (mean ± SD) | $AUC_{0\text{-}inf}$* (hr * μg/mL) (mean ± SD) | Bioavailability compared to IV |
|---|---|---|---|---|---|
| 0.3 | 3.21 ± 0.72 | 1.33 ± 0.58 | 1.69 ± 0.18 | 496.5 ± 81.29 | 55% |
| 0.6 | 7.2 ± 0.48 | 1.33 ± 0.58 | 2.82 ± 0.2 | 1417 ± 234 | 81.9% |
| 1 | 10.5 ± 1.76 | 2 ± 0 | 3.3 ± 1.43 | 2942 ± 300 | 89.5% |
| 6 | 102 ± 15.4 | 2.67 ± 1.15 | 7.95 ± 1.68 | 34439 ± 2,528 | 100% |

*extrapolation from AUCo-last was less than 3%.

85% identical to SEQ ID NO: 38, and/or a VL comprising an amino acid sequence at least 85% identical to SEQ ID NO: 39.

3. The method of embodiment 2, wherein the antibody comprises a VH comprising an amino acid sequence of SEQ ID NO: 38, and a VL comprising an amino acid sequence of SEQ ID NO: 39.

4. The method of any one of embodiments 1-3, wherein the antibody is a humanized antibody.

5. The method of embodiment 4, wherein the humanized antibody comprises a humanized VH and/or a humanized VL.

6. The method of any one of embodiments 1-5, wherein the antibody is selected from the group consisting of a full-length IgG, a Fab fragment, a F(ab') fragment, a F(ab')2 fragment, a scFv, and a Fv.

7. The method of embodiment 6, wherein the antibody is a full-length IgG.

8. The method of embodiment 9, wherein the antibody comprises a heavy chain constant region of the isotype IgG1, IgG2, IgG3, or IgG4.

9. The method of embodiment 8, wherein the antibody further comprises a heavy chain constant region set forth in SEQ ID NO: 46 or SEQ ID NO: 48.

10. The method of embodiment 9, wherein the antibody further comprises a light chain constant region set forth in SEQ ID NO: 47.

11. The method of any one of embodiments 1-10, wherein the antibody comprises: (i) a heavy chain comprising an amino acid sequence at least 85% identical to SEQ ID NO: 61, and/or a light chain comprising an amino acid sequence at least 85% identical to SEQ ID NO: 62; or (ii) a heavy chain comprising an amino acid sequence at least 85% identical to SEQ ID NO: 63, and/or a light chain comprising an amino acid sequence at least 85% identical to SEQ ID NO: 62.

12. The method of embodiment 11, wherein the antibody comprises a heavy chain comprising an amino acid sequence of SEQ ID NO: 61, and a light chain comprising an amino acid sequence of SEQ ID NO: 62.

13. The method of embodiment 11 wherein the antibody comprises a heavy chain comprising an amino acid sequence of SEQ ID NO: 63, and a light chain comprising an amino acid sequence of SEQ ID NO: 62.

14. The method of any one of embodiments 1-13, wherein the subject has myelofibrosis initiating mutations in JAK2, MPL, ASXL1, TET2, NFE2, SH2B3, SF3B1, or CALR.

15. The method of any one of embodiments 1-14, wherein the myelofibrosis is associated with increased levels of pro-inflammatory cytokines (e.g., IL-6, oncostatin-M) in the subject.

16. The method of any one of embodiments 1-15, wherein the subject presents with a serum hemoglobin level of less than 10 g/dL.

17. The method of any one of embodiments 1-16, wherein the subject presents with a serum hemoglobin level of less than 8 g/dL.

18. The method of any one of embodiments 1-17, wherein the subject is erythrocyte-transfusion dependent.

19. The method of embodiment 18, wherein the subject is anemic.

20. The method of any one of embodiments 1-19, wherein the subject has previously received an erythropoietin stimulating agent, a JAK-STAT inhibitor, a growth factor ligand trap, or an anti-fibrotic agent.

21. The method of any one of embodiments 1-19, further comprising administering to the subject one or more of an erythropoietin stimulating agent, a JAK-STAT inhibitor, a growth factor ligand trap, and an anti-fibrotic agent.

22. The method of embodiment 20 or embodiment 21, wherein the erythropoietin stimulating agent is selected from the group consisting of danazol, prednisone, thalidomide, lenalidomide, and pomalidomide.

23. The method of embodiment 20 or embodiment 21, wherein the JAK-STAT inhibitor is selected from the group consisting of ruxolitinib, momelotinib, pacritinib, INCB039110, AG490, and PpYLKTK (SEQ ID NO: 130).

24. The method of embodiment 20 or embodiment 21, wherein the growth factor ligand trap is sotatercept or luspatercept.

25. The method of embodiment 20 or embodiment 21, wherein the anti-fibrotic agent is PRM-151.

26. An isolated antibody that binds to human hemojuvelin (HJV), wherein the antibody comprises a VH comprising an amino acid sequence at least 85% identical to SEQ ID NO: 38, and/or a VL comprising an amino acid sequence at least 85% identical to SEQ ID NO: 39.

27. The isolated antibody of embodiment 26, wherein the antibody comprises a VH comprising an amino acid sequence of SEQ ID NO: 38, and a VL comprising an amino acid sequence of SEQ ID NO: 39.

28. The isolated antibody of embodiment 26 or embodiment 27, wherein the antibody is a humanized antibody.

28. The isolated antibody of embodiment 28, wherein the humanized antibody comprises a humanized VH and/or a humanized VL.

29. The isolated antibody of any one of embodiments 26-28, wherein the antibody is selected from the group consisting of a full-length IgG, a Fab fragment, a F(ab') fragment, a F(ab')2 fragment, a scFv, and a Fv.

30. The isolated antibody of embodiment 29, wherein the antibody is a full-length IgG.

31. The isolated antibody of embodiment 30, wherein the antibody comprises a heavy chain constant region of the isotype IgG1, IgG2, IgG3, or IgG4.

32. The isolated antibody of embodiment 31, wherein the antibody further comprises a heavy chain constant region set forth in SEQ ID NOs: 46, 48, 112 or 113.

33. The isolated antibody of embodiment 32, wherein the antibody further comprises a light chain constant region set forth in SEQ ID NO: 47.

34. The isolated antibody of any one of embodiments 26-33, wherein the antibody comprises: (i) a heavy chain comprising an amino acid sequence at least 85% identical to SEQ ID NO: 61 or 117, and/or a light chain comprising an amino acid sequence at least 85% identical to SEQ ID NO: 62; or (ii) a heavy chain comprising an amino acid sequence at least 85% identical to SEQ ID NO: 63 or 118, and/or a light chain comprising an amino acid sequence at least 85% identical to SEQ ID NO: 62.

35. The isolated antibody of embodiment 34, wherein the antibody comprises a heavy chain comprising an amino acid sequence of SEQ ID NOs: 61 or 117, and a light chain comprising an amino acid sequence of SEQ ID NO: 62.

36. The isolated antibody of embodiment 34, wherein the antibody comprises a heavy chain comprising an amino acid sequence of SEQ ID NOs: 63 or 118, and a light chain comprising an amino acid sequence of SEQ ID NO: 62.

37. An isolated antibody that binds to human hemojuvelin (HJV) produced by expressing in a host cell: (i) a nucleic acid sequence encoding a heavy chain, wherein the nucleic acid sequence is at least 90% identical to SEQ ID NO: 92;

and/or (ii) a nucleic acid sequence encoding a light chain, wherein the nucleic acid sequence is at least 90% identical to SEQ ID NO: 93.

38. An isolated antibody that binds to human hemojuvelin (HJV) produced by expressing in a host cell: (i) a nucleic acid sequence encoding a heavy chain, wherein the nucleic acid sequence is at least 90% identical to SEQ ID NO: 94; and/or (ii) a nucleic acid sequence encoding a light chain, wherein the nucleic acid sequence is at least 90% identical to SEQ ID NO: 93.

39. The isolated antibody of embodiments 37 or 38, wherein the host cell is Chinese hamster ovary (CHO) cells, dhfr-CHO cell, human embryonic kidney (HEK)-293 cells, verda reno (VERO) cells, nonsecreting null (NS0) cells, human embryonic retinal (PER.C6) cells, Sp2/0 cells, baby hamster kidney (BHK) cells, Madin-Darby Canine Kidney (MDCK) cells, Madin-Darby Bovine Kidney (MDBK) cells, or monkey kidney CV1 line transformed by SV40 (COS) cells.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B," the application also contemplates the alternative embodiments "a composition consisting of A and B" and "a composition consisting essentially of A and B."

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

```
                            SEQUENCE LISTING

Sequence total quantity: 130
SEQ ID NO: 1            moltype = AA  length = 5
FEATURE                 Location/Qualifiers
REGION                  1..5
                        note = Synthethic Polypeptide
source                  1..5
                        mol_type = protein
                        organism = synthetic construct
SEQUENCE: 1
NYGMN                                                                    5

SEQ ID NO: 2            moltype = AA  length = 17
FEATURE                 Location/Qualifiers
REGION                  1..17
                        note = Synthethic Polypeptide
source                  1..17
                        mol_type = protein
                        organism = synthetic construct
SEQUENCE: 2
MIYYDSSEKH YADSVKG                                                       17

SEQ ID NO: 3            moltype = AA  length = 6
FEATURE                 Location/Qualifiers
REGION                  1..6
                        note = Synthethic Polypeptide
source                  1..6
                        mol_type = protein
                        organism = synthetic construct
SEQUENCE: 3
GTTPDY                                                                   6

SEQ ID NO: 4            moltype = AA  length = 16
FEATURE                 Location/Qualifiers
REGION                  1..16
                        note = Synthethic Polypeptide
source                  1..16
                        mol_type = protein
                        organism = synthetic construct
SEQUENCE: 4
RSSQSLETSD GDTFLE                                                        16

SEQ ID NO: 5            moltype = AA  length = 7
FEATURE                 Location/Qualifiers
REGION                  1..7
                        note = Synthethic Polypeptide
source                  1..7
                        mol_type = protein
                        organism = synthetic construct
SEQUENCE: 5
EVSTRFS                                                                  7

SEQ ID NO: 6            moltype = AA  length = 9
```

```
FEATURE            Location/Qualifiers
REGION             1..9
                   note = Synthethic Polypeptide
source             1..9
                   mol_type = protein
                   organism = synthetic construct
SEQUENCE: 6
FQVTHDPMT                                                                    9

SEQ ID NO: 7       moltype = AA  length = 115
FEATURE            Location/Qualifiers
REGION             1..115
                   note = Synthethic Polypeptide
source             1..115
                   mol_type = protein
                   organism = synthetic construct
SEQUENCE: 7
EVQLVESGGG LVQPGGSLRL SCAASGFTFS NYGMNWIRQA PGKGLEWIGM IYYDSSEKHY            60
ADSVKGRFTI SRDNSKNTLY LQMNSLRAED TAVYYCAKGT TPDYWGQGTM VTVSS                115

SEQ ID NO: 8       moltype = AA  length = 112
FEATURE            Location/Qualifiers
REGION             1..112
                   note = Synthethic Polypeptide
source             1..112
                   mol_type = protein
                   organism = synthetic construct
SEQUENCE: 8
DVVLTQSPLS LPVTLGQPAS ISCRSSQSLE TSDGDTFLEW FQQRPGQSPR LLIYEVSTRF            60
SGVPDRFSGS GSGTDFTLKI SRVEAEDVGV YYCFQVTHDP MTFGQGTKLE IK                   112

SEQ ID NO: 9       moltype = AA  length = 5
FEATURE            Location/Qualifiers
REGION             1..5
                   note = Synthethic Polypeptide
source             1..5
                   mol_type = protein
                   organism = synthetic construct
SEQUENCE: 9
YYGMN                                                                        5

SEQ ID NO: 10      moltype = AA  length = 17
FEATURE            Location/Qualifiers
REGION             1..17
                   note = Synthethic Polypeptide
source             1..17
                   mol_type = protein
                   organism = synthetic construct
SEQUENCE: 10
MIYYDSSDKH YADSVKG                                                           17

SEQ ID NO: 11      moltype = AA  length = 6
FEATURE            Location/Qualifiers
REGION             1..6
                   note = Synthethic Polypeptide
source             1..6
                   mol_type = protein
                   organism = synthetic construct
SEQUENCE: 11
GTTPDV                                                                       6

SEQ ID NO: 12      moltype = AA  length = 6
FEATURE            Location/Qualifiers
REGION             1..6
                   note = Synthethic Polypeptide
source             1..6
                   mol_type = protein
                   organism = synthetic construct
SEQUENCE: 12
GTTPDK                                                                       6

SEQ ID NO: 13      moltype = AA  length = 6
FEATURE            Location/Qualifiers
REGION             1..6
                   note = Synthethic Polypeptide
source             1..6
                   mol_type = protein
                   organism = synthetic construct
SEQUENCE: 13
```

-continued

```
GSTPDY                                                              6

SEQ ID NO: 14         moltype = AA  length = 16
FEATURE               Location/Qualifiers
REGION                1..16
                      note = Synthethic Polypeptide
source                1..16
                      mol_type = protein
                      organism = synthetic construct
SEQUENCE: 14
RSSQSLESSD GDTFLE                                                   16

SEQ ID NO: 15         moltype = AA  length = 16
FEATURE               Location/Qualifiers
REGION                1..16
                      note = Synthethic Polypeptide
source                1..16
                      mol_type = protein
                      organism = synthetic construct
SEQUENCE: 15
RSSQSLEESD GYTFLE                                                   16

SEQ ID NO: 16         moltype = AA  length = 16
FEATURE               Location/Qualifiers
REGION                1..16
                      note = Synthethic Polypeptide
source                1..16
                      mol_type = protein
                      organism = synthetic construct
SEQUENCE: 16
RSSQSLEDSD GGTFLE                                                   16

SEQ ID NO: 17         moltype = AA  length = 16
FEATURE               Location/Qualifiers
REGION                1..16
                      note = Synthethic Polypeptide
source                1..16
                      mol_type = protein
                      organism = synthetic construct
SEQUENCE: 17
RSSQSLEESD GYTFLH                                                   16

SEQ ID NO: 18         moltype = AA  length = 7
FEATURE               Location/Qualifiers
REGION                1..7
                      note = Synthethic Polypeptide
source                1..7
                      mol_type = protein
                      organism = synthetic construct
SEQUENCE: 18
EVSNRFS                                                             7

SEQ ID NO: 19         moltype = AA  length = 7
FEATURE               Location/Qualifiers
REGION                1..7
                      note = Synthethic Polypeptide
source                1..7
                      mol_type = protein
                      organism = synthetic construct
SEQUENCE: 19
DVSTRFS                                                             7

SEQ ID NO: 20         moltype = AA  length = 7
FEATURE               Location/Qualifiers
REGION                1..7
                      note = Synthethic Polypeptide
source                1..7
                      mol_type = protein
                      organism = synthetic construct
SEQUENCE: 20
DVSERFS                                                             7

SEQ ID NO: 21         moltype = AA  length = 7
FEATURE               Location/Qualifiers
REGION                1..7
                      note = Synthethic Polypeptide
source                1..7
                      mol_type = protein
                      organism = synthetic construct
```

-continued

```
SEQUENCE: 21
DVSSRFS                                                                        7

SEQ ID NO: 22           moltype = AA  length = 7
FEATURE                 Location/Qualifiers
REGION                  1..7
                        note = Synthethic Polypeptide
source                  1..7
                        mol_type = protein
                        organism = synthetic construct
SEQUENCE: 22
AVSHRFS                                                                        7

SEQ ID NO: 23           moltype = AA  length = 7
FEATURE                 Location/Qualifiers
REGION                  1..7
                        note = Synthethic Polypeptide
source                  1..7
                        mol_type = protein
                        organism = synthetic construct
SEQUENCE: 23
EVSHRFS                                                                        7

SEQ ID NO: 24           moltype = AA  length = 9
FEATURE                 Location/Qualifiers
REGION                  1..9
                        note = Synthethic Polypeptide
source                  1..9
                        mol_type = protein
                        organism = synthetic construct
SEQUENCE: 24
MQVTHDPLT                                                                      9

SEQ ID NO: 25           moltype = AA  length = 9
FEATURE                 Location/Qualifiers
REGION                  1..9
                        note = Synthethic Polypeptide
source                  1..9
                        mol_type = protein
                        organism = synthetic construct
SEQUENCE: 25
FQVTHDPVT                                                                      9

SEQ ID NO: 26           moltype = AA  length = 9
FEATURE                 Location/Qualifiers
REGION                  1..9
                        note = Synthethic Polypeptide
source                  1..9
                        mol_type = protein
                        organism = synthetic construct
SEQUENCE: 26
FQATYDPLT                                                                      9

SEQ ID NO: 27           moltype = AA  length = 9
FEATURE                 Location/Qualifiers
REGION                  1..9
                        note = Synthethic Polypeptide
source                  1..9
                        mol_type = protein
                        organism = synthetic construct
SEQUENCE: 27
FQATHDPLT                                                                      9

SEQ ID NO: 28           moltype = AA  length = 9
FEATURE                 Location/Qualifiers
REGION                  1..9
                        note = Synthethic Polypeptide
source                  1..9
                        mol_type = protein
                        organism = synthetic construct
SEQUENCE: 28
FQATHDPVT                                                                      9

SEQ ID NO: 29           moltype = AA  length = 9
FEATURE                 Location/Qualifiers
REGION                  1..9
                        note = Synthethic Polypeptide
source                  1..9
                        mol_type = protein
```

```
                            organism = synthetic construct
SEQUENCE: 29
FQATHDPLS                                                               9

SEQ ID NO: 30           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 30
DVVLTQSPLS LPVTLGQPAS ISCRSSQSLE TSDGDTFLEW FQQRPGQSPR LLIYEVSSRF       60
SGVPDRFSGS GSGTDFTLKI SRVEAEDVGV YYCMQVTHDP LTFGQGTKLE IK              112

SEQ ID NO: 31           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 31
DVVLTQSPLS LPVTLGQPAS ISCRSSQSLE TSDGDTFLEW FQQRPGQSPR LLIYEVSNRF       60
SGVPDRFSGS GSGTDFTLKI SRVEAEDVGV YYCFQVTHDP VTFGQGTKLE IK              112

SEQ ID NO: 32           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 32
DVVLTQSPLS LPVTLGQPAS ISCRSSQSLE SSDGDTFLEW FQQRPGQSPR LLIYDVSTRF       60
SGVPDRFSGS GSGTDFTLKI SRVEAEDVGV YYCFQVTHDP VTFGQGTKLE IK              112

SEQ ID NO: 33           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 33
DVVLTQSPLS LPVTLGQPAS ISCRSSQSLE ESDGYTFLEW FQQRPGQSPR LLIYDVSERF       60
SGVPDRFSGS GSGTDFTLKI SRVEAEDVGV YYCFQATYDP LTFGQGTKLE IK              112

SEQ ID NO: 34           moltype = AA   length = 115
FEATURE                 Location/Qualifiers
REGION                  1..115
                        note = Synthethic Polypeptide
source                  1..115
                        mol_type = protein
                        organism = synthetic construct
SEQUENCE: 34
EVQLVESGGG LVQPGGSLRL SCAASGFTFS YYGMNWIRQA PGKGLEWIGM IYYDSSEKHY       60
ADSVKGRFTI SRDNSKNTLY LQMNSLRAED TAVYYCAKGT TPDYWGQGTM VTVSS           115

SEQ ID NO: 35           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 35
DVVLTQSPLS LPVTLGQPAS ISCRSSQSLE DSDGGTFLEW FQQRPGQSPR LLIYDVSSRF       60
SGVPDRFSGS GSGTDFTLKI SRVEAEDVGV YYCFQATHDP LTFGQGTKLE IK              112

SEQ ID NO: 36           moltype = AA   length = 115
FEATURE                 Location/Qualifiers
REGION                  1..115
                        note = Synthethic Polypeptide
source                  1..115
                        mol_type = protein
                        organism = synthetic construct
SEQUENCE: 36
EVQLVESGGG LVQPGGSLRL SCAASGFTFS NYGMNWIRQA PGKGLEWIGM IYYDSSDKHY       60
```

```
ADSVKGRFTI SRDNSKNTLY LQMNSLRAED TAVYYCAKGT TPDVWGQGTM VTVSS         115

SEQ ID NO: 37           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 37
DVVLTQSPLS LPVTLGQPAS ISCRSSQSLE ESDGYTFLHW FQQRPGQSPR LLIYEVSNRF    60
SGVPDRFSGS GSGTDFTLKI SRVEAEDVGV YYCFQATHDP VTFGQGTKLE IK           112

SEQ ID NO: 38           moltype = AA   length = 115
FEATURE                 Location/Qualifiers
REGION                  1..115
                        note = Synthethic Polypeptide
source                  1..115
                        mol_type = protein
                        organism = synthetic construct
SEQUENCE: 38
EVQLVESGGG LVQPGGSLRL SCAASGFTFS NYGMNWVRQA PGKGLEWIGM IYYDSSEKHY    60
ADSVKGRFTI SRDNSKNTLY LQMNSLRAED TAVYYCAKGT TPDYWGQGTM VTVSS         115

SEQ ID NO: 39           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 39
DVVLTQSPLS LPVTLGQPAS ISCRSSQSLE ESDGYTFLHW FQQRPGQSPR LLIYEVSTRF    60
SGVPDRFSGS GSGTDFTLKI SRVEAEDVGV YYCFQATHDP LTFGQGTKLE IK           112

SEQ ID NO: 40           moltype = DNA  length = 1338
FEATURE                 Location/Qualifiers
misc_feature            1..1338
                        note = Synthethic Polynucleotide
source                  1..1338
                        mol_type = other DNA
                        organism = synthetic construct
SEQUENCE: 40
gaagtacagt tggtagaaag cggcggagga cttgtgcagc caggtggatc tctcagactt    60
tcatgtgccg caagcggttt tactttagt aactatggaa tgaactgggt tagacaagcg    120
cccgaaaag gattggaatg gataggaatg atatactacg acagctccga aaacattat    180
gccgactcag ttaaaggaag atttacaata tcaagagaca atagcaaaaa cacactttat    240
cttcaaatga attcactgcg agccgaggat acagcagtct attattgcgc aaaaggctca    300
accccgatt actggggtca aggaacaatg gtaaccgtgt caagcgcgtc gaccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaagccgcgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agccccatc gagaaaacca tctccaaagc caaagggcag    1020
ccccgagaac cacaggtgta caccctgccc ccatcccgcg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaatga                                                 1338

SEQ ID NO: 41           moltype = AA   length = 112
FEATURE                 Location/Qualifiers
REGION                  1..112
                        note = Synthethic Polypeptide
source                  1..112
                        mol_type = protein
                        organism = synthetic construct
SEQUENCE: 41
DVVLTQSPLS LPVTLGQPAS ISCRSSQSLA DSDGDTFLHW FQQRPGQSPR LLIYAVSHRF    60
SGVPDRFSGS GSGTDFTLKI SRVEAEDVGV YYCFQATHDP VTFGQGTKLE IK           112

SEQ ID NO: 42           moltype = AA   length = 115
```

```
FEATURE                 Location/Qualifiers
REGION                  1..115
                        note = Synthethic Polypeptide
source                  1..115
                        mol_type = protein
                        organism = synthetic construct
SEQUENCE: 42
EVQLVESGGG LVQPGGSLRL SCAASGFTFS NYGMNWVRQA PGKGLEWIGM IYYDSSEKHY    60
ADSVKGRFTI SRDNSKNTLY LQMNSLRAED TAVYYCAKGT TPDKWGQGTM VTVSS        115

SEQ ID NO: 43           moltype = AA  length = 112
FEATURE                 Location/Qualifiers
REGION                  1..112
                        note = Synthethic Polypeptide
source                  1..112
                        mol_type = protein
                        organism = synthetic construct
SEQUENCE: 43
DVVLTQSPLS LPVTLGQPAS ISCRSSQSLE ESDGYTFLEW FQQRPGQSPR LLIYEVSHRF    60
SGVPDRFSGS GSGTDFTLKI SRVEAEDVGV YYCFQATHDP LTFGQGTKLE IK           112

SEQ ID NO: 44           moltype = AA  length = 115
FEATURE                 Location/Qualifiers
REGION                  1..115
                        note = Synthethic Polypeptide
source                  1..115
                        mol_type = protein
                        organism = synthetic construct
SEQUENCE: 44
EVQLVESGGG LVQPGGSLRL SCAASGFTFS NYGMNWVRQA PGKGLEWIGM IYYDSSEKHY    60
ADSVKGRFTI SRDNSKNTLY LQMNSLRAED TAVYYCAKGS TPDYWGQGTM VTVSS        115

SEQ ID NO: 45           moltype = AA  length = 112
FEATURE                 Location/Qualifiers
REGION                  1..112
                        note = Synthethic Polypeptide
source                  1..112
                        mol_type = protein
                        organism = synthetic construct
SEQUENCE: 45
DVVLTQSPLS LPVTLGQPAS ISCRSSQSLE DSDGGTFLEW FQQRPGQSPR LLIYDVSSRF    60
SGVPDRFSGS GSGTDFTLKI SRVEAEDVGV YYCFQATHDP LSFGQGTKLE IK           112

SEQ ID NO: 46           moltype = AA  length = 330
FEATURE                 Location/Qualifiers
REGION                  1..330
                        note = Synthethic Polypeptide
source                  1..330
                        mol_type = protein
                        organism = synthetic construct
SEQUENCE: 46
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 47           moltype = AA  length = 107
FEATURE                 Location/Qualifiers
source                  1..107
                        mol_type = protein
                        organism = Homo sapiens
SEQUENCE: 47
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 48           moltype = AA  length = 330
FEATURE                 Location/Qualifiers
REGION                  1..330
                        note = Synthetic Polypeptide
source                  1..330
                        mol_type = protein
                        organism = synthetic construct
SEQUENCE: 48
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDQLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
```

```
MTKNQVSLTC LVKGFYPSDI AVEWESNGQP ENNYKTTPPV LDSDGSFFLY SKLTVDKSRW   300
QQGNVFSCSV LHEALHNHYT QKSLSLSPGK                                   330

SEQ ID NO: 49           moltype = AA  length = 7
FEATURE                 Location/Qualifiers
REGION                  1..7
                        note = Synthethic Polypeptide
source                  1..7
                        mol_type = protein
                        organism = synthetic construct
SEQUENCE: 49
EVSSRFS                                                            7

SEQ ID NO: 50           moltype = AA  length = 16
FEATURE                 Location/Qualifiers
REGION                  1..16
                        note = Synthethic Polypeptide
source                  1..16
                        mol_type = protein
                        organism = synthetic construct
SEQUENCE: 50
RSSQSLADSD GDTFLH                                                  16

SEQ ID NO: 51           moltype = AA  length = 445
FEATURE                 Location/Qualifiers
REGION                  1..445
                        note = Synthethic Polypeptide
source                  1..445
                        mol_type = protein
                        organism = synthetic construct
SEQUENCE: 51
EVQLVESGGG LVQPGGSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGK                                        445

SEQ ID NO: 52           moltype = AA  length = 219
FEATURE                 Location/Qualifiers
REGION                  1..219
                        note = Synthethic Polypeptide
source                  1..219
                        mol_type = protein
                        organism = synthetic construct
SEQUENCE: 52
DVVLTQSPLS LPVTLGQPAS ISCRSSQSLE TSDGDTFLEW FQQRPGQSPR LLIYEVSTRF   60
SGVPDRFSGS GSGTDFTLKI SRVEAEDVGV YYCFQVTHDP MTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 53           moltype = AA  length = 219
FEATURE                 Location/Qualifiers
REGION                  1..219
                        note = Synthethic Polypeptide
source                  1..219
                        mol_type = protein
                        organism = synthetic construct
SEQUENCE: 53
DVVLTQSPLS LPVTLGQPAS ISCRSSQSLE TSDGDTFLEW FQQRPGQSPR LLIYEVSSRF   60
SGVPDRFSGS GSGTDFTLKI SRVEAEDVGV YYCMQVTHDP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 54           moltype = AA  length = 219
FEATURE                 Location/Qualifiers
REGION                  1..219
                        note = Synthethic Polypeptide
source                  1..219
                        mol_type = protein
                        organism = synthetic construct
SEQUENCE: 54
DVVLTQSPLS LPVTLGQPAS ISCRSSQSLE TSDGDTFLEW FQQRPGQSPR LLIYEVSNRF   60
SGVPDRFSGS GSGTDFTLKI SRVEAEDVGV YYCFQVTHDP VTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219
```

```
SEQ ID NO: 55              moltype = AA  length = 219
FEATURE                    Location/Qualifiers
REGION                     1..219
                           note = Synthethic Polypeptide
source                     1..219
                           mol_type = protein
                           organism = synthetic construct
SEQUENCE: 55
DVVLTQSPLS LPVTLGQPAS ISCRSSQSLE SSDGDTFLEW FQQRPGQSPR LLIYDVSTRF    60
SGVPDRFSGS GSGTDFTLKI SRVEAEDVGV YYCFQVTHDP VTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 56              moltype = AA  length = 219
FEATURE                    Location/Qualifiers
REGION                     1..219
                           note = Synthethic Polypeptide
source                     1..219
                           mol_type = protein
                           organism = synthetic construct
SEQUENCE: 56
DVVLTQSPLS LPVTLGQPAS ISCRSSQSLE ESDGYTFLEW FQQRPGQSPR LLIYDVSERF    60
SGVPDRFSGS GSGTDFTLKI SRVEAEDVGV YYCFQATYDP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 57              moltype = AA  length = 445
FEATURE                    Location/Qualifiers
REGION                     1..445
                           note = Synthethic Polypeptide
source                     1..445
                           mol_type = protein
                           organism = synthetic construct
SEQUENCE: 57
EVQLVESGGG LVQPGGSLRL SCAASGFTFS YYGMNWIRQA PGKGLEWIGM IYYDSSEKHY    60
ADSVKGRFTI SRDNSKNTLY LQMNSLRAED TAVYYCAKGT TPDYWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGK                                        445

SEQ ID NO: 58              moltype = AA  length = 219
FEATURE                    Location/Qualifiers
REGION                     1..219
                           note = Synthethic Polypeptide
source                     1..219
                           mol_type = protein
                           organism = synthetic construct
SEQUENCE: 58
DVVLTQSPLS LPVTLGQPAS ISCRSSQSLE DSDGGTFLEW FQQRPGQSPR LLIYDVSSRF    60
SGVPDRFSGS GSGTDFTLKI SRVEAEDVGV YYCFQATHDP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 59              moltype = AA  length = 445
FEATURE                    Location/Qualifiers
REGION                     1..445
                           note = Synthethic Polypeptide
source                     1..445
                           mol_type = protein
                           organism = synthetic construct
SEQUENCE: 59
EVQLVESGGG LVQPGGSLRL SCAASGFTFS NYGMNWIRQA PGKGLEWIGM IYYDSSDKHY    60
ADSVKGRFTI SRDNSKNTLY LQMNSLRAED TAVYYCAKGT TPDVWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGK                                        445

SEQ ID NO: 60              moltype = AA  length = 219
FEATURE                    Location/Qualifiers
REGION                     1..219
                           note = Synthethic Polypeptide
source                     1..219
                           mol_type = protein
```

```
                            organism = synthetic construct
SEQUENCE: 60
DVVLTQSPLS LPVTLGQPAS ISCRSSQSLE ESDGYTFLHW FQQRPGQSPR LLIYEVSNRF     60
SGVPDRFSGS GSGTDFTLKI SRVEAEDVGV YYCFQATHDP VTFGQGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 61           moltype = AA  length = 445
FEATURE                 Location/Qualifiers
REGION                  1..445
                        note = Synthethic Polypeptide
source                  1..445
                        mol_type = protein
                        organism = synthetic construct
SEQUENCE: 61
EVQLVESGGG LVQPGGSLRL SCAASGFTFS NYGMNWVRQA PGKGLEWIGM IYYDSSEKHY     60
ADSVKGRFTI SRDNSKNTLY LQMNSLRAED TAVYYCAKGT TPDYWGQGTM VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP EAAGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSREEMTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPGK                                         445

SEQ ID NO: 62           moltype = AA  length = 219
FEATURE                 Location/Qualifiers
REGION                  1..219
                        note = Synthethic Polypeptide
source                  1..219
                        mol_type = protein
                        organism = synthetic construct
SEQUENCE: 62
DVVLTQSPLS LPVTLGQPAS ISCRSSQSLE ESDGYTFLHW FQQRPGQSPR LLIYEVSTRF     60
SGVPDRFSGS GSGTDFTLKI SRVEAEDVGV YYCFQATHDP LTFGQGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 63           moltype = AA  length = 445
FEATURE                 Location/Qualifiers
REGION                  1..445
                        note = Synthethic Polypeptide
source                  1..445
                        mol_type = protein
                        organism = synthetic construct
SEQUENCE: 63
EVQLVESGGG LVQPGGSLRL SCAASGFTFS NYGMNWVRQA PGKGLEWIGM IYYDSSEKHY     60
ADSVKGRFTI SRDNSKNTLY LQMNSLRAED TAVYYCAKGT TPDYWGQGTM VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP EAAGGPSVFL    240
FPPKPKDQLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSREEMTKNQ    360
VSLTCLVKGF YPSDIAVEWE SNGQPENNYK TTPPVLDSDG SFFLYSKLTV DKSRWQQGNV    420
FSCSVLHEAL HNHYTQKSLS LSPGK                                         445

SEQ ID NO: 64           moltype = DNA  length = 660
FEATURE                 Location/Qualifiers
misc_feature            1..660
                        note = Synthethic Polynucleotide
source                  1..660
                        mol_type = other DNA
                        organism = synthetic construct
SEQUENCE: 64
gacgtagtac tgacccaaag ccccctttct ctcccagtaa ccctcggaca accagcctca     60
atttcatgca gatcatcaca atcacttgag gacagcgacg gaggcacttt tcttgagtgg    120
ttccaacaaa gacccggaca agcccacgc ctgcttattt acgacgtatc aagcagattc     180
tcaggagttc cagacagatt ttcaggcagc ggatccggca cagacttcac ccttaaaatt    240
agcagagtag aagcagaaga tgtaggagtg tattattgtt tccaagccac ccacgacccc    300
ctcagcttcg gacaaggaac taagctcgaa atcaaaagaa cggtggctgc accatctgtc    360
ttcatcttcc cgccatctga tgagcagttg aaatctgaca ctgccctcct tgtgtgcctg    420
ctgaataact ctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga    660

SEQ ID NO: 65           moltype = AA  length = 219
FEATURE                 Location/Qualifiers
REGION                  1..219
                        note = Synthethic Polypeptide
source                  1..219
```

```
                            mol_type = protein
                            organism = synthetic construct
SEQUENCE: 65
DVVLTQSPLS LPVTLGQPAS ISCRSSQSLA DSDGDTFLHW FQQRPGQSPR LLIYAVSHRF      60
SGVPDRFSGS GSGTDFTLKI SRVEAEDVGV YYCFQATHDP VTFGQGTKLE IKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 66               moltype = AA   length = 445
FEATURE                     Location/Qualifiers
REGION                      1..445
                            note = Synthethic Polypeptide
source                      1..445
                            mol_type = protein
                            organism = synthetic construct
SEQUENCE: 66
EVQLVESGGG LVQPGGSLRL SCAASGFTFS NYGMNWVRQA PGKGLEWIGM IYYDSSEKHY      60
ADSVKGRFTI SRDNSKNTLY LQMNSLRAED TAVYYCAKGT TPDKWGQGTM VTVSSASTKG     120
PSVFPLAPSS KSTSGGTAAL GCLVKDYFPE PVTVSWNSGA LTSGVHTFPA VLQSSGLYSL     180
SSVVTVPSSS LGTQTYICNV NHKPSNTKVD KKVEPKSCDK THTCPPCPAP EAAGGPSVFL     240
FPPKPKDTLM ISRTPEVTCV VVDVSHEDPE VKFNWYVDGV EVHNAKTKPR EEQYNSTYRV     300
VSVLTVLHQD WLNGKEYKCK VSNKALPAPI EKTISKAKGQ PREPQVYTLP PSREEMTKNQ     360
VSLTCLVKGF YPSDIAVEWE SNGQPENNYK TTPPVLDSDG SFFLYSKLTV DKSRWQQGNV     420
FSCSVMHEAL HNHYTQKSLS LSPGK                                          445

SEQ ID NO: 67               moltype = AA   length = 219
FEATURE                     Location/Qualifiers
REGION                      1..219
                            note = Synthethic Polypeptide
source                      1..219
                            mol_type = protein
                            organism = synthetic construct
SEQUENCE: 67
DVVLTQSPLS LPVTLGQPAS ISCRSSQSLE ESDGYTFLEW FQQRPGQSPR LLIYEVSHRF      60
SGVPDRFSGS GSGTDFTLKI SRVEAEDVGV YYCFQATHDP LTFGQGTKLE IKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 68               moltype = AA   length = 445
FEATURE                     Location/Qualifiers
REGION                      1..445
                            note = Synthethic Polypeptide
source                      1..445
                            mol_type = protein
                            organism = synthetic construct
SEQUENCE: 68
EVQLVESGGG LVQPGGSLRL SCAASGFTFS NYGMNWVRQA PGKGLEWIGM IYYDSSEKHY      60
ADSVKGRFTI SRDNSKNTLY LQMNSLRAED TAVYYCAKGS TPDYWGQGTM VTVSSASTKG     120
PSVFPLAPSS KSTSGGTAAL GCLVKDYFPE PVTVSWNSGA LTSGVHTFPA VLQSSGLYSL     180
SSVVTVPSSS LGTQTYICNV NHKPSNTKVD KKVEPKSCDK THTCPPCPAP EAAGGPSVFL     240
FPPKPKDTLM ISRTPEVTCV VVDVSHEDPE VKFNWYVDGV EVHNAKTKPR EEQYNSTYRV     300
VSVLTVLHQD WLNGKEYKCK VSNKALPAPI EKTISKAKGQ PREPQVYTLP PSREEMTKNQ     360
VSLTCLVKGF YPSDIAVEWE SNGQPENNYK TTPPVLDSDG SFFLYSKLTV DKSRWQQGNV     420
FSCSVMHEAL HNHYTQKSLS LSPGK                                          445

SEQ ID NO: 69               moltype = AA   length = 219
FEATURE                     Location/Qualifiers
REGION                      1..219
                            note = Synthethic Polypeptide
source                      1..219
                            mol_type = protein
                            organism = synthetic construct
SEQUENCE: 69
DVVLTQSPLS LPVTLGQPAS ISCRSSQSLE DSDGGTFLEW FQQRPGQSPR LLIYDVSSRF      60
SGVPDRFSGS GSGTDFTLKI SRVEAEDVGV YYCFQATHDP LSFGQGTKLE IKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 70               moltype = DNA   length = 345
FEATURE                     Location/Qualifiers
misc_feature                1..345
                            note = Synthethic Polynucleotide
source                      1..345
                            mol_type = other DNA
                            organism = synthetic construct
SEQUENCE: 70
gaagtacagt tggtagaaag cggcggagga cttgtgcagc caggtggatc tctcagactt      60
tcatgtgccg caagcggttt tactttagt aactatggaa tgaattggat tagacaagcg     120
cccggaaaag gattggaatg gataggaatg atatactacg atagctcaga aaaacattat     180
```

```
gccgactcag ttaaaggaag atttacaata tcaagagaca atagcaaaaa cacactttat    240
cttcaaatga attcactgcg agccgaggat acagcagtct attattgcgc aaaaggaaca    300
acaccagatt attggggtca aggaacaatg gtaaccgtgt caagc                    345

SEQ ID NO: 71           moltype = DNA  length = 1338
FEATURE                 Location/Qualifiers
misc_feature            1..1338
                        note = Synthethic Polynucleotide
source                  1..1338
                        mol_type = other DNA
                        organism = synthetic construct
SEQUENCE: 71
gaagtacagt tggtagaaag cggcggagga cttgtgcagc caggtggatc tctcagactt     60
tcatgtgccg caagcggttt tactttagt aactatgaa tgaattggat tagacaagcg      120
cccggaaaag gattggaatg gataggaatg atatactacg atagctcaga aaaacattat   180
gccgactcag ttaaaggaag atttacaata tcaagagaca atagcaaaaa cacactttat    240
cttcaaatga attcactgcg agccgaggat acagcagtct attattgcgc aaaaggaaca    300
acaccagatt attggggtca aggaacaatg gtaaccgtgt caagcgcgtc gaccaagggc    360
ccatcggtct tcccctggc accctcctcc aagagcacct ctgggggcac agcggccctc    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaagccgcgg ggggaccgtc agtcttcctc    720
ttccccccaa acccaagga caccctcatg atctcccgga ccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caagggggcag   1020
ccccgagaac cacaggtgta caccctgccc ccatcccgcg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338

SEQ ID NO: 72           moltype = DNA  length = 336
FEATURE                 Location/Qualifiers
misc_feature            1..336
                        note = Synthethic Polynucleotide
source                  1..336
                        mol_type = other DNA
                        organism = synthetic construct
SEQUENCE: 72
gacgtagtac tgacccaaag ccccctttct ctcccagtaa ccctcggaca accagcctca     60
atttcatgca gatcatcaca atcacttgag acgagcgacg gagacacttt tcttgagtgg    120
ttccaacaaa gacccggaca aagcccacgc ctgcttattt acgaggtatc aacgagattc    180
tcaggagttc cagacagatt ttcaggcagc ggatccggca cagacttcac ccttaaaatt    240
agcagagtag aagcagaaga tgtaggagtg tattattgtt ttcaagtcac ccacgacccc    300
atgacgttcg gacaaggaac taagctcgaa atcaaa                              336

SEQ ID NO: 73           moltype = DNA  length = 660
FEATURE                 Location/Qualifiers
misc_feature            1..660
                        note = Synthethic Polynucleotide
source                  1..660
                        mol_type = other DNA
                        organism = synthetic construct
SEQUENCE: 73
gacgtagtac tgacccaaag ccccctttct ctcccagtaa ccctcggaca accagcctca     60
atttcatgca gatcatcaca atcacttgag acgagcgacg gagacacttt tcttgagtgg    120
ttccaacaaa gacccggaca aagcccacgc ctgcttattt acgaggtatc aacgagattc    180
tcaggagttc cagacagatt ttcaggcagc ggatccggca cagacttcac ccttaaaatt    240
agcagagtag aagcagaaga tgtaggagtg tattattgtt ttcaagtcac ccacgacccc    300
atgacgttcg gacaaggaac taagctcgaa atcaaaagaa cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga    660

SEQ ID NO: 74           moltype = DNA  length = 336
FEATURE                 Location/Qualifiers
misc_feature            1..336
                        note = Synthethic Polynucleotide
source                  1..336
                        mol_type = other DNA
                        organism = synthetic construct
SEQUENCE: 74
```

```
gacgtagtac tgacccaaag ccccctttct ctcccagtaa ccctcggaca accagcctca   60
atttcatgca gatcatcaca atcacttgag acgagcgacg gagacacttt tcttgagtgg  120
ttccaacaaa gacccggaca aagcccacgc ctgcttattt acgaggtatc aagcagattc  180
tcaggagttc cagacagatt ttcaggcagc ggatccggca cagacttcac ccttaaaatt  240
agcagagtag aagcagaaga tgtaggagtg tattattgta tgcaagtcac ccacgacccc  300
ctgaccttcg gacaaggaac taagctcgaa atcaaa                            336

SEQ ID NO: 75          moltype = DNA  length = 660
FEATURE                Location/Qualifiers
misc_feature           1..660
                       note = Synthethic Polynucleotide
source                 1..660
                       mol_type = other DNA
                       organism = synthetic construct
SEQUENCE: 75
gacgtagtac tgacccaaag ccccctttct ctcccagtaa ccctcggaca accagcctca   60
atttcatgca gatcatcaca atcacttgag acgagcgacg gagacacttt tcttgagtgg  120
ttccaacaaa gacccggaca aagcccacgc ctgcttattt acgaggtatc aagcagattc  180
tcaggagttc cagacagatt ttcaggcagc ggatccggca cagacttcac ccttaaaatt  240
agcagagtag aagcagaaga tgtaggagtg tattattgta tgcaagtcac ccacgacccc  300
ctgaccttcg gacaaggaac taagctcgaa atcaaaagaa cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct caacaggggg agagtgttga  660

SEQ ID NO: 76          moltype = DNA  length = 336
FEATURE                Location/Qualifiers
misc_feature           1..336
                       note = Synthethic Polynucleotide
source                 1..336
                       mol_type = other DNA
                       organism = synthetic construct
SEQUENCE: 76
gacgtagtac tgacccaaag ccccctttct ctcccagtaa ccctcggaca accagcctca   60
atttcatgca gatcatcaca atcacttgag accagcgacg gagatacttt tcttgagtgg  120
ttccaacaaa gacccggaca aagcccacgc ctgcttattt acgaggtatc aaacagattc  180
tcaggagttc cagacagatt ttcaggcagc ggatccggca cagacttcac ccttaaaatt  240
agcagagtag aagcagaaga tgtaggagtg tattattgtt tccaagtcac ccacgacccc  300
gtcacgttcg gacaaggaac taagctcgaa atcaaa                            336

SEQ ID NO: 77          moltype = DNA  length = 660
FEATURE                Location/Qualifiers
misc_feature           1..660
                       note = Synthethic Polynucleotide
source                 1..660
                       mol_type = other DNA
                       organism = synthetic construct
SEQUENCE: 77
gacgtagtac tgacccaaag ccccctttct ctcccagtaa ccctcggaca accagcctca   60
atttcatgca gatcatcaca atcacttgag accagcgacg gagatacttt tcttgagtgg  120
ttccaacaaa gacccggaca aagcccacgc ctgcttattt acgaggtatc aaacagattc  180
tcaggagttc cagacagatt ttcaggcagc ggatccggca cagacttcac ccttaaaatt  240
agcagagtag aagcagaaga tgtaggagtg tattattgtt tccaagtcac ccacgacccc  300
gtcacgttcg gacaaggaac taagctcgaa atcaaaagaa cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct caacaggggg agagtgttga  660

SEQ ID NO: 78          moltype = DNA  length = 336
FEATURE                Location/Qualifiers
misc_feature           1..336
                       note = Synthethic Polynucleotide
source                 1..336
                       mol_type = other DNA
                       organism = synthetic construct
SEQUENCE: 78
gacgtagtac tgacccaaag ccccctttct ctcccagtaa ccctcggaca accagcctca   60
atttcatgca gatcatcaca atcacttgag tccagcgacg gagacacttt tcttgagtgg  120
ttccaacaaa gacccggaca aagcccacgc ctgcttattt acgatgtatc aactagattc  180
tcaggagttc cagacagatt ttcaggcagc ggatccggca cagacttcac ccttaaaatt  240
agcagagtag aagcagaaga tgtaggagtg tattattgtt ttcaagtcac ccatgacccc  300
gtgaccttcg gacaaggaac taagctcgaa atcaaa                            336

SEQ ID NO: 79          moltype = DNA  length = 660
FEATURE                Location/Qualifiers
```

```
misc_feature            1..660
                        note = Synthethic Polynucleotide
source                  1..660
                        mol_type = other DNA
                        organism = synthetic construct
SEQUENCE: 79
gacgtagtac tgacccaaag ccccctttct ctcccagtaa ccctcggaca accagcctca   60
atttcatgca gatcatcaca atcacttgag tccagcgacg gagacacttt tcttgagtgg  120
ttccaacaaa gacccggaca aagcccacgc ctgcttattt acgatgtatc aactagattc  180
tcaggagttc cagacagatt ttcaggcagc ggatccggca cagacttcac ccttaaaatt  240
agcagagtag aagcagaaga tgtaggagtg tattattgtt ttcaagtcac ccatgacccc  300
gtgaccttcg gacaaggaac taagctcgaa atcaaaagaa cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct caacaggggg agagtgttga  660

SEQ ID NO: 80            moltype = DNA  length = 336
FEATURE                  Location/Qualifiers
misc_feature             1..336
                         note = Synthethic Polynucleotide
source                   1..336
                         mol_type = other DNA
                         organism = synthetic construct
SEQUENCE: 80
gacgtagtac tgacccaaag ccccctttct ctcccagtaa ccctcggaca accagcctca   60
atttcatgca gatcatcaca atcacttgag gaaagcgacg gatacacttt tcttgaatgg  120
ttccaacaaa gacccggaca aagcccacgc ctgcttattt acgatgtatc agaaagattc  180
tcaggagttc cagacagatt ttcaggcagc ggatccggca cagacttcac ccttaaaatt  240
agcagagtag aagcagaaga tgtaggagtg tattattgtt tccaagcgac ctacgacccc  300
ctcaccttcg gacaaggaac taagctcgaa atcaaa                            336

SEQ ID NO: 81            moltype = DNA  length = 660
FEATURE                  Location/Qualifiers
misc_feature             1..660
                         note = Synthethic Polynucleotide
source                   1..660
                         mol_type = other DNA
                         organism = synthetic construct
SEQUENCE: 81
gacgtagtac tgacccaaag ccccctttct ctcccagtaa ccctcggaca accagcctca   60
atttcatgca gatcatcaca atcacttgag gaaagcgacg gatacacttt tcttgaatgg  120
ttccaacaaa gacccggaca aagcccacgc ctgcttattt acgatgtatc agaaagattc  180
tcaggagttc cagacagatt ttcaggcagc ggatccggca cagacttcac ccttaaaatt  240
agcagagtag aagcagaaga tgtaggagtg tattattgtt tccaagcgac ctacgacccc  300
ctcaccttcg gacaaggaac taagctcgaa atcaaaagaa cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct caacaggggg agagtgttga  660

SEQ ID NO: 82            moltype = DNA  length = 345
FEATURE                  Location/Qualifiers
misc_feature             1..345
                         note = Synthethic Polynucleotide
source                   1..345
                         mol_type = other DNA
                         organism = synthetic construct
SEQUENCE: 82
gaagtacagt tggtagaaag cggcggagga cttgtgcagc caggtggatc tctcagactt   60
tcatgtgccg caagcggttt tactttttagt tactatggaa tgaactggat tagacaagcg  120
cccggaaaag gattggaatg gataggcatg atatatacg acagctcgga gaaacattat  180
gccgactcag ttaaaggaag atttacaata tcaagagaca atagcaaaaa cacactttat  240
cttcaaatga attcactgcg agccgaggat acagcagtct attattgcgc aaaagggacg  300
acgcccgatt actggggtca aggaacaatg gtaaccgtgt caagc                  345

SEQ ID NO: 83            moltype = DNA  length = 336
FEATURE                  Location/Qualifiers
misc_feature             1..336
                         note = Synthethic Polynucleotide
source                   1..336
                         mol_type = other DNA
                         organism = synthetic construct
SEQUENCE: 83
gacgtagtac tgacccaaag ccccctttct ctcccagtaa ccctcggaca accagcctca   60
atttcatgca gatcatcaca atcacttgag gacagcgacg gaggaacttt tcttgagtgg  120
ttccaacaaa gacccggaca aagcccacgc ctgcttattt acgacgtatc aagcagattc  180
```

-continued

```
tcaggagttc cagacagatt ttcaggcagc ggatccggca cagacttcac ccttaaaatt    240
agcagagtag aagcagaaga tgtaggagtg tattattgtt ttcaagcgac ccacgacccc    300
ctgacgttcg gacaaggaac taagctcgaa atcaaa                              336

SEQ ID NO: 84           moltype = DNA  length = 1338
FEATURE                 Location/Qualifiers
misc_feature            1..1338
                        note = Synthethic Polynucleotide
source                  1..1338
                        mol_type = other DNA
                        organism = synthetic construct
SEQUENCE: 84
gaagtacagt tggtagaaag cggcggagga cttgtgcagc caggtggatc tctcagactt     60
tcatgtgccg caagcggttt tacttttagt tactatggaa tgaactggat tagacaagcg    120
cccggaaaag gattggaatg gataggcatg atatactacg acagctcgga gaaacattat    180
gccgactcag ttaaaggaag atttacaata tcaagagaca atagcaaaaa cacactttat    240
cttcaaatga attcactgcg agccgaggat acagcagtct attattgcgc aaaagggacg    300
acgcccgatt actggggtca aggaacaatg gtaaccgtgt caagccgcgt gaccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaagccgcgg ggggaccgtc agtcttcctc    720
ttcccccaa acccaaggac accctcatg atctcccgga cccctgaggt cacatgcgtg     780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caagggcag    1020
ccccgagaac cacaggtgta ccccctgccc catcccgcg agagatgac caagaaccag    1080
gtcagcctga cctgcctggt caaaggcttc tatcccagc acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaatga                                                  1338

SEQ ID NO: 85           moltype = DNA  length = 660
FEATURE                 Location/Qualifiers
misc_feature            1..660
                        note = Synthethic Polynucleotide
source                  1..660
                        mol_type = other DNA
                        organism = synthetic construct
SEQUENCE: 85
gacgtagtac tgacccaaag ccccctttct ctcccagtaa ccctcggaca accagcctca     60
atttcatgca gatcatcaca atcacttgag gacagcgacg gaggaacttt tcttgagtgg    120
ttccaacaaa gacccggaca aagcccacgc ctgcttattt acgacgtatc aagcagattc    180
tcaggagttc cagacagatt ttcaggcagc ggatccggca cagacttcac ccttaaaatt    240
agcagagtag aagcagaaga tgtaggagtg tattattgtt ttcaagcgac ccacgacccc    300
ctgacgttcg gacaaggaac taagctcgaa atcaaaagaa cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga    660

SEQ ID NO: 86           moltype = DNA  length = 345
FEATURE                 Location/Qualifiers
misc_feature            1..345
                        note = Synthethic Polynucleotide
source                  1..345
                        mol_type = other DNA
                        organism = synthetic construct
SEQUENCE: 86
gaagtacagt tggtagaaag cggcggagga cttgtgcagc caggtggatc tctcagactt     60
tcatgtgccg caagcggttt tacttttagt aactatggaa tgaactggat aagacaagcg    120
cccggaaaag gattggaatg gataggcatg atatactacg acagctcgga caaacattat    180
gccgactcag ttaaaggaag atttacaata tcaagagaca atagcaaaaa cacactttat    240
cttcaaatga attcactgcg agccgaggat acagcagtct attattgcgc aaaagggacg    300
acgccggatg tatgggggtca aggaacaatg gtaaccgtgt caagc                   345

SEQ ID NO: 87           moltype = DNA  length = 336
FEATURE                 Location/Qualifiers
misc_feature            1..336
                        note = Synthethic Polynucleotide
source                  1..336
                        mol_type = other DNA
                        organism = synthetic construct
SEQUENCE: 87
```

```
gacgtagtac tgacccaaag ccccctttct ctcccagtaa ccctcggaca accagcctca    60
atttcatgca gatcatcaca atcacttgaa gagagcgacg gatacacttt tcttcattgg   120
ttccaacaaa gacccggaca aagcccacgc ctgcttattt acgaggtatc aaacagattc   180
tcaggagttc cagacagatt ttcaggcagc ggatccggca cagacttcac ccttaaaatt   240
agcagagtag aagcagaaga tgtaggagtg tattattgtt ccaagccac ccacgacccc    300
gtgacgttcg gacaaggaac taagctcgaa atcaaa                             336
```

| SEQ ID NO: 88 | moltype = DNA length = 1338 |
|---|---|
| FEATURE | Location/Qualifiers |
| misc_feature | 1..1338 |
| | note = Synthethic Polynucleotide |
| source | 1..1338 |
| | mol_type = other DNA |
| | organism = synthetic construct |

```
SEQUENCE: 88
gaagtacagt tggtagaaag cggcggagga cttgtgcagc caggtggatc tctcagactt    60
tcatgtgccg caagcggttt tactttagt aactatggaa tgaactggat aagacaagcg    120
cccggaaaag gattggaatg gataggcatg atatactacg acagctcgga caaacattat   180
gccgactcag ttaaaggaag atttacaata tcaagagaca atagcaaaaa cacactttat   240
cttcaaatga attcactgcg agccgaggat acagcagtct attattgcgc aaaagggacg   300
acgccggatg tatgggtca aggaacaatg gtaaccgtgt caagcgcgtc gaccaagggc    360
ccatccggtct tcccccctgc accctcctcc aagagcacct ctgggggcac agcggccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcaccc agacctacat ctgcaacgtg   600
aatcacaagc ccagcaacac caaggtggac aagaaagttg agcccaaatc ttgtgacaaa   660
actcacacat gcccaccgtg cccagcacct gaagccgcgg ggggaccgtc agtcttcctc   720
ttcccccccaa aacccaagga caccctcatg atctcccgga cccctgaggt cacatgcgtg   780
gtggtggacg tgagccacga agaccctgag gtcaagttca actggtacgt ggacggcgtg   840
gaggtgcata atgccaagac aaagccgcgg gaggagcagt acaacagcac gtaccgtgtg   900
gtcagcgtcc tcaccgtcct gcaccaggac tggctgaatg gcaaggagta caagtgcaag   960
gtctccaaca aagcccctcc cagccccatc gagaaaacca tctccaaagc caaagggcag  1020
ccccgagaac cacaggtgta caccctgccc ccatcccgcg aggagatgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gtaaatga                                                 1338
```

| SEQ ID NO: 89 | moltype = DNA length = 660 |
|---|---|
| FEATURE | Location/Qualifiers |
| misc_feature | 1..660 |
| | note = Synthethic Polynucleotide |
| source | 1..660 |
| | mol_type = other DNA |
| | organism = synthetic construct |

```
SEQUENCE: 89
gacgtagtac tgacccaaag ccccctttct ctcccagtaa ccctcggaca accagcctca    60
atttcatgca gatcatcaca atcacttgaa gagagcgacg gatacacttt tcttcattgg   120
ttccaacaaa gacccggaca aagcccacgc ctgcttattt acgaggtatc aaacagattc   180
tcaggagttc cagacagatt ttcaggcagc ggatccggca cagacttcac ccttaaaatt   240
agcagagtag aagcagaaga tgtaggagtg tattattgtt ccaagccac ccacgacccc    300
gtgacgttcg gacaaggaac taagctcgaa atcaaaagaa cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttga   660
```

| SEQ ID NO: 90 | moltype = DNA length = 345 |
|---|---|
| FEATURE | Location/Qualifiers |
| misc_feature | 1..345 |
| | note = Synthethic Polynucleotide |
| source | 1..345 |
| | mol_type = other DNA |
| | organism = synthetic construct |

```
SEQUENCE: 90
gaagtacagt tggtagaaag cggcggagga cttgtgcaac caggtggatc tctcagactt    60
tcatgtgccg caagcggttt tactttagt aactatggaa tgaactgggt tagacaagcg    120
cccggaaaag gattggaatg gataggcatg atatattacg acagctcgga gaaacattat   180
gccgactcag ttaaaggaag atttacaata tcaagagaca atagcaaaaa cacactttat   240
cttcaaatga attcactgcg agccgaggat acagcagtct attattgcgc aaaagggacc   300
acccccgatt actggggtca aggaacaatg gtaaccgtgt caagc                   345
```

| SEQ ID NO: 91 | moltype = DNA length = 336 |
|---|---|
| FEATURE | Location/Qualifiers |
| misc_feature | 1..336 |
| | note = Synthethic Polynucleotide |
| source | 1..336 |

```
                       mol_type = other DNA
                       organism = synthetic construct
SEQUENCE: 91
gacgtagtac tgacccaaag cccccttttct ctcccagtaa ccctcggaca accagcctca    60
atttcatgca gatcatcaca atcacttgaa gaaagcgacg gatacacttt tcttcactgg   120
ttccaacaaa gacccggaca aagcccacgc ctgcttattt acgaggtatc aaccagattc   180
tcaggagttc cagacagatt ttcaggcagc ggatccggca cagacttcac ccttaaaatt   240
agcagagtag aagcagaaga tgtaggagtg tattattgtt ccaagccac ccacgacccc    300
ctgaccttcg gacaaggaac taagctcgaa atcaaa                             336

SEQ ID NO: 92           moltype = DNA  length = 1338
FEATURE                 Location/Qualifiers
misc_feature            1..1338
                       note = Synthethic Polynucleotide
source                  1..1338
                       mol_type = other DNA
                       organism = synthetic construct
SEQUENCE: 92
gaagtacagt tggtagaaag cggcggagga cttgtgcaac caggtggatc tctcagactt    60
tcatgtgccg caagcggttt tacttttagt aactatggaa tgaactgggt tagacaagcg   120
cccggaaaag gattggaatg gataggcatg atatattacg acagctcgga gaaacattat   180
gccgactcag ttaaaggaag atttacaata tcaagagaca atagcaaaaa cacactttat   240
cttcaaatga attcactgcg agccgaggat acagcagtct attattgcgc aaaagggacc   300
acccccgatt actgggtca aggaacaatg gtaaccgtgt caagcgcgtc gaccaagggc    360
ccatcggtct tccccctggc accctcctcc aagagcacct ctgggggcac agcggccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcaccc agacctacat ctgcaacgtg   600
aatcacaagc ccagcaacac caaggtggac aagaaagttg agcccaaatc ttgtgacaaa   660
actcacacat gcccaccgtg cccagcacct gaagccgtcg ggggaccgtc agtcttcctc   720
ttccccccaa acccaaggga caccctcatg atctcccgga cccctgaggt cacatgcgtg   780
gtggtggacg tgagccacga agaccctgag gtcaagttca actggtacgt ggacggcgtg   840
gaggtgcata atgccaagac aaagccgcgg gaggagcagt acaacagcac gtaccgtgtg   900
gtcagcgtcc tcaccgtcct gcaccaggac tggctgaatg gcaaggagta caagtgcaag   960
gtctccaaca aagccctccc agcccccatc gagaaaacca tctccaaagc caagggcag   1020
ccccgagaac cacaggtgta caccctgccc ccatcccgcg aggagatgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gtaaatga                                                1338

SEQ ID NO: 93           moltype = DNA  length = 660
FEATURE                 Location/Qualifiers
misc_feature            1..660
                       note = Synthethic Polynucleotide
source                  1..660
                       mol_type = other DNA
                       organism = synthetic construct
SEQUENCE: 93
gacgtagtac tgacccaaag cccccttttct ctcccagtaa ccctcggaca accagcctca    60
atttcatgca gatcatcaca atcacttgaa gaaagcgacg gatacacttt tcttcactgg   120
ttccaacaaa gacccggaca aagcccacgc ctgcttattt acgaggtatc aaccagattc   180
tcaggagttc cagacagatt ttcaggcagc ggatccggca cagacttcac ccttaaaatt   240
agcagagtag aagcagaaga tgtaggagtg tattattgtt ccaagccac ccacgacccc    300
ctgaccttcg gacaaggaac taagctcgaa atcaaaagaa cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttga   660

SEQ ID NO: 94           moltype = DNA  length = 1338
FEATURE                 Location/Qualifiers
misc_feature            1..1338
                       note = Synthethic Polynucleotide
source                  1..1338
                       mol_type = other DNA
                       organism = synthetic construct
SEQUENCE: 94
gaagtacagt tggtagaaag cggcggagga cttgtgcaac caggtggatc tctcagactt    60
tcatgtgccg caagcggttt tacttttagt aactatggaa tgaactgggt tagacaagcg   120
cccggaaaag gattggaatg gataggcatg atatattacg acagctcgga gaaacattat   180
gccgactcag ttaaaggaag atttacaata tcaagagaca atagcaaaaa cacactttat   240
cttcaaatga attcactgcg agccgaggat acagcagtct attattgcgc aaaagggacc   300
acccccgatt actgggtca aggaacaatg gtaaccgtgt caagcgcgtc gaccaagggc    360
ccatcggtct tccccctggc accctcctcc aagagcacct ctgggggcac agcggccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
```

```
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaagccgcgg ggggaccgtc agtcttcctc    720
ttccccccaa acccaagga ccaactcatg atctcccgga cccctgaggt cacatgcgtg     780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caagggcag    1020
ccccgagaac cacaggtgta cacctgccc catcccgcg aggaatgac caagaaccag       1080
gtcagcctga cctgcctggt caaaggcttc tatcccagc acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgctgca tgaggctctg cacaaccact acacgcagaa gagcctctcc    1320
ctgtctccgg gtaaatga                                                  1338

SEQ ID NO: 95          moltype = DNA   length = 336
FEATURE                Location/Qualifiers
misc_feature           1..336
                       note = Synthethic Polynucleotide
source                 1..336
                       mol_type = other DNA
                       organism = synthetic construct
SEQUENCE: 95
gacgtagtac tgacccaaag ccccctttct ctcccagtaa ccctcggaca accagcctca     60
atttcatgca gatcatcaca atcacttgcg gacagcgacg gagatacttt tcttcactgg    120
ttccaacaaa gacccggaca aagcccacgc ctgcttattt acgcggtatc acacagattc    180
tcaggagttc cagacagatt ttcaggcagc ggatccggca cagacttcac ccttaaaatt    240
agcagagtag aagcagaaga tgtaggagtg tattattgtt ccaagccac ccatgacccc     300
gtcacgttcg gacaaggaac taagctcgaa atcaaa                              336

SEQ ID NO: 96          moltype = DNA   length = 660
FEATURE                Location/Qualifiers
misc_feature           1..660
                       note = Synthethic Polynucleotide
source                 1..660
                       mol_type = other DNA
                       organism = synthetic construct
SEQUENCE: 96
gacgtagtac tgacccaaag ccccctttct ctcccagtaa ccctcggaca accagcctca     60
atttcatgca gatcatcaca atcacttgcg gacagcgacg gagatacttt tcttcactgg    120
ttccaacaaa gacccggaca aagcccacgc ctgcttattt acgcggtatc acacagattc    180
tcaggagttc cagacagatt ttcaggcagc ggatccggca cagacttcac ccttaaaatt    240
agcagagtag aagcagaaga tgtaggagtg tattattgtt ccaagccac ccatgacccc     300
gtcacgttcg gacaaggaac taagctcgaa atcaaaagaa cggtggctgc caccatctgtc   360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga    660

SEQ ID NO: 97          moltype = DNA   length = 345
FEATURE                Location/Qualifiers
misc_feature           1..345
                       note = Synthethic Polynucleotide
source                 1..345
                       mol_type = other DNA
                       organism = synthetic construct
SEQUENCE: 97
gaagtacagt tggtagaaag cggcggagga cttgtgcagc caggtggatc tctcagactt    60
tcatgtgccg caagcggttt tacttttagt aactatgaa tgaactgggt tagacaagcg    120
cccgaaaag gattgaatg gataggcatg atatactacg acagctccga gaaacattat     180
gccgactcag ttaaaggaag atttacaata tcaagagaca atagcaaaaa cacacttat    240
cttcaaatga attcactgcg agccgaggat acagcagtct attattgcgc aaaaggcacg    300
acgcccgata aatgggtca aggaacaatg gtaaccgtgt caagc                    345

SEQ ID NO: 98          moltype = DNA   length = 336
FEATURE                Location/Qualifiers
misc_feature           1..336
                       note = Synthethic Polynucleotide
source                 1..336
                       mol_type = other DNA
                       organism = synthetic construct
SEQUENCE: 98
gacgtagtac tgacccaaag ccccctttct ctcccagtaa ccctcggaca accagcctca     60
atttcatgca gatcatcaca atcacttgag gagagcgacg gatacacttt tcttgagtgg    120
ttccaacaaa gacccggaca aagcccacgc ctgcttattt acgaggtatc acatagattc    180
tcaggagttc cagacagatt ttcaggcagc ggatccggca cagacttcac ccttaaaatt    240
agcagagtag aagcagaaga tgtaggagtg tattattgtt ccaagcgac ccacgacccc     300
ctgacgttcg gacaaggaac taagctcgaa atcaaa                              336
```

```
SEQ ID NO: 99              moltype = DNA  length = 1338
FEATURE                    Location/Qualifiers
misc_feature               1..1338
                           note = Synthethic Polynucleotide
source                     1..1338
                           mol_type = other DNA
                           organism = synthetic construct
SEQUENCE: 99
gaagtacagt tggtagaaag cggcggagga cttgtgcagc caggtggatc tctcagactt   60
tcatgtgccg caagcggttt tactttagt aactatggaa tgaactgggt tagacaagcg   120
cccgaaaag gattggaatg gataggcatg atatactacg acagctccga gaaacattat    180
gccgactcag ttaaaggaag atttacaata tcaagacaca atagcaaaaa cacactttat   240
cttcaaatga attcactgcg agccgaggat acagcagtct attattgcgc aaaaggcacg   300
acgcccgata aatggggtca aggaacaatg gtaaccgtgt caagcgcgtc gaccaagggc   360
ccatcggtct tccccctggc accctcctcc aagagcacct ctggggggcac agcggccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcaccc agacctacat ctgcaacgtg   600
aatcacaagc ccagcaacac caaggtggac aagaaagttg agcccaaatc ttgtgacaaa   660
actcacacat gcccaccgtg cccagcacct gaagccgcgg ggggaccgtc agtcttcctc   720
ttcccccca aacccaagga caccctcatg atctcccgga cccctgaggt cacatgcgtg    780
gtggtggacg tgagccacga agaccctgag gtcaagttca actggtacgt ggacggcgtg   840
gaggtgcata atgccaagac aaagccgcgg gaggagcagt acaacagcac gtaccgtgtg   900
gtcagcgtcc tcaccgtcct gcaccaggac tggctgaatg gcaaggagta caagtgcaag   960
gtctccaaca aagccctccc agcccccatc gagaaaacca tctccaaagc caaagggcag   1020
ccccgagaac cacaggtgta caccctgccc ccatcccgcg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338

SEQ ID NO: 100             moltype = DNA  length = 660
FEATURE                    Location/Qualifiers
misc_feature               1..660
                           note = Synthethic Polynucleotide
source                     1..660
                           mol_type = other DNA
                           organism = synthetic construct
SEQUENCE: 100
gacgtagtac tgacccaaag cccccttct ctcccagtaa ccctcggaca accagcctca    60
atttcatgca gatcatcaca atcacttgag gagagcgacg gatacacttt tcttgagtgg   120
ttccaacaaa gacccggaca agcccacgc ctgcttattt acgaggtatc acatagattc    180
tcaggagttc cagacagatt ttcaggcagc ggatccggca cagacttcac ccttaaaatt   240
agcagagtag aagcagaaga tgtaggagtg tattattgtt tccaagcgac ccacgacccc   300
ctgacgttcg gacaaggaac taagctcgaa atcaaaagaa cggtggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttga   660

SEQ ID NO: 101             moltype = DNA  length = 345
FEATURE                    Location/Qualifiers
misc_feature               1..345
                           note = Synthethic Polynucleotide
source                     1..345
                           mol_type = other DNA
                           organism = synthetic construct
SEQUENCE: 101
gaagtacagt tggtagaaag cggcggagga cttgtgcagc caggtggatc tctcagactt   60
tcatgtgccg caagcggttt tactttagt aactatggaa tgaactgggt tagacaagcg   120
cccggaaaag gattggaatg gataggaatg atatactacg acagctccga gaaacattat   180
gccgactcag ttaaaggaag atttacaata tcaagacaca atagcaaaaa cacactttat   240
cttcaaatga attcactgcg agccgaggat acagcagtct attattgcgc aaaaggctcg   300
accccgatt actggggtca aggaacaatg gtaaccgtgt caagc                    345

SEQ ID NO: 102             moltype = DNA  length = 336
FEATURE                    Location/Qualifiers
misc_feature               1..336
                           note = Synthethic Polynucleotide
source                     1..336
                           mol_type = other DNA
                           organism = synthetic construct
SEQUENCE: 102
gacgtagtac tgacccaaag cccccttct ctcccagtaa ccctcggaca accagcctca    60
atttcatgca gatcatcaca atcacttgag gacagcgacg gagcacttt tcttgagtgg   120
ttccaacaaa gacccggaca agcccacgc ctgcttattt acgacgtatc aagcagattc   180
```

```
tcaggagttc cagacagatt ttcaggcagc ggatccggca cagacttcac ccttaaaatt   240
agcagagtag aagcagaaga tgtaggagtg tattattgtt tccaagccac ccacgacccc   300
ctcagcttcg gacaaggaac taagctcgaa atcaaa                             336
```

```
SEQ ID NO: 103             moltype = AA   length = 330
FEATURE                    Location/Qualifiers
source                     1..330
                           mol_type = protein
                           organism = Homo sapiens
SEQUENCE: 103
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 104             moltype = AA   length = 19
FEATURE                    Location/Qualifiers
REGION                     1..19
                           note = Synthethic Polypeptide
source                     1..19
                           mol_type = protein
                           organism = synthetic construct
SEQUENCE: 104
MEFGLSWLFL VAILKGVQC                                                 19

SEQ ID NO: 105             moltype = AA   length = 5
FEATURE                    Location/Qualifiers
REGION                     1..5
                           note = Synthethic Polypeptide
VARIANT                    1
                           note = X can be Asn or Tyr
source                     1..5
                           mol_type = protein
                           organism = synthetic construct
SEQUENCE: 105
XYGMN                                                                 5

SEQ ID NO: 106             moltype = AA   length = 17
FEATURE                    Location/Qualifiers
REGION                     1..17
                           note = Synthethic Polypeptide
VARIANT                    8
                           note = X can be Glu or Asp
source                     1..17
                           mol_type = protein
                           organism = synthetic construct
SEQUENCE: 106
MIYYDSSXKH YADSVKG                                                   17

SEQ ID NO: 107             moltype = AA   length = 6
FEATURE                    Location/Qualifiers
REGION                     1..6
                           note = Synthethic Polypeptide
VARIANT                    2
                           note = X can be Thr or Ser
VARIANT                    6
                           note = X can be Tyr, Val, or Lys
source                     1..6
                           mol_type = protein
                           organism = synthetic construct
SEQUENCE: 107
GXTPDX                                                                6

SEQ ID NO: 108             moltype = AA   length = 16
FEATURE                    Location/Qualifiers
REGION                     1..16
                           note = Synthethic Polypeptide
VARIANT                    7
                           note = X can be Ala or Glu
VARIANT                    8
                           note = X can be Thr, Ser, Glu, or Asp
VARIANT                    12
                           note = X can be Asp, Tyr, or Gly
VARIANT                    16
                           note = X can be Glu or His
source                     1..16
                           mol_type = protein
```

-continued

```
                            organism = synthetic construct
SEQUENCE: 108
RSSQSLXXSD GXTFLX                                                    16

SEQ ID NO: 109              moltype = AA   length = 7
FEATURE                     Location/Qualifiers
REGION                      1..7
                            note = Synthethic Polypeptide
VARIANT                     1
                            note = X can be Glu, Asp, or Ala
VARIANT                     4
                            note = Xaa can Asn, Ser, Thr, Glu, or His
source                      1..7
                            mol_type = protein
                            organism = synthetic construct
SEQUENCE: 109
XVSXRFS                                                              7

SEQ ID NO: 110              moltype = AA   length = 9
FEATURE                     Location/Qualifiers
REGION                      1..9
                            note = Synthethic Polypeptide
VARIANT                     1
                            note = X can be Phe or Met
VARIANT                     3
                            note = X can be Val or Ala
VARIANT                     5
                            note = X can be His or Tyr
VARIANT                     8
                            note = X can be Met, Leu, or Val
VARIANT                     9
                            note = X can be Thr or Ser
source                      1..9
                            mol_type = protein
                            organism = synthetic construct
SEQUENCE: 110
XQXTXDPXX                                                            9

SEQ ID NO: 111              moltype = AA   length = 329
FEATURE                     Location/Qualifiers
REGION                      1..329
                            note = Synthetic Polypeptide
source                      1..329
                            mol_type = protein
                            organism = synthetic construct
SEQUENCE: 111
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 112              moltype = AA   length = 329
FEATURE                     Location/Qualifiers
REGION                      1..329
                            note = Synthetic Polypeptide
source                      1..329
                            mol_type = protein
                            organism = synthetic construct
SEQUENCE: 112
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 113              moltype = AA   length = 329
FEATURE                     Location/Qualifiers
REGION                      1..329
                            note = Synthetic Polypeptide
source                      1..329
                            mol_type = protein
                            organism = synthetic construct
SEQUENCE: 113
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDQLMISRTP EVTCVVVDVS HEDPEVKFNW YVDGVEVHNA KTKPREEQYN   180
```

```
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV LHEALHNHYT QKSLSLSPG                                     329

SEQ ID NO: 114          moltype = AA   length = 444
FEATURE                 Location/Qualifiers
REGION                  1..444
                        note = Synthetic Polypeptide
source                  1..444
                        mol_type = protein
                        organism = synthetic construct
SEQUENCE: 114
EVQLVESGGG LVQPGGSLRL SCAASGFTFS NYGMNWIRQA PGKGLEWIGM IYYDSSEKHY    60
ADSVKGRFTI SRDNSKNTLY LQMNSLRAED TAVYYCAKGT TPDYWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 115          moltype = AA   length = 444
FEATURE                 Location/Qualifiers
REGION                  1..444
                        note = Synthetic Polypeptide
source                  1..444
                        mol_type = protein
                        organism = synthetic construct
SEQUENCE: 115
EVQLVESGGG LVQPGGSLRL SCAASGFTFS YYGMNWIRQA PGKGLEWIGM IYYDSSEKHY    60
ADSVKGRFTI SRDNSKNTLY LQMNSLRAED TAVYYCAKGT TPDYWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 116          moltype = AA   length = 444
FEATURE                 Location/Qualifiers
REGION                  1..444
                        note = Synthetic Polypeptide
source                  1..444
                        mol_type = protein
                        organism = synthetic construct
SEQUENCE: 116
EVQLVESGGG LVQPGGSLRL SCAASGFTFS NYGMNWIRQA PGKGLEWIGM IYYDSSDKHY    60
ADSVKGRFTI SRDNSKNTLY LQMNSLRAED TAVYYCAKGT TPDVWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 117          moltype = AA   length = 444
FEATURE                 Location/Qualifiers
REGION                  1..444
                        note = Synthetic Polypeptide
source                  1..444
                        mol_type = protein
                        organism = synthetic construct
SEQUENCE: 117
EVQLVESGGG LVQPGGSLRL SCAASGFTFS NYGMNWVRQA PGKGLEWIGM IYYDSSEKHY    60
ADSVKGRFTI SRDNSKNTLY LQMNSLRAED TAVYYCAKGT TPDYWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 118          moltype = AA   length = 444
FEATURE                 Location/Qualifiers
REGION                  1..444
                        note = Synthetic Polypeptide
source                  1..444
                        mol_type = protein
                        organism = synthetic construct
```

```
SEQUENCE: 118
EVQLVESGGG LVQPGGSLRL SCAASGFTFS NYGMNWVRQA PGKGLEWIGM IYYDSSEKHY    60
ADSVKGRFTI SRDNSKNTLY LQMNSLRAED TAVYYCAKGT TPDYWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDQLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVLHEAL HNHYTQKSLS LSPG                                          444

SEQ ID NO: 119          moltype = AA   length = 444
FEATURE                 Location/Qualifiers
REGION                  1..444
                        note = Synthetic Polypeptide
source                  1..444
                        mol_type = protein
                        organism = synthetic construct
SEQUENCE: 119
EVQLVESGGG LVQPGGSLRL SCAASGFTFS NYGMNWVRQA PGKGLEWIGM IYYDSSEKHY    60
ADSVKGRFTI SRDNSKNTLY LQMNSLRAED TAVYYCAKGT TPDKWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                          444

SEQ ID NO: 120          moltype = AA   length = 444
FEATURE                 Location/Qualifiers
REGION                  1..444
                        note = Synthetic Polypeptide
source                  1..444
                        mol_type = protein
                        organism = synthetic construct
SEQUENCE: 120
EVQLVESGGG LVQPGGSLRL SCAASGFTFS NYGMNWVRQA PGKGLEWIGM IYYDSSEKHY    60
ADSVKGRFTI SRDNSKNTLY LQMNSLRAED TAVYYCAKGS TPDYWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                          444

SEQ ID NO: 121          moltype = AA   length = 14
FEATURE                 Location/Qualifiers
REGION                  1..14
                        note = Synthetic
source                  1..14
                        mol_type = protein
                        organism = synthetic construct
SEQUENCE: 121
SSPMALGANA TATR                                                      14

SEQ ID NO: 122          moltype = AA   length = 14
FEATURE                 Location/Qualifiers
REGION                  1..14
                        note = Synthetic
source                  1..14
                        mol_type = protein
                        organism = synthetic construct
SEQUENCE: 122
TSSPMALGAN ATAT                                                      14

SEQ ID NO: 123          moltype = AA   length = 364
FEATURE                 Location/Qualifiers
REGION                  1..364
                        note = Synthetic
source                  1..364
                        mol_type = protein
                        organism = synthetic construct
SEQUENCE: 123
QCKILRCNAE YVSSTLSLRG GGSSGALRGG GGGGRGGGVG SGGLCRALRS YALCTRRTAR    60
TCRGDLAFHS AVHGIEDLMI QHNCSRQGPT PPPPRGPALP GAGSGLPAPD PCDYEGRFSR   120
LHGRPPGFLH CASFGDPHVR SFHHHFHTCR VQGAWPLLDN DFLFVQATSS PMALGANATA   180
TRKLTIIFKN MQECIDQKVY QAEVDNLPVA FEDGSINGGD RPGGSSLSIQ TANPGNHVEI   240
QAAYIGTTII IRQTAGQLSF SIKVAEDVAM AFSAEQDLQL CVGGCPPSQR LSRSERNRRG   300
AITIDTARRL CKEGLPVEDA YFHSCVFDVL ISGDPNFTVA AQAALEDARA FLPDLEKLHL   360
FPSD                                                                364
```

```
SEQ ID NO: 124          moltype = AA   length = 21
FEATURE                 Location/Qualifiers
REGION                  1..21
                        note = Synthetic
source                  1..21
                        mol_type = protein
                        organism = synthetic construct
SEQUENCE: 124
SSPMALGANA TATRKLTIIF K                                                   21

SEQ ID NO: 125          moltype = AA   length = 30
FEATURE                 Location/Qualifiers
REGION                  1..30
                        note = Synthetic
source                  1..30
                        mol_type = protein
                        organism = synthetic construct
SEQUENCE: 125
DNDFLFVQAT SSPMALGANA TTRKLTIIFK                                          30

SEQ ID NO: 126          moltype = AA   length = 21
FEATURE                 Location/Qualifiers
REGION                  1..21
                        note = Synthetic
source                  1..21
                        mol_type = protein
                        organism = synthetic construct
SEQUENCE: 126
QLCVGGCPPS QRLSRSERNR R                                                   21

SEQ ID NO: 127          moltype = AA   length = 12
FEATURE                 Location/Qualifiers
REGION                  1..12
                        note = Synthetic
source                  1..12
                        mol_type = protein
                        organism = synthetic construct
SEQUENCE: 127
SQRLSRSERN RR                                                             12

SEQ ID NO: 128          moltype = AA   length = 426
FEATURE                 Location/Qualifiers
source                  1..426
                        mol_type = protein
                        organism = Homo sapiens
SEQUENCE: 128
MGEPGQSPSP RSSHGSPPTL STLTLLLLLC GHAHSQCKIL RCNAEYVSST LSLRGGGSSG          60
ALRGGGGGGR GGGVGSGGLC RALRSYALCT RRTARTCRGD LAFHSAVHGI EDLMIQHNCS         120
RQGPTAPPPP RGPALPGAGS GLPAPDPCDY EGRFSRLHGR PPGFLHCASF GDPHVRSFHH         180
HFHTCRVQGA WPLLDNDFLF VQATSSPMAL GANATATRKL TIIFKNMQEC IDQKVYQAEV         240
DNLPVAFEDG SINGGDRPGG SSLSIQTANP GNHVEIQAAY IGTTIIIRQT AGQLSFSIKV         300
AEDVAMAFSA EQDLQLCVGG CPPSQRLSRS ERNRRGAITI DTARRLCKEG LPVEDAYFHS         360
CVFDVLISGD PNFTVAAQAA LEDARAFLPD LEKLHLFPSD AGVPLSSATL LAPLLSGLFV         420
LWLCIQ                                                                  426

SEQ ID NO: 129          moltype = AA   length = 25
FEATURE                 Location/Qualifiers
REGION                  1..25
                        note = Synthetic
source                  1..25
                        mol_type = protein
                        organism = synthetic construct
SEQUENCE: 129
DTHFPICIFC CGCCHRSKCG MCCKT                                               25

SEQ ID NO: 130          moltype = AA   length = 6
FEATURE                 Location/Qualifiers
source                  1..6
                        mol_type = protein
                        organism = synthetic construct
MOD_RES                 2
                        note = Phosphorylated Tyrosine
SEQUENCE: 130
PYLKTK                                                                     6
```

What is claimed is:

1. A method of treating anemia in a subject having myelofibrosis, the method comprising:
   administering to the subject an effective amount of a composition comprising an isolated antibody that binds to human hemojuvelin (HJV) and a pharmaceutically acceptable carrier, wherein the isolated antibody comprises:
   a heavy chain comprising the amino acid sequence of SEQ ID NO: 117, and a light chain comprising the amino acid sequence of SEQ ID NO: 62.

2. The method of claim 1, wherein the composition is administered to the subject via subcutaneous injection.

3. The method of claim 1, wherein the composition is administered to the subject once monthly.

4. The method of claim 1, wherein the anemia results from hepcidin expression that is induced by at least one pro-inflammatory cytokine.

5. The method of claim 4, wherein the administration of the composition reduces the anemia.

6. The method of claim 4, wherein the at least one pro-inflammatory cytokine comprises Interleukin-6 (IL-6).

7. The method of claim 1, wherein the administration reduces hepcidin-25 in the subject within 24 hours of the administration.

8. The method of claim 7, wherein the administration reduces a hepcidin-25 level by at least 50% compared to the hepcidin-25 level in the subject prior to the administration.

9. The method of claim 1, wherein the subject has one or more myelofibrosis-initiating mutations in JAK2, MPL, ASXL1, TET2, NFE2, SH2B3, SF3B1, and/or CALR.

10. The method of claim 1, wherein the subject has primary myelofibrosis, post-essential thrombocythemia (ET) myelofibrosis, or post-polycythemia vera (PV) myelofibrosis.

11. The method of claim 10, wherein the subject has a Dynamic International Prognostic Scoring System (DIPSS) score of more than 1.

12. The method of claim 10, wherein the subject has a DIPSS score of 3-4.

13. The method of claim 10, wherein the subject has a DIPSS score of at least 5.

14. The method of claim 1, wherein the subject has a serum hemoglobin level of less than 10 g/dL.

15. The method of claim 1, wherein the subject has a serum hemoglobin level of less than 8 g/dL.

16. The method of claim 1, wherein the subject is erythrocyte transfusion-dependent.

17. The method of claim 1, wherein the subject has previously received or is receiving a selective JAK-STAT inhibitor.

18. The method of claim 17, the selective JAK-STAT inhibitor is ruxolitinib, fedratinib, pacritinib, INCB039110, AG490, or PpYLKTK (SEQ ID NO: 130).

19. A method of treating anemia in a subject having myelofibrosis, the method comprising administering to the subject an effective amount of a composition comprising:
   (i) an isolated anti-human hemojuvelin (HJV) antibody comprising a heavy chain comprising the amino acid sequence of SEQ ID NO: 61, and a light chain comprising the amino acid sequence of SEQ ID NO: 62; and/or
   (ii) an isolated anti-human hemojuvelin (HJV) antibody comprising a heavy chain comprising the amino acid sequence of SEQ ID NO: 117, and a light chain comprising the amino acid sequence of SEQ ID NO: 62,
   wherein the composition further comprises a pharmaceutically acceptable carrier.

20. The method of claim 19, wherein the composition is administered to the subject via subcutaneous injection.

21. The method of claim 19, wherein the anemia results from hepcidin expression that is induced by at least one pro-inflammatory cytokine.

22. The method of claim 19, wherein the subject has primary myelofibrosis, post-essential thrombocythemia (ET) myelofibrosis, or post-polycythemia vera (PV) myelofibrosis.

23. The method of claim 19, wherein the subject is erythrocyte transfusion-dependent.

24. The method of claim 19, wherein the subject has previously received or is receiving a selective JAK-STAT inhibitor.

25. A method of treating anemia in a subject having myelofibrosis, the method comprising:
   administering to the subject an effective amount of a composition comprising an isolated antibody that binds to human hemojuvelin (HJV) and a pharmaceutically acceptable carrier, wherein the isolated antibody comprises:
   a heavy chain comprising the amino acid sequence of SEQ ID NO: 61, and a light chain comprising the amino acid sequence of SEQ ID NO: 62.

26. The method of claim 25, wherein the composition is administered to the subject via subcutaneous injection.

27. The method of claim 25, wherein the anemia results from hepcidin expression that is induced by at least one pro-inflammatory cytokine.

28. The method of claim 25, wherein the subject has primary myelofibrosis, post-essential thrombocythemia (ET) myelofibrosis, or post-polycythemia vera (PV) myelofibrosis.

29. The method of claim 25, wherein the subject is erythrocyte transfusion-dependent.

30. The method of claim 25, wherein the subject has previously received or is receiving a selective JAK-STAT inhibitor.

* * * * *

UNITED STATES PATENT AND TRADEMARK OFFICE
CERTIFICATE OF CORRECTION

| | |
|---|---|
| PATENT NO. | : 12,365,729 B2 |
| APPLICATION NO. | : 18/896718 |
| DATED | : July 22, 2025 |
| INVENTOR(S) | : Maria Beconi et al. |

Page 1 of 1

It is certified that error appears in the above-identified patent and that said Letters Patent is hereby corrected as shown below:

On the Title Page

In item (71), the third Applicant's name is hereby corrected as shown below:
(71) Applicants: Disc Medicine, Inc., Watertown, MA (US); AbbVie Inc., North Chicago, IL (US); AbbVie Deutschland GmbH & Co. KG, Wiesbaden (DE)

In item (73), the second and third Assignees' names are hereby corrected as shown below:
(73) Assignees: Disc Medicine, Inc., Watertown, MA (US); AbbVie Inc., North Chicago, IL (US); AbbVie Deutschland GmbH & Co. KG, Wiesbaden (DE)

Signed and Sealed this
Sixteenth Day of September, 2025

Coke Morgan Stewart
*Acting Director of the United States Patent and Trademark Office*